US009085527B2

(12) United States Patent
Vu et al.

(10) Patent No.: US 9,085,527 B2
(45) Date of Patent: *Jul. 21, 2015

(54) FATTY ACID ACYLATED SALICYLATES AND THEIR USES

(75) Inventors: Chi B. Vu, Arlington, MA (US); Jean E. Bemis, Arlington, MA (US); Michael R. Jirousek, Cambridge, MA (US); Jill C. Milne, Brookline, MA (US); Jesse J. Smith, Waltham, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 850 days.

This patent is subject to a terminal disclaimer.

(21) Appl. No.: 12/714,308

(22) Filed: Feb. 26, 2010

(65) Prior Publication Data
US 2010/0184730 A1    Jul. 22, 2010

Related U.S. Application Data

(63) Continuation-in-part of application No. 12/499,779, filed on Jul. 8, 2009, now Pat. No. 8,173,831.

(60) Provisional application No. 61/078,983, filed on Jul. 8, 2008, provisional application No. 61/104,363, filed on
(Continued)

(51) Int. Cl.
*C07C 69/86* (2006.01)
*A61K 31/60* (2006.01)
(Continued)

(52) U.S. Cl.
CPC .......... *C07C 69/86* (2013.01); *C07C 69/65* (2013.01); *C07C 69/94* (2013.01); *C07C 233/20* (2013.01); *C07C 233/49* (2013.01); *C07C 233/55* (2013.01); *C07C 235/60* (2013.01); *C07C 237/22* (2013.01); *C07C 271/28* (2013.01);
(Continued)

(58) Field of Classification Search
CPC ..... A61K 8/368; A61K 31/60; A61K 31/616; C07D 307/77; C07C 69/65; C07C 69/86; C07C 69/94
See application file for complete search history.

(56) References Cited

U.S. PATENT DOCUMENTS

| 4,036,951 A | 7/1977 | Halpern et al. |
| 4,199,576 A | 4/1980 | Reller et al. |

(Continued)

FOREIGN PATENT DOCUMENTS

| EP | 0675103 | 10/1995 |
| ES | 428254 | 7/1974 |

(Continued)

OTHER PUBLICATIONS

Higdon, J. et al., Essential Fatty acids, 2005, Linus Pauling Institute, Oregon State University, 46 pages (pp. 1-46).*

(Continued)

*Primary Examiner* — Yate K Cutliff
(74) *Attorney, Agent, or Firm* — Goodwin Procter LLP

(57) ABSTRACT

The invention relates to fatty acid acylated salicylate derivatives; compositions comprising an effective amount of a fatty acid acylated salicylate derivative; and methods for treating or preventing an inflammatory disorder comprising the administration of an effective amount of a fatty acid acylated salicylate derivative.

54 Claims, 3 Drawing Sheets

Related U.S. Application Data

Oct. 10, 2008, provisional application No. 61/104,364, filed on Oct. 10, 2008, provisional application No. 61/104,366, filed on Oct. 10, 2008, provisional application No. 61/148,658, filed on Jan. 30, 2009.

(51) Int. Cl.

| | | |
|---|---|---|
| *C07D 307/77* | (2006.01) | |
| *C07C 69/65* | (2006.01) | |
| *C07C 69/94* | (2006.01) | |
| *C07C 233/20* | (2006.01) | |
| *C07C 233/49* | (2006.01) | |
| *C07C 233/55* | (2006.01) | |
| *C07C 235/60* | (2006.01) | |
| *C07C 237/22* | (2006.01) | |
| *C07C 271/28* | (2006.01) | |
| *C07C 275/42* | (2006.01) | |
| *C07C 323/42* | (2006.01) | |
| *C07D 207/416* | (2006.01) | |
| *C07D 295/192* | (2006.01) | |

(52) U.S. Cl.
CPC .............. *C07C 275/42* (2013.01); *C07C 323/42* (2013.01); *C07D 207/416* (2013.01); *C07D 295/192* (2013.01); *C07D 307/77* (2013.01)

(56) References Cited

U.S. PATENT DOCUMENTS

| | | | |
|---|---|---|---|
| 4,264,517 A | 4/1981 | Liang | |
| 4,276,430 A | 6/1981 | Reller et al. | |
| 4,551,279 A | 11/1985 | Mueller et al. | |
| 4,670,465 A | 6/1987 | Guzman et al. | |
| 5,603,959 A * | 2/1997 | Horrobin et al. | 424/490 |
| 5,728,732 A | 3/1998 | Corey et al. | |
| 5,760,261 A | 6/1998 | Guttag | |
| 5,792,786 A | 8/1998 | Whittaker et al. | |
| 6,245,811 B1 * | 6/2001 | Horrobin et al. | 514/547 |
| 6,353,124 B1 | 3/2002 | Whittaker et al. | |
| 6,387,945 B2 | 5/2002 | Packer et al. | |
| 6,602,902 B2 | 8/2003 | Shashoua et al. | |
| 6,956,077 B1 | 10/2005 | Akiyama et al. | |
| RE40,546 E | 10/2008 | Clarkson et al. | |
| 7,560,473 B2 | 7/2009 | Wang et al. | |
| 8,173,831 B2 | 5/2012 | Milne et al. | |
| 8,729,293 B2 | 5/2014 | Milne et al. | |
| 8,735,378 B2 | 5/2014 | Milne et al. | |
| 8,735,379 B2 | 5/2014 | Milne et al. | |
| 2001/0002404 A1 | 5/2001 | Webb et al. | |
| 2003/0059865 A1 | 3/2003 | Nelson | |
| 2004/0254357 A1 | 12/2004 | Zaloga et al. | |
| 2007/0155747 A1 | 7/2007 | Dasse et al. | |
| 2010/0041748 A1 | 2/2010 | Milne et al. | |
| 2011/0082192 A1 | 4/2011 | Milne et al. | |
| 2012/0238530 A1 | 9/2012 | Milne et al. | |
| 2012/0238585 A1 | 9/2012 | Milne et al. | |
| 2012/0238586 A1 | 9/2012 | Milne et al. | |
| 2012/0238756 A1 | 9/2012 | Milne et al. | |
| 2014/0221323 A1 | 8/2014 | Milne et al. | |

FOREIGN PATENT DOCUMENTS

| | | |
|---|---|---|
| GB | 1581443 | 12/1980 |
| JP | 562223159 A | 10/1987 |
| JP | 2004168024 A | 6/2004 |
| WO | WO 86/03199 | 6/1986 |
| WO | WO 96/33155 | 10/1996 |
| WO | 96/34846 A1 | 11/1996 |
| WO | 96/34855 A1 | 11/1996 |
| WO | WO-96/34858 A1 | 11/1996 |
| WO | 98/18751 A1 | 5/1998 |
| WO | 01/45744 | 6/2001 |
| WO | WO-2006/066894 A1 | 6/2006 |
| WO | WO 2007/116027 | 10/2007 |
| WO | WO-2009/138437 A1 | 11/2009 |
| WO | WO-2011/089529 A1 | 7/2011 |
| WO | WO-2012/003563 A1 | 1/2012 |
| WO | WO-2013/175357 A2 | 11/2013 |

OTHER PUBLICATIONS

Hyo-Kyung Han et al.; "Targeted Prodrug Design to Optimize Drug Delivery;" AAPS Pharmsci 2000, 2(1) Article 6, (http://www.pharmsci.org/); Mar. 21, 2000; 11 pages).

"L-DOPA;" Retrieved from "http://en.wikipedia.org/wiki/L-DOPA;" (http://en.wikipedia.org/wiki/Levodopa; Aug. 28, 2008; 5 pages.

"Prodrug;" Retrieved from "http://en.wikipedia.org/wiki/Prodrug;" (http://en.wikipedia.org/wiki/Prodrug); Aug. 28, 2008; 2 pages.

Ferrucci, L. et al., "Relationship of plasma polyunsaturated fatty acids to circulating inflammatory markers," Journal of Clinical Endocrinology and Metabolism, 2006, vol. 91(2), pp. 439-446.

International Search Report and Written Opinion for International Application No. PCT/US2009/049982, mailed Oct. 14, 2009, 10 pages.

Zhu et al. "Synthesis of One N-Methylaminocarbamate Containing Disulfide Linkage" Huaxue Shiji, vol. 29, pp. 389-393, 2007.

Extended European Search Report for European Patent Application No. 14176625.3 dated Nov. 13, 2014 (5 pages).

Opposition filed by Chilean Pharmaceutical Labs Industrial Association in Chilean Patent Application No. 24-2011 dated Aug. 11, 2011 (English translation; 4 pages).

Gerwick et al. "Phenolic Lipids From Related Marine Algae Of The Order Dictyotales" Phytochemistry, vol. 21, No. 3, pp. 633-637, 1982.

\* cited by examiner

FATTY ACID ACYLATED SALICYLATES AND THEIR USES

1. PRIORITY

This application is a continuation-in-part of U.S. application Ser. No. 12/499,779, filed Jul. 8, 2009, and claims the benefit of U.S. Provisional Application No. 61/148,658, filed Jan. 30, 2009, U.S. Provisional Application No. 61/104,363, filed Oct. 10, 2008, U.S. Provisional Application No. 61/104,364, filed Oct. 10, 2008, U.S. Provisional Application No. 61/104,366, filed Oct. 10, 2008, and U.S. Provisional Application No. 61/078,983, filed Jul. 8, 2008. The entire disclosures of those applications are relied on and incorporated into this application by reference.

2. FIELD OF THE INVENTION

The invention relates to fatty acid acylated salicylate derivatives, fatty acid acylated diflunisal derivatives, and fatty acid acylated triflusal derivatives (compounds of the invention); compositions comprising an effective amount of a fatty acid acylated salicylate derivative, a fatty acid acylated diflunisal derivative, and/or a fatty acid acylated triflusal derivative (compound of the invention); and methods for treating or preventing an inflammatory disease comprising the administration of an effective amount of a compound of the invention. All patents, patent applications and publications cited herein are hereby incorporated by reference in their entireties.

3. BACKGROUND OF THE INVENTION

Inflammatory pathways underlie the key pathophysiology of many chronic and acute diseases. Unresolved inflammation is important in many chronic disorders, including, but not limited to, heart disease, atherosclerosis, type 1 and type 2 diabetes, dyslipidemia, asthma, arthritis (including rheumatoid arthritis (RA)), osteoarthritis, cystic fibrosis, muscle wasting disease (including muscular dystrophy), pain, insulin resistance, oxidative stress, inflammatory bowel disease (IBD) (including colitis and Crohn's disease), and neurodegenerative disease (including Alzheimer's disease).

In more recent years, the study of inflammation has gone deeper into the cell. Cell-signaling molecules have been identified that modulate the expression of genes that control the inflammatory response, including the pro-inflammatory response and the anti-inflammatory response. One of the central regulators that balance the genes encoding anti- and pro-inflammation factors is Nuclear Factor Kappa Beta (NFκB). NFκB is a family of transcriptions factors that include p50 (NFκB1), p52 (NFκB2), p65 (RelA), c-Rel and RelB. These nuclear factors are held as complexes or dimeric pairs in an inactive state in the cytoplasm as a complex by a NFκB inhibitory factor IκB. The IκB proteins include IκBα, IκBβ, and IκBε, but others also exist. The inactive NFκB complex is released from the cytoplasm by phosphorylation of the IκB protein through kinases such as IKKβ. The kinases regulating NFκB activity are activated by immune responses or cellular stresses. Thus, in the cytoplasmic NFκB complex such as IκB/p65/p50, IκB becomes phosphorylated through kinases such as IKKβ and releases dimeric pairs of NFκB to the nucleus such as p65/p50. In the nucleus, NFκB regulates genetic expression of proinflammatory factors such as cytokines like TNFα, IL-6, and IL-1β in addition to enzymes such as cyclooxygenase-2 (COX-2) one of the enzymes that converts arachidonic acid to prostaglandin H2 (PGH2). These factors induce inflammation in various tissues. In addition, depending upon the cellular context and the NFκB nuclear factors released NFκB can cause the expression of anti-inflammatory genes.

Salicylates and other non-steroidal anti-inflammatory drugs (NSAIDs) can influence the NFκB pathway, allowing people to derive relief and reduced inflammation from these drugs. Aspirin and COX inhibitors act to reduce inflammation by reversibly or irreversibly blocking access to the hydrophobic channel via acetylation of serine 530 (COX-1) or Serine 516 (COX-2). For some selective NSAIDs with a carboxylate group, there is significant charge-charge interaction with Arginine 120. This binding or interaction blocks the cyclooxygenase enzyme that forms $PGH_2$. Salicylate does not irreversibly inhibit cyclooxygenase because it lacks the ability to acylate the COX enzyme and has little, if any, direct inhibitory action on the COX enzyme at concentrations that are relevant in vivo. Salicylate has been shown to inhibit the activity of IKKβ and thereby inhibit NFκB leading to reduced expression of COX-2 in an inflammatory state where COX-2 expression has been induced.

Another example of an NSAID is diflunisal:

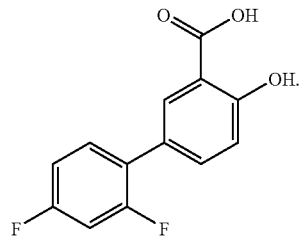 [SMILES: O=C(O)c1cc(-c2ccc(F)cc2F)ccc1O]

Yet another example of an NSAID is triflusal:

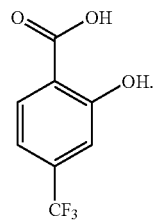 [SMILES: O=C(O)c1ccc(C(F)(F)F)cc1O]

Diflunisal and Triflusal are commonly used to relieve pain, tenderness, swelling and stiffness caused by osteoarthritis and rheumatoid arthritis, and to relieve mild to moderate pain generally.

Problems arise in salicylate therapy due to side effects, which means alternative ways need to be developed and pursued to reduce NFκB activity. Some salicylates, when given orally, have a key disadvantage of causing gastric ulcers over the long term in chronic administration. In addition, salicylates can be strong irritants, thought to be caused by the high local concentration of these COX inhibitors. Many of the unwanted effects of aspirin are caused by the inappropriate inhibition of COX or the NFκB pathway. Although NSAIDs inhibit COX and are efficacious anti-inflammatory agents, adverse effects limit their use.

Other anti-inflammatory agents that modulate NFκB activity are omega-3 polyunsaturated fatty acids (PUFA). Omega-3 fatty acids also reduce IL-1, which is an activator of NFκB, and increase anti-inflammatory cytokines, such as IL-10, and adipokines, such as adiponectin. Oily cold water fish, such as salmon, trout, herring, and tuna are the source of dietary marine omega-3 fatty acids with eicosapentaenoic acid (EPA) and docosahexaenoic acid (DHA) being the key marine derived omega-3 fatty acids. Leafy green vegetables, and certain beans, nuts or oils, such as soybeans, walnuts, flaxseed, and canola oil, are also rich dietary sources of omega-3 fatty acids.

The anti-inflammatory effects of omega-3 fatty acids have been widely studied with positive results for several chronic inflammatory diseases. TNFα and IL-6 are cytokines that increase dramatically during inflammatory processes and are commonly measured as markers of inflammation. Greater intake of omega-3 PUFA has been shown to associate strongly with lower levels of circulating TNFα and IL-6 (Ferrucci, L. et al. *J Clin. Endocrinol. Metab.* 2006, 91, 439-446). Furthermore, higher intake of omega-3 PUFA has also been associated with increased levels of markers of anti-inflammation, including the well-characterized anti-inflammatory cytokine IL-10 (Ferrucci, L. et al. *J. Clin. Endocrinol. Metab.* 2006, 91, 439-446). Animal models of colitis indicate that fish oil decreases colonic damage and inflammation, weight loss, and mortality. Fish oil supplements in patients with IBD have shown to modulate levels of inflammatory mediators and may be beneficial for the induction and maintenance of remission in ulcerative colitis.

In the management of RA and other inflammatory conditions, side effects limit the use of NSAIDs. A clinical trial showed that 39 percent of patients with RA supplemented with cod liver oil were able to reduce their daily NSAID requirement by greater than 30 percent. Omega-3 fatty acids have been used to reduce the risk for sudden death caused by cardiac arrhythmias, have been taken as dietary supplements, and the ethyl ester of omega-3 fatty acids as a combination therapy is used to treat dyslipidemia.

Furthermore, omega-3 fatty acids have been shown to improve insulin sensitivity and glucose tolerance in normoglycemic men and in obese individuals. Omega-3 fatty acids have also been shown to improve insulin resistance in obese and non-obese patients with an inflammatory phenotype. Lipid, glucose and insulin metabolism have been show to be improved in overweight hypertensive subjects through treatment with omega-3 fatty acids.

DHA or EPA, C22 and C20 omega-3 fatty acids, are metabolized to active anti-inflammatory metabolites, some of which include resolvins and protectins, and activate various anti-inflammatory pathways.

The ability to simultaneously blunt proinflammatory pathways, for example those that affect levels of C-reactive protein (CRP), TNFα and IL-6 cytokines, while stimulating anti-inflammatory pathways by shunting omega-3 fatty acids, such as DHA and EPA, into metabolic pathways that ultimately produce resolvins, protectins and other metabolites that resolve inflammation would be a great benefit in treating the aforementioned diseases. Inflammation could be particularly vulnerable to a two-pronged attack, inhibiting pro-inflammatory pathways and upregulating anti-inflammatory pathways.

4. SUMMARY OF THE INVENTION

The invention is based in part on the discovery of fatty acid acylated salicylate derivatives and their demonstrated effects in the simultaneous upregulation of anti-inflammatory pathways and down regulation of proinflammatory pathways. The invention is also based in part on the discovery of fatty acid acylated diflunisal derivatives and their upregulation of anti-inflammatory pathways and down regulation of proinflammatory pathways. Additionally, the invention is based in part on the discovery of fatty acid acylated triflusal derivatives and their upregulation of anti-inflammatory pathways and down regulation of proinflammatory pathways. These novel compounds of the invention are useful in the treatment or prevention of diseases associated with inflammation.

Accordingly in one aspect, a molecular conjugate is described which comprises a salicylate and a fatty acid covalently linked, wherein the fatty acid is selected from the group consisting of omega-3 fatty acids and fatty acids that are metabolized in vivo to omega-3 fatty acids, and the conjugate is capable of hydrolysis to produce free salicylate and free fatty acid.

In another aspect, compounds of the Formula I are described:

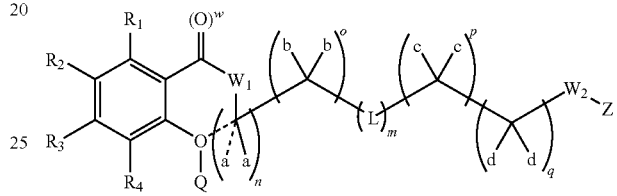

Formula I and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each symbol ----- represents an optional bond, which when present between the phenolic oxygen and the methylene containing substituent a, requires that Q is null, or when present between substituent a and the carbon of the methylene containing substituent a, requires that Q not be null;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$—, —S—S—,

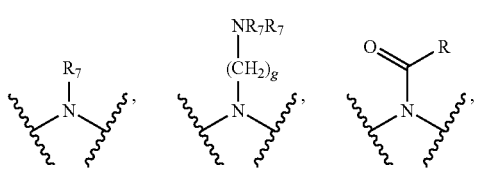

[Structural formulas shown]

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H, or

[Structural formula]

with the proviso that there is at least one

[Structural formula]

in the compound;
each r is independently 2 or 3;
each s is independently 5 or 6;
w is 0 or 1;
each t is independently 0 or 1;
Q is null, $C(O)CH_3$, Z,

[Structural formulas]

each e is independently H or any one of the side chains of the naturally occurring amino acids;
$W_3$ is null, —O—, or —N(R)—; and
T is H, $C(O)CH_3$, or Z;
provided that
when m, n, o, p, and q are each 0, $W_1$ and $W_2$ are each null, w is 1, and Z is

[Structural formula]

then t must be 0; and
when w is 0, then $W_1$ is O or NH.

In another aspect, compounds of the Formula Ia are described:

Formula Ia

[Structural formula]

and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —$NH(C_1-C_3$ alkyl), —$N(C_1-C_3$ alkyl)$_2$, —$NH(C(O)C_1-C_3$ alkyl), —$N(C(O)C_1-C_3$ alkyl)$_2$, —C(O)H, —C(O)$C_1-C_3$ alkyl, —C(O)O$C_1-C_3$ alkyl, —C(O)$NH_2$, —C(O)NH($C_1-C_3$ alkyl), —C(O)N($C_1-C_3$ alkyl)$_2$, —$C_1-C_3$ alkyl, —O—$C_1-C_3$ alkyl, —S(O)$C_1-C_3$ alkyl, —S(O)$_2C_1-C_3$ alkyl, difluorophenyl, and trifluoromethyl;

r is 2 or 3; and s is 5 or 6.

In another aspect, compounds of the Formula Ib are described:

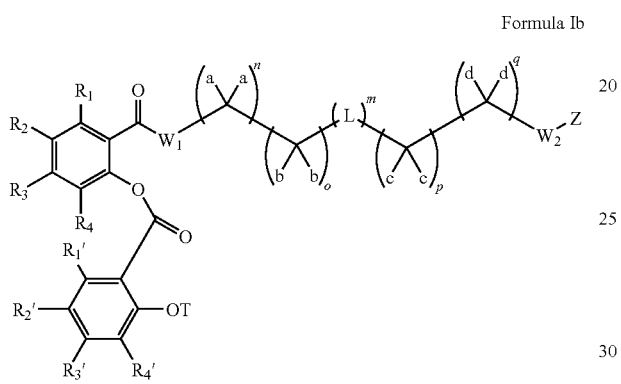

Formula Ib and pharmaceutically acceptable salts, hydrates, solvates, prodrugs, enantiomers, and stereoisomers thereof;

wherein $R_1$, $R_2$, $R_3$, $R_4$, $R_1'$, $R_2'$, $R_3'$, and $R_4'$ are each independently selected from the group consisting of H, Cl, F, CN, $NH_2$, —$NH(C_1-C_3$ alkyl), —$N(C_1-C_3$ alkyl)$_2$, —$NH(C(O)C_1-C_3$ alkyl), —$N(C(O)C_1-C_3$ alkyl)$_2$, —C(O)H, —C(O)$C_1-C_3$ alkyl, —C(O)O$C_1-C_3$ alkyl, —C(O)$NH_2$, —C(O)NH($C_1-C_3$ alkyl), —C(O)N($C_1-C_3$ alkyl)$_2$, —$C_1-C_3$ alkyl, —O—$C_1-C_3$ alkyl, —S(O)$C_1-C_3$ alkyl, —S(O)$_2C_1-C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$—, —S—S—,

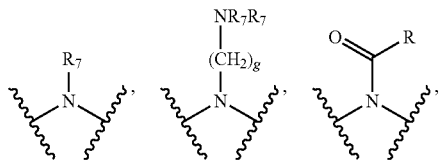

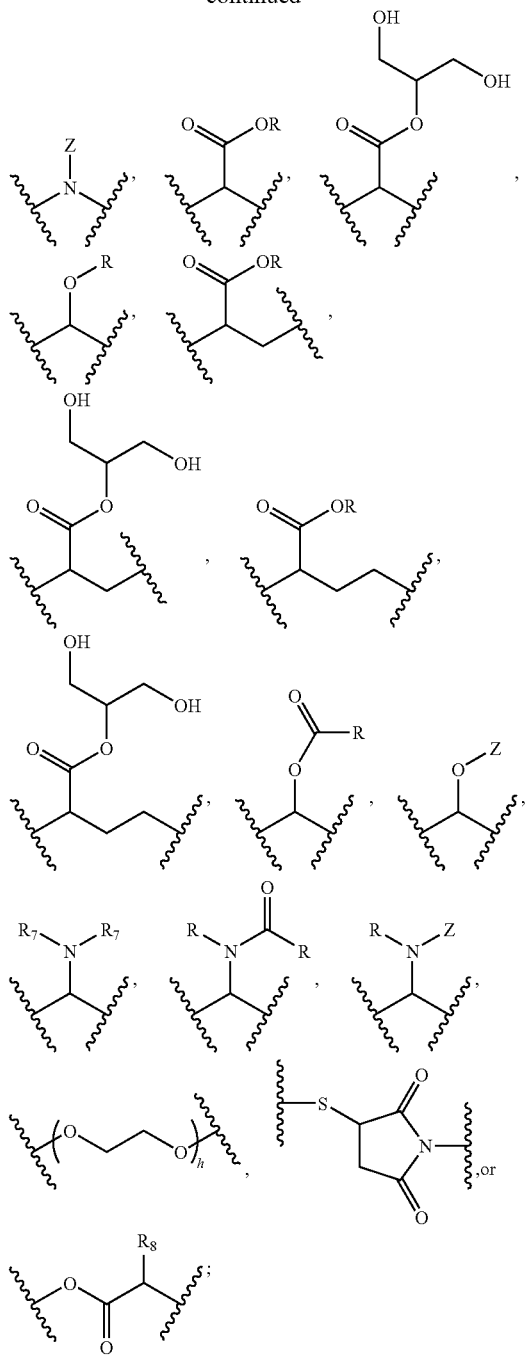

each g is independently 2, 3 or 4;

each h is independently 1, 2, 3 or 4;

m is 0, 1, 2, or 3;

each $R_7$ is independently H or $C_1-C_6$ alkyl, or both $R_7$ groups, when taken together with the nitrogen to which they are attached, can form a heterocycle;

each $R_8$ is independently e, H or straight or branched $C_1-C_{10}$ which can be optionally substituted with OH, $NH_2$, $CO_2R$, $CONH_2$, phenyl, $C_6H_4OH$, imidazole or arginine;

each R is independently H, —C(O)—$C_1-C_3$ alkyl, or straight or branched $C_1-C_4$ alkyl optionally substituted with OR, $NR_2$, or halogen;

each Z is independently H, or

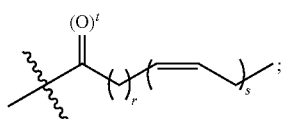

with the proviso that there is at least one

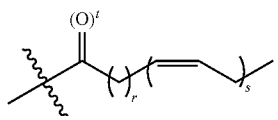

in the compound;
each r is independently 2 or 3;
each s is independently 5 or 6;
each t is independently 0 or 1;
each e is independently H or any one of the side chains of the naturally occurring amino acids; and
T is H, C(O)CH$_3$, or Z;
provided that
when m, n, o, p, and q are each 0, W$_1$ and W$_2$ are each null, and Z is

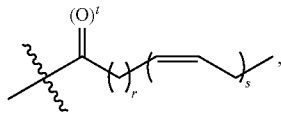

then t must be 0.

In another aspect, compounds of the Formula Ic are described:

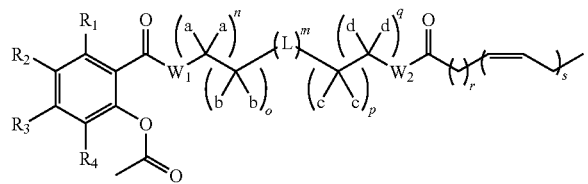

Formula Ic and pharmaceutically acceptable salts, hydrates, solvates, enantiomers, and stereoisomers thereof,
wherein
R$_1$, R$_2$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, —S(O)$_2$C$_1$-C$_3$ alkyl, difluorophenyl, and trifluoromethyl;
W$_1$ and W$_2$ are each null, O, or NH, or when W$_1$ and W$_2$ are both NH, then both W$_1$ and W$_2$ can be taken together to form a piperidine moiety;
each a and c is independently H, CH$_3$, —OCH$_3$, —OCH$_2$CH$_3$, C(O)OH, C(O)OR or benzyl;
each b is independently H, CH$_3$, C(O)OH, O—Z, C(O)OR or benzyl;
each d is independently H, C(O)OH, C(O)OR or benzyl;
each n, o, p, and q is independently 0 or 1;
each L is independently —O—, —S—, —S(O)—, —S(O)$_2$—, —S—S—,

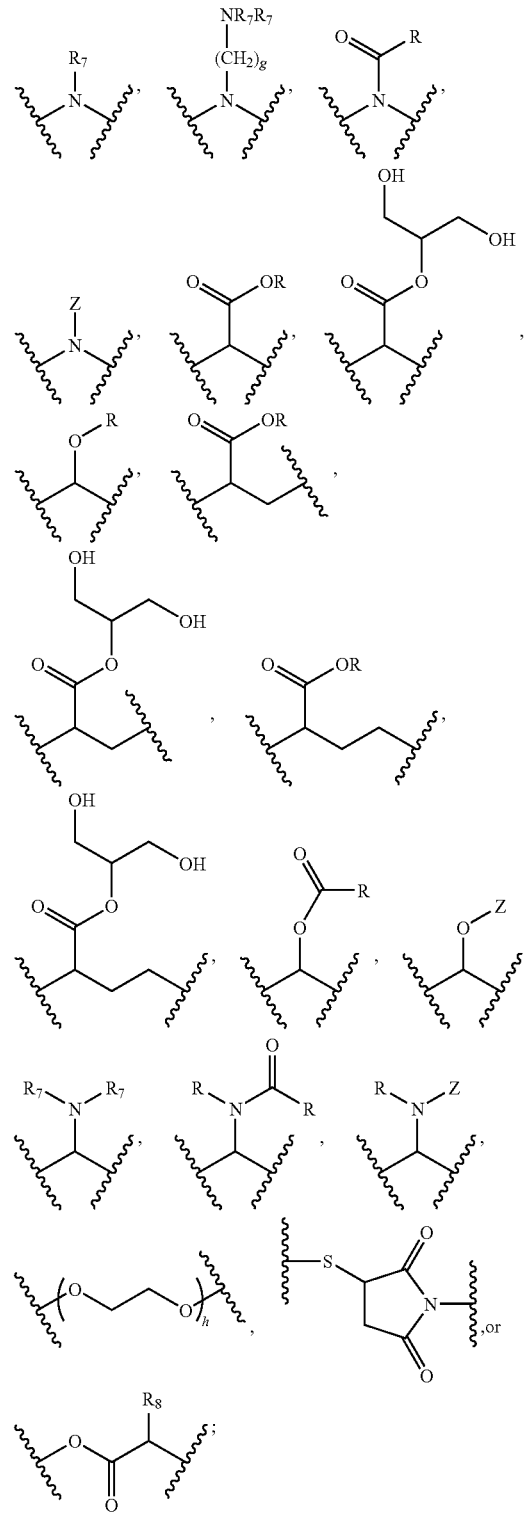

each g is independently 2, 3 or 4;
each h is independently 1, 2, 3 or 4;

m is 0, 1, 2, or 3;

each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H, or

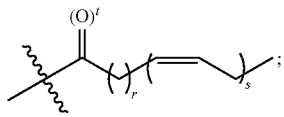

each r is independently 2 or 3;
each s is independently 5 or 6;
each t is independently 0 or 1, and
each e is independently H or any one of the side chains of the naturally occurring amino acids;

provided that
when m, n, o, p, and q are each 0, $W_1$ and $W_2$ must not both be null; and
when $W_1$ and $W_2$ are each null, one of m, n, o, p, and q must be at least 1.

In another aspect, compounds of the Formula Id are described:

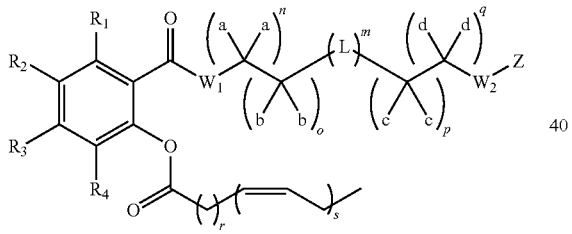

Formula Id and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;
each b is independently H, $CH_3$, C(O)OH, O—Z, C(O)OR or benzyl;
each d is independently H, C(O)OH, C(O)OR or benzyl;
each n, o, p, and q is independently 0 or 1;
each L is independently —O—, —S—, —S(O)—, —S(O)$_2$—, —S—S—,

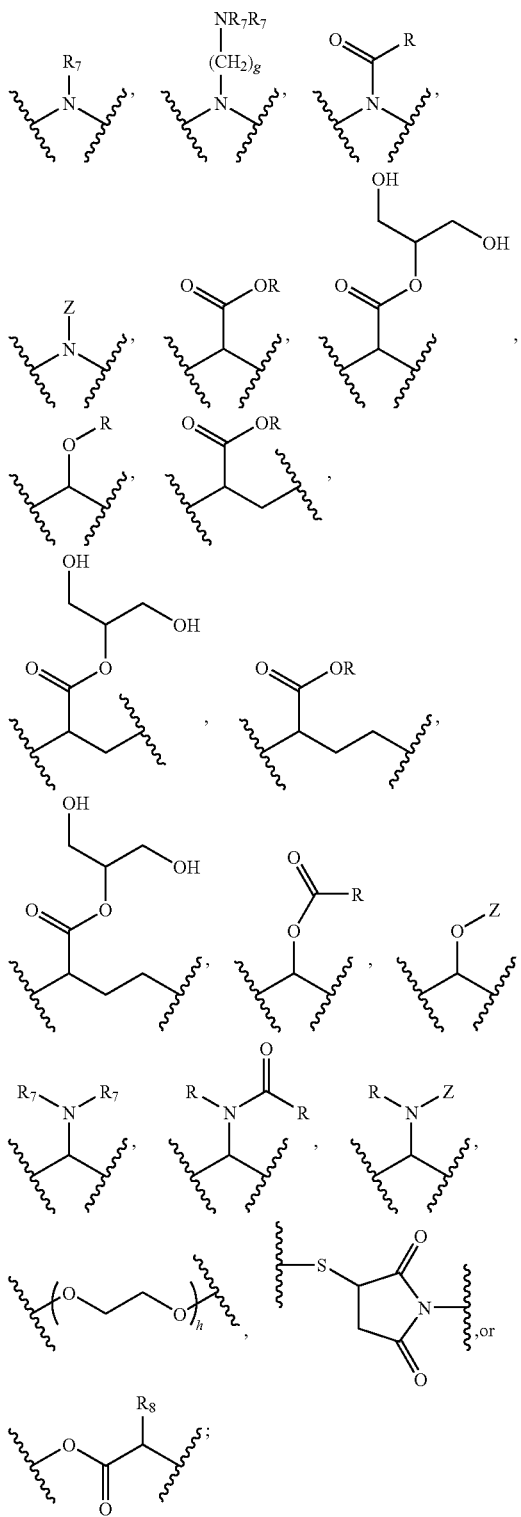

each g is independently 2, 3 or 4;
each h is independently 1, 2, 3 or 4;
m is 0, 1, 2, or 3;

each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H, or

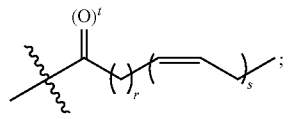

each r is independently 2 or 3;
each s is independently 5 or 6;
each t is independently 0 or 1, and
each e is independently H or any one of the side chains of the naturally occurring amino acids;
provided that
when m, n, o, p, and q are each 0, $W_1$ and $W_2$ are each null, and Z is

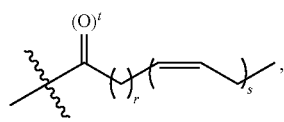

then t must be 0.

In another aspect, compounds of the Formula If are described:

Formula If

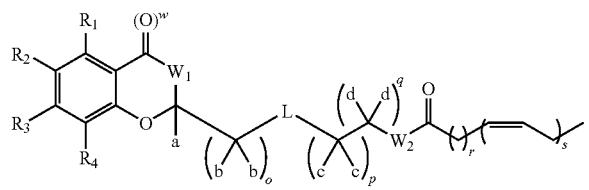

and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2C_1$-$C_3$ alkyl, difluorophenyl, and trifluoromethyl;
$W_1$ and $W_2$ are each null, O, or NH;
each a and c is independently H, $CH_3$, —$OCH_3$, —$OCH_2CH_3$, C(O)OH, C(O)OR or benzyl;
each b is independently H, $CH_3$, C(O)OH, O—Z, C(O)OR or benzyl;
each d is independently H, C(O)OH, C(O)OR or benzyl;
each o, p, and q is independently 0 or 1;
each L is independently —O—, —S—, —S(O)—, —S(O)$_2$—, —S—S—,

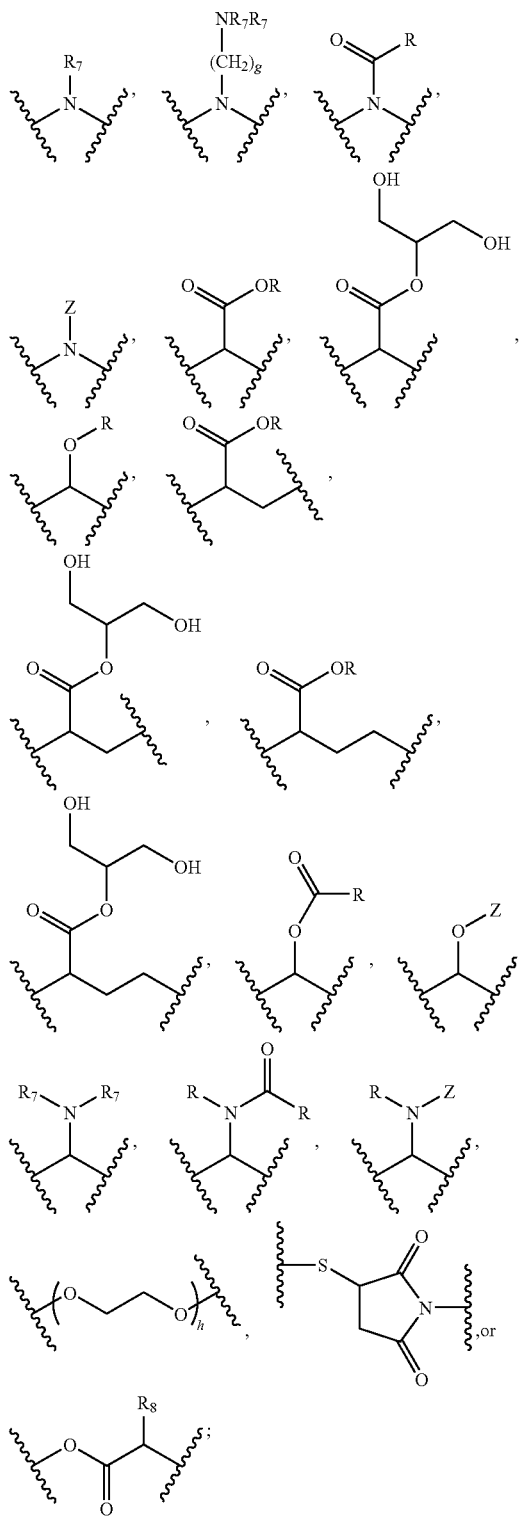

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H, or

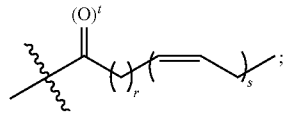

each r is independently 2 or 3;
each s is independently 5 or 6;
each t is independently 0 or 1;
w is 0 or 1; and
each e is independently H or any one of the side chains of the naturally occurring amino acids.

In another aspect, compounds of the Formula Ih are described:

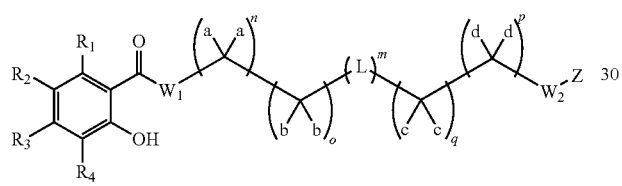

Formula Ih and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;
each n, o, p, and q is independently 0 or 1;
each L is independently —O—, —S—, —S(O)—, —S(O)$_2$—, —S—S—,

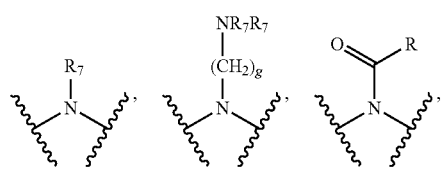

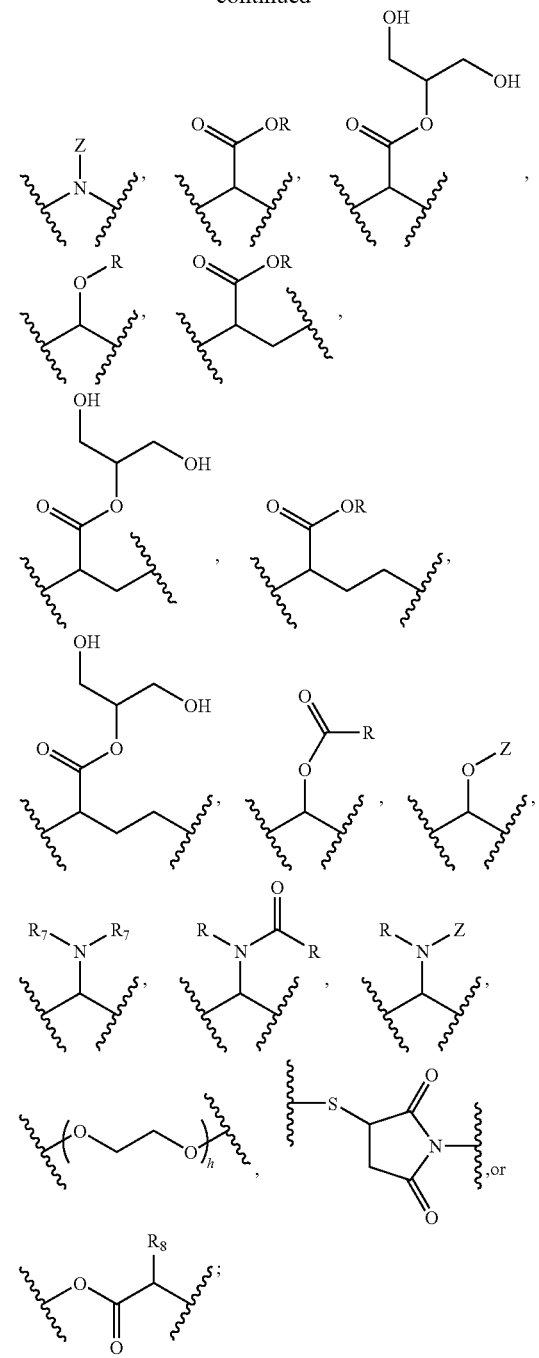

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H, or

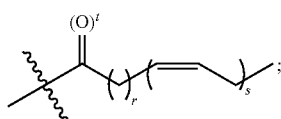

with the proviso that there is at least one

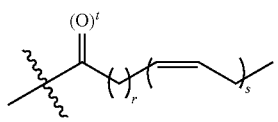

in the compound;
each r is independently 2 or 3;
each s is independently 5 or 6;
each t is independently 0 or 1; and
each e is independently H or any one of the side chains of the naturally occurring amino acids;
provided that
when m, n, o, p, and q are each 0, $W_1$ and $W_2$ are each null, and Z is

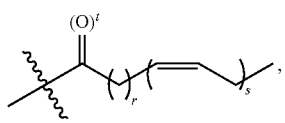

then t must be 0.

In another aspect, compounds of the Formula Ii are described:

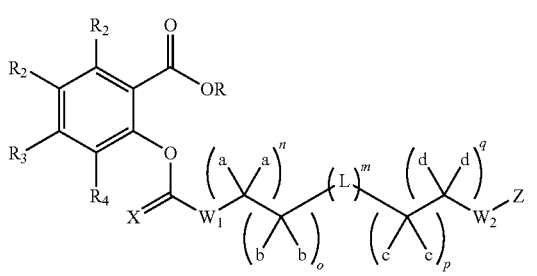

Formula Ii and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2C_1$-$C_3$ alkyl, difluorophenyl and trifluoromethyl;
$W_1$ and $W_2$ are each independently null, O, or NH, or when $W_1$ and $W_2$ are both NH, then both $W_1$ and $W_2$ can be taken together to form a piperidine moiety;
X is O or S;
each a and c is independently H, $CH_3$, —$OCH_3$, —$OCH_2CH_3$, C(O)OH, C(O)OR or benzyl;
each b is independently H, $CH_3$, C(O)OH, O—Z, C(O)OR or benzyl;
each d is independently H, C(O)OH, C(O)OR or benzyl;
each n, o, p, and q is independently 0 or 1;
each L is independently —O—, —S—, —S(O)—, —S(O)$_2$—, —S—S—,

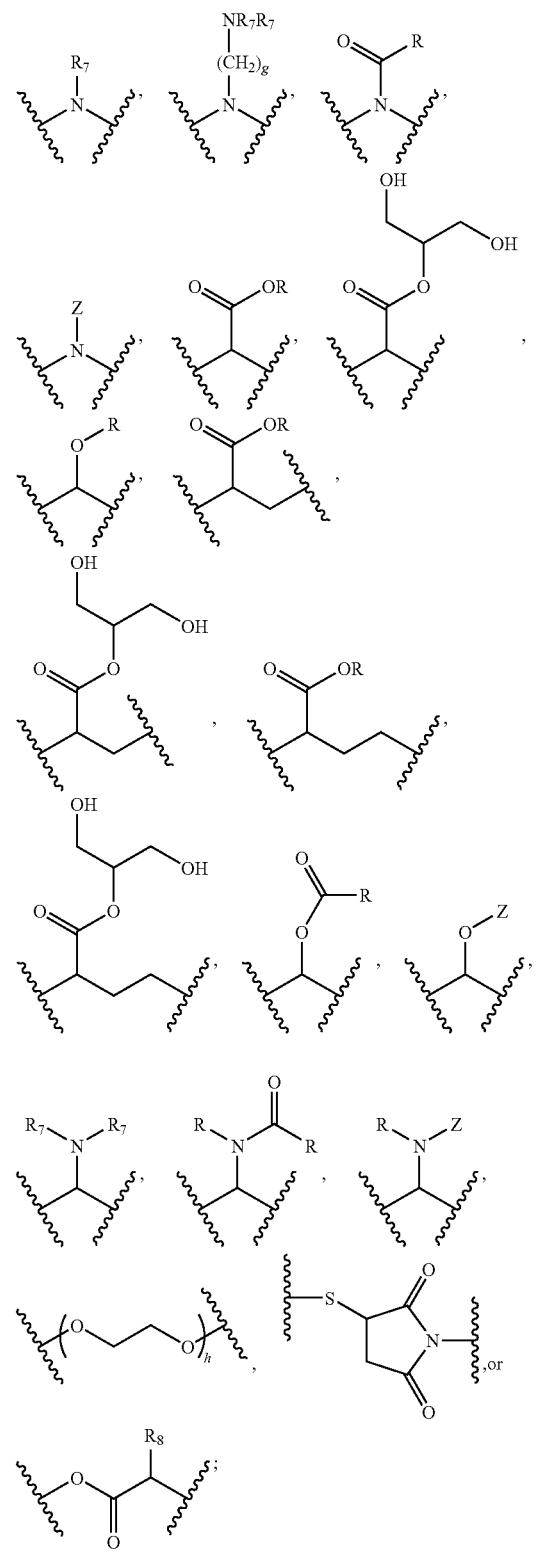

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H, or

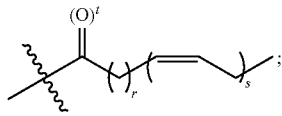

each r is independently 2 or 3;
each s is independently 5 or 6;
each t is independently 0 or 1, and
each e is independently H or any one of the side chains of the naturally occurring amino acids;
provided that
when m, n, o, p, and q are each 0, $W_1$ and $W_2$ are each null, and Z is

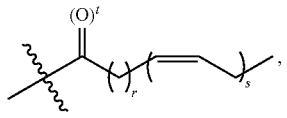

then t must be 6.

In another aspect, compounds of the Formula II are described:

Formula II

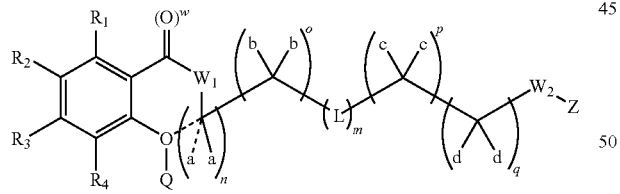

and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2C_1$-$C_3$ alkyl, difluorophenyl, and trifluoromethyl;
$W_1$ and $W_2$ are each independently null, O, or NH, or when $W_1$ and $W_2$ are both NH, then both $W_1$ and $W_2$ can be taken together to form a piperidine moiety;

each symbol represents ----- an optional bond, which when present between the phenolic oxygen and the methylene containing substituent a, requires that Q is null, or when present between substituent a and the carbon of the methylene containing substituent a, requires that Q not be null;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$—, —S—S—,

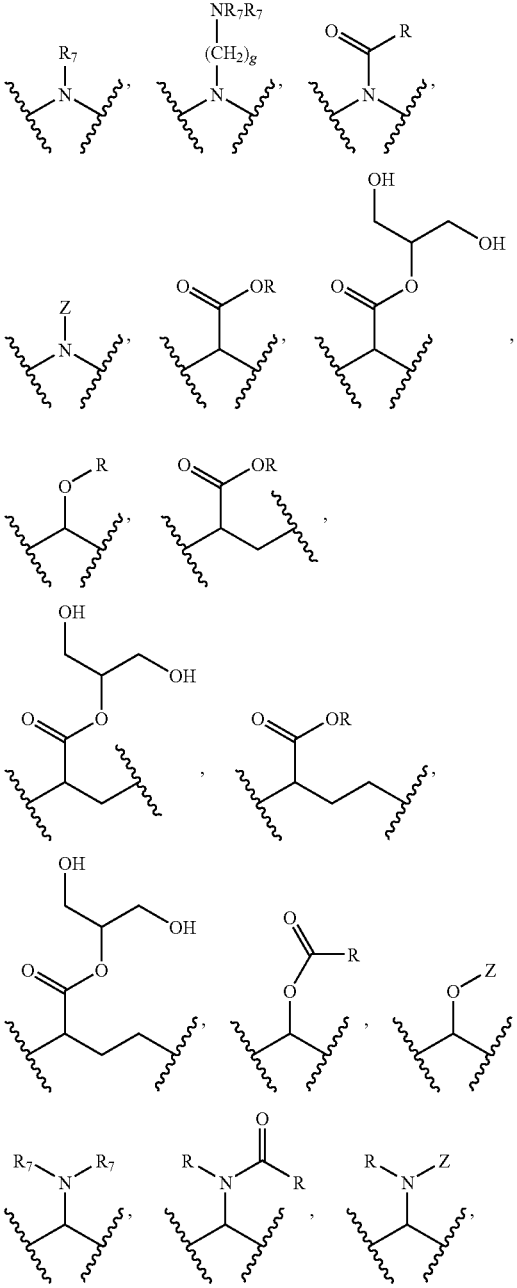

-continued

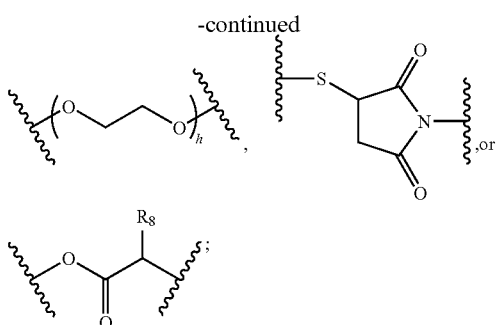

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H, or

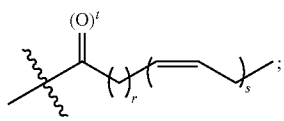

with the proviso that there is at least one

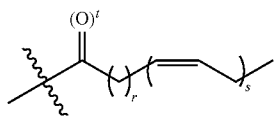

in the compound;
r is 7;
s is 3;
each t is independently 0 or 1;
w is 0 or 1;
Q is null, H, $C(O)CH_3$, Z,

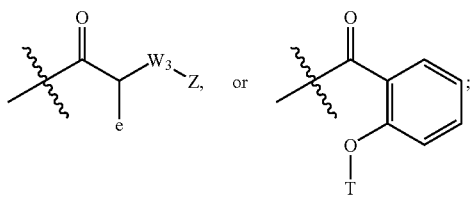

each e is independently H or any one of the side chains of the naturally occurring amino acids;
$W_3$ is null, —O—, or —N(R)—; and
T is H, $C(O)CH_3$, or Z;
provided that
when m, n, o, p, and q are each 0, $W_1$ and $W_2$ are each null, w is 1, and Z is

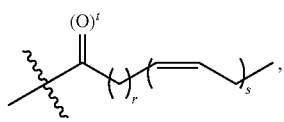

then t must be 0;
when w is 0, then $W_1$ is O or NH; and
when w is 1, and Z is

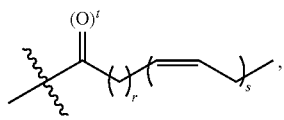

then t is 1, with the proviso that it is then impermissible that m, n, o, p, and q are each 0 and $W_1$ and $W_2$ are each null.

In another aspect, compounds of the Formula III are described:

Formula III

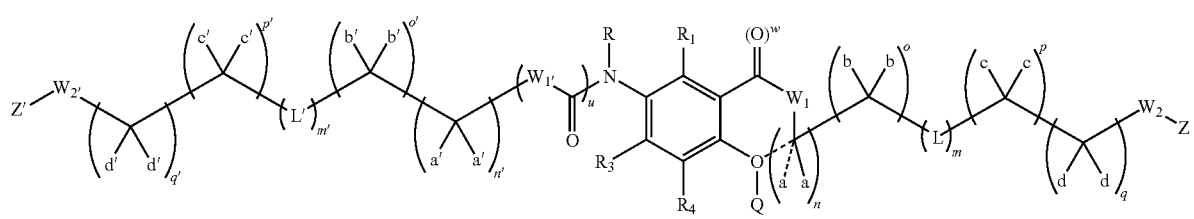

and pharmaceutically acceptable salts, hydrates, solvates, prodrugs, enantiomers, and stereoisomers thereof;
wherein $R_1$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;

each $W_1$, $W_{1'}$, $W_2$ and $W_{2'}$ is independently null, O, or NH, or when $W_1$ and $W_2$ or $W_{1'}$ and $W_{2'}$ are both NH, then both $W_1$ and $W_2$ or $W_{1'}$ and $W_{2'}$ can be taken together to form a piperidine moiety;

each symbol - - - - represents an optional bond, which when present between the phenolic oxygen and the methylene containing substituent a, requires that Q is null, or when present between substituent a and the carbon of the methylene containing substituent a, requires that Q not be null;

each a, a', c, and c' is independently H, $CH_3$, —$OCH_3$, —$OCH_2CH_3$, C(O)OH, C(O)OR or benzyl;

each b and b' is independently H, $CH_3$, C(O)OH, O—Z, C(O)OR or benzyl;

each d and d' is independently H, C(O)OH, C(O)OR or benzyl;

each n, n', o, o', p, p', q, and q' is independently 0 or 1;

each L and L' is independently —O—, —S—, —S(O)—, —S(O)$_2$—, —S—S—,

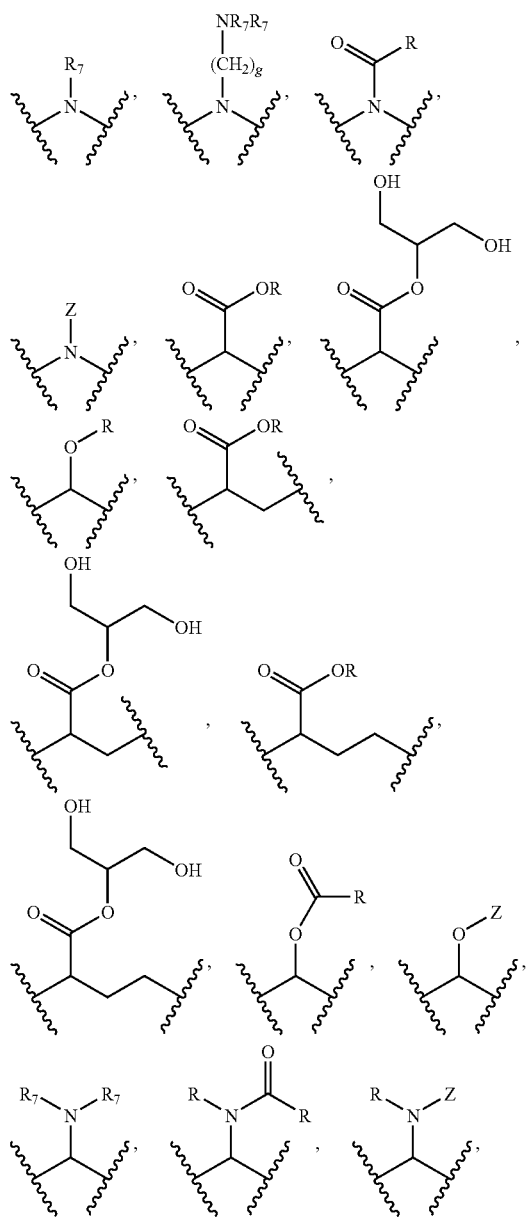

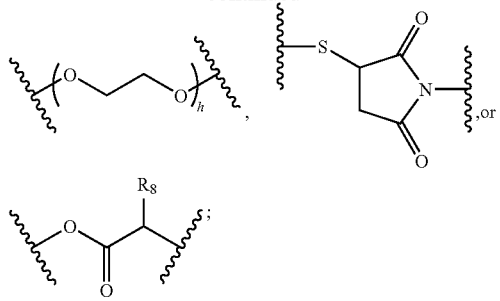

each g is independently 2, 3 or 4;
each h is independently 1, 2, 3 or 4;
each m and m' is independently 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z and Z' is independently H, or

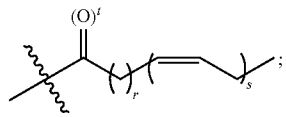

with the proviso that there is at least one

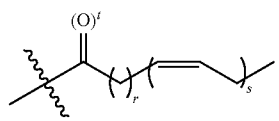

in the compound;
each r is independently 2, 3, or 7;
each s is independently 3, 5, or 6;
each t is independently 0 or 1;
w is 0 or 1;
u is 0 or 1;
Q is null, C(O)$CH_3$, Z,

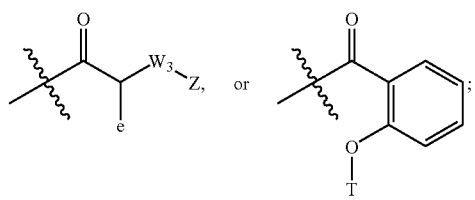

each e is independently H or any one of the side chains of the naturally occurring amino acids;
$W_3$ is null, —O—, or —N(R)—; and
T is H, C(O)$CH_3$, or Z;
provided that when m, n, o, p, and q are each 0, $W_1$ and $W_2$ are each null, w is 1, and Z is

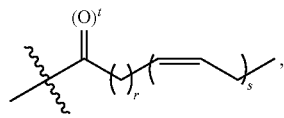

then t must be 0;
when m', n', o', p', and q' are each 0, u is 1, $W_{1'}$ and $W_{2'}$ are each null, and Z' is

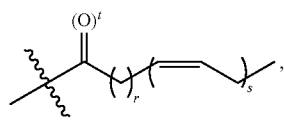

then t must be 0;
when w is 0, then $W_1$ is O or NH; and
when w is 1, Z is

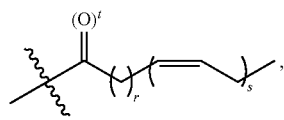

and r is 7, then t is 1.

In yet another aspect, compounds of the Formula IIIa are described:

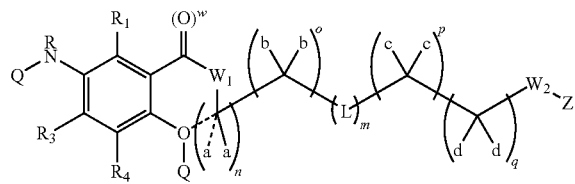

Formula IIIa and pharmaceutically acceptable salts, hydrates, solvates, prodrugs, enantiomers, and stereoisomers thereof;
wherein
$R_1$, $R_3$, and $R_4$ are each independently selected from the group consisting of H, Cl, F, CN, $NH_2$, $-NH(C_1-C_3$ alkyl), $-N(C_1-C_3$ alkyl$)_2$, $-NH(C(O)C_1-C_3$ alkyl), $-N(C(O)C_1-C_3$ alkyl$)_2$, $-C(O)H$, $-C(O)C_1-C_3$ alkyl, $-C(O)OC_1-C_3$ alkyl, $-C(O)NH_2$, $-C(O)NH(C_1-C_3$ alkyl), $-C(O)N(C_1-C_3$ alkyl$)_2$, $-C_1-C_3$ alkyl, $-O-C_1-C_3$ alkyl, $-S(O)C_1-C_3$ alkyl, $-S(O)_2C_1-C_3$ alkyl, difluorophenyl, and trifluoromethyl;
$W_1$ and $W_2$ are each independently null, O, or NH, or when $W_1$ and $W_2$ are both NH, then both $W_1$ and $W_2$ can be taken together to form a piperidine moiety;
each symbol ----- represents an optional bond, which when present between the phenolic oxygen and the methylene containing substituent a, requires that Q is null, or when present between substituent a and the carbon of the methylene containing substituent a, requires that Q not be null;
each a and c is independently H, $CH_3$, $-OCH_3$, $-OCH_2CH_3$, C(O)OH, C(O)OR or benzyl;

each b is independently H, $CH_3$, C(O)OH, O—Z, C(O)OR or benzyl;
each d is independently H, C(O)OH, C(O)OR or benzyl;
each n, o, p, and q is independently 0 or 1;
each L is independently —O—, —S—, —S(O)—, —S(O)$_2$—, —S—S—,

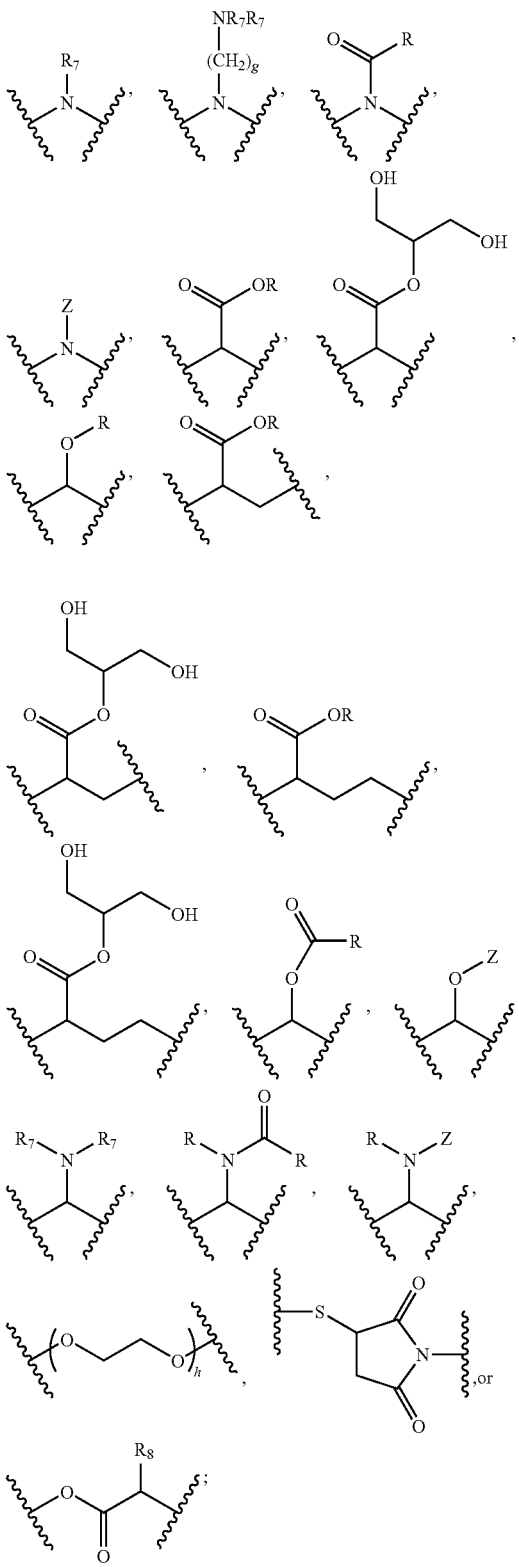

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H, or with the proviso that there is at least one in the compound;
each r is independently 2, 3, or 7;
each s is independently 3, 5, or 6;
each t is independently 0 or 1;
w is 0 or 1;
each Q is independently null, H, $C(O)CH_3$, Z, each e is independently H or any one of the side chains of the naturally occurring amino acids;
each $W_3$ is independently null, —O—, or —N(R)—; and
each T is independently H, $C(O)CH_3$, or Z;
provided that
when m, n, o, p, and q are each 0, $W_1$ and $W_2$ are each null, w is 1, and Z is then t must be 0;
when w is 0, then $W_1$ is O or NH; and
when w is 1, Z is and r is 7, then t is 1.

In another aspect, compounds of the Formula IIIb are described:

Formula IIIb and pharmaceutically acceptable salts, hydrates, solvates, prodrugs, enantiomers, and stereoisomers thereof;
wherein
$R_1$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;
$W_1$ and $W_2$ are each independently null, O, or NH, or when $W_1$ and $W_2$ are both NH, then both $W_1$ and $W_2$ can be taken together to form a piperidine moiety;
each a and c is independently H, $CH_3$, —$OCH_3$, —$OCH_2CH_3$ or C(O)OH, C(O)OR or benzyl;
each b is independently H, $CH_3$, C(O)OH, O—Z, C(O)OR or benzyl;
each d is independently H, C(O)OH, C(O)OR or benzyl;
each n, o, p, and q is independently 0 or 1;
each L is independently —O—, —S—, —S(O)—, —S(O)$_2$—, —S—S—,

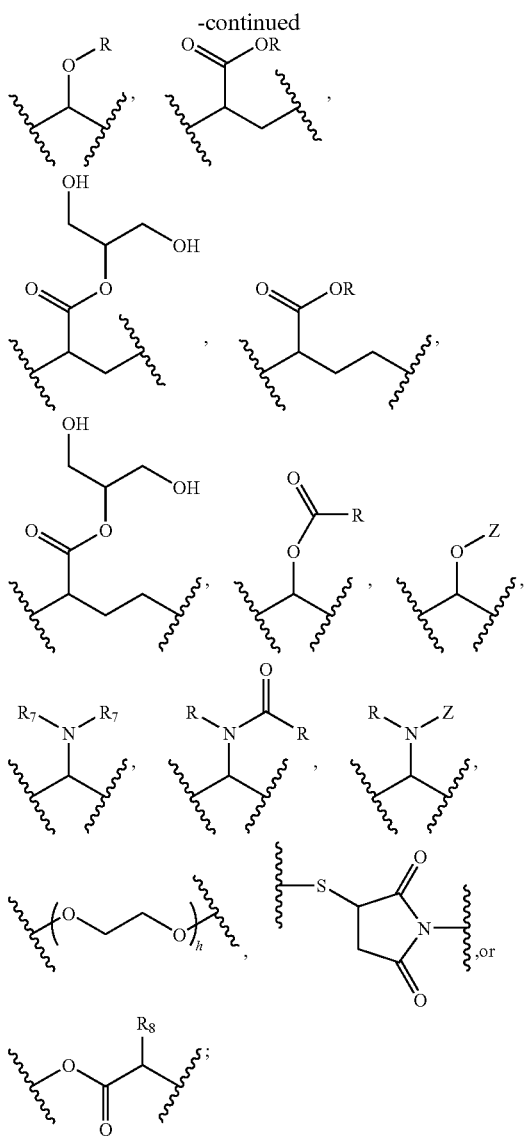

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H, or in the compound;
each r is independently 2 or 3;
each s is independently 5 or 6;
each t is independently 0 or 1;
Q is null, H, C(O)CH$_3$, Z, or each e is independently H or any one of the side chains of the naturally occurring amino acids;
$W_3$ is null, —O—, or —N(R)—;
provided that
when m, n, o, p, and q are each 0, $W_1$ and $W_2$ are each null, and Z is then t must be 0.

In another aspect, compounds of the Formula IIIc are described:

Formula IIIc and pharmaceutically acceptable salts, hydrates, solvates, prodrugs, enantiomers, and stereoisomers thereof;
wherein
$R_1$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)NH$_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2C_1$-$C_3$ alkyl, difluorophenyl, and trifluoromethyl;
$W_1$ and $W_2$ are each independently null, O, or NH, or when $W_1$ and $W_2$ are both NH, then both $W_1$ and $W_2$ can be taken together to form a piperidine moiety;
each a and c is independently H, CH$_3$, —OCH$_3$, —OCH$_2$CH$_3$, C(O)OH, C(O)OR or benzyl;

each b is independently H, CH$_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$—, —S—S—,

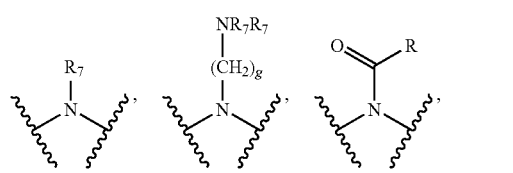

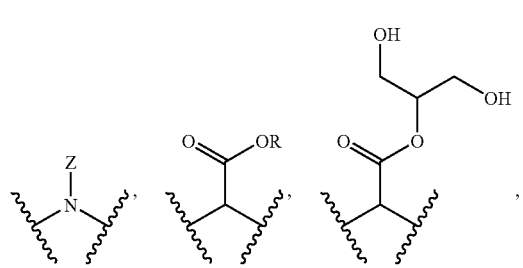

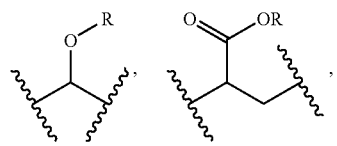

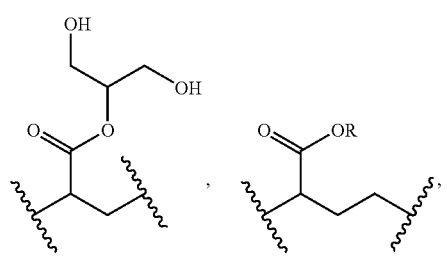

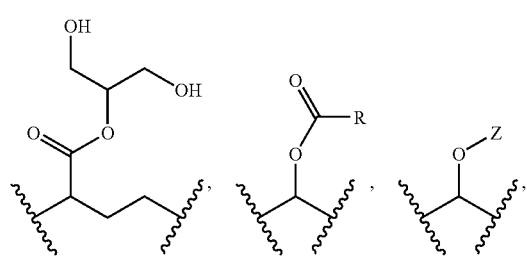

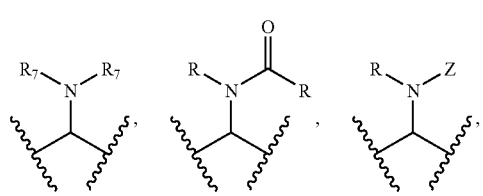

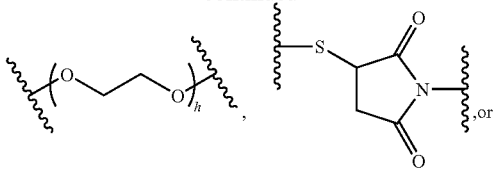

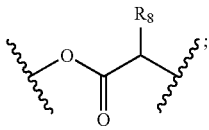

each g is independently 2, 3 or 4;

each h is independently 1, 2, 3 or 4;

m is 0, 1, 2, or 3;

each R$_7$ is independently H or C$_1$-C$_6$ alkyl, or both R$_7$ groups, when taken together with the nitrogen to which they are attached, can form a heterocycle;

each R$_8$ is independently e, H or straight or branched C$_1$-C$_{10}$ which can be optionally substituted with OH, NH$_2$, CO$_2$R, CONH$_2$, phenyl, C$_6$H$_4$OH, imidazole or arginine;

each R is independently H, —C(O)—C$_1$-C$_3$ alkyl, or straight or branched C$_1$-C$_4$ alkyl optionally substituted with OR, NR$_2$, or halogen;

each Z is independently H, or

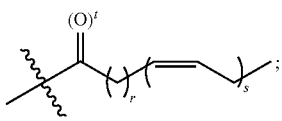

with the proviso that there is at least one

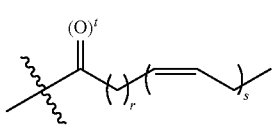

in the compound;

each r is independently 2 or 3;

each s is independently 5 or 6;

each t is independently 0 or 1;

Q is null, H, C(O)CH$_3$, Z, or

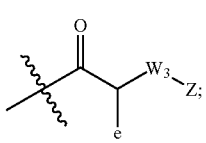

each e is independently H or any one of the side chains of the naturally occurring amino acids;

W$_3$ is null, —O—, or —N(R)—; and

T is H, C(O)CH$_3$, or Z.

In another aspect, compounds of the Formula IIId are described:

Formula IIId and pharmaceutically acceptable salts, hydrates, solvates, prodrugs, enantiomers, and stereoisomers thereof;
wherein
$R_1$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;

each $W_1$, and $W_2$ is independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;
each n, o, p, and q is independently 0 or 1;
each L is independently —O—, —S—, —S(O)—, —S(O)$_2$—, —S—S—, each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H, or with the proviso that there is at least one

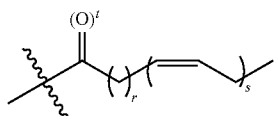

in the compound;
each r is independently 2, 3, or 7;
each s is independently 3, 5, or 6;
each t is independently 0 or 1;
u is 0 or 1;
Q is null, C(O)CH$_3$, Z,

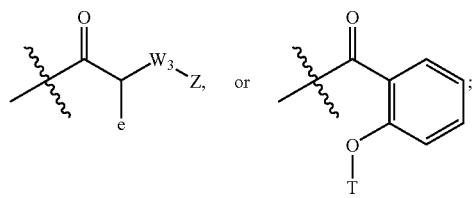

each e is independently H or any one of the side chains of the naturally occurring amino acids;
W$_3$ is null, —O—, or —N(R)—; and
T is H, C(O)CH$_3$, or Z;
provided that
when m, n, o, p, and q are each 0, u is 1, W$_1$ and W$_2$ are each null, and Z is

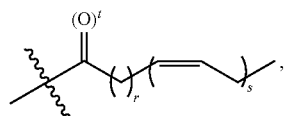

then t must be 0.

In yet another aspect, compounds of the Formula IIIe are described:

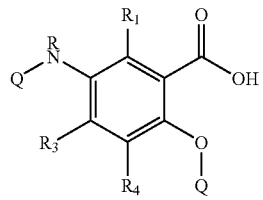

Formula IIIe and pharmaceutically acceptable salts, hydrates, solvates, prodrugs, enantiomers, and stereoisomers thereof;

wherein
R$_1$, R$_3$, and R$_4$ are each independently selected from the group consisting of H, Cl, F, CN, NH$_2$, —NH(C$_1$-C$_3$ alkyl), —N(C$_1$-C$_3$ alkyl)$_2$, —NH(C(O)C$_1$-C$_3$ alkyl), —N(C(O)C$_1$-C$_3$ alkyl)$_2$, —C(O)H, —C(O)C$_1$-C$_3$ alkyl, —C(O)OC$_1$-C$_3$ alkyl, —C(O)NH$_2$, —C(O)NH(C$_1$-C$_3$ alkyl), —C(O)N(C$_1$-C$_3$ alkyl)$_2$, —C$_1$-C$_3$ alkyl, —O—C$_1$-C$_3$ alkyl, —S(O)C$_1$-C$_3$ alkyl, —S(O)$_2$C$_1$-C$_3$ alkyl, difluorophenyl, and trifluoromethyl;

R is H, —C(O)—C$_1$-C$_3$ alkyl, or straight or branched C$_1$-C$_4$ alkyl optionally substituted with OR, NR$_2$, or halogen;

each Q is independently null, H, C(O)CH$_3$, Z,

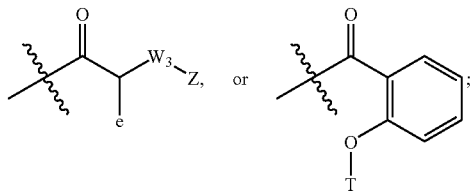

each e is independently H or any one of the side chains of the naturally occurring amino acids;
each W$_3$ is independently null, —O—, or —N(R)—;
each T is independently H, C(O)CH$_3$, or Z;
each Z is independently H, or

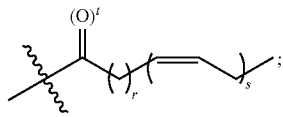

with the proviso that there is at least one

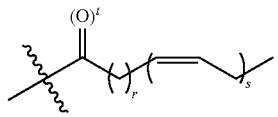

in the compound;
each r is independently 2, 3, or 7;
each s is independently 3, 5, or 6; and
each t is independently 0 or 1.

In another aspect, compounds of the Formula IIIf are described:

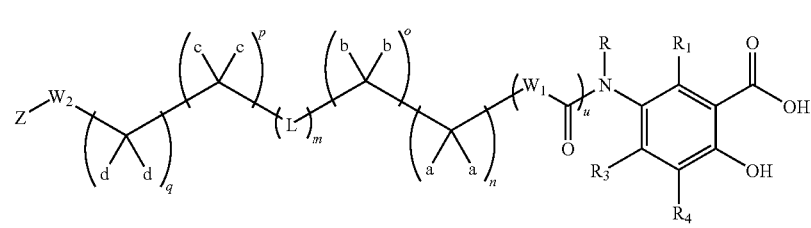

Formula IIIf and pharmaceutically acceptable salts, hydrates, solvates, prodrugs, enantiomers, and stereoisomers thereof;

wherein $R_1$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2C_1$-$C_3$ alkyl, difluorophenyl, and trifluoromethyl;

each $W_1$, and $W_2$ is independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$—, —S—S—,

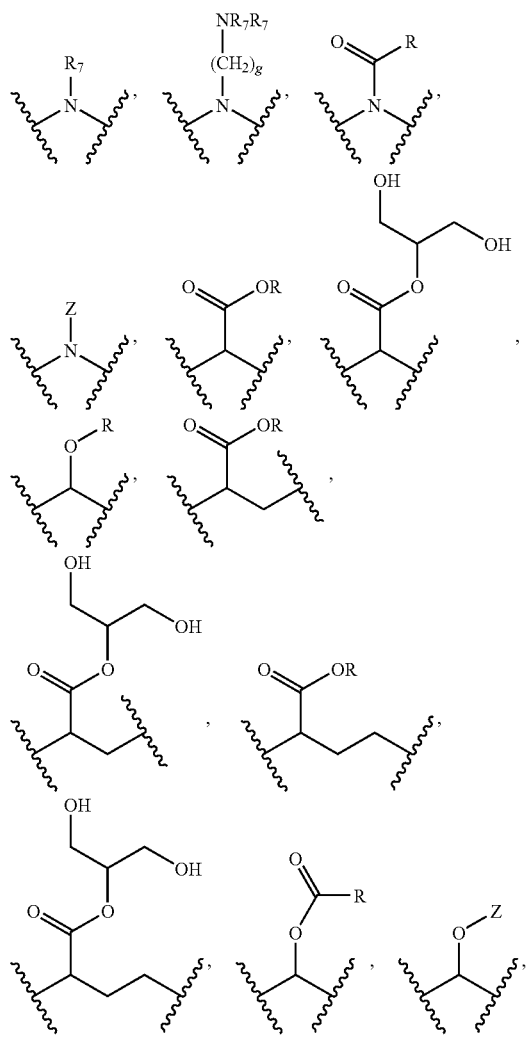

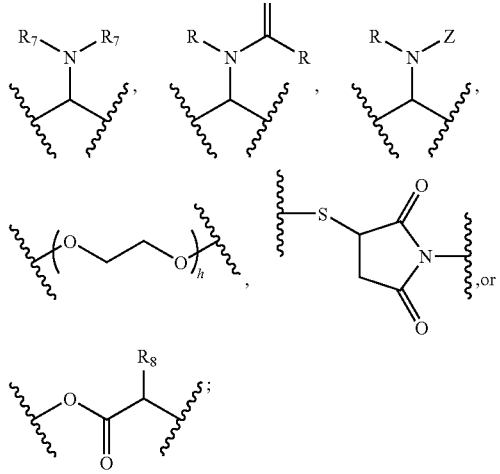

each g is independently 2, 3 or 4;

each h is independently 1, 2, 3 or 4;

m is 0, 1, 2, or 3;

each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H, or

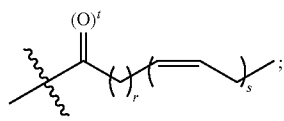

with the proviso that there is at least one

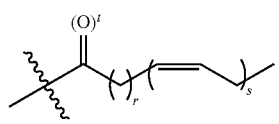

in the compound;

each r is independently 2, 3, or 7;

each s is independently 3, 5, or 6;

each t is independently 0 or 1;

u is 0 or 1; and each e is independently H or any one of the side chains of the naturally occurring amino acids;

provided that when m, n, o, p, and q are each 0, u is 1, $W_1$ and $W_2$ are each null, and Z is

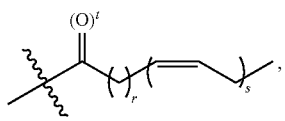

then t must be 0.

In yet another aspect, compounds of the Formula IIIg are described:

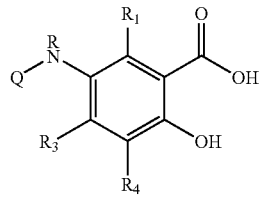

Formula IIIg and pharmaceutically acceptable salts, hydrates, solvates, prodrugs, enantiomers, and stereoisomers thereof;

wherein $R_1$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, —$S(O)_2C_1$-$C_3$ alkyl, difluorophenyl, and trifluoromethyl;

R is H, —C(O)—$C_1$-$C_3$ alkyl, or straight or branched $C_1$-$C_4$ alkyl optionally substituted with OR, $NR_2$, or halogen;

Q is H, $C(O)CH_3$, Z,

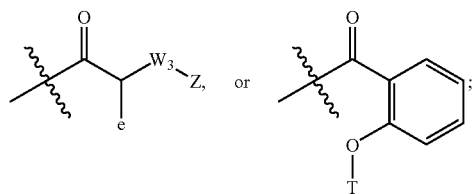

e is H or any one of the side chains of the naturally occurring amino acids;

$W_3$ is null, —O—, or —N(R)—; and

T is H, $C(O)CH_3$, or Z.

Z is H, or

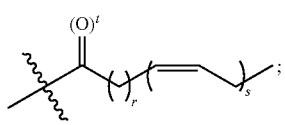

with the proviso that there is at least one

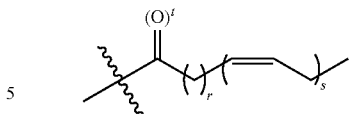

in the compound;

r is 2, 3, or 7;

s is 3, 5, or 6; and t is 0 or 1.

In a further aspect, compounds of the Formula I' are described:

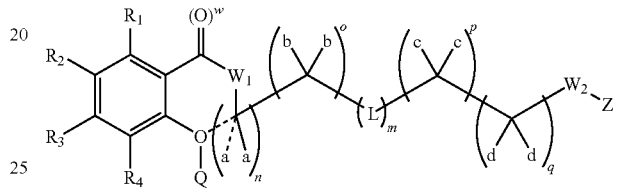

Formula I' and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, —$S(O)_2C_1$-$C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each symbol ----- represents an optional bond, which when present between the phenolic oxygen and the methylene containing substituent a, requires that Q is null, or when present between substituent a and the carbon of the methylene containing substituent a, requires that Q not be null;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —$S(O)_2$—, —S—S—,

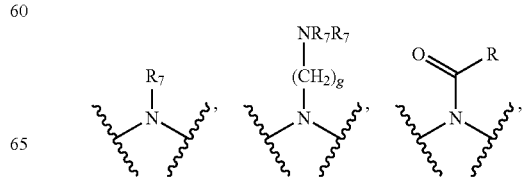

-continued

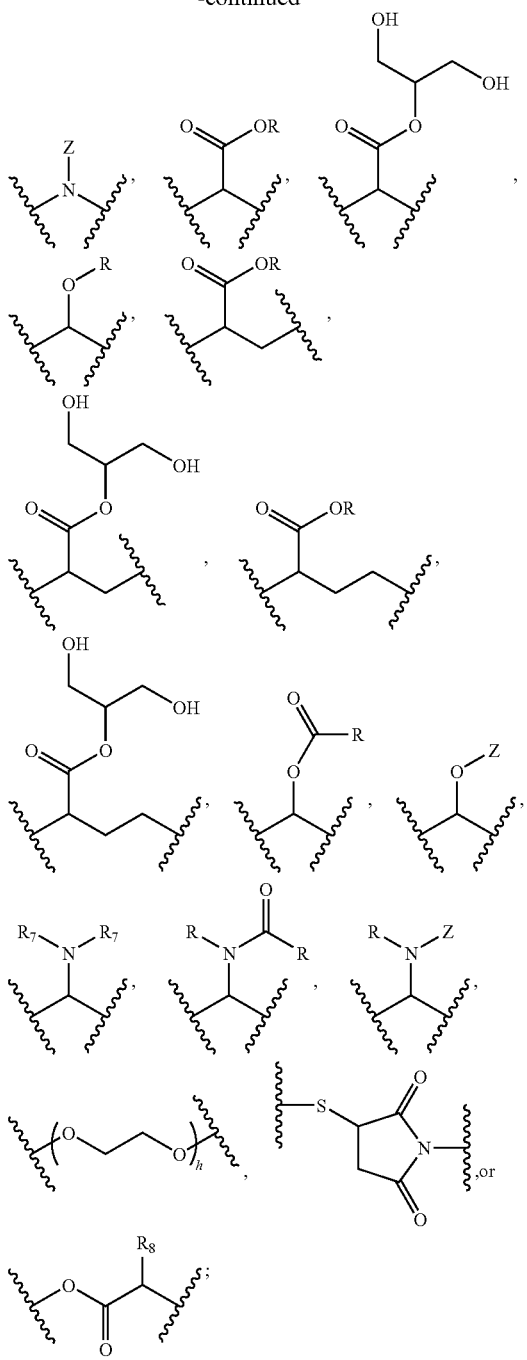

, or

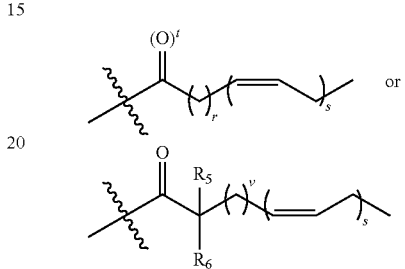;

with the proviso that there is at least one

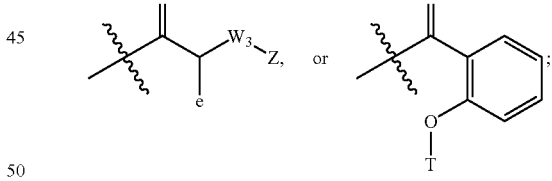

in the compound;
each r is independently 2 or 3;
each s is independently 5 or 6;
each t is independently 0 or 1;
w is 0 or 1;
each v is independently 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl;
Q is null, C(O)CH$_3$, Z,

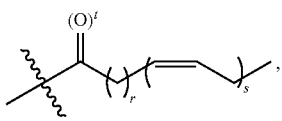, or each e is independently H or any one of the side chains of the naturally occurring amino acids;
$W_3$ is null, —O—, or —N(R)—; and
T is H, C(O)CH$_3$, or Z;
provided that
when m, n, o, p, and q are each 0, $W_1$ and $W_2$ are each null, w is 1, and Z is then t must be 0;

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H, when m, n, o, p, and q are each 0, and $W_1$ and $W_2$ are each null, then Z must not be

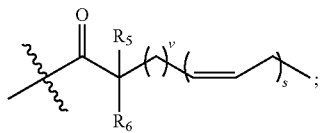

;

when w is 0, then $W_1$ is O or NH; and
when Q is Z, t=1.

In another aspect, compounds of the Formula Ia' are described:

Formula Ia'

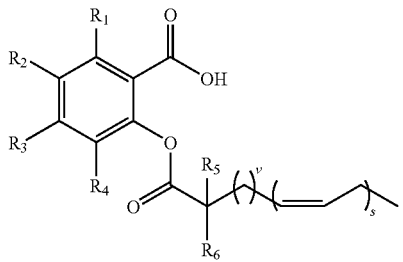

and pharmaceutically acceptable salts, hydrates, solvates, prodrugs, enantiomers, and stereoisomers thereof;
wherein
$R_1$, $R_2$, $R_3$, and $R_4$ are each independently selected from the group consisting of H, Cl, F, CN, $NH_2$, —$NH(C_1-C_3$ alkyl), —$N(C_1-C_3$ alkyl)$_2$, —$NH(C(O)C_1-C_3$ alkyl), —$N(C(O)C_1-C_3$ alkyl)$_2$, —C(O)H, —$C(O)C_1-C_3$ alkyl, —$C(O)OC_1-C_3$ alkyl, —$C(O)NH_2$, —$C(O)NH(C_1-C_3$ alkyl), —$C(O)N(C_1-C_3$ alkyl)$_2$, —$C_1-C_3$ alkyl, —O—$C_1-C_3$ alkyl, —$S(O)C_1-C_3$ alkyl, —$S(O)_2C_1-C_3$ alkyl, difluorophenyl, and trifluoromethyl;

s is 5 or 6;
v is 1 or 2; and
$R_5$ and $R_6$ are each independently hydrogen, deuterium, $C_1-C_4$ alkyl, halogen, —OH, —$C(O)C_1-C_4$ alkyl, —O-aryl, —O-benzyl, —$OC(O)C_1-C_4$ alkyl, —$C_1-C_3$ alkene, —$C_1-C_3$ alkyne, —$C(O)C_1-C_4$ alkyl, $NH_2$, —$NH(C_1-C_3$ alkyl), —$N(C_1-C_3$ alkyl)$_2$, —$NH(C(O)C_1-C_3$ alkyl), —$N(C(O)C_1-C_3$ alkyl)$_2$, —SH, —$S(C_1-C_3$ alkyl), —$S(O)C_1-C_3$ alkyl, —$S(O)_2C_1-C_3$ alkyl.

In another aspect compounds of the Formula Ib' are described:

Formula Ib'

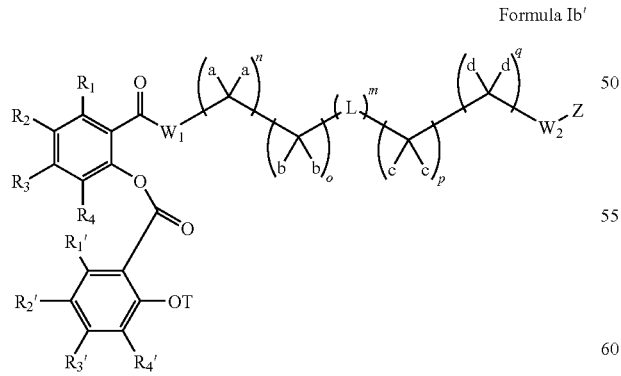

and pharmaceutically acceptable salts, hydrates, solvates, prodrugs, enantiomers, and stereoisomers thereof;
wherein
$R_1$, $R_2$, $R_3$, $R_4$, $R_1'$, $R_2'$, $R_3'$, and $R_4'$ are each independently selected from the group consisting of H, Cl, F, CN, $NH_2$, —$NH(C_1-C_3$ alkyl), —$N(C_1-C_3$ alkyl)$_2$, —$NH(C(O)C_1-C_3$ alkyl), —$N(C(O)C_1-C_3$ alkyl)$_2$, —C(O)H, —$C(O)C_1-C_3$ alkyl, —$C(O)OC_1-C_3$ alkyl, —$C(O)NH_2$, —$C(O)NH(C_1-C_3$ alkyl), —$C(O)N(C_1-C_3$ alkyl)$_2$, —$C_1-C_3$ alkyl, —O—$C_1-C_3$ alkyl, —$S(O)C_1-C_3$ alkyl, —$S(O)_2C_1-C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —$S(O)_2$—, —S—S—,

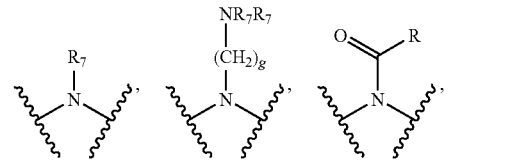

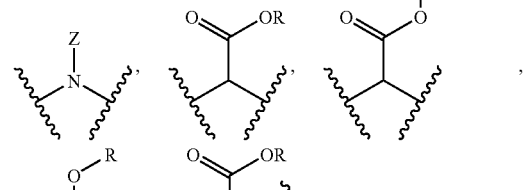

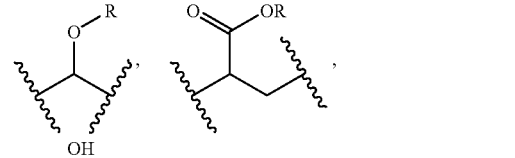

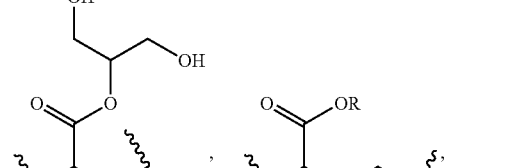

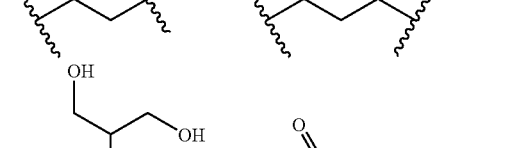

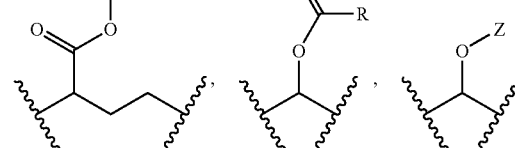

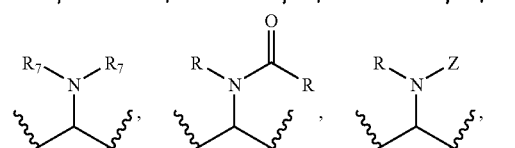

-continued

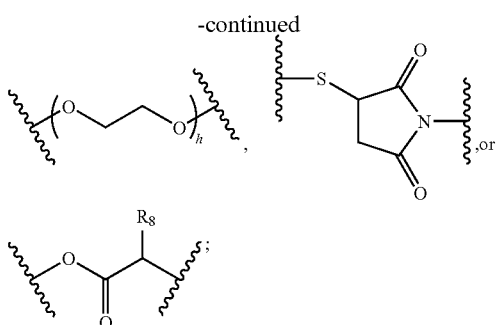

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H,

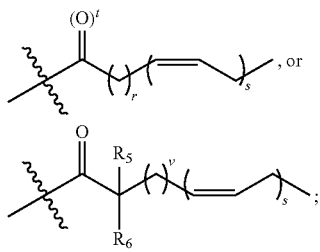

with the proviso that there is at least one

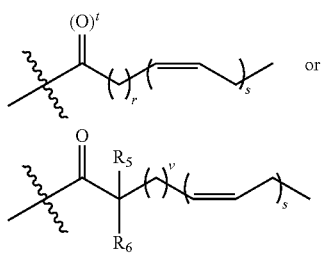

in the compound;
each r is independently 2 or 3;
each s is independently 5 or 6;
each t is independently 0 or 1;
each v is independently 1 or 2;
$R_5$ and $R_6$ are each independently hydrogen, deuterium, $C_1$-$C_4$ alkyl, halogen, —OH, —C(O)$C_3$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl;
T is H, C(O)$CH_3$, or Z; and each e is independently H or any one of the side chains of the naturally occurring amino acids;
provided that
when m, n, o, p, and q are each 0, $W_1$ and $W_2$ are each null, and Z is

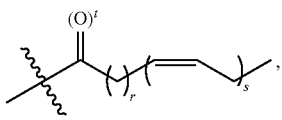

then t must be 0; and
when m, n, o, p, and q are each 0, and $W_1$ and $W_2$ are each null, then Z must not be

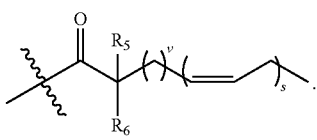

In another aspect compounds of the Formula Ic' are described:

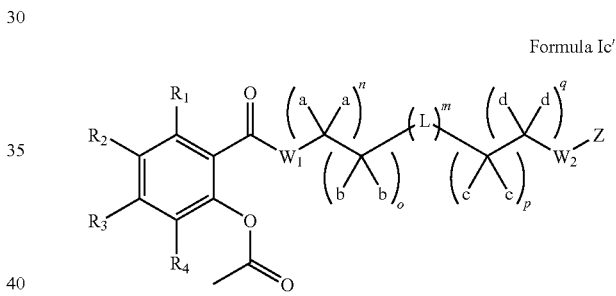

Formula Ic' and pharmaceutically acceptable salts, hydrates, solvates, enantiomers, and stereoisomers thereof,
wherein
$R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2C_1$-$C_3$ alkyl, difluorophenyl, and trifluoromethyl;
$W_1$ and $W_2$ are each independently null, O, or NH, or when $W_1$ and $W_2$ are both NH, then both $W_1$ and $W_2$ can be taken together to form a piperidine moiety;
each a and c is independently H, $CH_3$, —$OCH_3$, —$OCH_2CH_3$, C(O)OH, C(O)OR or benzyl;
each b is independently H, $CH_3$, C(O)OH, O—Z, C(O)OR or benzyl;
each d is independently H, C(O)OH, C(O)OR or benzyl;
each n, o, p, and q is each 0 or 1;
each L is independently —O—, —S—, —S(O)—, —S(O)$_2$—, —S—S—,

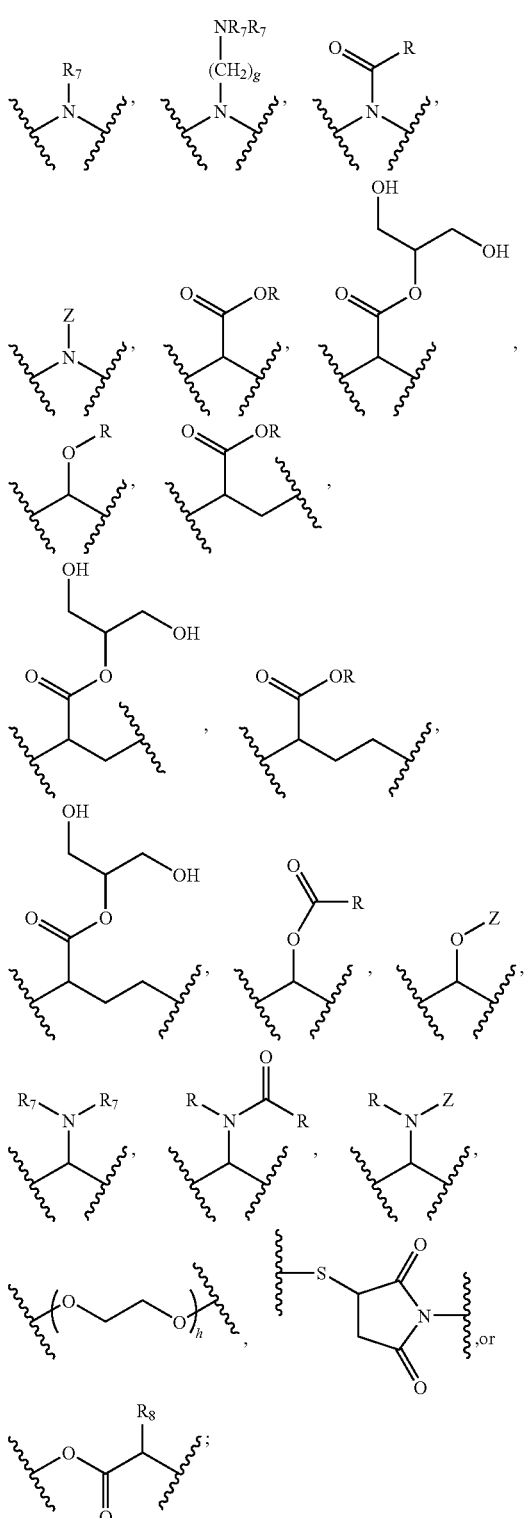

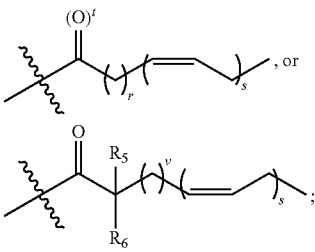

each g is independently 2, 3 or 4;

each h is independently 1, 2, 3 or 4;

m is 0, 1, 2, or 3;

each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H,

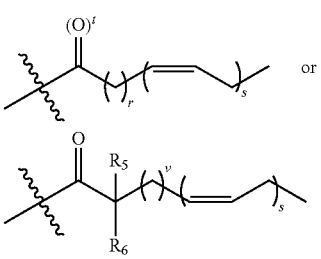

with the proviso that there is at least one

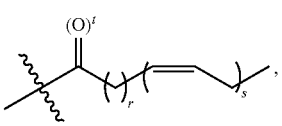

in the compound;

each r is independently 2 or 3;

each s is independently 5 or 6;

each t is independently 0 or 1;

each v is independently 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2C_1$-$C_3$ alkyl; and each e is independently H or any one of the side chains of the naturally occurring amino acids, provided that when m, n, o, p, and q are each 0, $W_1$ and $W_2$ are each null, and Z is

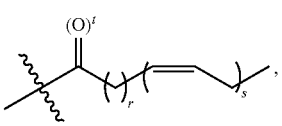

then t must be 0;

when m, n, o, p, and q are each 0, and $W_1$ and $W_2$ are each null, then Z must not be

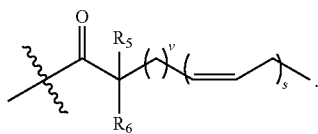

In another aspect, compounds of the Formula Id' are described:

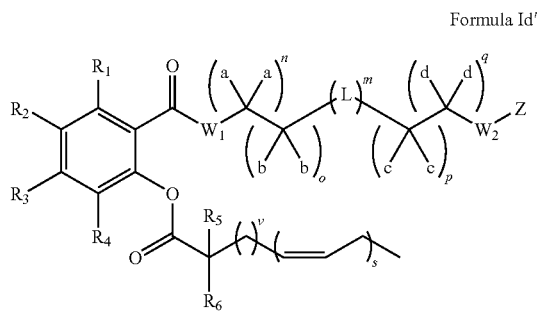

Formula Id' and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2C_1$-$C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$—, —S—S—,

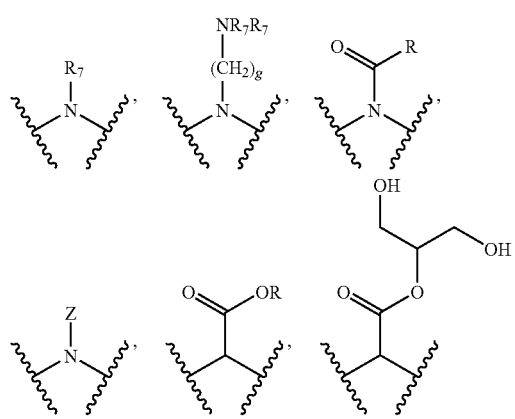

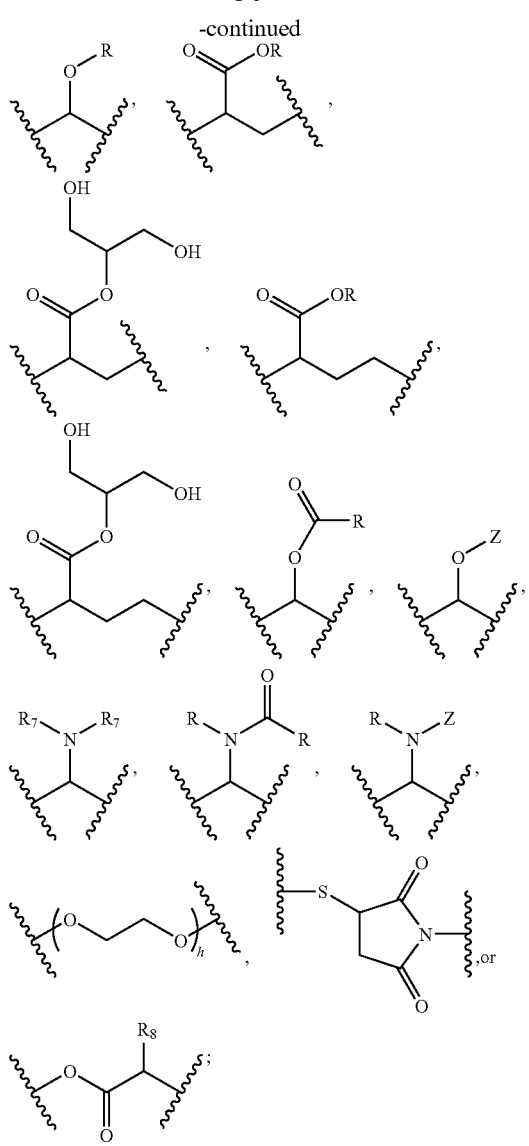

each g is independently 2, 3 or 4;

each h is independently 1, 2, 3 or 4;

m is 0, 1, 2, or 3;

each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H,

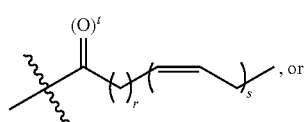

-continued

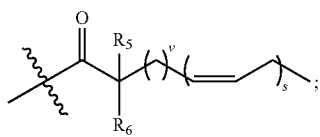

with the proviso that there is at least one

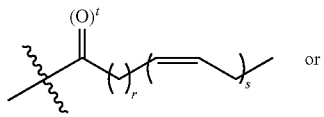

or

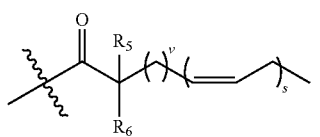

in the compound;

each r is independently 2 or 3;

each s is independently 5 or 6;

each t is independently 0 or 1;

each v is independently 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl; and each e is independently H or any one of the side chains of the naturally occurring amino acids;

provided that when m, n, o, p, and q are each 0, $W_1$ and $W_2$ are each null, and Z is

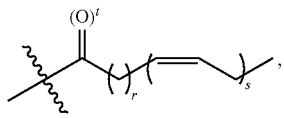

then t must be 0;

when m, n, o, p, and q are each 0, and $W_1$ and $W_2$ are each null, then Z must not be

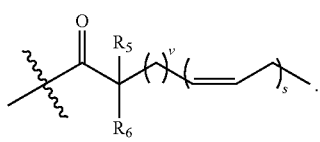

In another aspect, compounds of the Formula If' are described:

Formula If'

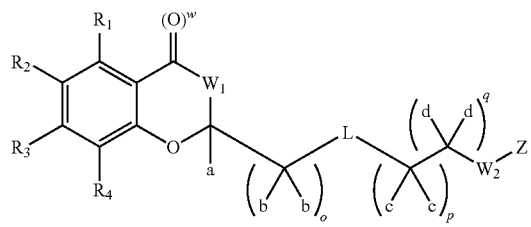

and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)NH$_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;

$W_1$ and $W_2$ are each independently null, O, or NH;

each a and c is independently H, CH$_3$, —OCH$_3$, —OCH$_2$CH$_3$, C(O)OH, C(O)OR or benzyl;

each b is independently H, CH$_3$, C(O)OH, O—Z, C(O)OR or benzyl;

each d is independently H, C(O)OH, C(O)OR or benzyl;

each o, p, and q is independently 0 or 1;

each L is independently —O—, —S—, —S(O)—, —S(O)$_2$—, —S—S—,

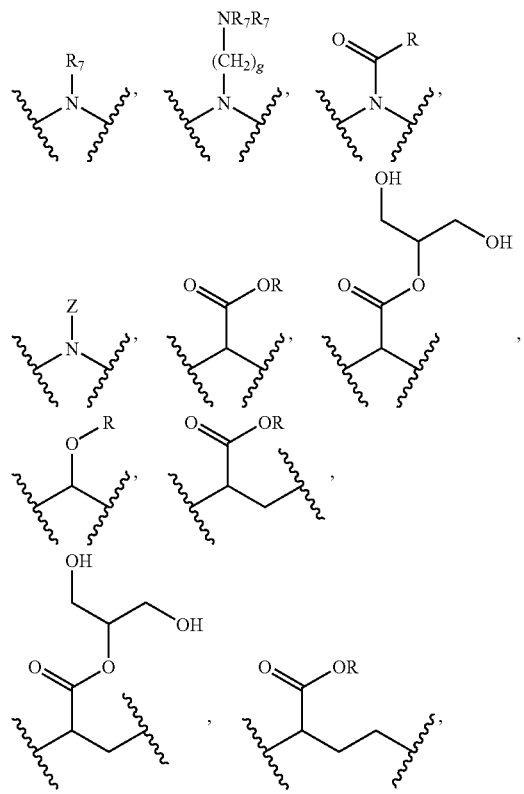

-continued

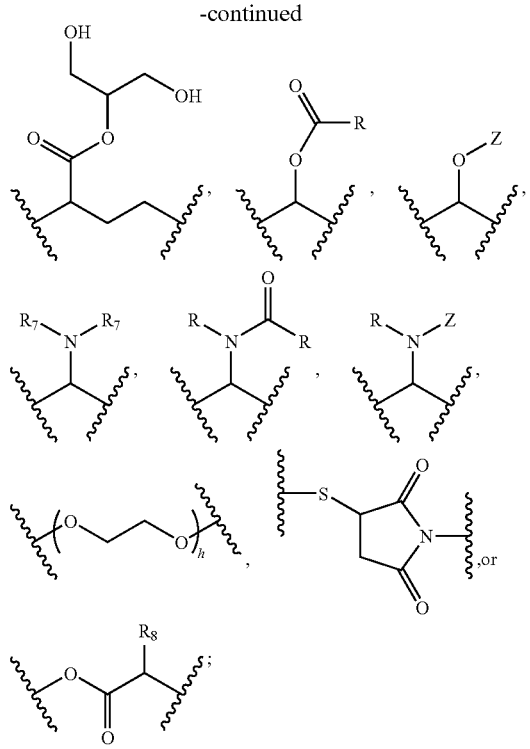

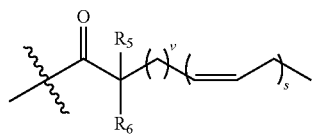

each g is independently 2, 3 or 4;

each h is independently 1, 2, 3 or 4;

m is 0, 1, 2, or 3;

each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H,

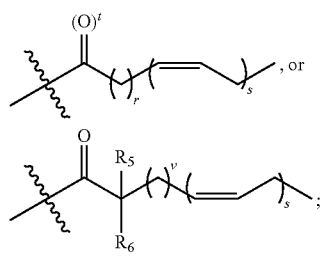

with the proviso that there is at least one

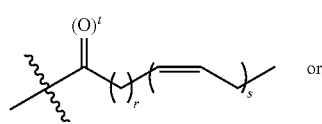

-continued

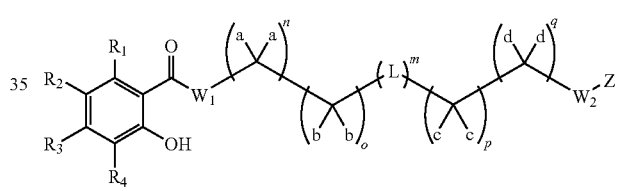

in the compound;

each r is independently 2 or 3;

each s is independently 5 or 6;

each t is independently 0 or 1;

w is 0 or 1;

each v is independently 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl; and each e is independently H or any one of the side chains of the naturally occurring amino acids.

In another aspect, compounds of the Formula Ih' are described:

Formula Ih' and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$—, —S—S—,

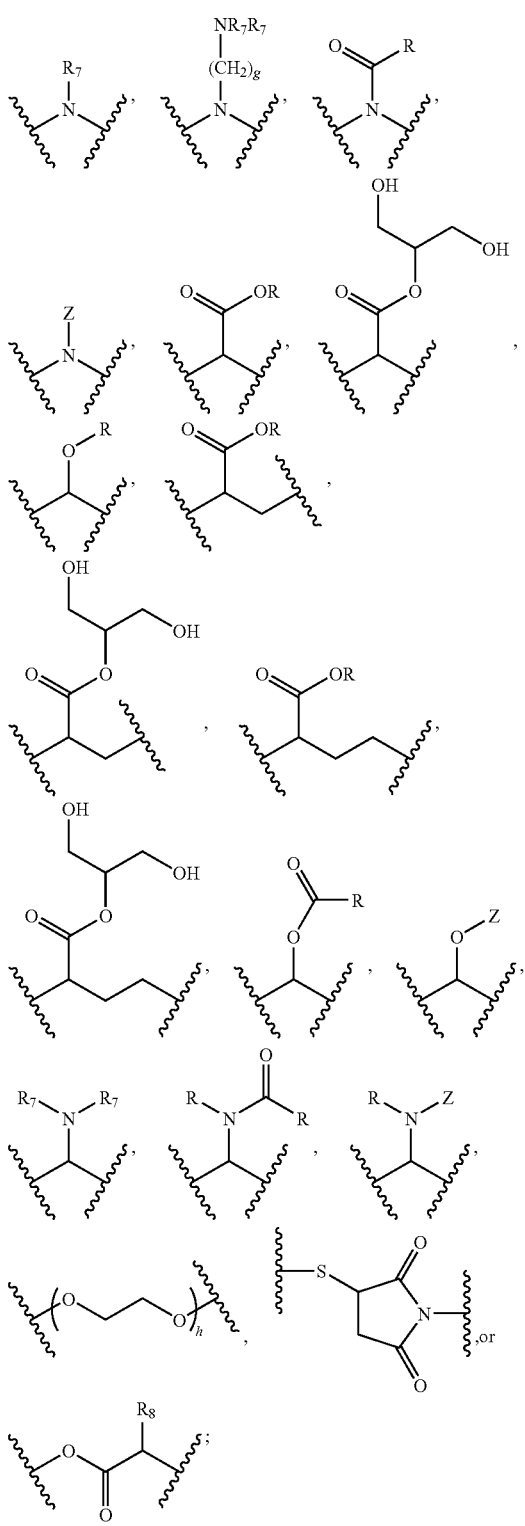

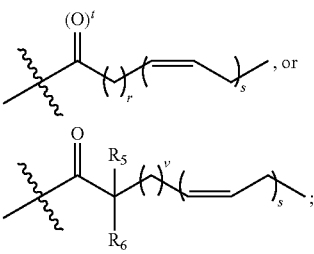

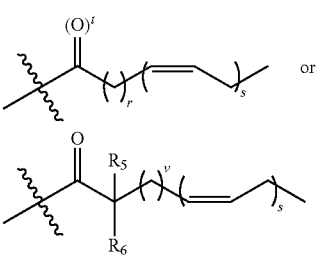

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H, with the proviso that there is at least one in the compound;
each r is independently 2 or 3;
each s is independently 5 or 6;
each t is independently 0 or 1;
each v is independently 1 or 2;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl; and
each e is independently H or any one of the side chains of the naturally occurring amino acids;
provided that
when m, n, o, p, and q are each 0, $W_1$ and $W_2$ are each null, and Z is

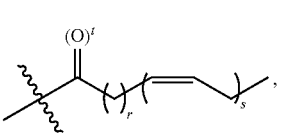

then t must be 0;
when m, n, o, p, and q are each 0, and $W_1$ and $W_2$ are each null, then Z must not be

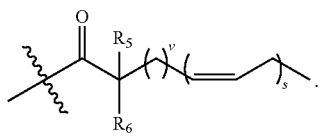

In another aspect, compounds of the Formula Ii' are described:

Formula Ii'

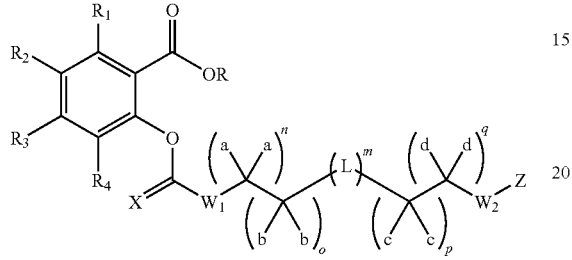

and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, $NH_2$, —$NH(C_1-C_3$ alkyl), —$N(C_1-C_3$ alkyl$)_2$, —$NH(C(O)C_1-C_3$ alkyl), —$N(C(O)C_1-C_3$ alkyl$)_2$, —C(O)H, —$C(O)C_1-C_3$ alkyl, —$C(O)OC_1-C_3$ alkyl, —$C(O)NH_2$, —$C(O)NH(C_1-C_3$ alkyl), —$C(O)N(C_1-C_3$ alkyl$)_2$, —$C_1-C_3$ alkyl, —O—$C_1-C_3$ alkyl, —$S(O)C_1-C_3$ alkyl, —$S(O)_2C_1-C_3$ alkyl, difluorophenyl and trifluoromethyl;

$W_1$ and $W_2$ are each independently null, O, or NH, or when $W_1$ and $W_2$ are both NH, then both $W_1$ and $W_2$ can be taken together to form a piperidine moiety;

X is O or S;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —$S(O)_2$—, —S—S—,

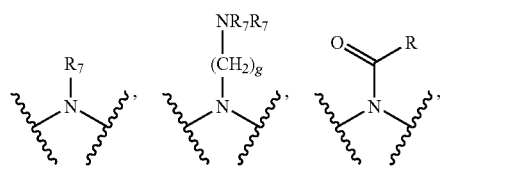

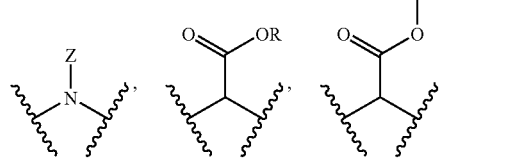

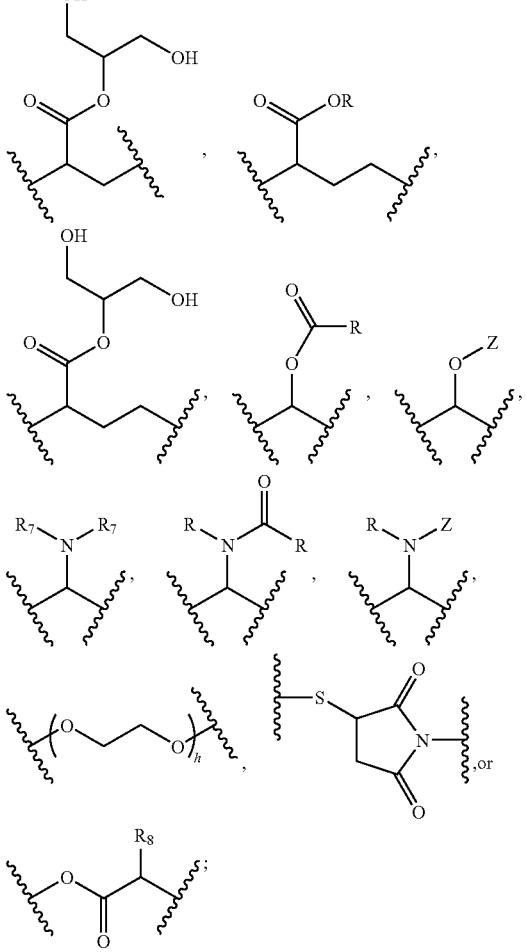

each g is independently 2, 3 or 4;

each h is independently 1, 2, 3 or 4;

m is 0, 1, 2, or 3;

each $R_7$ is independently H or $C_1-C_6$ alkyl, or both $R_7$ groups, when taken together with the nitrogen to which they are attached, can form a heterocycle;

each $R_8$ is independently e, H or straight or branched $C_1-C_{10}$ which can be optionally substituted with OH, $NH_2$, $CO_2R$, $CONH_2$, phenyl, $C_6H_4OH$, imidazole or arginine;

each R is independently H, —C(O)—$C_1-C_3$ alkyl, or straight or branched $C_1-C_4$ alkyl optionally substituted with OR, $NR_2$, or halogen;

each Z is independently H,

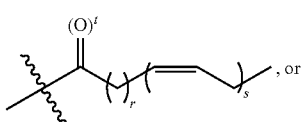

-continued

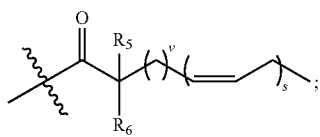

with the proviso that there is at least one

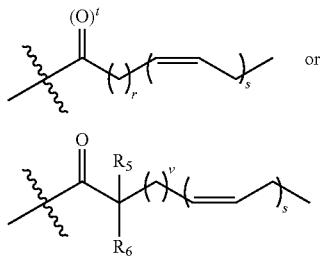

in the compound;

each r is independently 2 or 3;

each s is independently 5 or 6;

each t is independently 0 or 1;

each v is independently 1 or 2;

$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl; and each e is independently H or any one of the side chains of the naturally occurring amino acids;

provided that when m, n, o, p, and q are each 0, $W_1$ and $W_2$ are each null, and Z is

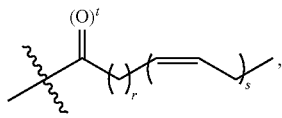

then t must be 0;

when m, n, o, p, and q are each 0, and $W_1$ and $W_2$ are each null, then Z must not be

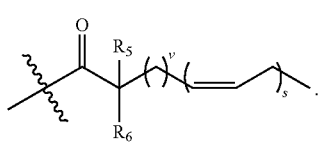

In another aspect, compounds of the Formula II' are described:

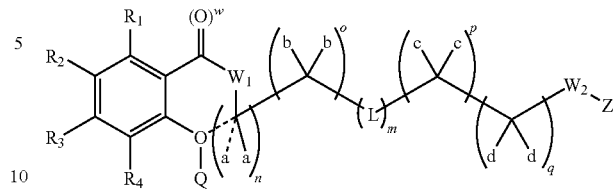

Formula II' and pharmaceutically acceptable salts, hydrates, solvates, prodrugs, enantiomers, and stereoisomers thereof;

wherein $R_1$, $R_2$, $R_3$, and $R_4$ are each independently selected from the group consisting of H, Cl, F, CN, NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)NH$_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each symbol ----- represents an optional bond, which when present between the phenolic oxygen and the methylene containing substituent a, requires that Q is null, or when present between substituent a and the carbon of the methylene containing substituent a, requires that Q not be null;

each a and c is independently H, CH$_3$, —OCH$_3$, —OCH$_2$CH$_3$, C(O)OH, C(O)OR or benzyl;

each b is independently H, CH$_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$, —S—S—,

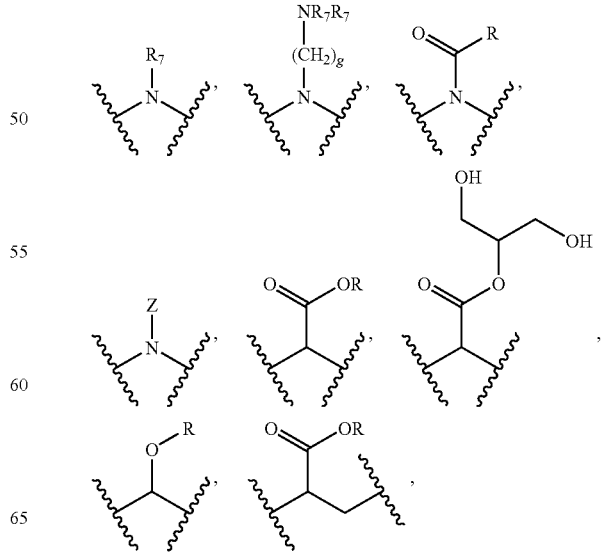

-continued

[chemical structures shown]

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H,

[chemical structure], or

[chemical structure];

with the proviso that there is at least one

[chemical structure] or

[chemical structure]

in the compound;
r is 7;
s is 3;
each t is independently 0 or 1;
w is 0 or 1;
each v is 6;
$R_5$ and $R_6$ are each independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2C_1$-$C_3$ alkyl;
Q is null, C(O)$CH_3$, Z,

[chemical structure], or [chemical structure];

each e is independently H or any one of the side chains of the naturally occurring amino acids;
$W_3$ is null, —O—, or —N(R) and
T is H, C(O)$CH_3$, or Z;
provided that
when m, n, o, p, and q are each 0, $W_1$ and $W_2$ are each null, w is 1, and Z is

[chemical structure], then t must be 0;
when m, n, o, p, and q are each 0, and $W_1$ and $W_2$ are each null, then Z must not be

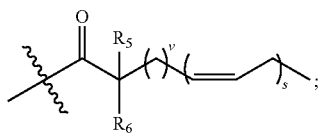

when w is 0, then $W_1$ is O or NH; and
when w is 1, and Z is

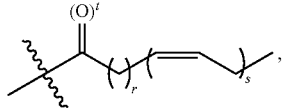

then t is 1, with the proviso that it is then impermissible that m, n, o, p, and q are each 0 and $W_1$ and $W_2$ are each null.

In another aspect, compounds of the Formula III' are described:

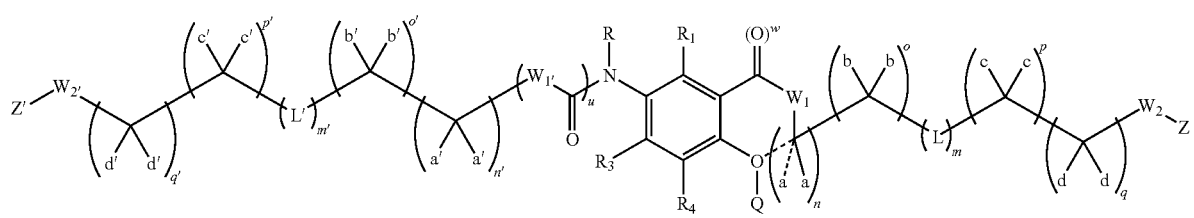

Formula III' and pharmaceutically acceptable salts, hydrates, solvates, prodrugs, enantiomers, and stereoisomers thereof;

wherein $R_1$, $R_3$, and $R_4$ are each independently selected from the group consisting of H, Cl, F, CN, $NH_2$, $NH(C_1-C_3$ alkyl), $N(C_1-C_3$ alkyl$)_2$, $NH(C(O)C_1-C_3$ alkyl), $N(C(O)C_1-C_3$ alkyl$)_2$, $C(O)H$, $C(O)C_1-C_3$ alkyl, $C(O)OC_1-C_3$ alkyl, $C(O)NH_2$, $C(O)NH(C_1-C_3$ alkyl), $C(O)N(C_1-C_3$ alkyl$)_2$, $C_1-C_3$ alkyl, $OC_1-C_3$ alkyl, $S(O)C_1-C_3$ alkyl, $S(O)_2C_1-C_3$ alkyl, difluorophenyl, and trifluoromethyl;

each $W_1$, $W_{1'}$, $W_2$ and $W_{2'}$ is independently null, O, or NH, or when $W_1$ and $W_2$ or $W_{1'}$ and $W_{2'}$ are both NH, then both $W_1$ and $W_2$ or $W_{1'}$ and $W_{2'}$ can be taken together to form a piperidine moiety;

each symbol ----- represents an optional bond, which when present between the phenolic oxygen and the methylene containing substituent a, requires that Q is null, or when present between substituent a and the carbon of the methylene containing substituent a, requires that Q not be null;

each a, a', c, and c' is independently H, $CH_3$, $-OCH_3$, $-OCH_2CH_3$, $C(O)OH$, $C(O)OR$ or benzyl;

each b and b' is independently H, $CH_3$, $C(O)OH$, $O-Z$, $C(O)OR$ or benzyl;

each d and d' is independently H, $C(O)OH$, $C(O)OR$ or benzyl;

each n, n', o, o', p, p', q, and q' is independently 0 or 1;

each L and L' is independently $-O-$, $-S-$, $-S(O)-$, $-S(O)_2-$, $-S-S-$,

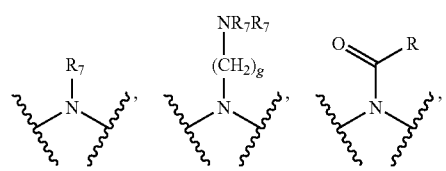

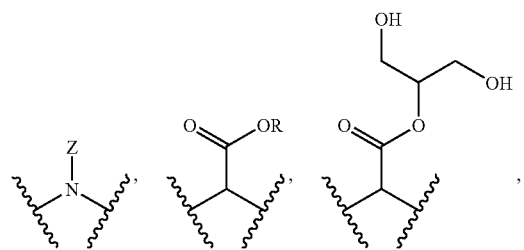

-continued

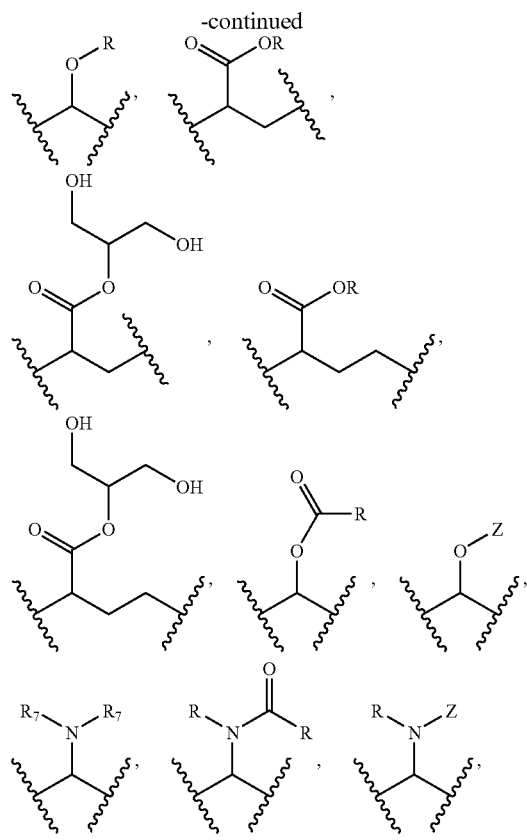

-continued

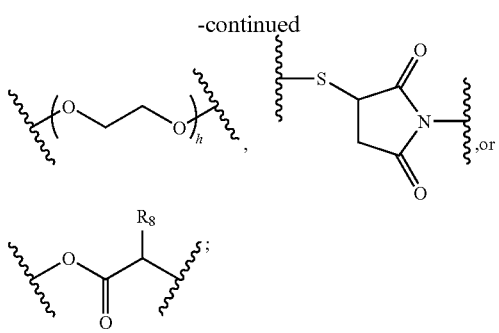

each g is independently 2, 3 or 4;
each h is independently 1, 2, 3 or 4;
each m and m' is independently 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z and Z' is independently H,

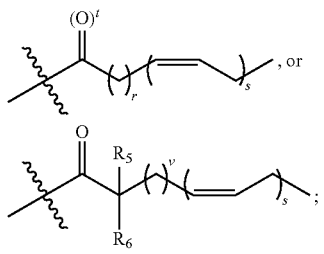

with the proviso that there is at least one

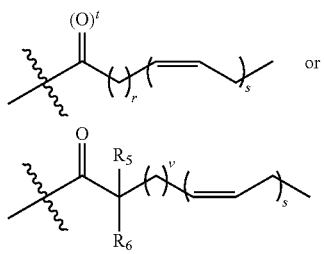

in the compound;
each r is independently 2, 3, or 7;
each s is independently 3, 5, or 6;
each t is independently 0 or 1;
w is 0 or 1;
each v is independently 1, 2, or 6;
each $R_5$ and $R_6$ is independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl;

u is 0 or 1;
each Q is independently null, C(O)$CH_3$, Z,

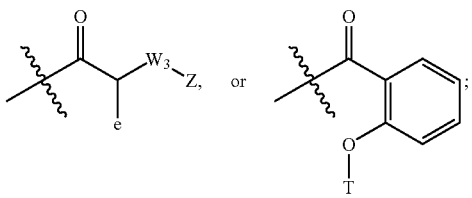

each e is independently H or any one of the side chains of the naturally occurring amino acids;
each $W_3$ is independently null, —O—, or —N(R)—; and
each T is independently H, C(O)$CH_3$, or Z;
provided that
when m, n, o, p, and q are each 0, $W_1$ and $W_2$ are each null, w is 1, and Z is

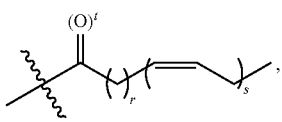

then t must be 0;
when m', n', o', p', and q' are each 0, u is 1, $W_{1'}$ and $W_{2'}$ are each null, and Z' is

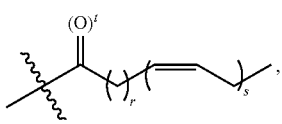

then t must be 0;
when m, n, o, p, and q are each 0, and $W_1$ and $W_2$ are each null, then Z must not be

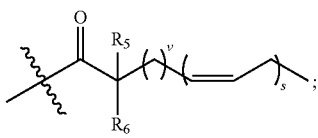

when m', n', p', q', and u' are each 0, and $W_{2'}$ is null, Z' must not be

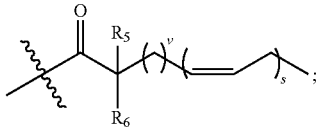

when w is 0, then $W_1$ is O or NH; and
when w is 1, Z is

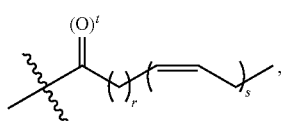

and r is 7, then t is 1.

In yet another aspect, compounds of the Formula IIIa' are described:

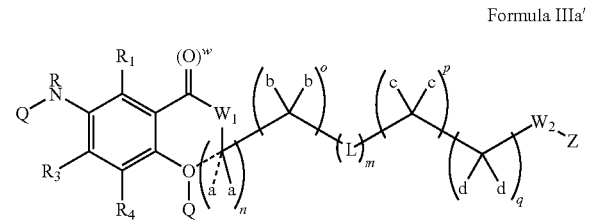

Formula IIIa' and pharmaceutically acceptable salts, hydrates, solvates, prodrugs, enantiomers, and stereoisomers thereof; wherein $R_1$, $R_3$, and $R_4$ are each independently selected from the group consisting of H, Cl, F, CN, $NH_2$, $NH(C_1-C_3$ alkyl), $N(C_1-C_3$ alkyl$)_2$, $NH(C(O)C_1-C_3$ alkyl), $N(C(O)C_1-C_3$ alkyl$)_2$, C(O)H, $C(O)C_1-C_3$ alkyl, $C(O)OC_1-C_3$ alkyl, $C(O)NH_2$, $C(O)NH(C_1-C_3$ alkyl), $C(O)N(C_1-C_3$ alkyl$)_2$, $C_1-C_3$ alkyl, $OC_1-C_3$ alkyl, $S(O)C_1-C_3$ alkyl, $S(O)_2C_1-C_3$ alkyl, difluorophenyl, and trifluoromethyl;

each $W_1$ and $W_2$ is independently null, O, or NH, or when $W_1$ and $W_2$ are both NH, then both $W_1$ and $W_2$ can be taken together to form a piperidine moiety;

each symbol ----- represents an optional bond, which when present between the phenolic oxygen and the methylene containing substituent a, requires that Q is null, or when present between substituent a and the carbon of the methylene containing substituent a, requires that Q not be null;

each a and c is independently H, $CH_3$, $-OCH_3$, $-OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)$_2$—, —S—S—,

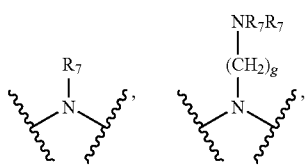 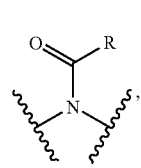

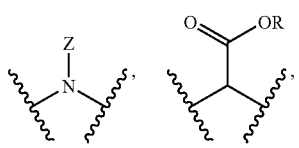 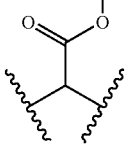

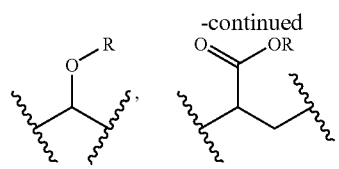

each g is independently 2, 3 or 4;

each h is independently 1, 2, 3 or 4;

m is 0, 1, 2, or 3;

each $R_7$ is independently H or $C_1-C_6$ alkyl, or both $R_7$ groups, when taken together with the nitrogen to which they are attached, can form a heterocycle;

each $R_8$ is independently e, H or straight or branched $C_1-C_{10}$ which can be optionally substituted with OH, $NH_2$, $CO_2R$, $CONH_2$, phenyl, $C_6H_4OH$, imidazole or arginine;

each R is independently H, —C(O)—$C_1-C_3$ alkyl, or straight or branched $C_1-C_4$ alkyl optionally substituted with OR, $NR_2$, or halogen;

each Z is independently H,

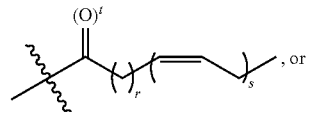, or

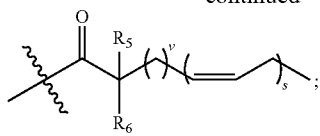

with the proviso that there is at least one

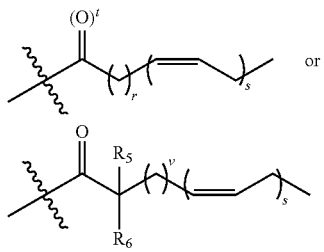

in the compound;

each r is independently 2, 3, or 7;
each s is independently 3, 5, or 6;
each t is independently 0 or 1;
w is 0 or 1;
each v is independently 1, 2, or 6;
each $R_5$ and $R_6$ are independently hydrogen, deuterium, $C_1$-$C_4$ alkyl, halogen, —OH, —C(O)$C_3$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl;
each Q is independently null, C(O)$CH_3$, Z,

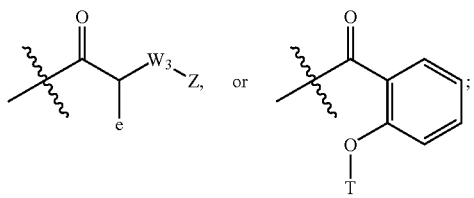

each e is independently H or any one of the side chains of the naturally occurring amino acids;
each $W_3$ is independently null, —O—, or —N(R)—; and each T is independently H, C(O)$CH_3$, or Z;
provided that
when m, n, o, p, and q are each 0, $W_1$ and $W_2$ are each null, w is 1, and Z is

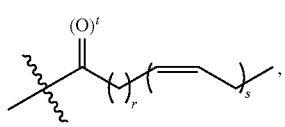

then t must be 0;
when m, n, o, p, and q are each 0, and $W_1$ and $W_2$ are each null, then Z must not be

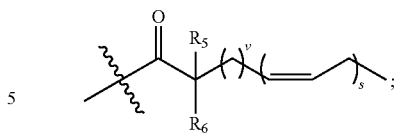

when w is 0, then $W_1$ is O or NH; and
when w is 1, Z is

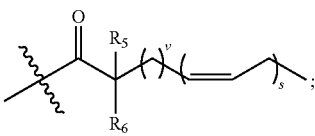

and r is 7, then t is 1.
In another aspect, compounds of the Formula IIIb' are described:

Formula IIIb'

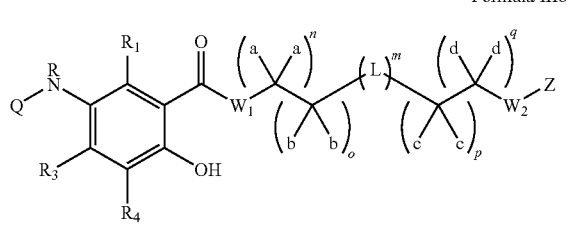

and pharmaceutically acceptable salts, hydrates, solvates, prodrugs, enantiomers, and stereoisomers thereof;
wherein
$R_1$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;
$W_1$ and $W_2$ are each independently null, O, or NH, or when $W_1$ and $W_2$ are both NH, then both $W_1$ and $W_2$ can be taken together to form a piperidine moiety;
each a and c is independently H, $CH_3$, —$OCH_3$, —$OCH_2CH_3$ or C(O)OH, C(O)OR or benzyl;
each b is independently H, $CH_3$, C(O)OH, O—Z, C(O)OR or benzyl;
each d is independently H, C(O)OH, C(O)OR or benzyl;
each n, o, p, and q is independently 0 or 1;
each L is independently —O—, —S—, —S(O)—, —S(O)$_2$—, —S—S—,

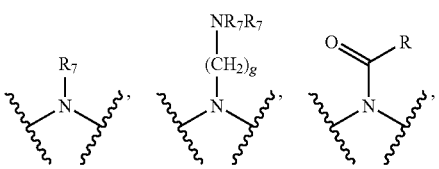

-continued

[structures shown]

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H,

[structures shown]

with the proviso that there is at least one

[structures shown]

in the compound;
each r is independently 2, 3, or 7;
each s is independently 3, 5, or 6;
each t is independently 0 or 1;
each v is independently 1, 2, or 6;
each $R_5$ and $R_6$ are independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2C_1$-$C_3$ alkyl;
Q is null, H, C(O)CH$_3$, Z,

[structure shown]

each e is independently H or any one of the side chains of the naturally occurring amino acids;
$W_3$ is null, —O—, or —N(R)—;
provided that
when m, n, o, p, and q are each 0, $W_1$ and $W_2$ are each null, and Z is

[structure shown]

then t must be 0;
when m, n, o, p, and q are each 0, and $W_1$ and $W_2$ are each null, then Z must not be

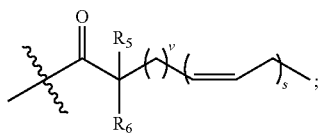

when w is 1, Z is

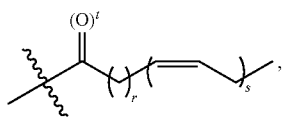

and r is 7, then t is 1.

In another aspect, compounds of the Formula IIIc' are described:

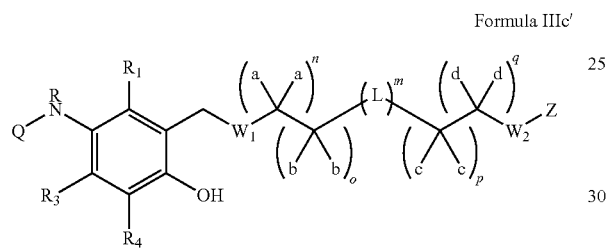

Formula IIIc' and pharmaceutically acceptable salts, hydrates, solvates, prodrugs, enantiomers, and stereoisomers thereof;

wherein $R_1$, $R_3$, and $R_4$ are each independently selected from the group consisting of H, Cl, F, CN, $NH_2$, —$NH(C_1-C_3$ alkyl), —$N(C_1-C_3$ alkyl)$_2$, —$NH(C(O)C_1-C_3$ alkyl), —$N(C(O)C_1-C_3$ alkyl)$_2$, —C(O)H, —$C(O)C_1-C_3$ alkyl, —$C(O)OC_1-C_3$ alkyl, —$C(O)NH_2$, —$C(O)NH(C_1-C_3$ alkyl), —$C(O)N(C_1-C_3$ alkyl)$_2$, —$C_1-C_3$ alkyl, —O—$C_1-C_3$ alkyl, —$S(O)C_1-C_3$ alkyl, —$S(O)_2C_1-C_3$ alkyl, difluorophenyl, and trifluoromethyl;

$W_1$ and $W_2$ are each independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —$S(O)_2$—, —S—S—,

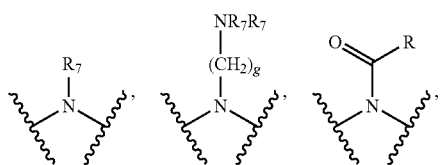

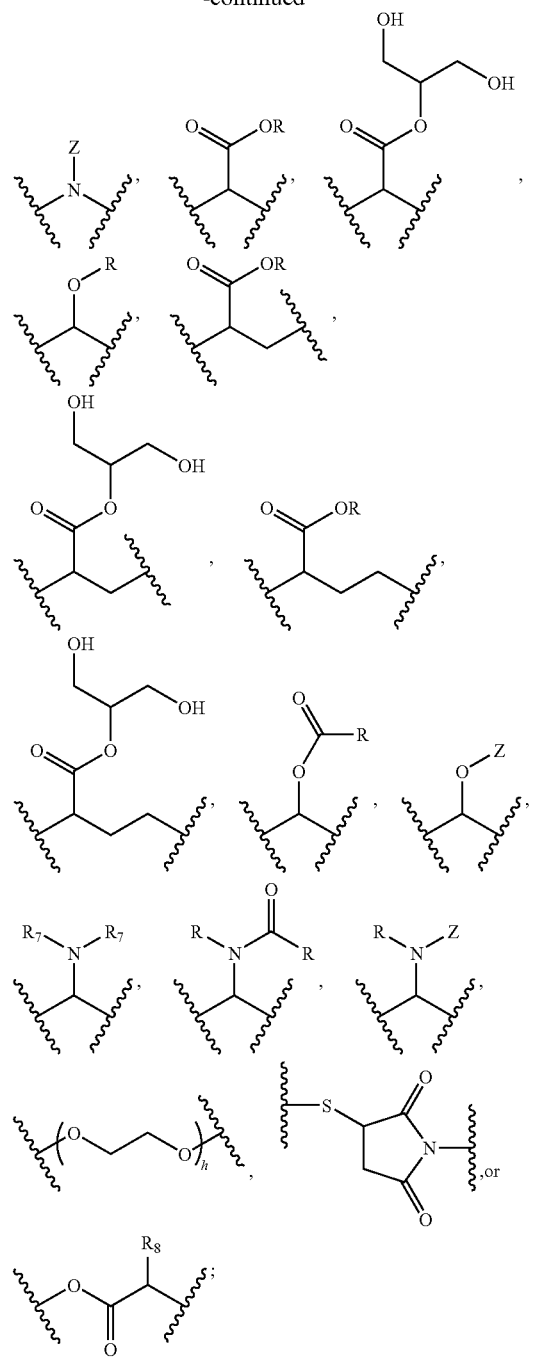

each g is independently 2, 3 or 4;
each h is independently 1, 2, 3 or 4;
m is 0, 1, 2, or 3;
each $R_7$ is independently H or $C_1-C_6$ alkyl, or both $R_7$ groups, when taken together with the nitrogen to which they are attached, can form a heterocycle;
each $R_8$ is independently e, H or straight or branched $C_1-C_{10}$ which can be optionally substituted with OH, $NH_2$, $CO_2R$, $CONH_2$, phenyl, $C_6H_4OH$, imidazole or arginine;
each R is independently H, —C(O)—$C_1-C_3$ alkyl, or straight or branched $C_1-C_4$ alkyl optionally substituted with OR, $NR_2$, or halogen;
each Z is independently H,

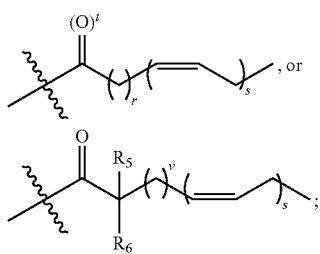

with the proviso that there is at least one

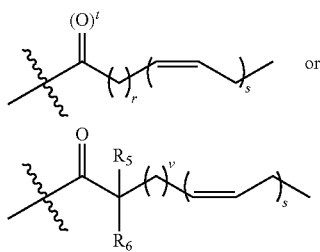

in the compound;
each r is independently 2, 3, or 7;
each s is independently 3, 5, or 6;
each t is independently 0 or 1;
each v is independently 1, 2, or 6;
each $R_5$ and $R_6$ are independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl;
Q is null, H, C(O)$CH_3$, Z,

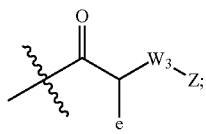

each e is independently H or any one of the side chains of the naturally occurring amino acids;
$W_3$ is null, —O—, or —N(R)—; and
T is H, C(O)$CH_3$, or Z.
In another aspect, compounds of the Formula IIId' are described:

and pharmaceutically acceptable salts, hydrates, solvates, prodrugs, enantiomers, and stereoisomers thereof;
wherein
$R_1$, $R_3$, and $R_4$ are each independently selected from the group consisting of H, Cl, F, CN, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, —S(O)$_2$$C_1$-$C_3$ alkyl, difluorophenyl, and trifluoromethyl;
each $W_1$, and $W_2$ is independently null, O, or NH, or when $W_1$ and $W_2$ are both NH, then both $W_1$ and $W_2$ can be taken together to form a piperidine moiety;
each a and c is independently H, $CH_3$, —$OCH_3$, —$OCH_2CH_3$, C(O)OH, C(O)OR or benzyl;
each b is independently H, $CH_3$, C(O)OH, O—Z, C(O)OR or benzyl;
each d is independently H, C(O)OH, C(O)OR or benzyl;
each n, o, p, and q is independently 0 or 1;
each L is independently —O—, —S—, —S(O)—, —S(O)$_2$—, —S—S—,

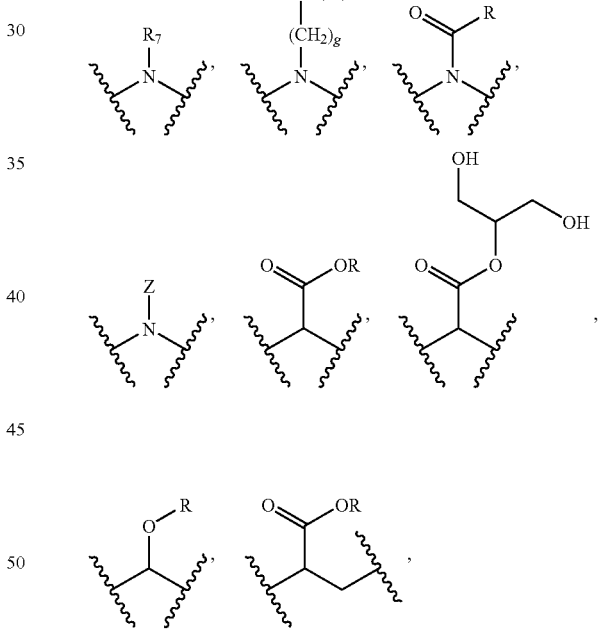

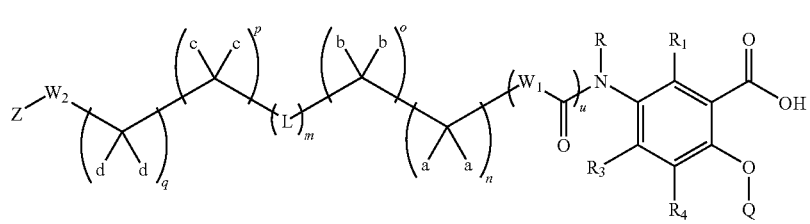

Formula IIId'

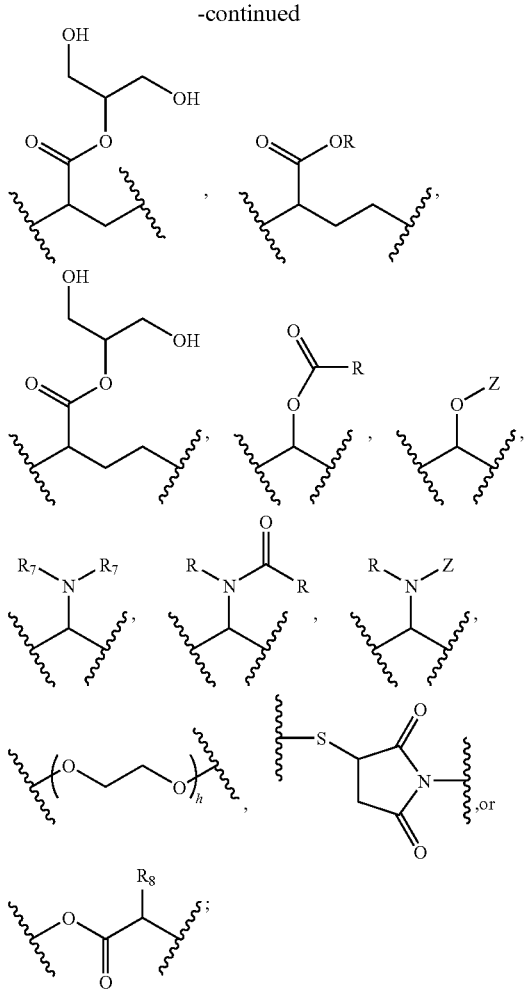

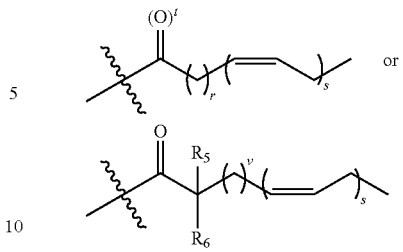

in the compound;

each r is independently 2, 3, or 7;
each s is independently 3, 5, or 6;
each t is independently 0 or 1;
each v is independently 1, 2, or 6;
each $R_5$ and $R_6$ are independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl;

u is 0 or 1;
Q is null, C(O)$CH_3$, Z,

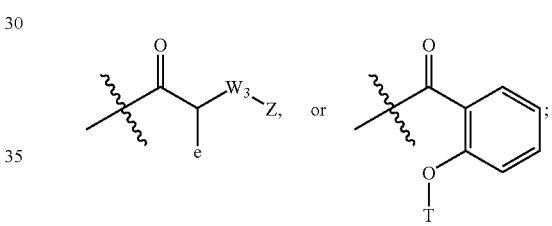

each e is independently H or any one of the side chains of the naturally occurring amino acids;
$W_3$ is null, —O—, or —N(R)—; and
T is H, C(O)$CH_3$, or Z;
provided that
when m, n, o, p, and q are each 0, u is 1, $W_1$ and $W_2$ are each null, and Z is

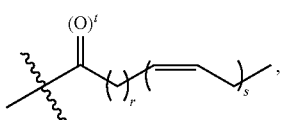

then t must be 0; and
when m, n, o, p, q, and u are each 0, and $W_2$ is null, then Z must not be

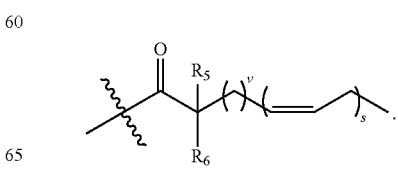

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with OR, $NR_2$, or halogen;
each Z is independently H,

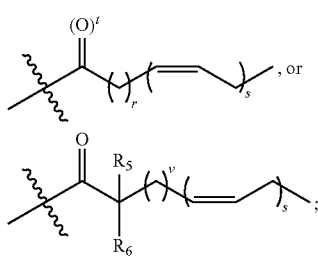

with the proviso that there is at least one

In yet another aspect, compounds of the Formula IIIe' are described:

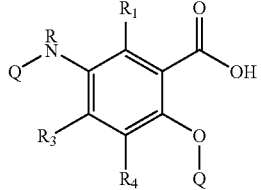

Formula IIIe' and pharmaceutically acceptable salts, hydrates, solvates, prodrugs, enantiomers, and stereoisomers thereof;

wherein $R_1$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, —$S(O)_2C_1$-$C_3$ alkyl, difluorophenyl, and trifluoromethyl;

R is H, —C(O)—$C_1$-$C_3$ alkyl, or straight or branched $C_1$-$C_4$ alkyl optionally substituted with OR, $NR_2$, or halogen;

each Q is independently null, H, $C(O)CH_3$, Z,

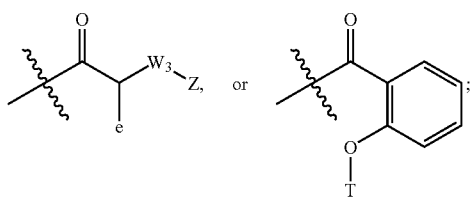

each e is independently H or any one of the side chains of the naturally occurring amino acids;

each $W_3$ is independently null, —O—, or —N(R)—;

each T is independently H, $C(O)CH_3$, or Z;

each Z is independently H,

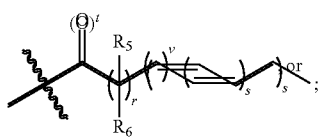

with the proviso that there is at least one

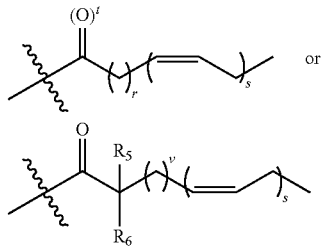

in the compound;

each r is independently 2, 3, or 7;

each s is independently 3, 5, or 6;

each t is independently 0 or 1;

each v is independently 1, 2, or 6; and each $R_5$ and $R_6$ are independently hydrogen, deuterium, $C_1$-$C_4$ alkyl, halogen, —OH, —$C(O)C_1$-$C_4$ alkyl, —O-aryl, —O-benzyl, —$OC(O)C_1$-$C_4$ alkyl, —$C_1$-$C_3$ alkene, —$C_1$-$C_3$ alkyne, —$C(O)C_1$-$C_4$ alkyl, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —SH, —$S(C_1$-$C_3$ alkyl), —$S(O)C_1$-$C_3$ alkyl, or —$S(O)_2C_1$-$C_3$ alkyl.

In another aspect, compounds of the Formula IIIf' are described:

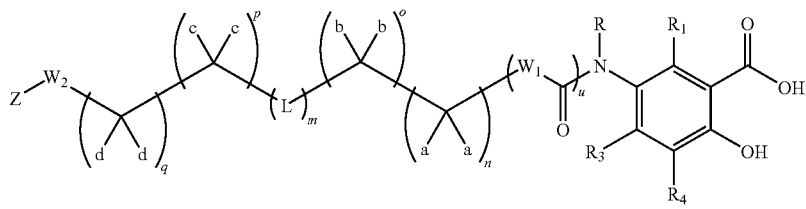

Formula IIIf' and pharmaceutically acceptable salts, hydrates, solvates, prodrugs, enantiomers, and stereoisomers thereof;

wherein $R_1$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, —$S(O)_2C_3$-$C_3$ alkyl, difluorophenyl, and trifluoromethyl;

each $W_1$, and $W_2$ is independently null, O, or NH, or when $W_1$ and $W_2$ are both NH, then both $W_1$ and $W_2$ can be taken together to form a piperidine moiety;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —$S(O)_2$—, —S—S—,

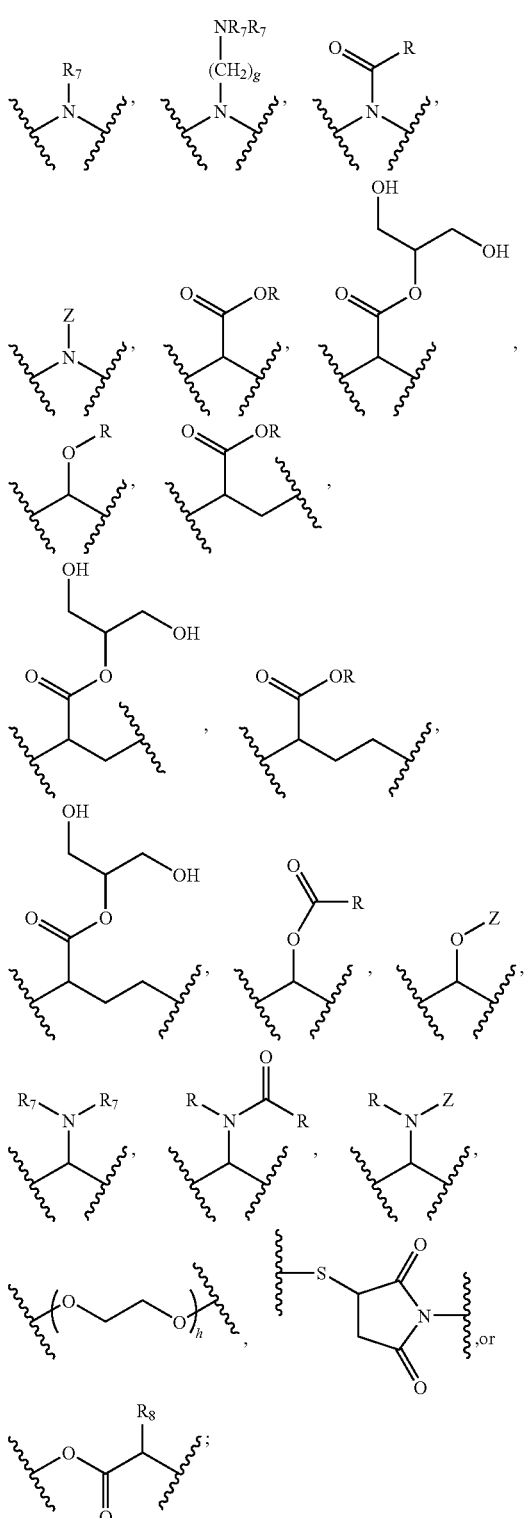

each g is independently 2, 3 or 4;

each h is independently 1, 2, 3 or 4;

m is 0, 1, 2, or 3;

each $R_7$ is independently H or $C_1$-$C_6$ alkyl, or both $R_7$ groups, when taken together with the nitrogen to which they are attached, can form a heterocycle;

each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;

each R is independently H, —C(O)—$C_1$-$C_3$ alkyl, or straight or branched $C_1$-$C_4$ alkyl optionally substituted with OR, $NR_2$, or halogen;

each Z is independently H,

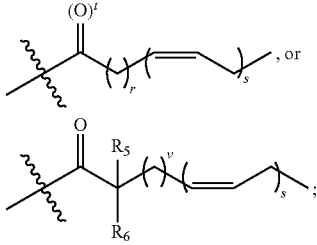

with the proviso that there is at least one

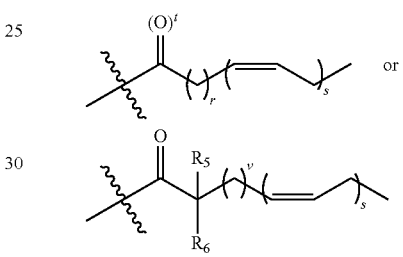

in the compound;

each r is independently 2, 3, or 7;

each s is independently 3, 5, or 6;

each t is independently 0 or 1;

each v is independently 1, 2, or 6;

each $R_5$ and $R_6$ are independently hydrogen, deuterium, $C_1$-$C_4$ alkyl, halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, $NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2C_1$-$C_3$ alkyl;

u is 0 or 1; and each e is independently H or any one of the side chains of the naturally occurring amino acids;

provided that when m, n, o, p, and q are each 0, u is 1, $W_1$ and $W_2$ are each null, and Z is

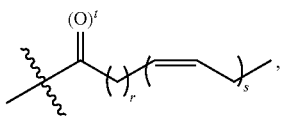

then t must be 0; and when m, n, o, p, q, and u are each 0, and $W_2$ is null, then Z must not be

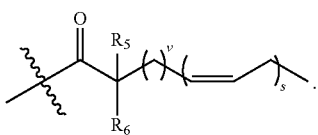

In yet another aspect, compounds of the Formula IIIg' are described:

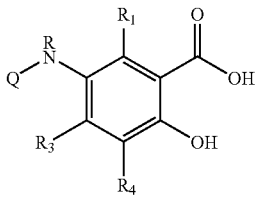

Formula IIIg' and pharmaceutically acceptable salts, hydrates, solvates, prodrugs, enantiomers, and stereoisomers thereof;

wherein $R_1$, $R_3$, and $R_4$ are each independently selected from the group consisting of H, Cl, F, CN, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —C(O)H, —$C(O)C_1$-$C_3$ alkyl, —$C(O)OC_1$-$C_3$ alkyl, —$C(O)NH_2$, —$C(O)NH(C_1$-$C_3$ alkyl), —$C(O)N(C_1$-$C_3$ alkyl)$_2$, —$C_1$-$C_3$ alkyl, —O—$C_1$-$C_3$ alkyl, —$S(O)C_1$-$C_3$ alkyl, —$S(O)_2C_1$-$C_3$ alkyl, difluorophenyl, and trifluoromethyl;

R is H, —C(O)—$C_1$-$C_3$ alkyl, or straight or branched $C_1$-$C_4$ alkyl optionally substituted with OR, $NR_2$, or halogen;

Q is H, $C(O)CH_3$, Z,

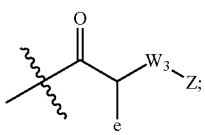

e is H or any one of the side chains of the naturally, occurring amino acids;

$W_3$ is null, —O—, or —N(R)—; and

T is H, $C(O)CH_3$, or Z.

each Z is independently H,

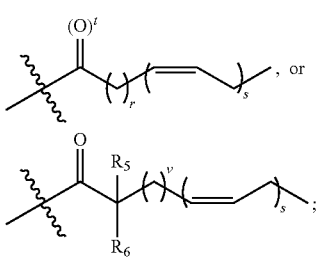

with the proviso that there is at least one

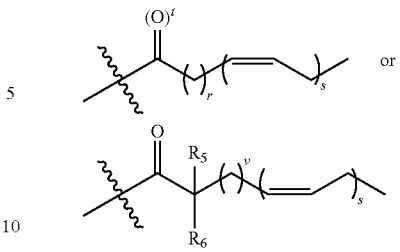

in the compound;

each r is independently 2, 3, or 7;
each s is independently 3, 5, or 6;
each t is independently 0 or 1;
each v is independently 1, 2, or 6; and
each $R_5$ and $R_6$ are independently hydrogen, deuterium, $C_1$-$C_4$ alkyl, halogen, —OH, —$C(O)C_1$-$C_4$ alkyl, —O-aryl, —O-benzyl, —$OC(O)C_1$-$C_4$ alkyl, —$C_1$-$C_3$ alkene, —$C_1$-$C_3$ alkyne, —$C(O)C_1$-$C_4$ alkyl, $NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —SH, —$S(C_1$-$C_3$ alkyl), —$S(O)C_1$-$C_3$ alkyl, or —$S(O)_2C_1$-$C_3$ alkyl;

provided that
when r is 7, s is 3.

In any of the above Formulae, any one or more of H may be substituted with a deuterium. It is also understood in any of the above Formulae that a methyl substituent can be substituted with a $C_1$-$C_6$ alkyl.

Also described are pharmaceutical formulations comprising at least one compound of the invention.

Also described herein are methods of simultaneously up regulating antiinflammation pathways and down regulating proinflammation pathways in a cell by administering to the cell a compound of the invention.

Also described herein are methods of simultaneously up regulating antiinflammation pathways and down regulating proinflammation pathways in a patient in need thereof, by administering to the patient an effective amount of a compound of the invention.

Also described herein are methods of treating a disease susceptible to treatment with a compound of the invention in a patient in need thereof by administering to the patient an effective amount of a compound of the invention.

Also described herein are methods of treating diseases associated with inflammation by administering to a patient in need thereof an effective amount of a compound of the invention.

The invention also includes pharmaceutical compositions that comprise an effective amount of a compound of the invention and a pharmaceutically acceptable carrier. The compositions are useful for treating or preventing an inflammatory disease. The invention includes a compound of the invention provided as a pharmaceutically acceptable prodrug, hydrate, salt, such as a pharmaceutically acceptable salt, enantiomer, stereoisomer, or mixtures thereof.

The details of the invention are set forth in the accompanying description below. Although any methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

5. BRIEF DESCRIPTION OF THE FIGURES

DETAILED DESCRIPTION OF THE INVENTION

Figure 1:
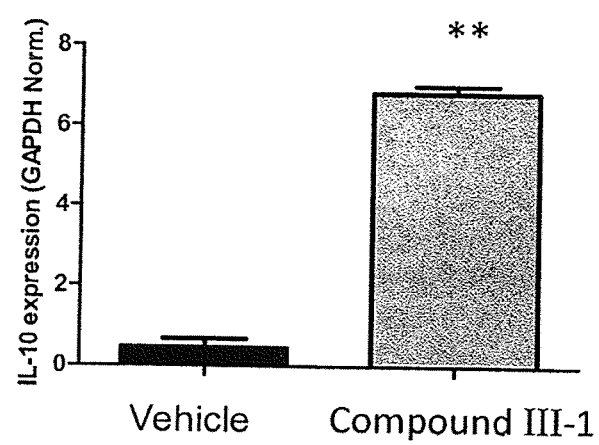
FIG. 1 is a graphic representation of the data showing the effects of the Compound III-1 of the invention on IL-10 levels in 3T3-L1 adipocytes.

Inflammation is the underlying cause of and pathological contributor to many chronic diseases including type 2 diabetes, rheumatoid arthritis, psoriasis, inflammatory bowel disease, Parkinson's disease, Alzheimer's disease, multiple sclerosis, epilepsy, and cancer, and the like. Inflammation is the body's natural protective response to insult, injury and infection. The normal inflammatory process is highly regulated. The process is initiated by a stimulus which leads to the induction of pro-inflammatory pathways. The response persists while the stimulus is present and is turned off during the resolving phase of inflammation. During each of these phases of the inflammatory response different enzymes, receptors, and effectors, are activated and inactivated. If the stimulus persists, chronic inflammation ensues and results in an imbalance in the pro- and anti-inflammatory pathways. Current therapies that target inflammation have been directed in general at single molecular targets or effectors in single pathways. For example, TNFα antibodies, TNFα soluble receptors, COX-2 inhibitors, CCR2 antagonists, p38 inhibitors, etc. target just the pro-inflammatory arm of inflammation. In general these approaches are not disease modifying and are associated with side effects that result from an imbalanced inflammatory response. The simultaneous targeting of both the pro- and anti-inflammatory pathways in the normal inflammatory response provides superior activity in targeting inflammation, disease modifying activity, and a reduced side effect profile. The compounds of the invention possess the ability to inhibit pro-inflammatory pathways, while simultaneously activating anti-inflammatory pathways. The simultaneous targeting of these pathways leads to synergistic efficacy and thus the two activities must be delivered to the target cell and/or tissue together.

The compounds of the invention have been designed to bring together salicylate analogs and omega 3 fatty acids into a single molecular conjugate. Salicylate analogs inhibit the pro-inflammatory pathway through inhibition of NFκB. The omega 3 fatty acids including DHA, EPA, and ALA activate the anti-inflammatory pathway. The compounds of the invention thus possess two activities—the ability to blunt pro-inflammatory activity and the ability to activate anti-inflammatory activity compounds of the invention exhibit potent NFκB and TNFα inhibitory activity in a mouse macrophage cell line, RAW264.7, while the individual components, a salicylate analog and a EFA, alone or in combination together, do not. The activity of the compounds of the invention is substantially greater than the sum of the components suggesting that the activity induced by the compounds of the invention is synergistic.

DEFINITIONS

The following definitions are used in connection with the fatty acid acylated salicylate derivatives, the fatty acid acylated diflunisal derivatives, and fatty acid acylated triflusal derivatives:

The term "compound of the invention" refers to a fatty acid acylated salicylate derivative described herein, wherein salicylate derivative includes, without limitation, salicylic acid and substituted salicylates such as aminosalicylic acid, a fatty acid acylated diflunisal derivative described herein, or a fatty acid acylated triflusal derivative described herein. The term "compounds of the invention" refers to more than one compound of the invention and may be fatty acid acylated salicylate derivatives, fatty acid acylated diflunisal derivatives, fatty acid acylated triflusal derivatives, or some combination thereof. The compounds of the invention include any and all possible isomers, stereoisomers, enantiomers, diastereomers, tautomers, pharmaceutically acceptable salts, hydrates, solvates, and prodrugs thereof.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "heterocycle" as used herein refers to a cyclic hydrocarbon containing 3-6 atoms wherein at least one of the atoms is an O, N, or S. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine, and Tyrosine.

The term "fatty acid" as used herein means an omega-3 fatty acid and fatty acids that are metabolized in vivo to omega-3 fatty acids. Non-limiting examples of fatty acids are all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid).

The term "salicylic acid" as used herein means the molecule known as salicylic acid and any derivative thereof.

The term "salicylate" as used herein means the esters or salts of salicylic acid and any derivative thereof.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a compound of the invention and a pharmaceutically acceptable carrier. The invention includes a compound of the invention when provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

An "effective amount" when used in connection with a compound of the invention is an amount effective for treating or preventing an inflammatory disease.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating" with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a compound of the invention.

The following abbreviations are used herein and have the indicated definitions: ALT is Alanine immunotransferase, 5-ASA is 5-aminosalicylic acid, AcOK is potassium acetate, Bn is benzyl, Boc and BOC are tert-butyl dicarbonate, $Boc_2O$ is di-tert-butyl dicarbonate, BSA is bovine serum albumin, $Bu_4NBr$ is tetra-n-butylammonium bromide, Cbz is carboxybenzyl, CDI is 1,1'-carbonyldiimidazole, CPS is counts per second, DCC is N,N'-dicyclohexylcarbodiimide, DCM is dichloromethane, DIEA is N,N-diisopropylethylamine, dimethoxyethane is 1,2-dimethoxyethane, DMAP is 4-dimethylaminopyridine, DMEM is Dulbecco's Modified Eagle Medium, DMF is N,N-dimethylformamide, DMSO is dimethyl sulfoxide, DOSS is sodium dioctyl sulfosuccinate, EDC and EDCI are 1-ethyl-3-(3-dimethylaminopropyl)carbodiimide hydrochloride, ELISA is enzyme-linked immunosorbent assay, ethylenediamine is 1,2-diaminoethane, EtOAc is ethyl acetate, FFA is free fatty acid, GAPDH is glyceraldehyde 3-phosphate dehydrogenase, h is hour, HATU is 2-(7-aza-1H-benzotriazole-1-yl)-1,1,3,3-tetramethyluronium hexafluorophosphate, HPLC is high performance liquid chromatography, HPMC is hydroxypropyl methylcellulose, $NaHB(AcO)_3$ is sodium triacetoxyborohydride, oxone is potassium peroxymonosulfate, PCR is polymerase chain reaction, Pd/C is palladium on carbon, PE is petroleum ether, Pivaloyl and Piv are 2,2-dimethylpropanoyl, RT is room temperature, SA is salicylic acid, SDS is dodecyl sulfate sodium salt, TFA is trifluoroacetic acid, TGPS is tocopherol propylene glycol succinate, THF is tetrahydrofuran, and TNF is tumor necrosis factor.

Compounds

Accordingly in one aspect, a molecular conjugate is described which comprises a salicylate and a fatty acid covalently linked, wherein the fatty acid is selected from the group consisting of omega-3 fatty acids and fatty acids that are metabolized in vivo to omega-3 fatty acids, and the conjugate is capable of hydrolysis to produce free salicylate and free fatty acid.

In some embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, and tetracosahexaenoic acid. In other embodiments, the fatty acid is selected from eicosapentaenoic acid and docosahexaenoic acid. In some embodiments, the hydrolysis is enzymatic.

In another aspect, the present invention provides fatty acid acylated salicylate derivatives according to Formula I, Formula Ia, Formula Ib, Formula Ic, Formula Id, Formula If, Formula Ih, Formula II, Formula II, Formula III, Formula IIIa, Formula IIIb, Formula IIIc, Formula IIId, Formula IIIe, Formula IIIf, Formula IIIg, Formula I', Formula Ia', Formula Ib', Formula Ic', Formula Id', Formula If', Formula Ih', Formula Ii', Formula II', Formula III', Formula IIIa', Formula IIIb', Formula IIIc', Formula IIId', Formula IIIe', Formula IIIf' and Formula IIIg' as set forth below. The present invention also provides fatty acid acylated diflunisal derivatives according to Formula I, Formula Ia, Formula Ib, Formula Ic, Formula Id, Formula If, Formula Ih, Formula II, Formula II, Formula III, Formula IIIa, Formula IIIb, Formula IIIc, Formula IIId, Formula IIIe, Formula IIf, Formula IIIg, Formula I', Formula Ia', Formula Ib', Formula Ic', Formula Id', Formula If', Formula Ih', Formula Ii', Formula II', Formula III', Formula IIIa', Formula IIIb', Formula IIIc', Formula IIId', Formula IIIe', Formula IIIf' and Formula IIIg' as set forth below. The present invention additionally provides fatty acid acylated triflusal derivatives according to Formula I, Formula Ia, Formula Ib, Formula Ic, Formula Id, Formula If, Formula Ih, Formula Ii, Formula II, Formula III, Formula IIIa, Formula IIIb, Formula IIIc, Formula IIId, Formula IIIe, Formula IIIf, Formula IIIg, Formula I', Formula Ia', Formula Ib', Formula Ic', Formula Id', Formula If', Formula Ih', Formula Ii', Formula II', Formula III', Formula IIIa', Formula IIIb', Formula IIIc', Formula IIId', Formula IIIe', Formula IIIf' and Formula IIIg' as set forth below.

Described herein are compounds of the Formula I:

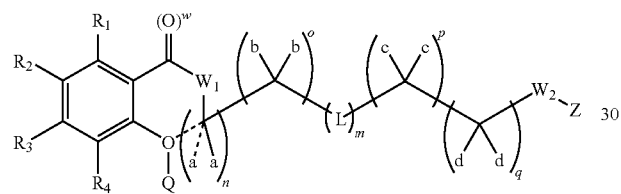

Formula I and pharmaceutically acceptable salts, hydrates, solvates, prodrugs, enantiomers, and stereoisomers thereof;
wherein
$R_1$, $R_2$, $R_3$, $R_4$, $R_7$, $R_8$, R, $W_1$, $W_2$, $W_3$, a, b, c, d, e, g, h, the symbol -----, L, Z, m, n, o, p, q, r, s, t, w, Q, and T are as defined above for compounds of Formula I.

In some embodiments, $R_2$ is Cl or F.
In other embodiments, $R_2$ or $R_3$ is difluorophenyl.
In other embodiments, $R_3$ is trifluoromethyl.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, one symbol ----- represents a bond. In some embodiments, the bond is present between the phenolic oxygen and the methylene containing substituent a. In other embodiments, the bond is present between substituent a and the carbon of the methylene containing substituent a.
In some embodiments, one a is C(O)OR.
In other embodiments, one R is straight or branched $C_1$-$C_4$ alkyl optionally substituted with OR, $NR_2$, or halogen.
In some embodiments, one b is O—Z, Z is

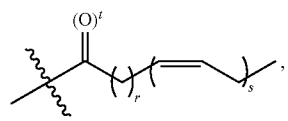

and t is 1.
In some embodiments, one d is C(O)OR.

In some embodiments n, o, p, and q are each 1.
In some embodiments, two of n, o, p, and q are each 1.
In other embodiments, three of n, o, p, and q are each 1.
In some embodiments, m is 0.
In some embodiments, each L is independently —S—, —S(O)—, —S(O)$_2$—, or —S—S—.
In some embodiments, each L is independently —O—,

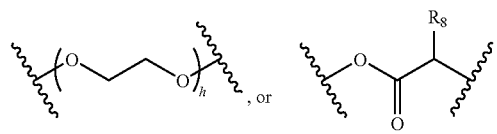

In some embodiments, each L is independently

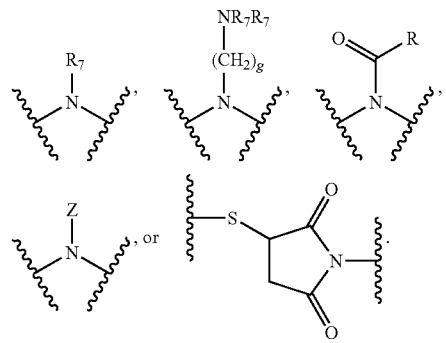

In some embodiments, each L is independently

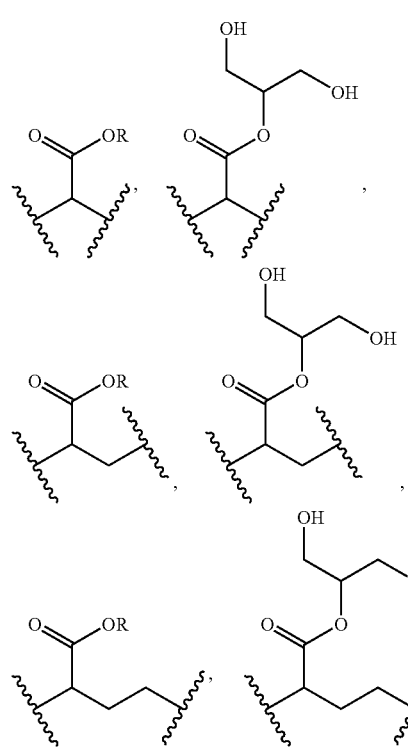

91
-continued
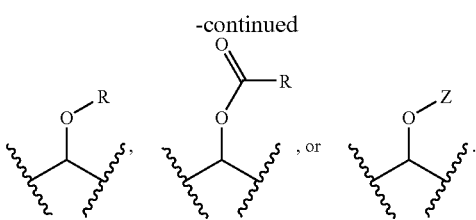
In some embodiments, each L is independently
92
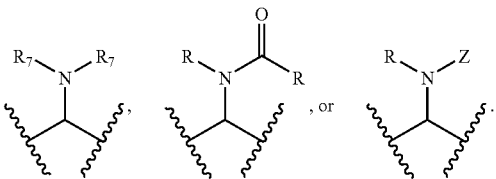
In some embodiments, $R_8$ is e.
In some embodiments, t is 1.
In some embodiments, w is 1.
In other illustrative embodiments, compounds of the Formula I are as set forth below:
I-1
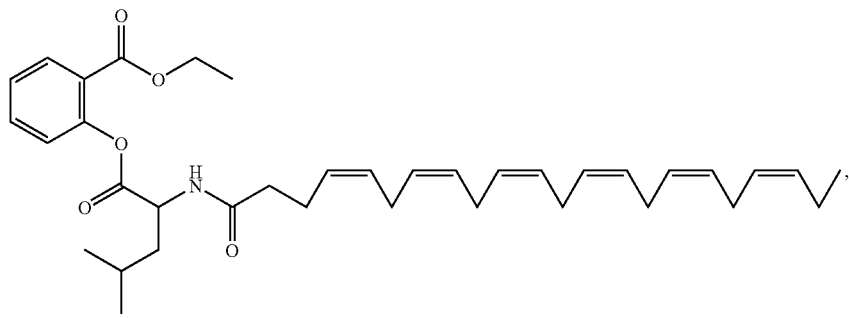
I-2
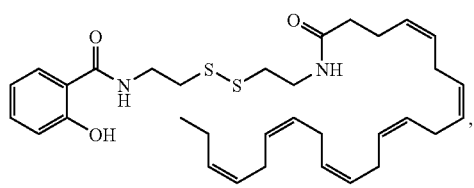
I-3
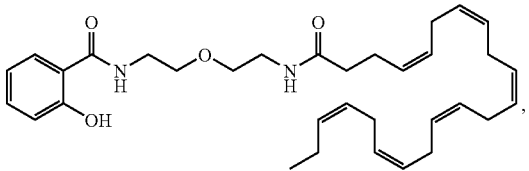
I-4
I-5
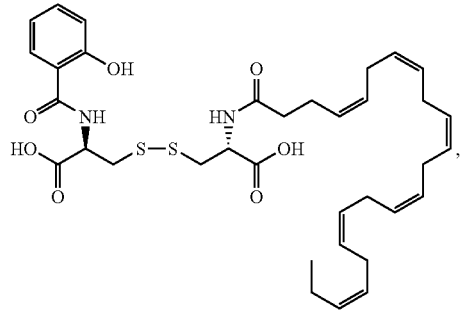
I-6
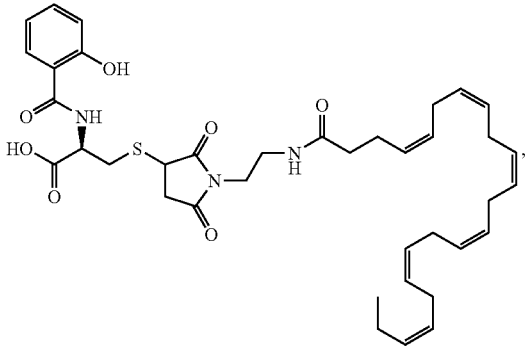
I-7
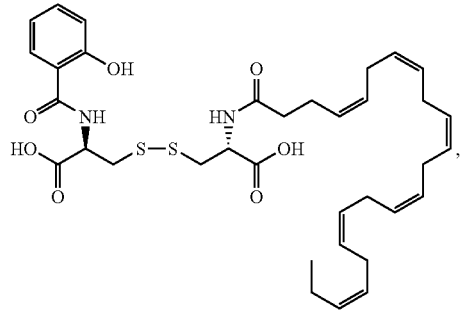
I-8
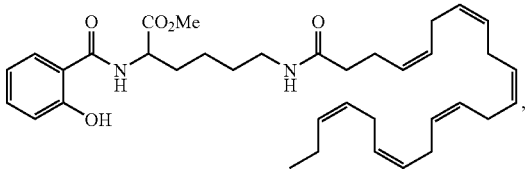

-continued
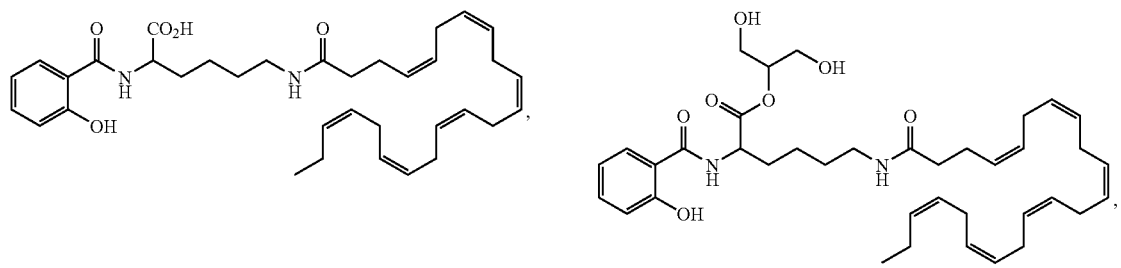
I-9
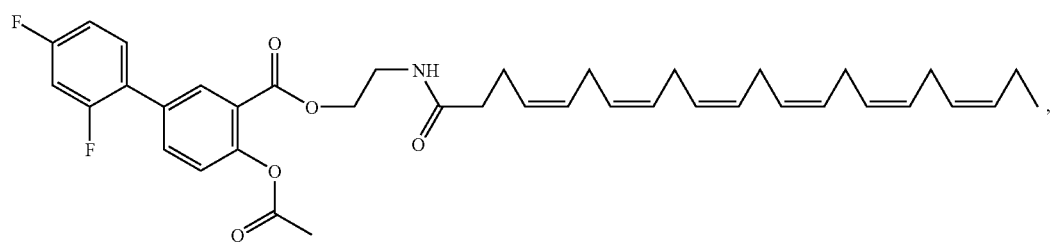
I-10
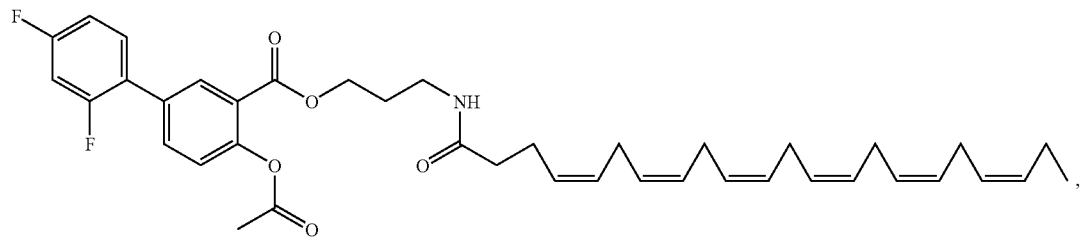
I-11
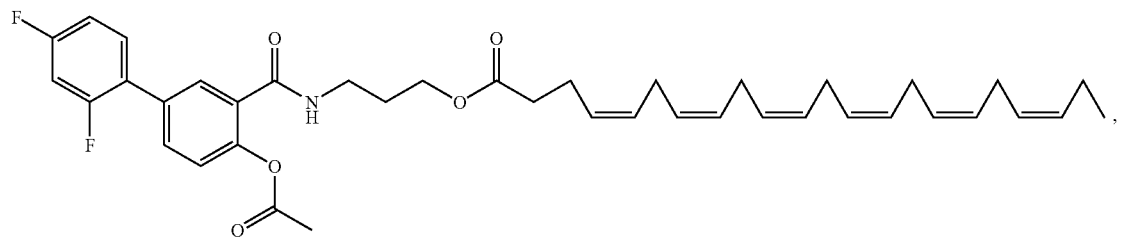
I-12
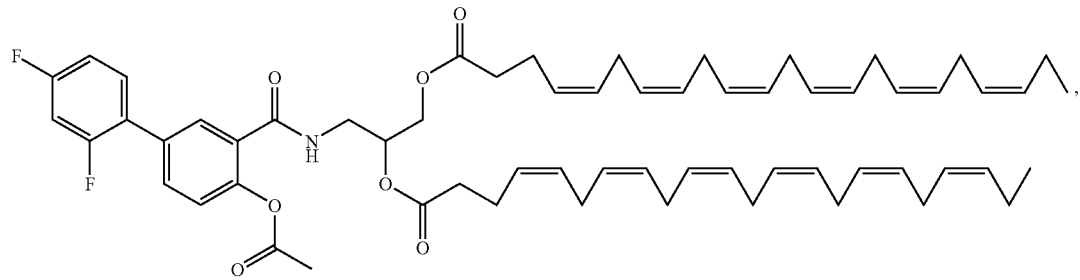
I-13
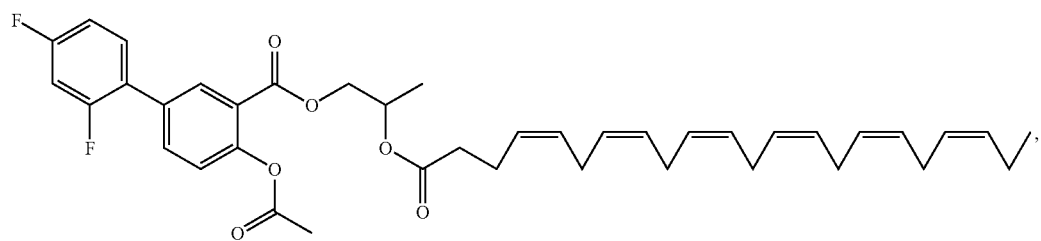
I-14
I-15

-continued
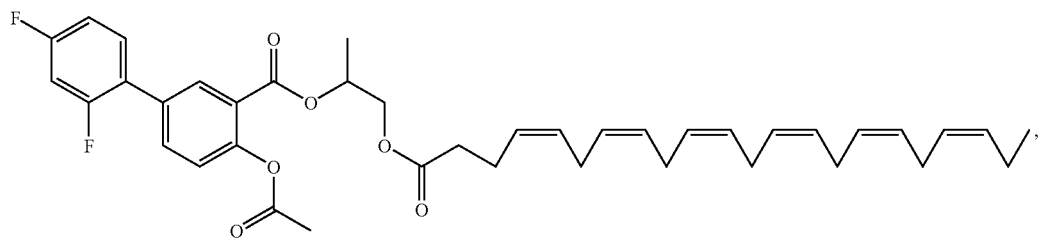
I-16
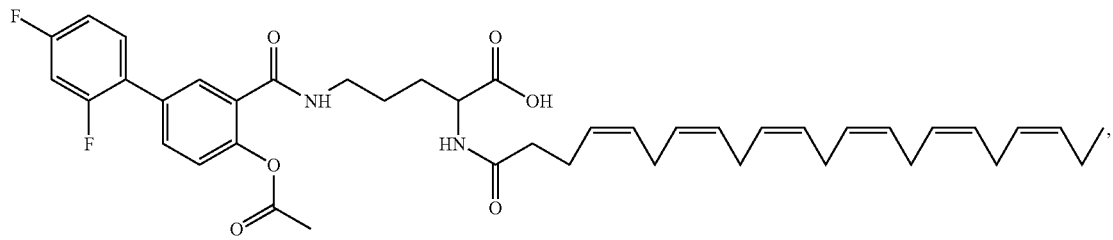
I-17
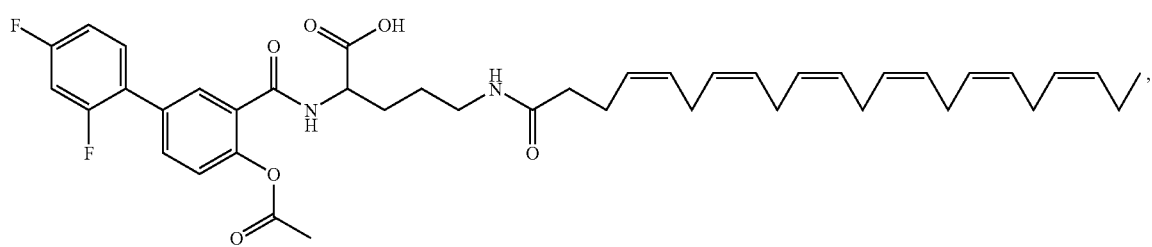
I-18
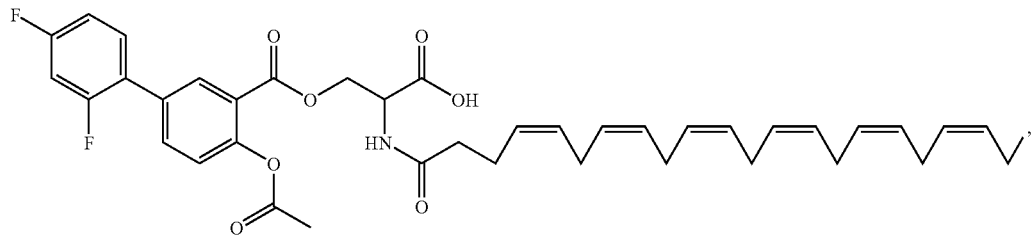
I-19
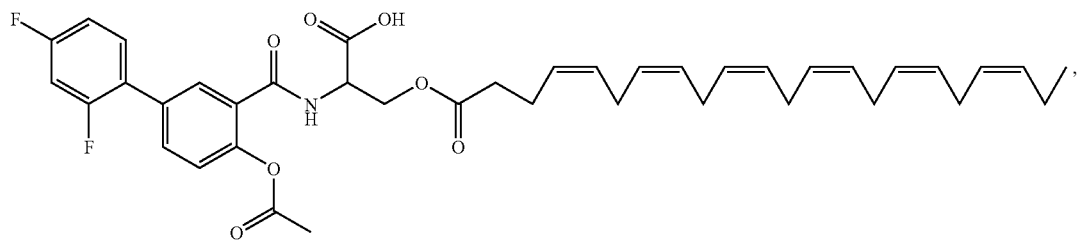
I-20
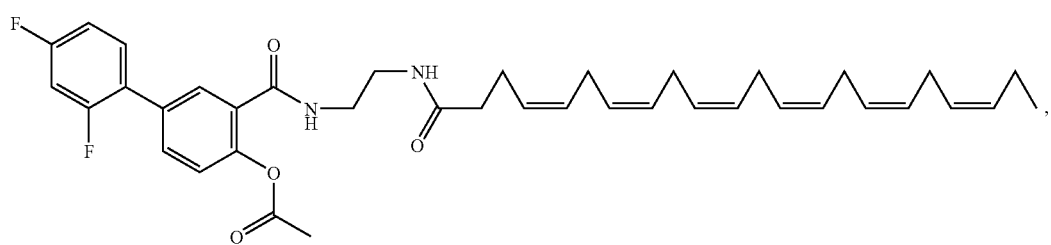
I-21

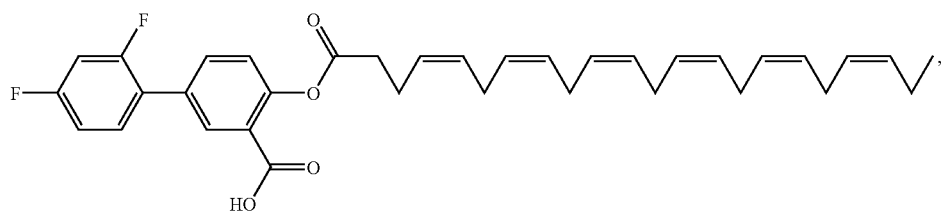
I-22
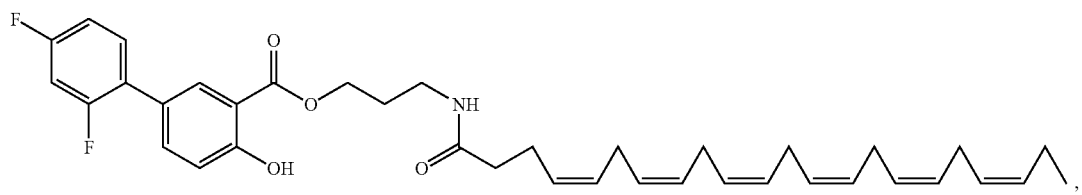
I-24
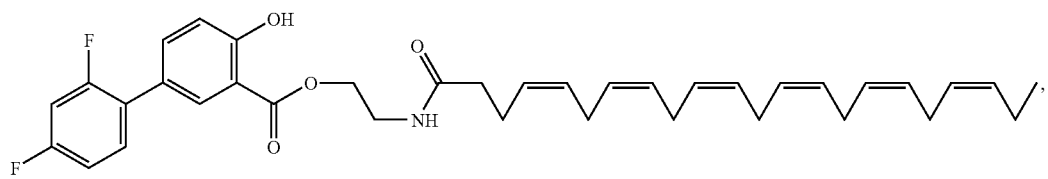
I-25
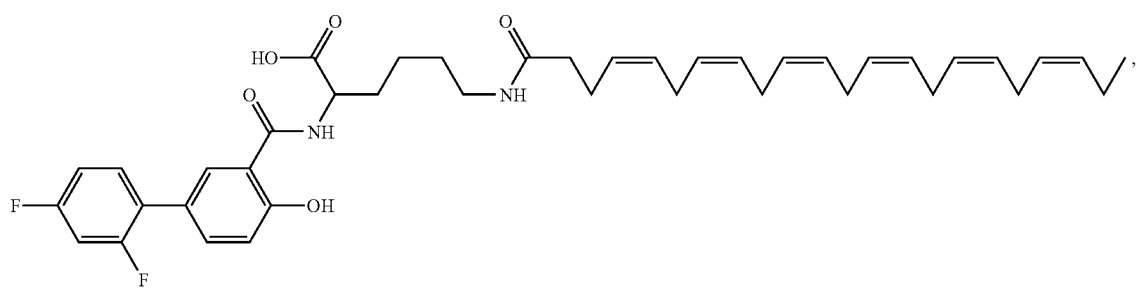
I-26
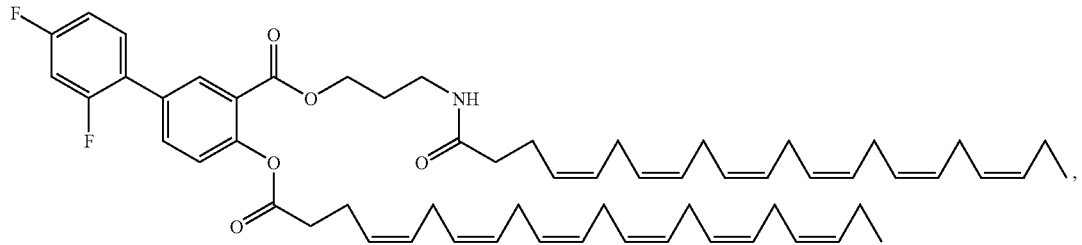
I-27
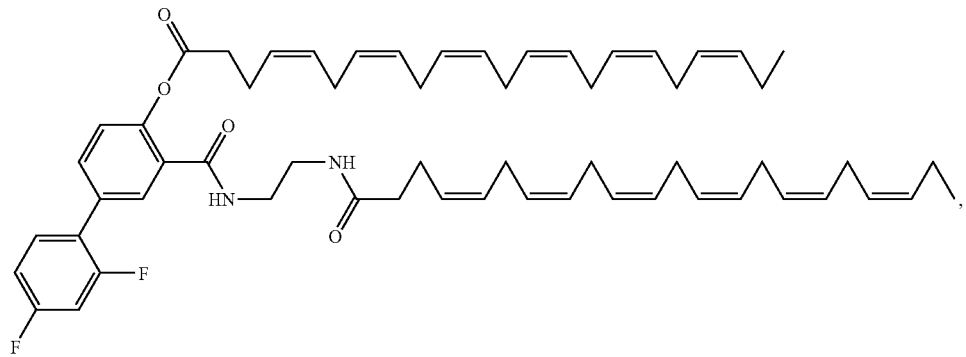
I-28

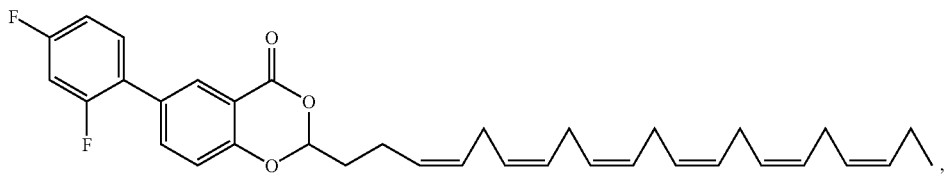
I-29
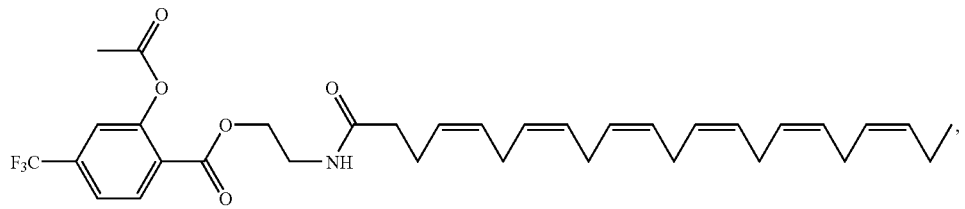
I-30
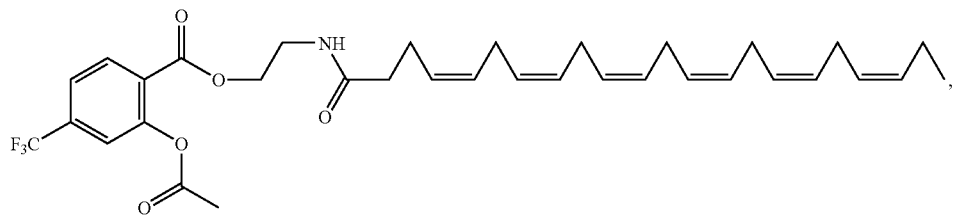
I-31
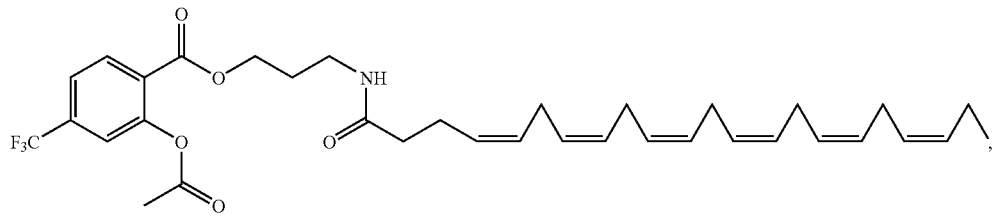
I-32
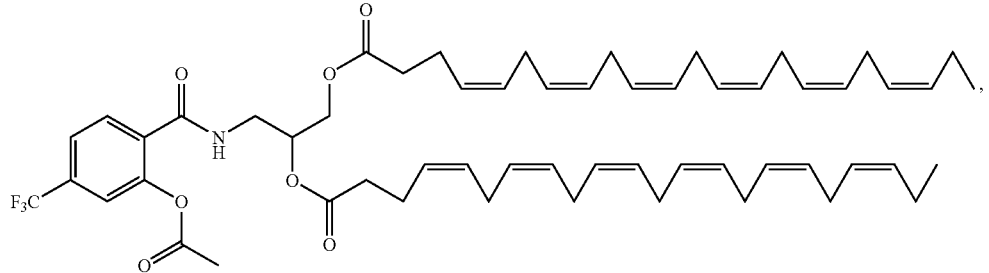
I-33
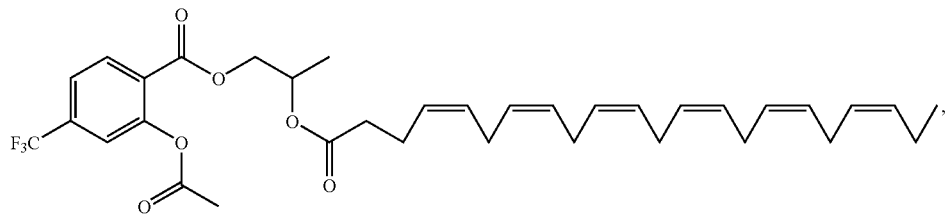
I-34
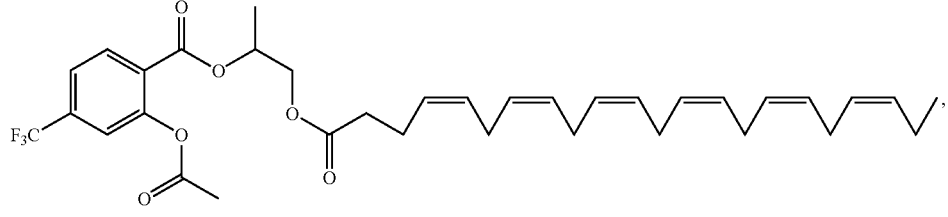
I-35

-continued
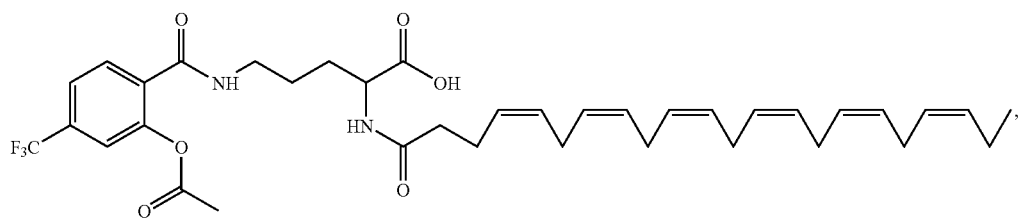
I-36
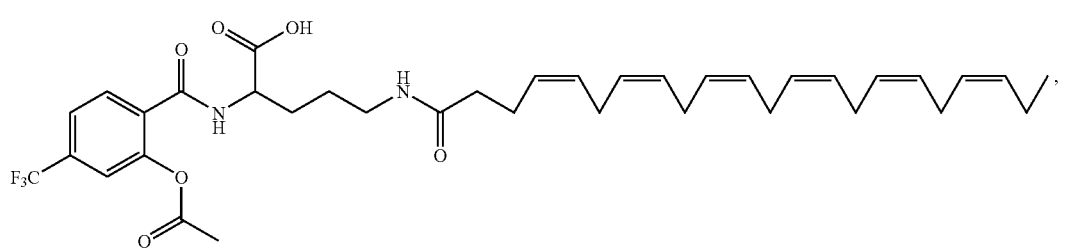
I-37
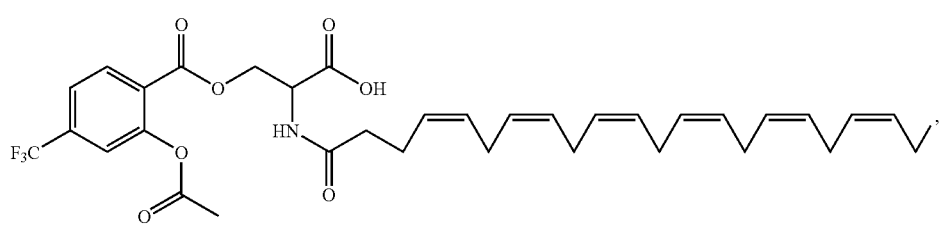
I-38
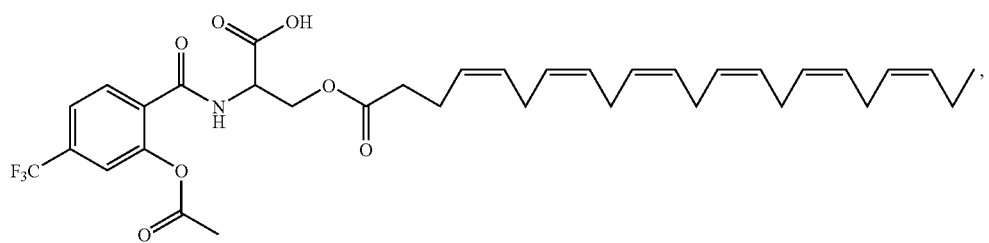
I-39
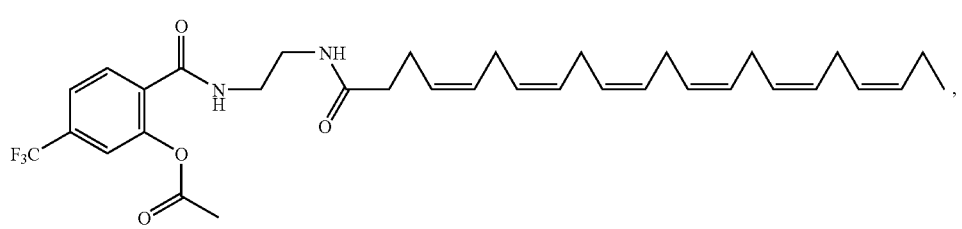
I-40
I-41
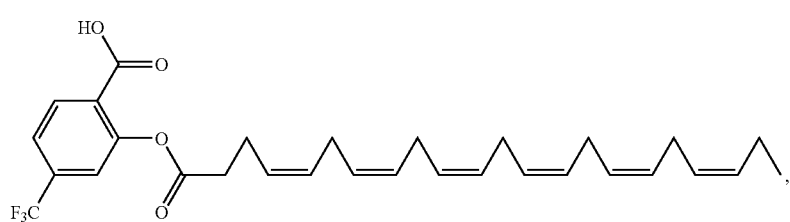
I-42

-continued
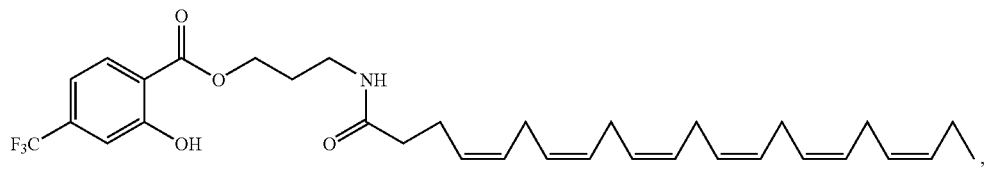
I-44
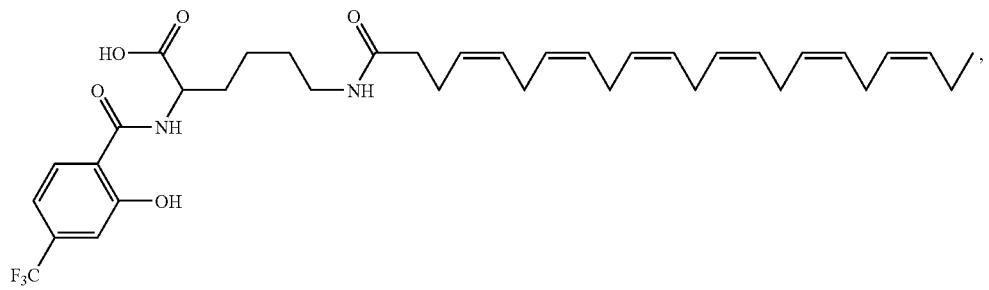
I-45
I-46
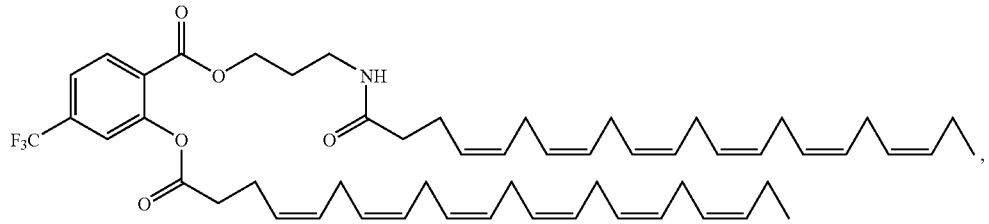
I-47
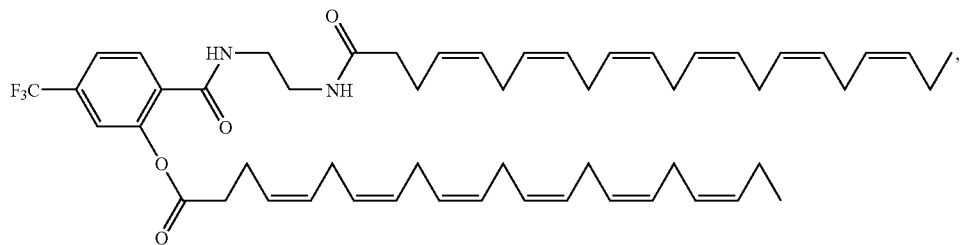
I-48
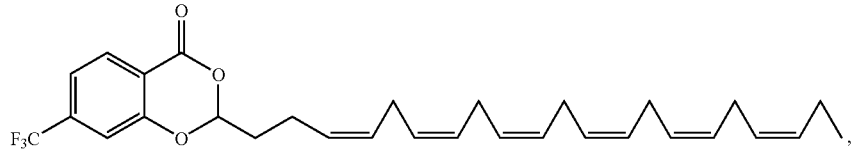
I-49
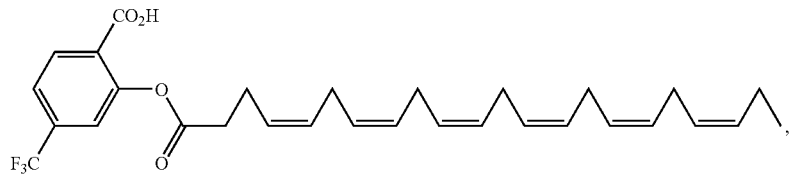
I-50

-continued
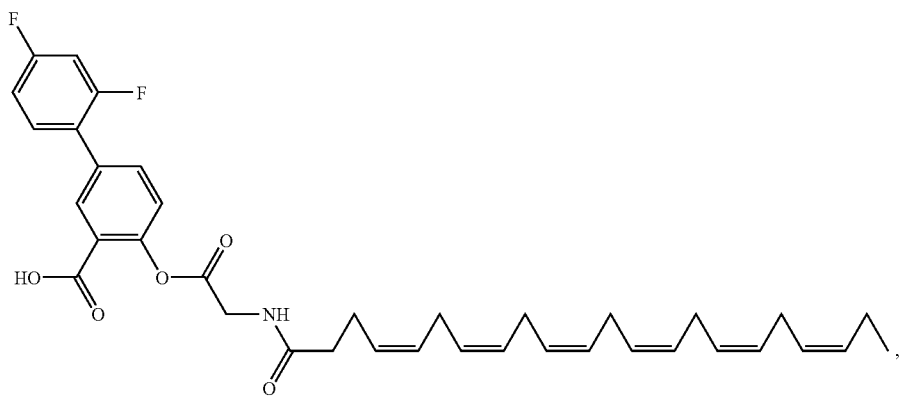
I-51
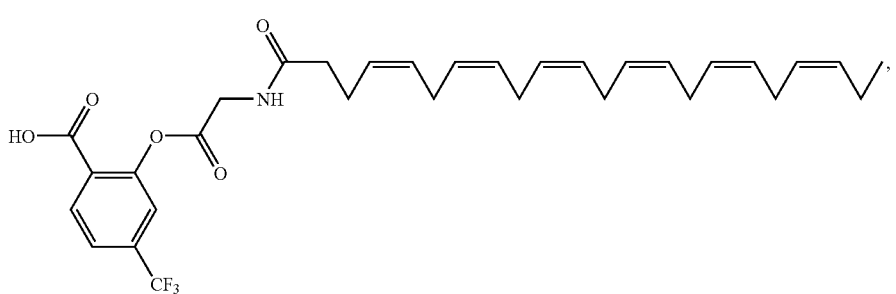
I-52
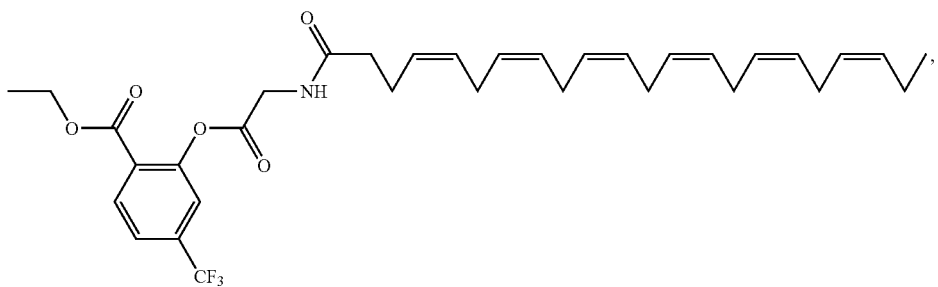
I-53
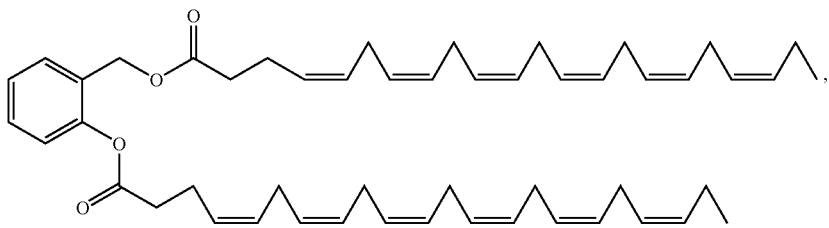
Ie-1
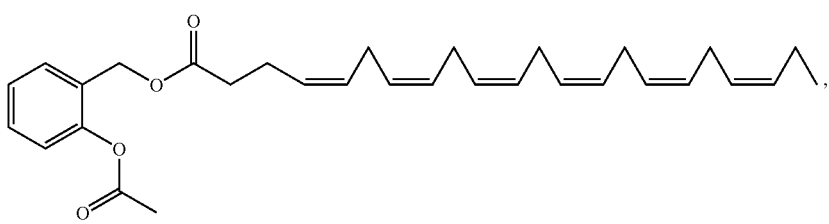
Ie-2
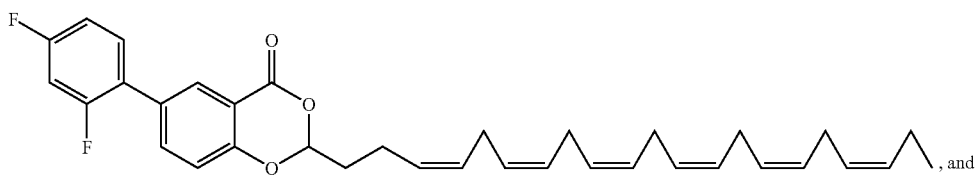
, and
IVe-1

VIe-1

In a further aspect, compounds of the Formula Ia are described:

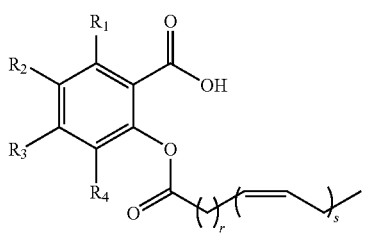

Formula Ia and pharmaceutically acceptable salts, hydrates, solvates, prodrugs, enantiomers, and stereoisomers thereof;

wherein $R_1, R_2, R_3, R_4, R_5, R_6$, r, and s are as defined above for Formula Ia.

In some embodiments, $R_2$ or $R_3$ is Cl or F.

In some embodiments, $R_2$ is difluorophenyl.

In other embodiments, $R_3$ is trifluoromethyl.

In some embodiments, r is 2, and s is 6.

In some embodiments, r is 3, and s is 5.

In other illustrative embodiments, compounds of Formula Ia are as set forth below:

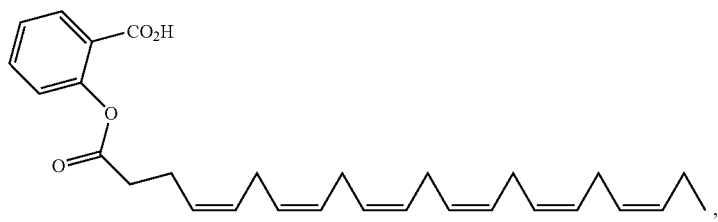

Ia-1

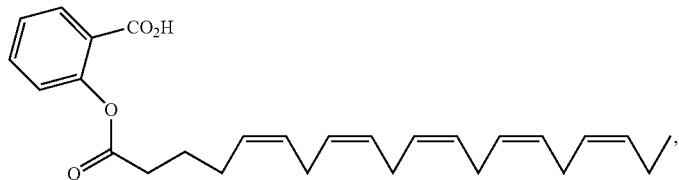

Ia-2

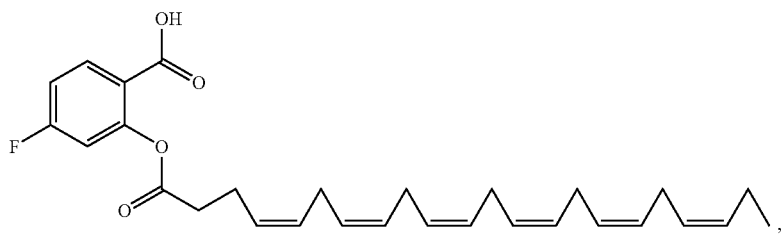

Ia-3

Ia-4

Ia-5
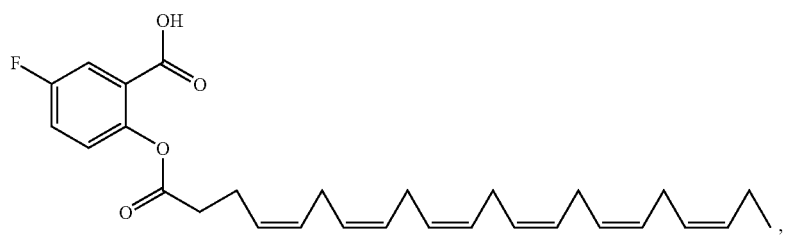
Ia-6
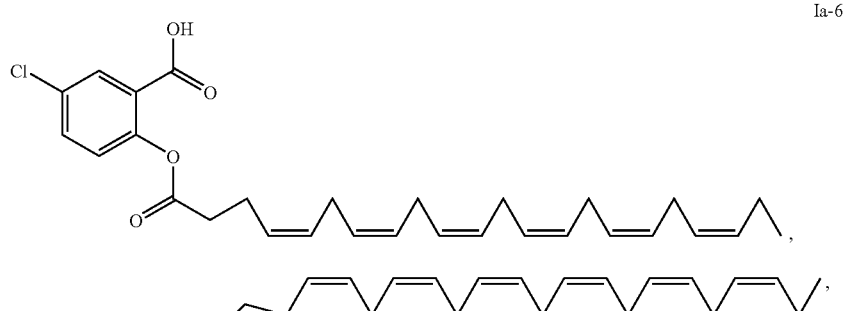
IVa-1
IVa-2
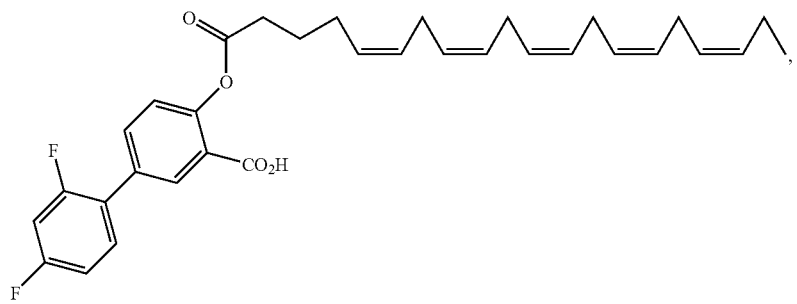
IVc-1
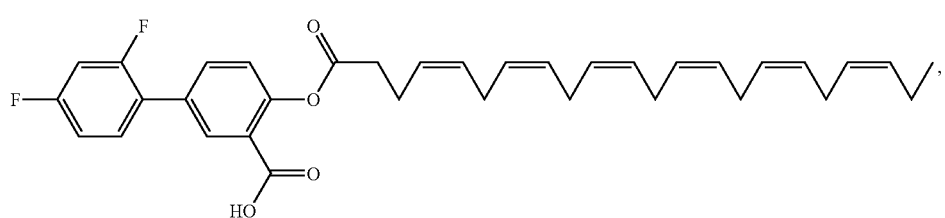
VIa-1
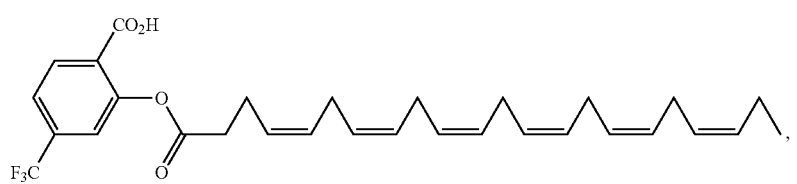

VIa-2

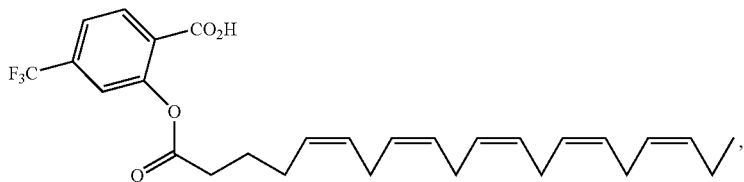

VIc-2

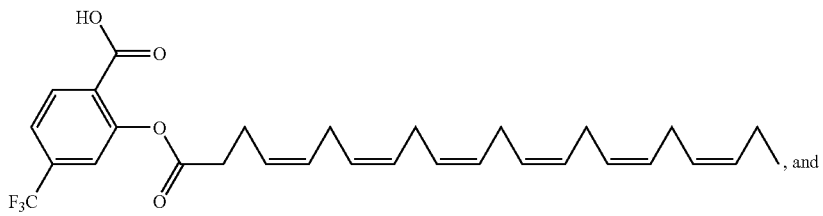
, and

VIg-2

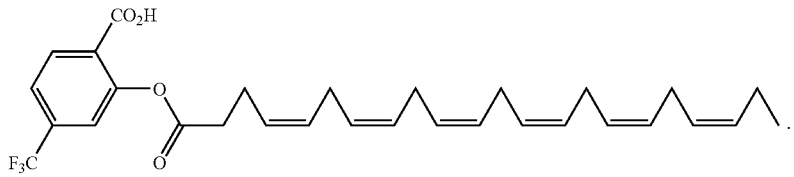
.

Described herein are compounds of the Formula Ib:

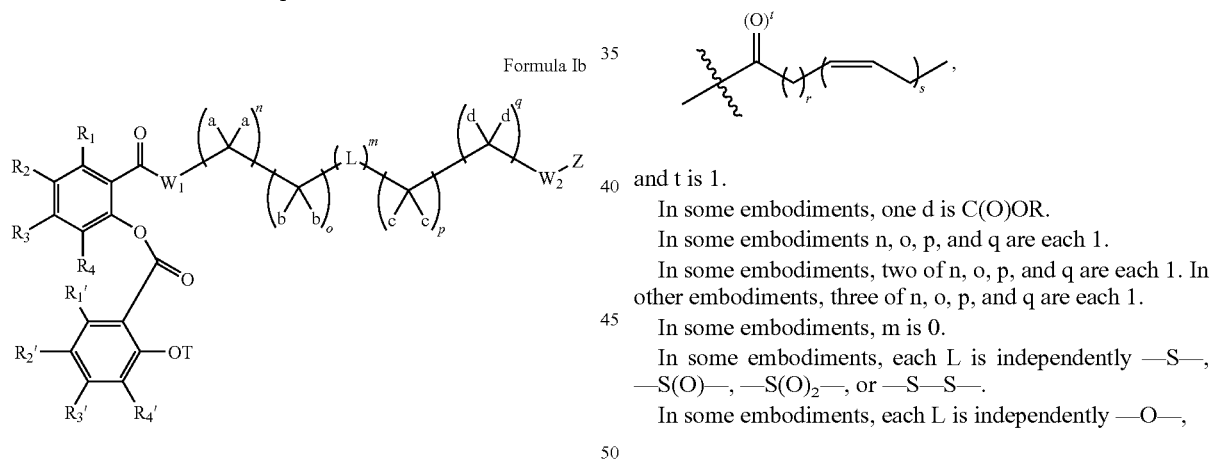

Formula Ib and pharmaceutically acceptable salts, hydrates, solvates, prodrugs, enantiomers, and stereoisomers thereof;
wherein
$R_1, R_2, R_3, R_4, R_7, R_8, R_1', R_2', R_3', R_4', R, L, W_1, W_2$, a, c, b, d, e, g, h, m, n, o, p, q, Z, r, s, t, and T are as defined above for the compounds of Formula Ib.

In some embodiments, $R_2$ or $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, or C(O)OR.

In some embodiments, one b is O—Z, Z is $$\begin{array}{c}(O)^t\\ \vphantom{X}\\ \end{array}$$

and t is 1.

In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —S(O)$_2$—, or —S—S—.
In some embodiments, each L is independently —O—, , or

.

In some embodiments, each L is independently

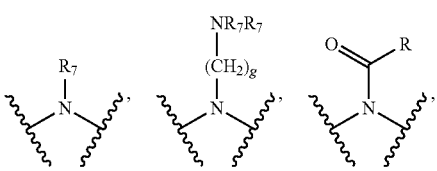

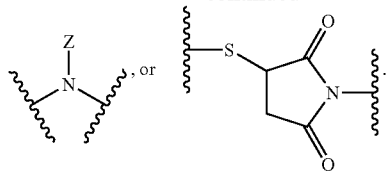
In some embodiments, each L is independently
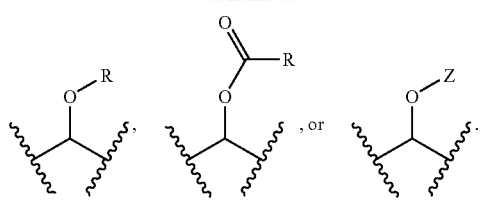
In some embodiments, each L is independently
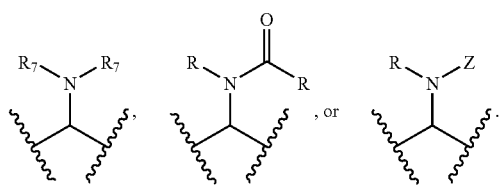
In some embodiments, $R_8$ is e.
In some embodiments, t is 1.
In some embodiments, T is H.
In some embodiments, T is C(O)CH$_3$.
In some embodiments, T is Z.
In other illustrative embodiments, compounds of Formula Ib are as set forth below:
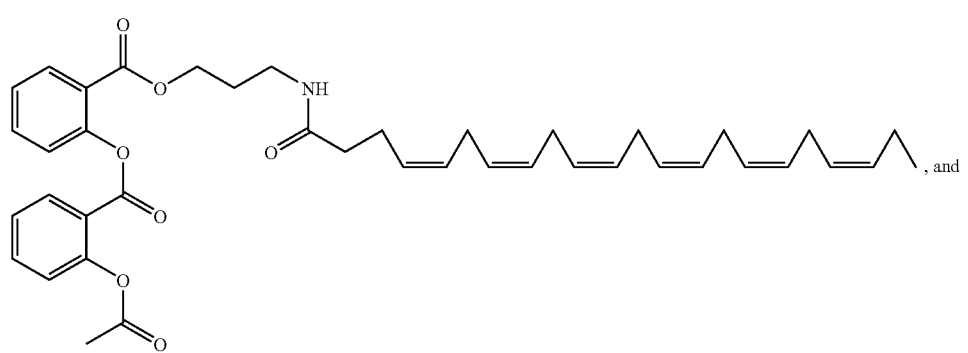
Ib-1
, and -continued Ib-2

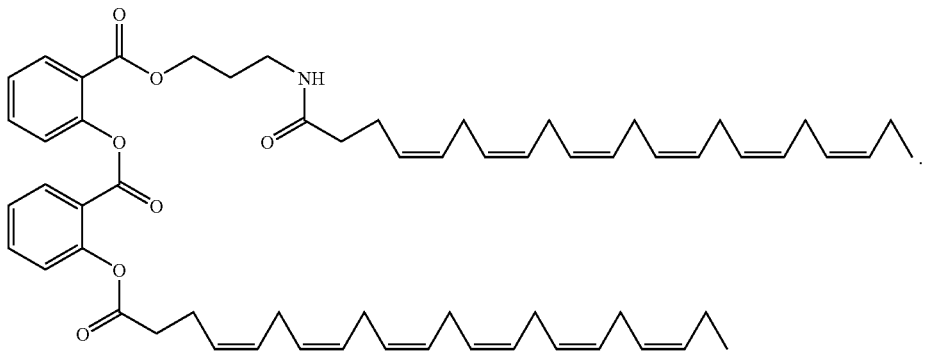

In another aspect, compounds of the Formula Ic are described:

Formula Ic

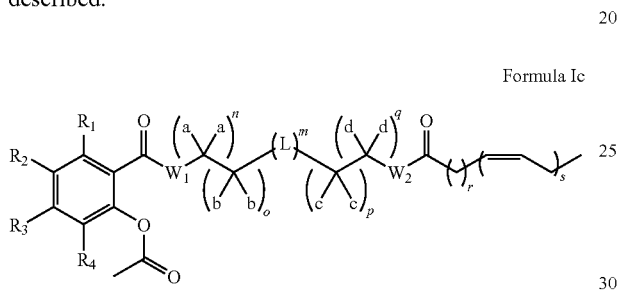

and pharmaceutically acceptable salts, hydrates, solvates, prodrugs, enantiomers, and stereoisomers thereof;

wherein $R_1$, $R_2$, $R_3$, $R_4$, $R_7$, $R_8$, R, $W_1$, $W_2$, L, a, c, b, d, e, g, h, m, n, o, p, q, Z, r, s, and t are as defined above for the compounds of the Formula Ic.

In some embodiments, $R_2$ or $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, —$OCH_2CH_3$, or C(O)OR.

In some embodiments, one b is O—Z, Z is

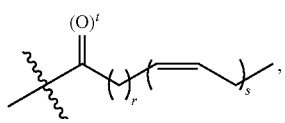

and t is 1.

In some embodiments, one d is C(O)OR.

In some embodiments, n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —$S(O)_2$—, or —S—S—.

In some embodiments, each L is independently —O—,

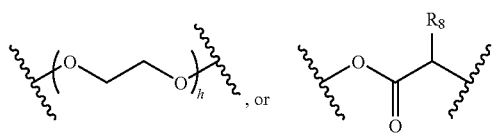

In some embodiments, each L is independently

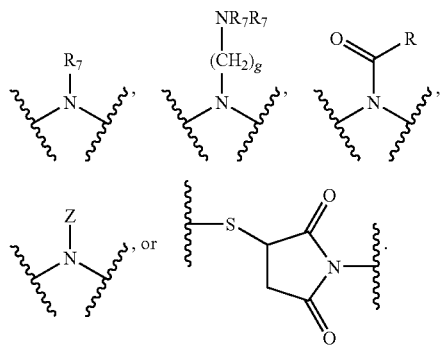

In some embodiments, each L is independently

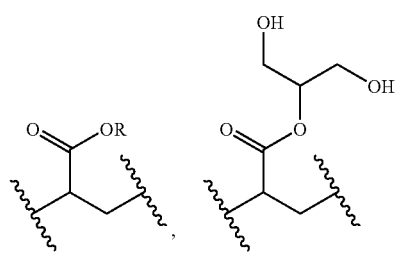

-continued
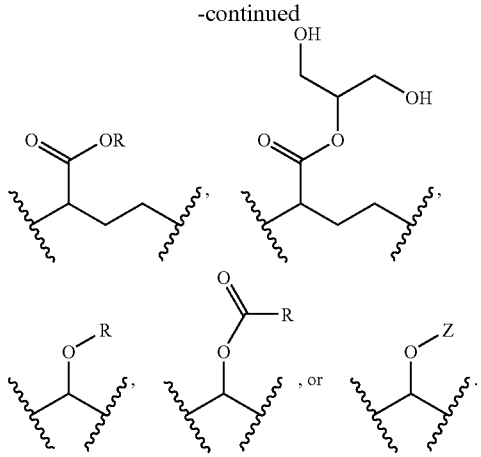
In some embodiments, each L is independently
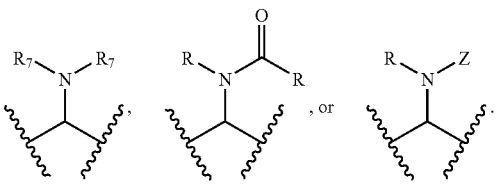
In some embodiments, $R_8$ is e.
In some embodiments, t is 1.
In some embodiments, r is 2, and s is 6.
In some embodiments, r is 3, and s is 5.
In other illustrative embodiments, compounds of Formula Ic are as set forth below:
Ic-1
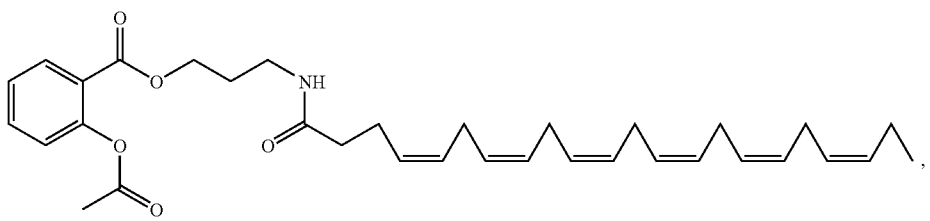
Ic-2
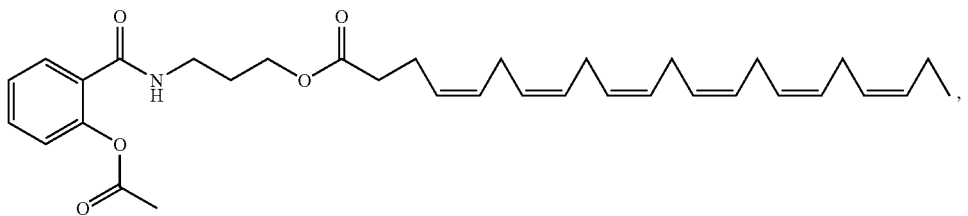
Ic-3
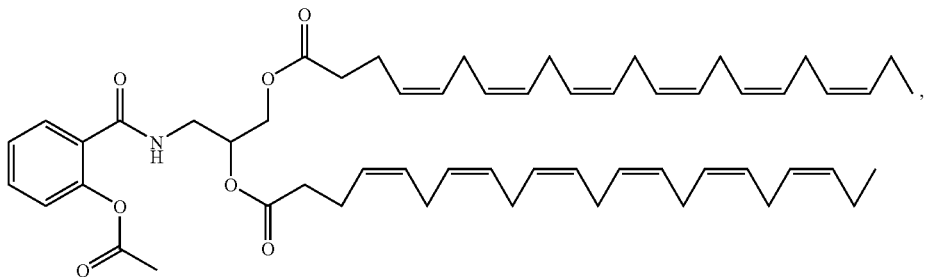
Ic-4
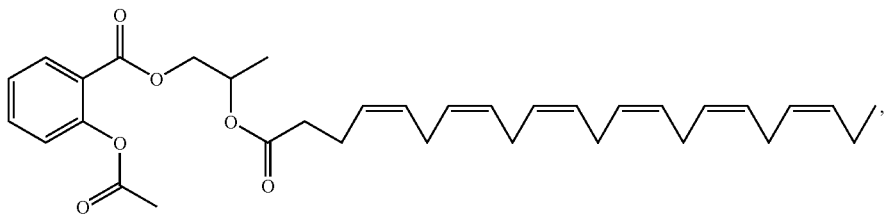

-continued
Ic-5
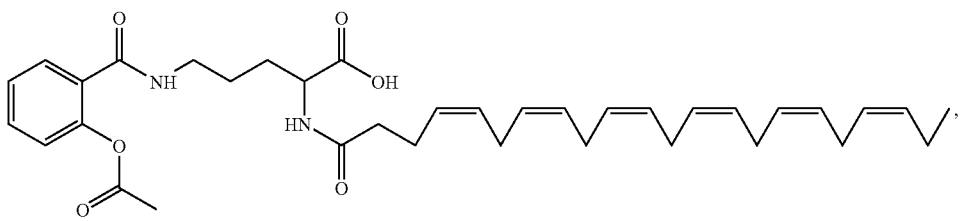
Ic-6
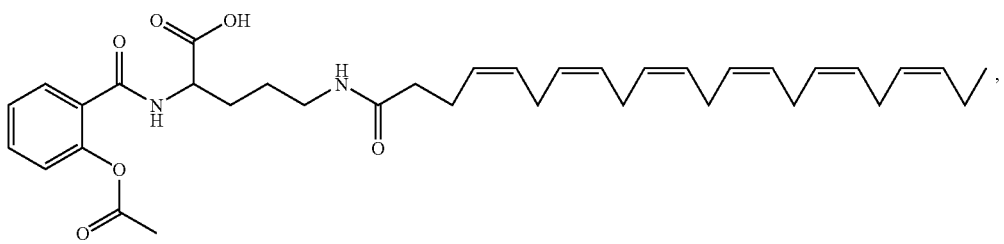
Ic-7
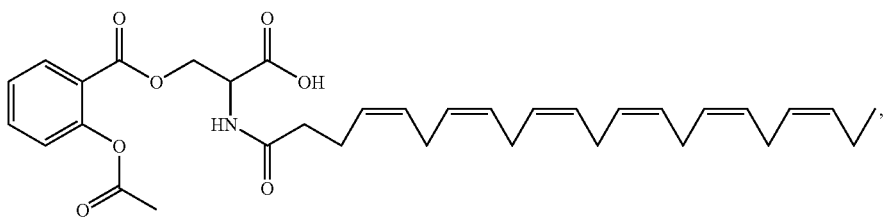
Ic-8
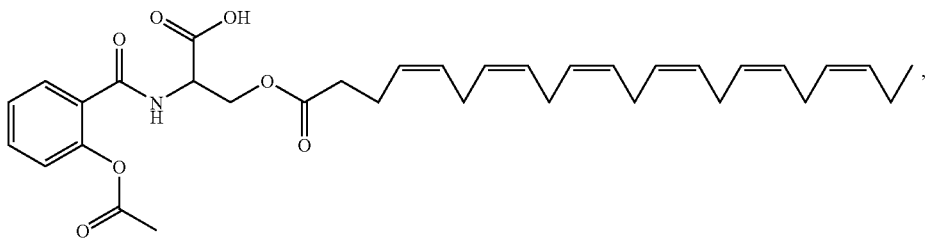
Ic-9
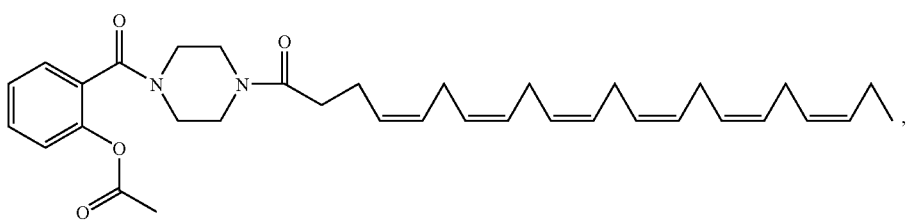
Ic-11
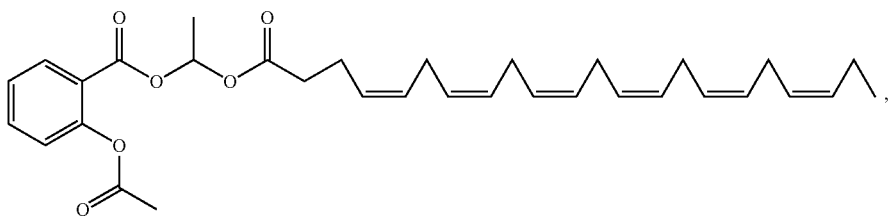
Ic-12

-continued
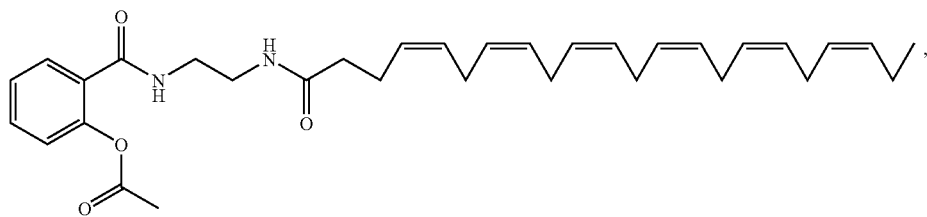
Ic-13
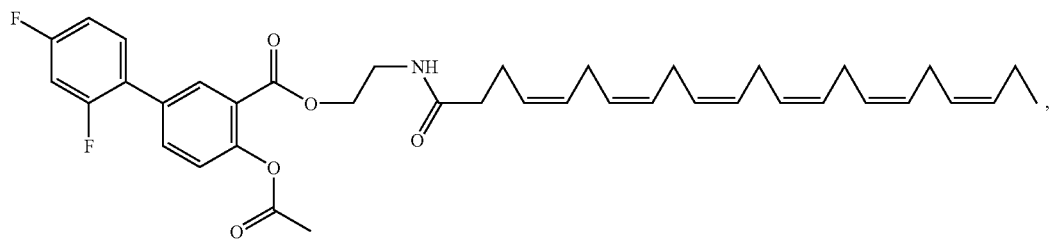
IVb-1
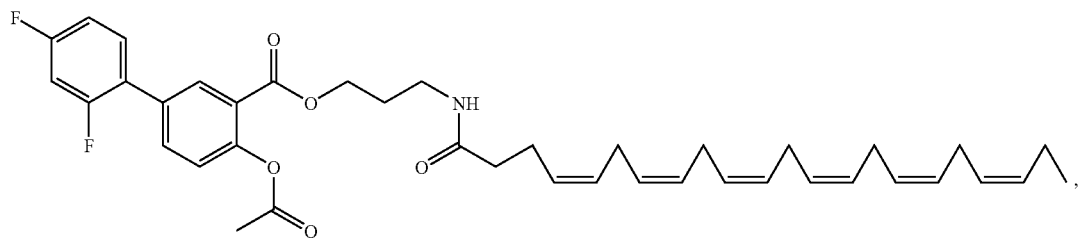
IVb-2
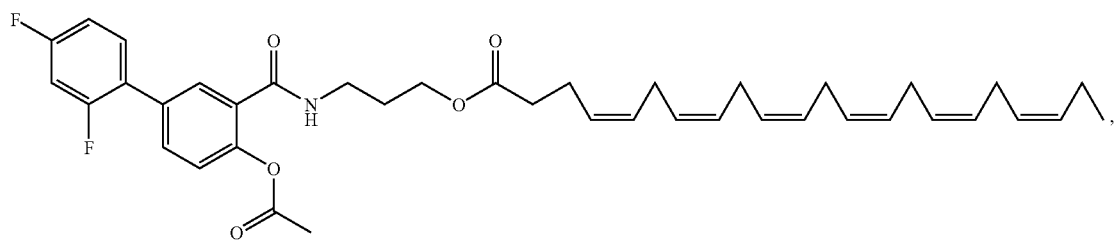
IVb-3
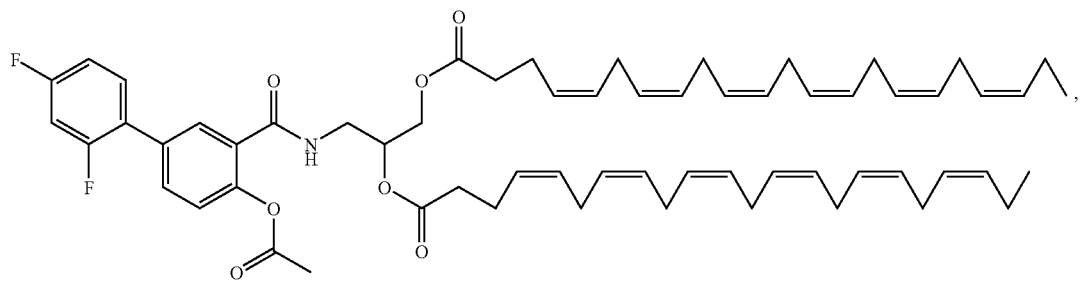
IVb-4
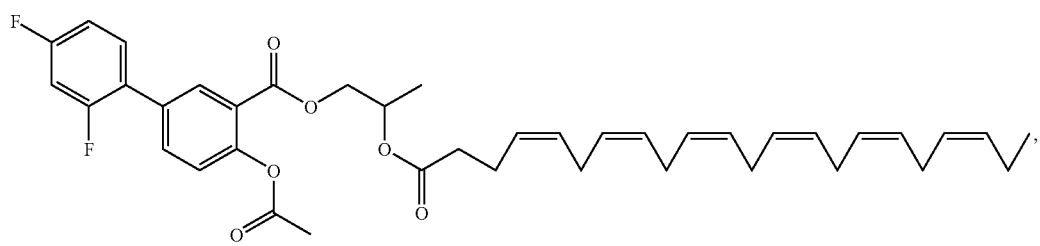
IVb-5

-continued
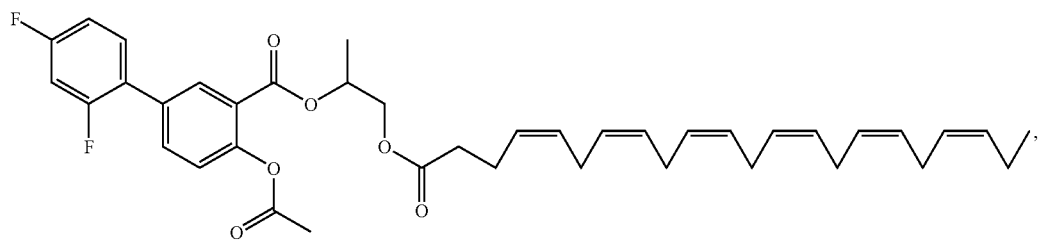
IVb-6
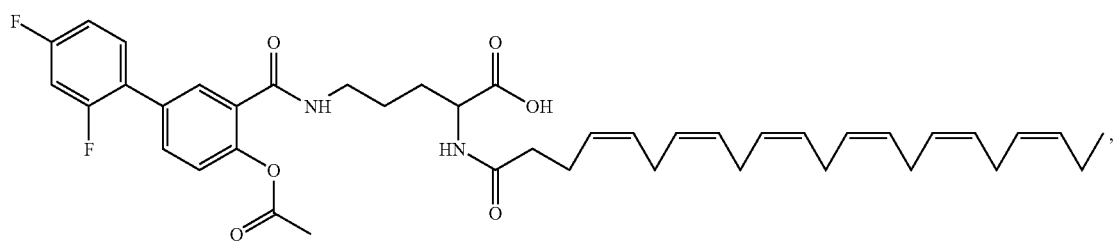
IVb-7
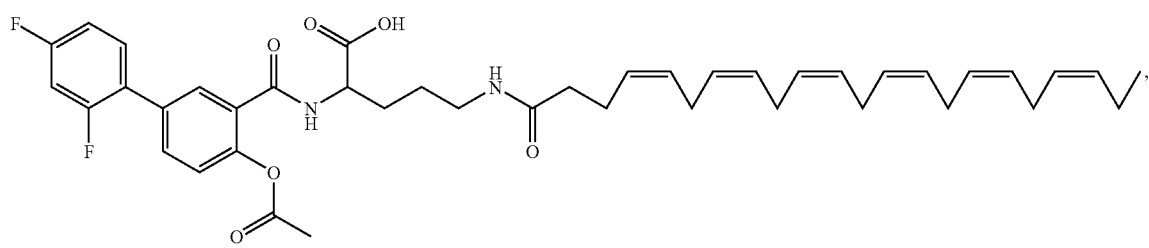
IVb-8
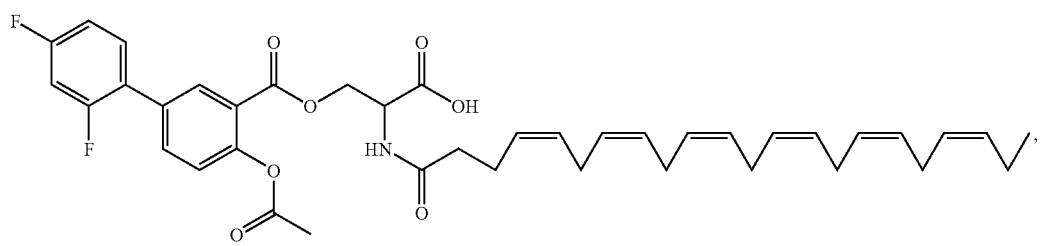
IVb-9
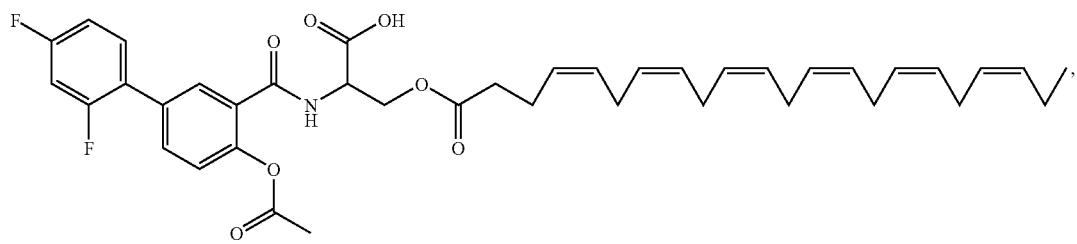
IVb-10
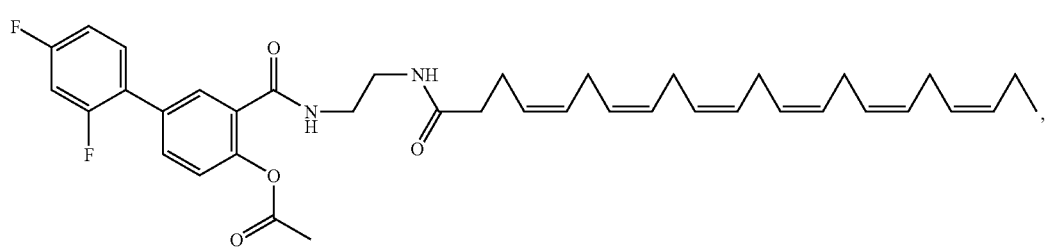
IVb-11

-continued
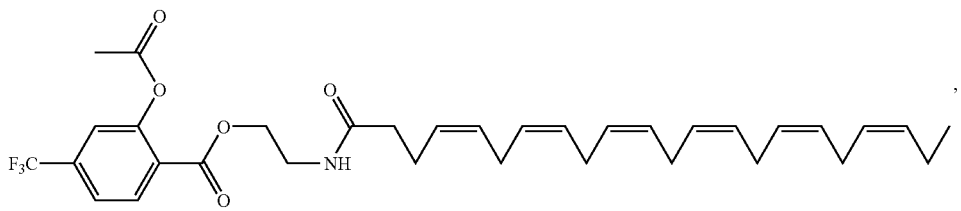
VIb-1
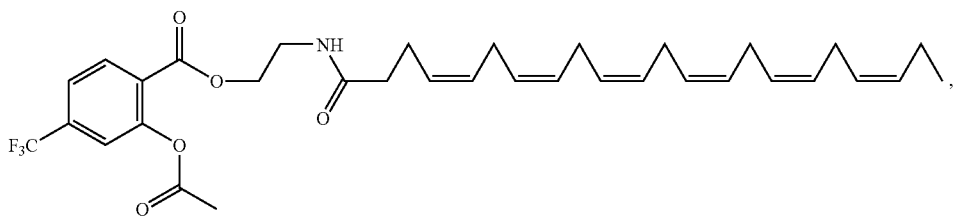
VIb-2
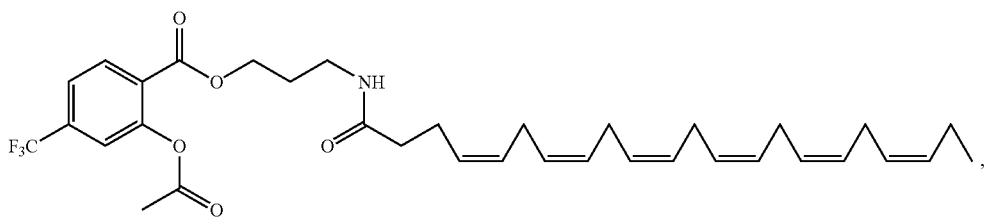
VIb-3
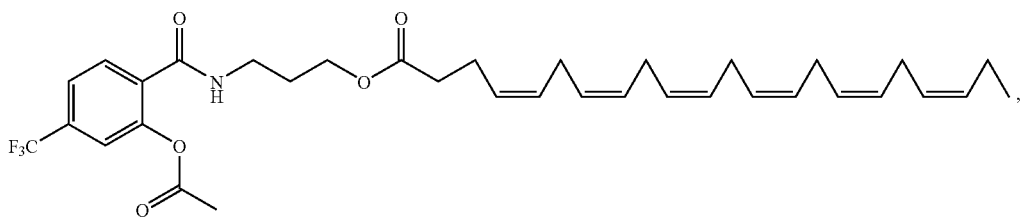
VIb-4
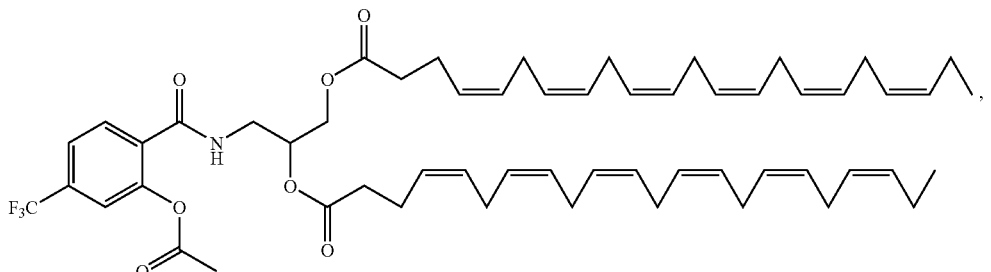
VIb-5
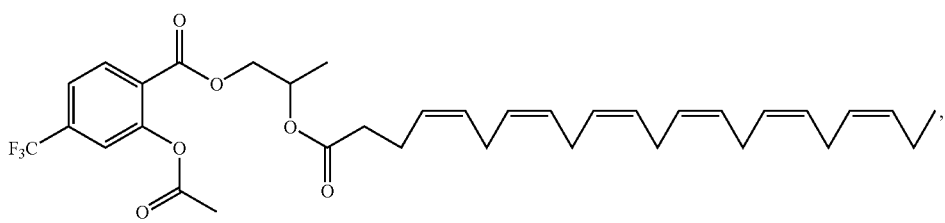
VIb-6
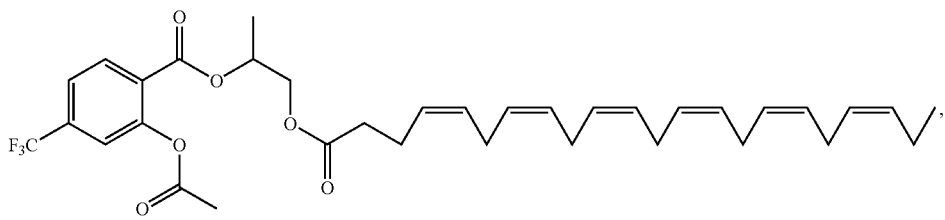
VIb-7

-continued

VIb-8
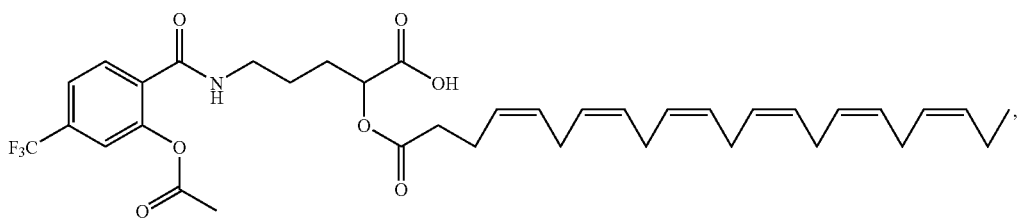

VIb-9
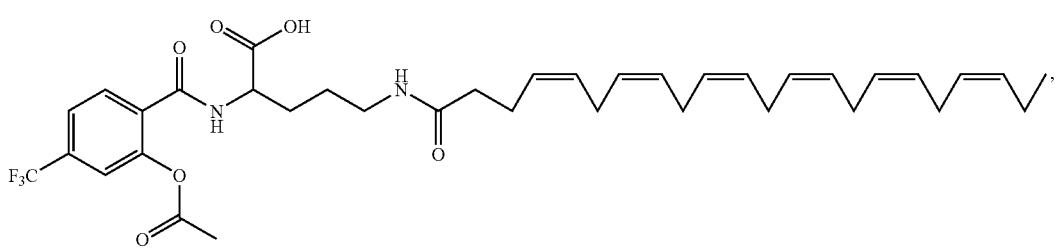

VIb-10
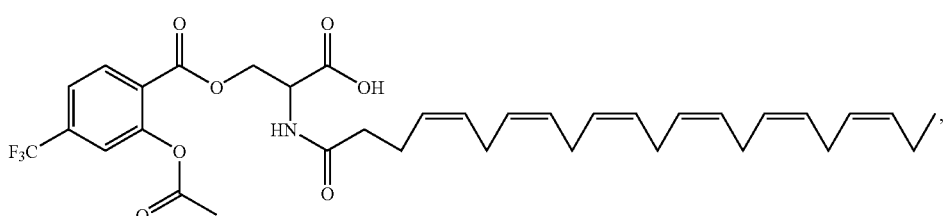

VIb-11
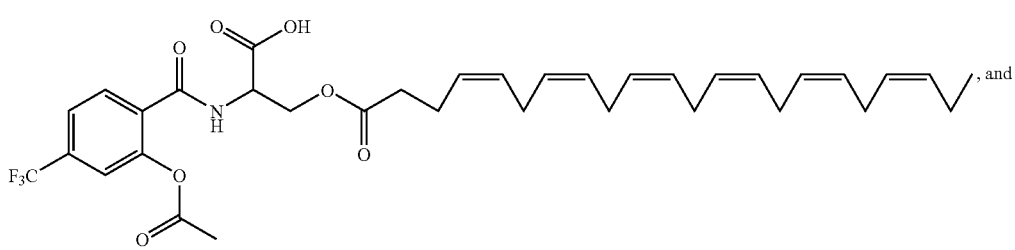

VIb-12
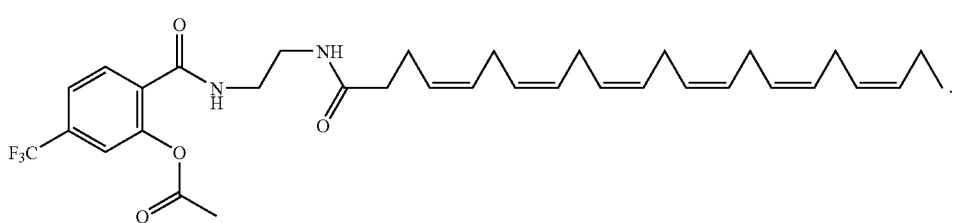

In another aspect, compounds of the Formula Id are described:

Formula Id
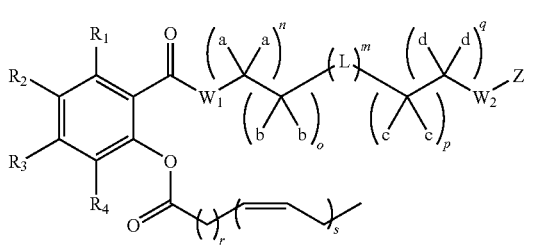

and pharmaceutically acceptable salts, hydrates, solvates, prodrugs, enantiomers, and stereoisomers thereof;

wherein $R_1$, $R_2$, $R_3$, $R_4$, $R_7$, $R_8$, R, $W_1$, $W_2$, L, a, b, c, d, e, g, h, m, n, o, p, q, Z, r, s, and t are as defined above for the compounds of the Formula Id.

In some embodiments, $R_2$ or $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, —$OCH_2CH_3$, or C(O)OR.

In some embodiments, one b is O—Z, Z is

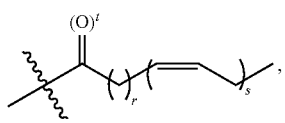

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

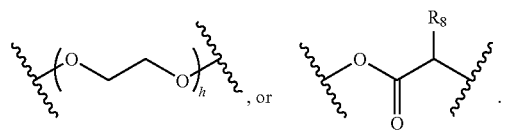

In some embodiments, each L is independently

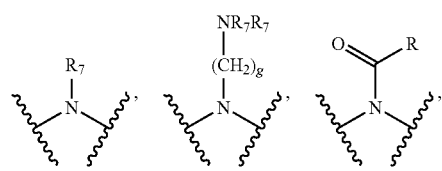

In some embodiments, each L is independently

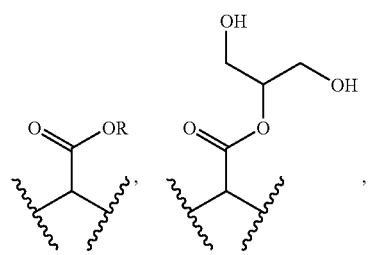

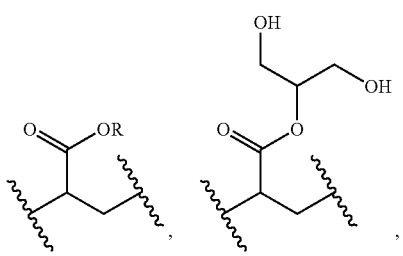

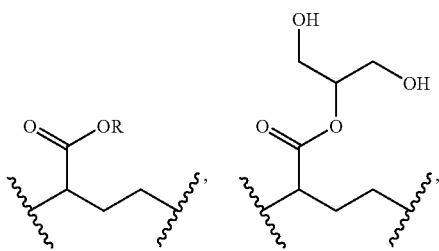

In some embodiments, each L is independently

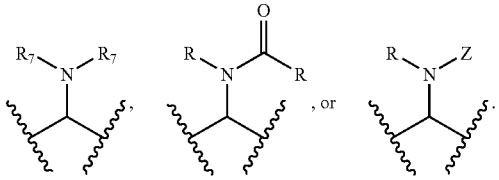

In some embodiments, $R_8$ is e.

In some embodiments, t is 1.

In some embodiments, r is 2, and s is 6.

In some embodiments, r is 3, and s is 5.

In other illustrative embodiments, compounds of Formula Id are as set forth below:

Id-1

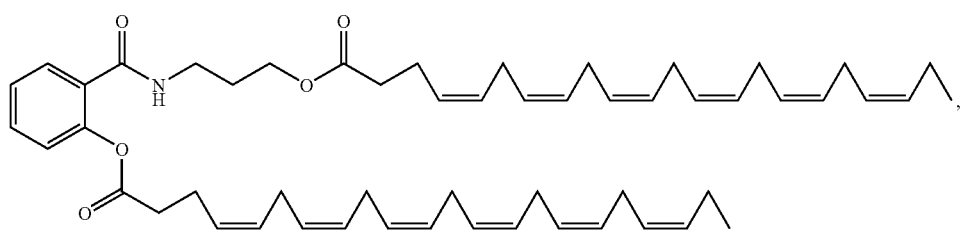

-continued
Id-2
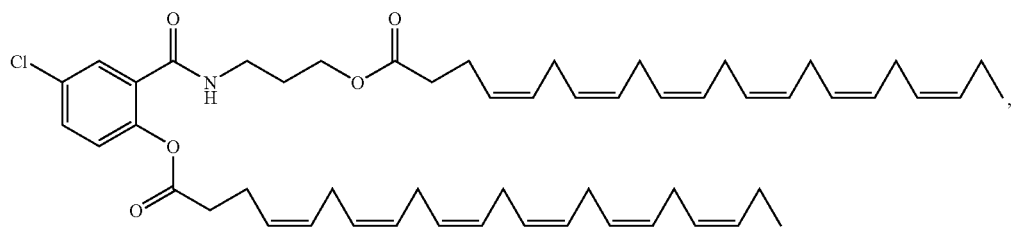
Id-3
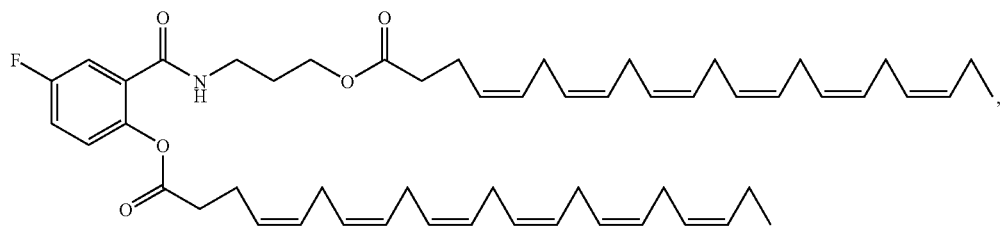
Id-4
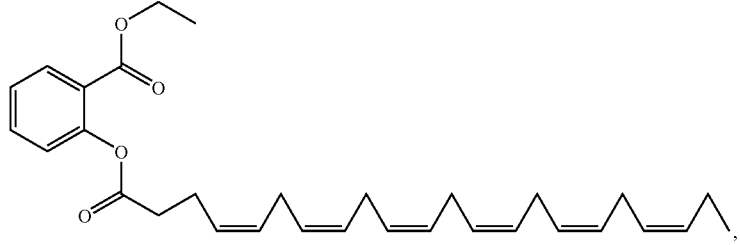
Id-5
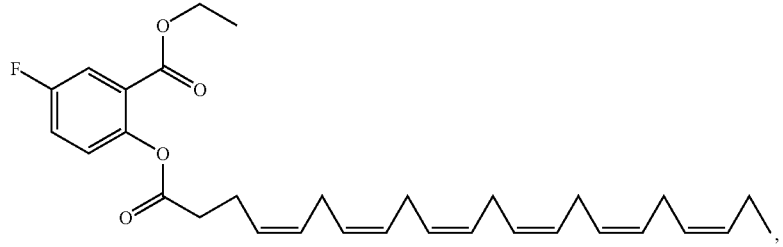
Id-6
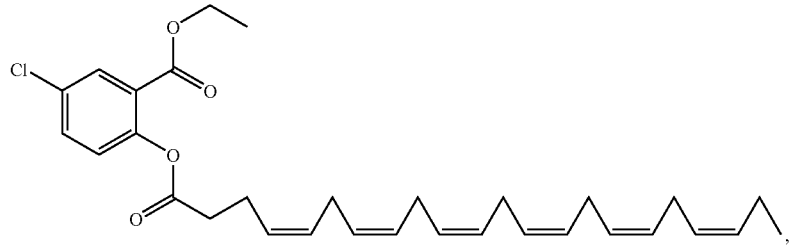
IVc-2
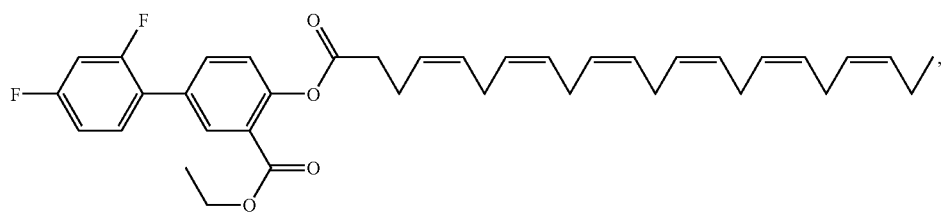
IVc-2
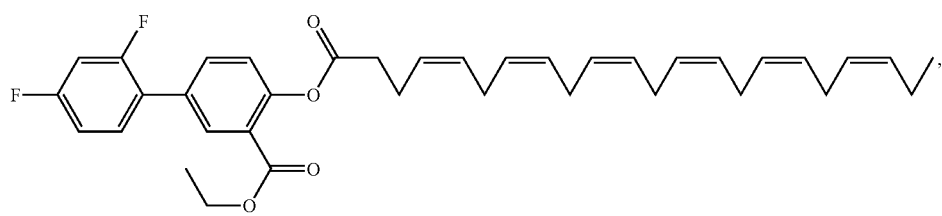

-continued
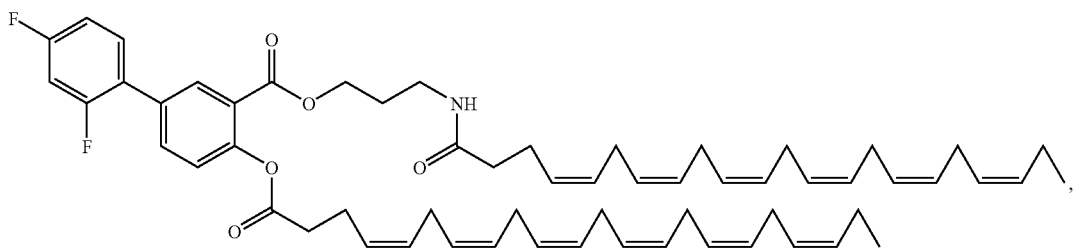
IVc-6
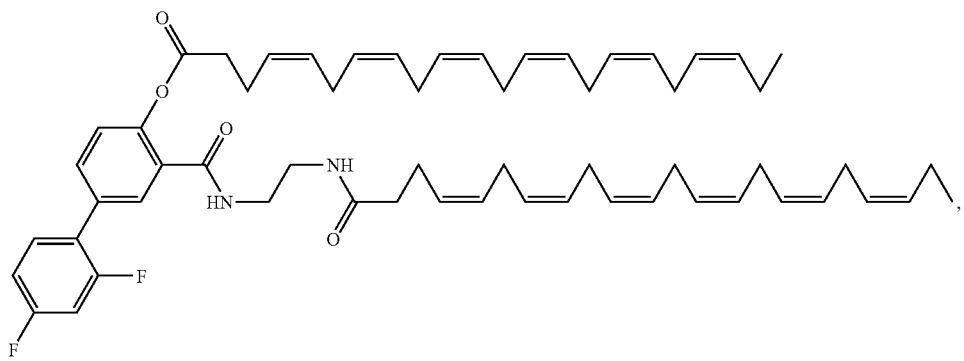
IVc-7
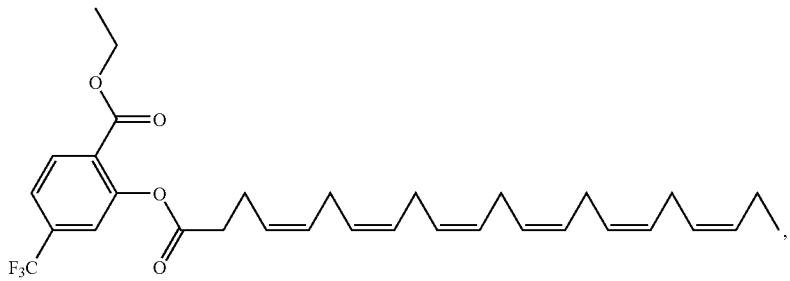
VIc-3
VIc-6
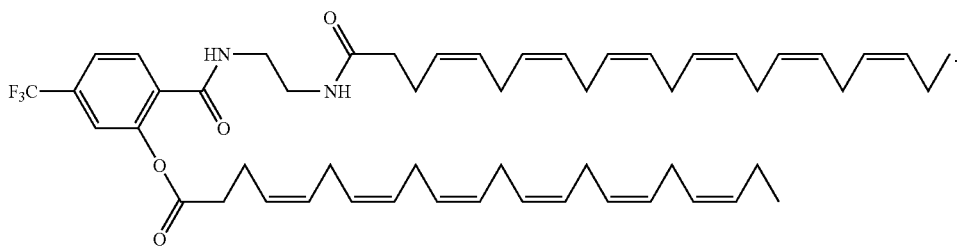
VIc-7

In another aspect, compounds of the Formula If are described:

Formula If

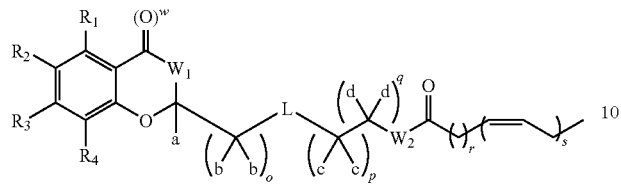

and pharmaceutically acceptable salts, hydrates, solvates, prodrugs, enantiomers, and stereoisomers thereof;
wherein
$R_1$, $R_2$, $R_3$, $R_4$, $R_7$, $R_8$, R, $W_1$, $W_2$, L, a, b, c, d, e, g, h, Z, m, o, p, q, r, s, t, and w are as defined above for the compounds of the Formula If.

In some embodiments, $R_2$ or $R_2$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, —$OCH_2CH_3$, or C(O)OR.

In some embodiments, one b is O—Z, Z is

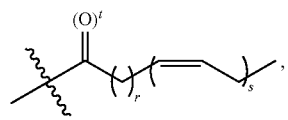

and t is 1.

In some embodiments, one d is C(O)OR.

In some embodiments o, p, and q are each 1.

In some embodiments, one of o, p, and q is 1. In other embodiments, two of o, p, and q are each 1.

In some embodiments, m is 0.

In some embodiments, each L is independently —S—, —S(O)—, —S(O)$_2$—, or —S—S—.

In some embodiments, each L is independently —O—,

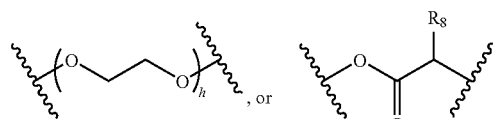

In some embodiments, each L is independently

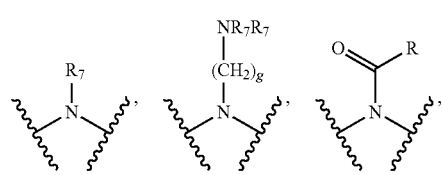

In some embodiments, each L is independently

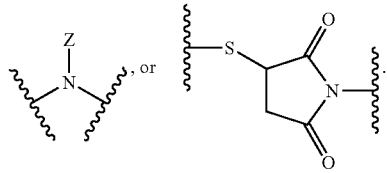

In some embodiments, each L is independently

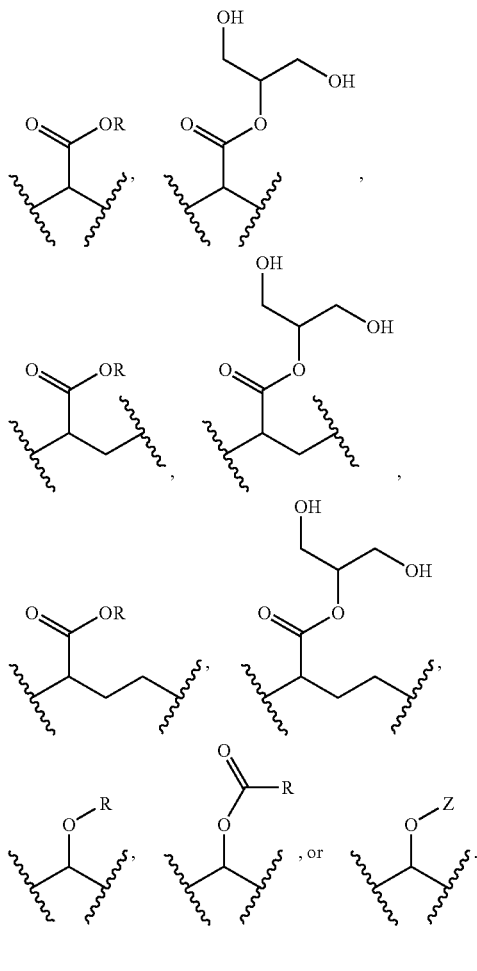

In some embodiments, each L is independently

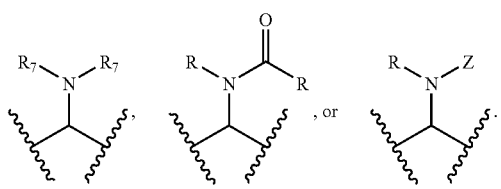

In some embodiments, $R_8$ is e.
In some embodiments, t is 1.
In some embodiments, w is 1.
In some embodiments, r is 2, and s is 6.
In some embodiments, r is 3, and s is 5.
In other illustrative embodiments, compounds of Formula If are as set forth below:

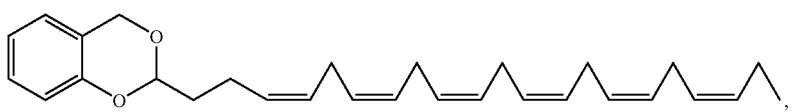, If-1

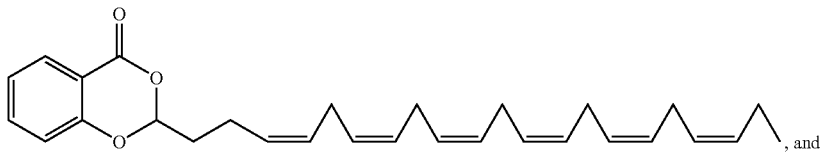, If-2, and

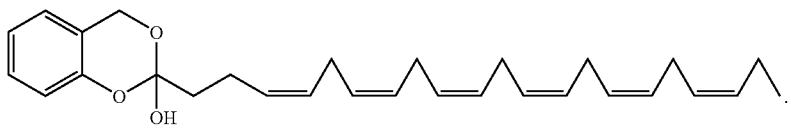, If-3.

In another aspect, compounds of the Formula Ih are described

Formula Ih

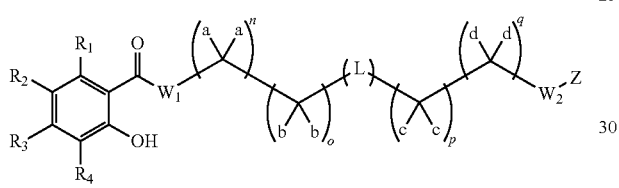

and pharmaceutically acceptable salts, hydrates, solvates, prodrugs, enantiomers, and stereoisomers thereof;
wherein
$R_1$, $R_2$, $R_3$, $R_4$, $R_7$, $R_8$, R, $W_1$, $W_2$, a, b, c, d, e, g, h, L, Z, m, n, o, p, q, r, s, and t, are as defined above for compounds of Formula Ih.

In some embodiments, $R_2$ or $R_2$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, —$OCH_2CH_3$, or C(O)OR.

In some embodiments, one b is O—Z, Z is

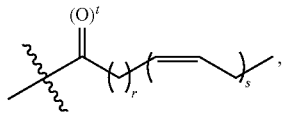

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —$S(O)_2$—, or —S—S—.

In some embodiments, each L is independently —O—,

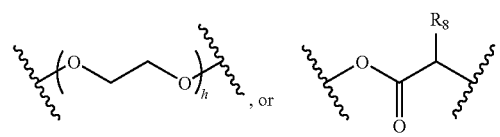, or .

In some embodiments, each L is independently

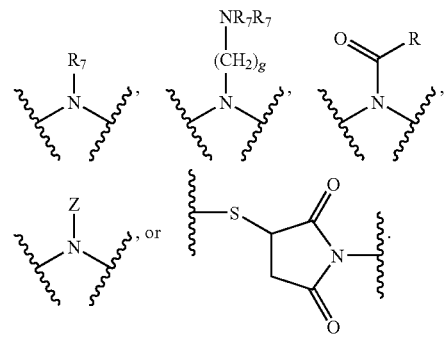

In some embodiments, each L is independently

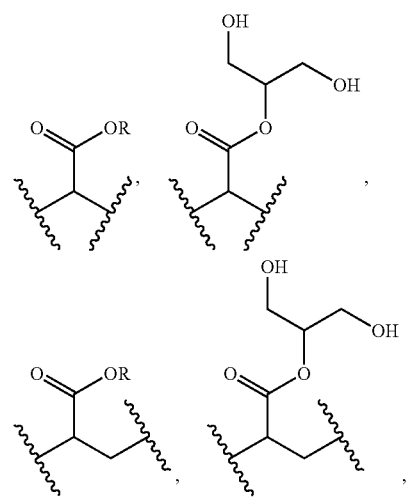

,

,

,

,

-continued

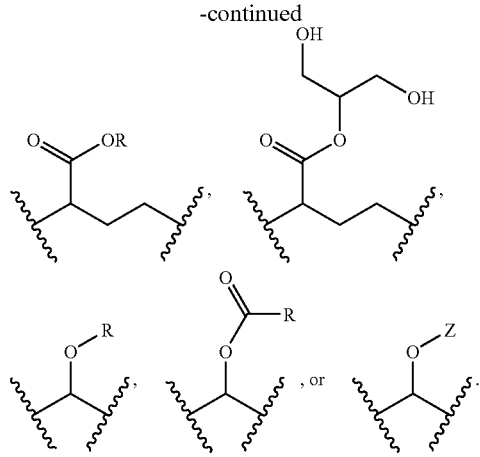

In some embodiments, each L is independently

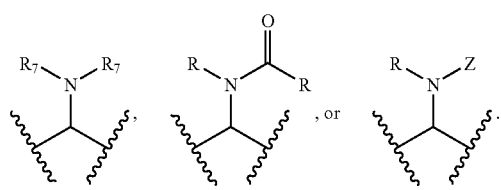

In some embodiments, $R_8$ is e.
In some embodiments, t is 1.
In some embodiments, each e is independently any one of the side chains of the naturally occurring amino acids. In other embodiments, e is H.

In some embodiments, r is 2, and s is 6.
In some embodiments, r is 3, and s is 5.
In some embodiments, the compounds have the formulas:

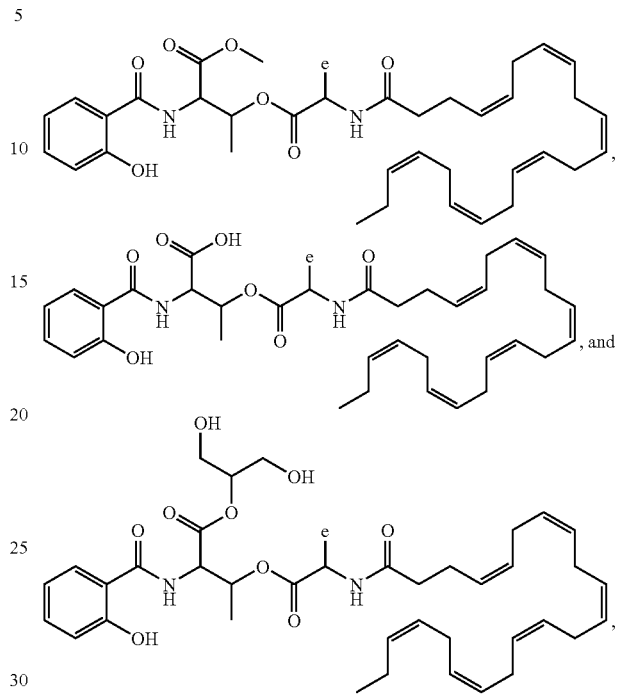

wherein e is as defined above for Formula Ih.

In other illustrative embodiments, compounds of Formula Ih areas set forth below:

Ih-1

Ih-2

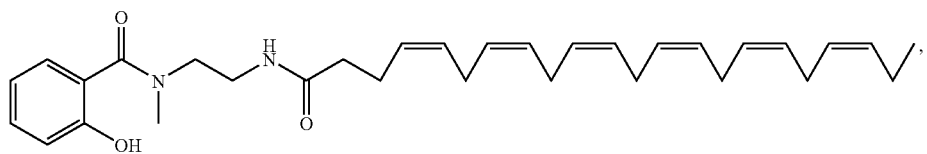
Ih-3

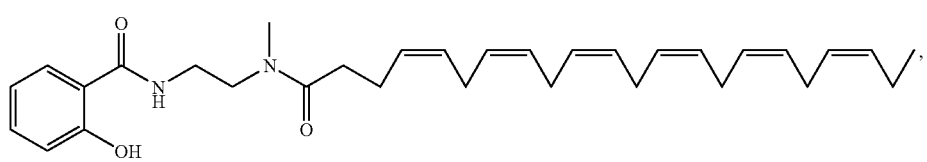
Ih-4

-continued
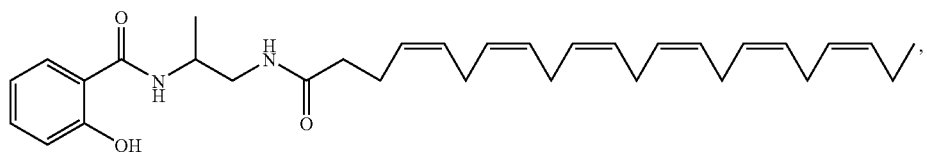
Ih-5
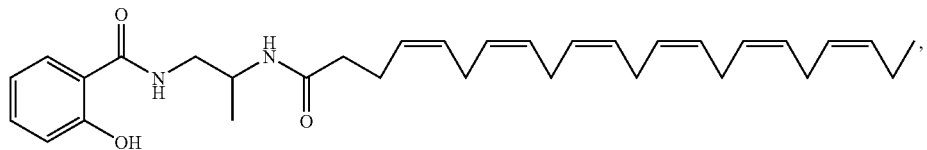
Ih-6
Ih-7
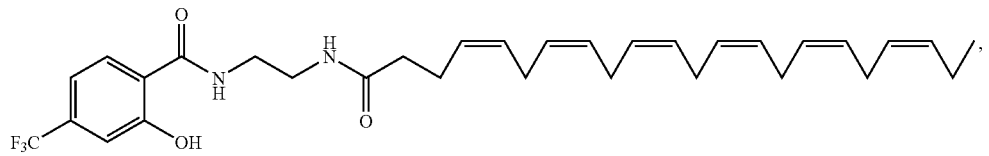
Ih-8
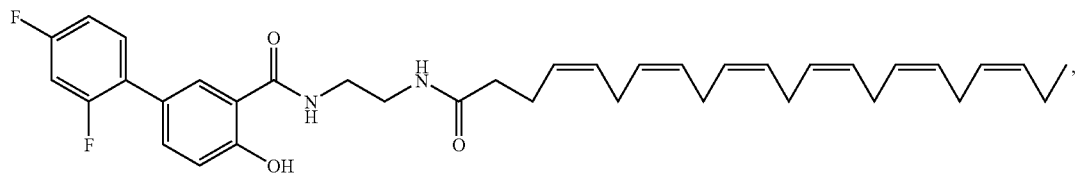
Ih-9
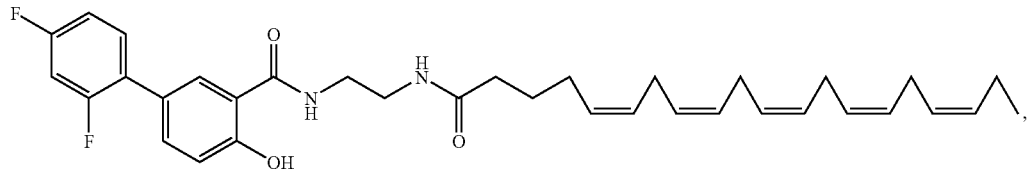
Ih-10
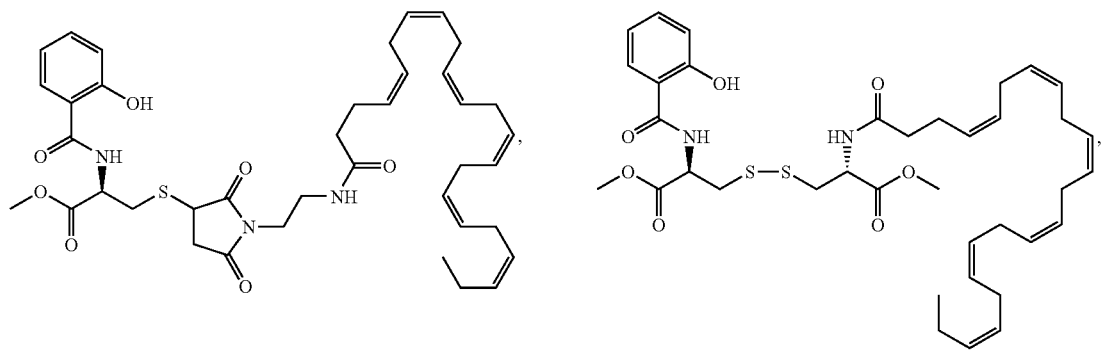
Ih-11                               Ih-12

-continued
Ih-13
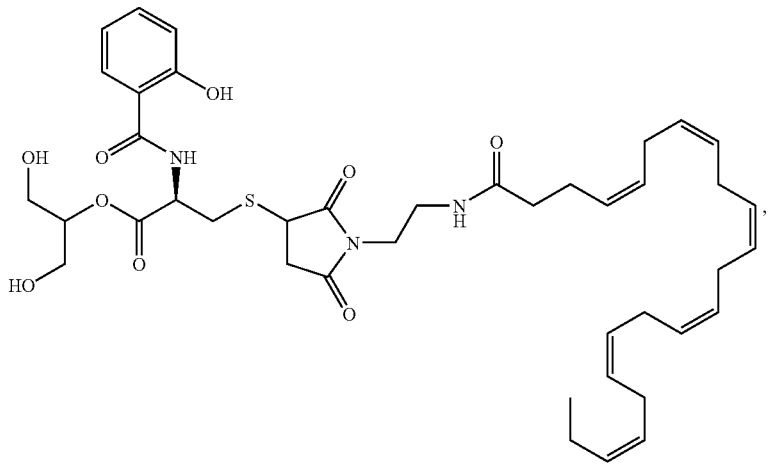
Ih-14
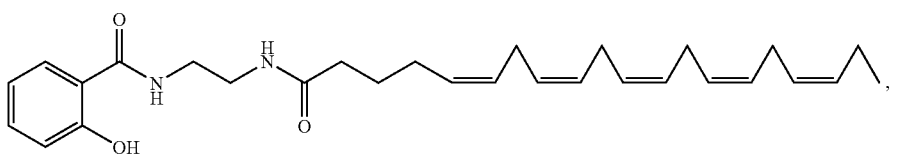
Ih-15
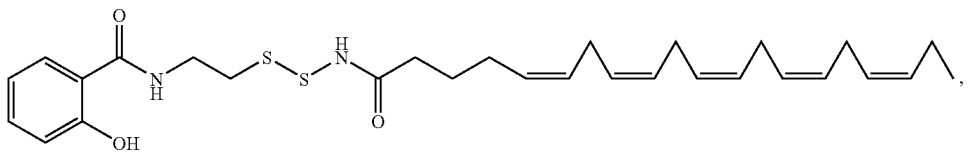
IVc-3
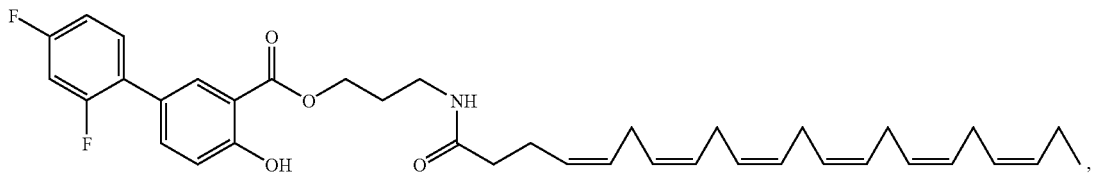
IVc-4
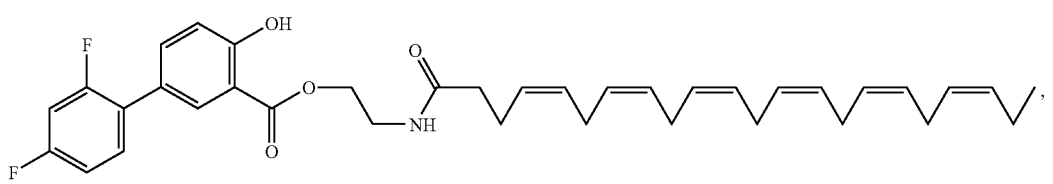
IVc-5
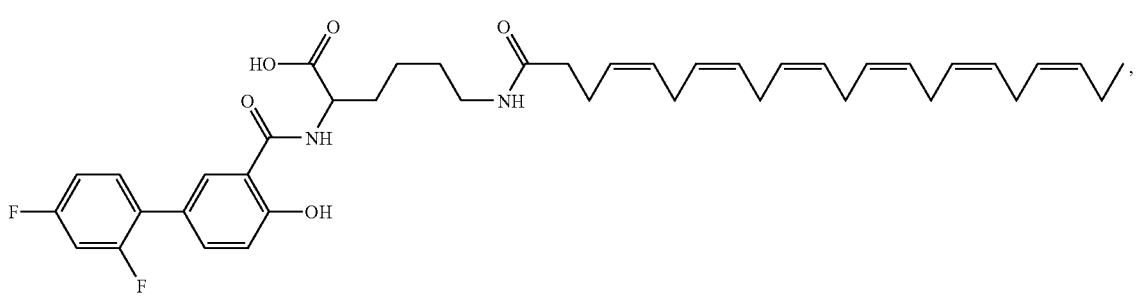
VIc-1

-continued

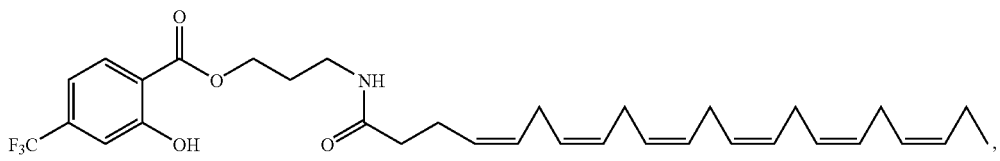
VIc-4

VIc-5

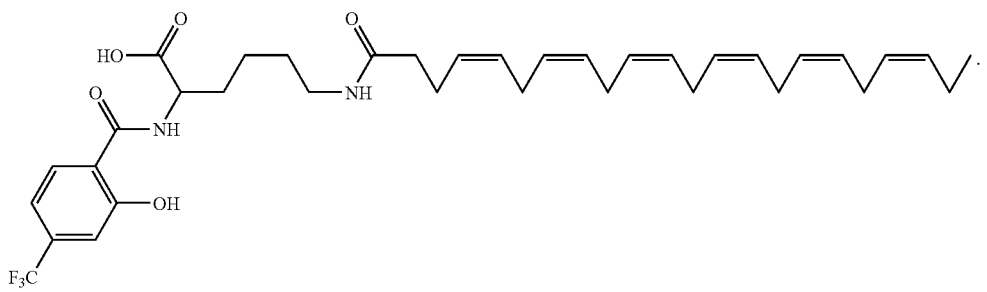
VIc-5'

In another aspect, compounds of the Formula Ii are described

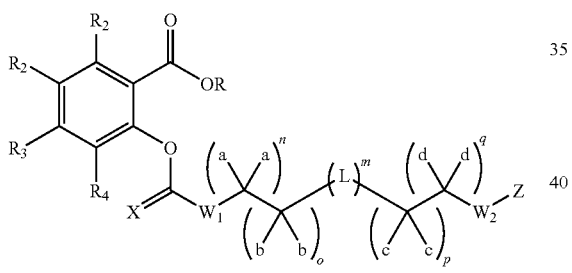
Formula Ii and pharmaceutically acceptable salts, hydrates, solvates, prodrugs, enantiomers, and stereoisomers thereof;
wherein
$R_1$, $R_2$, $R_3$, $R_4$, $R_7$, $R_8$, R, $W_1$, $W_2$, a, b, c, d, e, g, h, L, X, Z, m, n, o, p, q, r, s, and t, are as defined above for compounds of Formula II.

In some embodiments, $R_2$ or $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, each a and c is independently H, $CH_3$, —$OCH_3$, —$OCH_2CH_3$, or C(O)OR.
In some embodiments, one b is O—Z, Z is

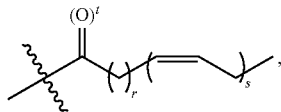

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —S(O)$_2$—, or —S—S—.
In some embodiments, each L is independently —O—,

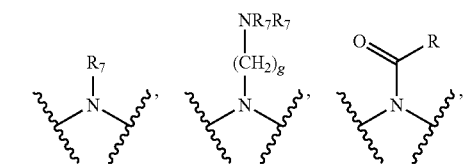

In some embodiments, each L is independently

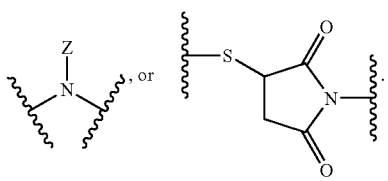

In some embodiments, each L is independently

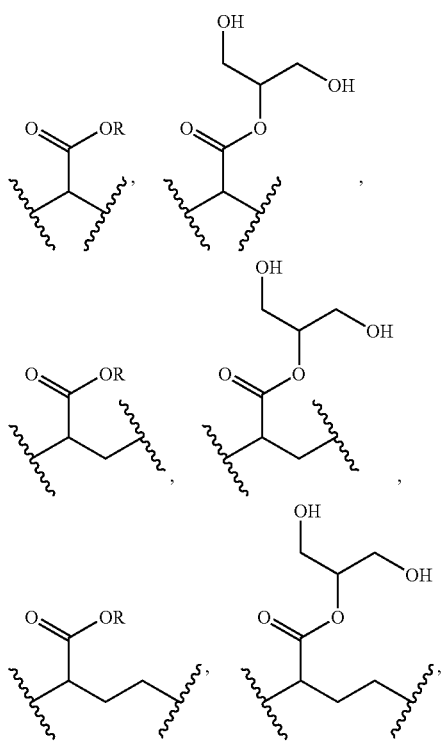

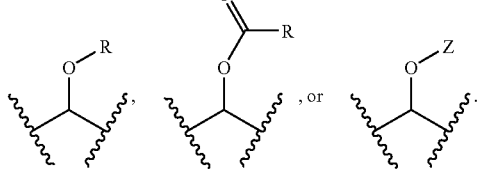

In some embodiments, each L is independently

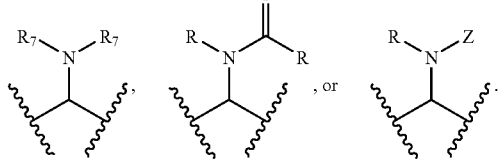

In some embodiments, $R_8$ is e.
In some embodiments, t is 1.
In some embodiments, X is S.
In some embodiments, each e is independently any one of the side chains of the naturally occurring amino acids. In other embodiments, e is H.
In some embodiments, r is 2, and s is 6.
In some embodiments, r is 3, and s is 5.
Illustrative compounds of Formula Ii include:

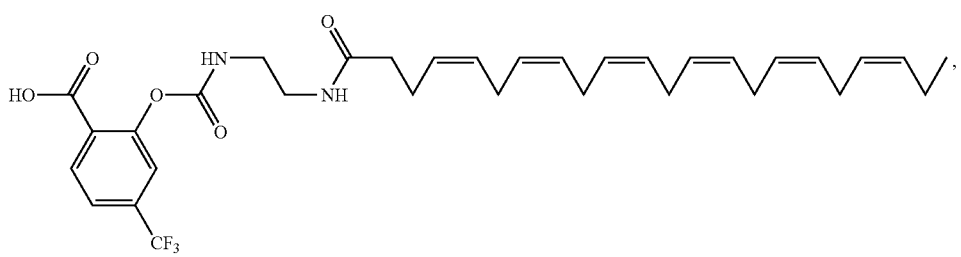

Ii-1

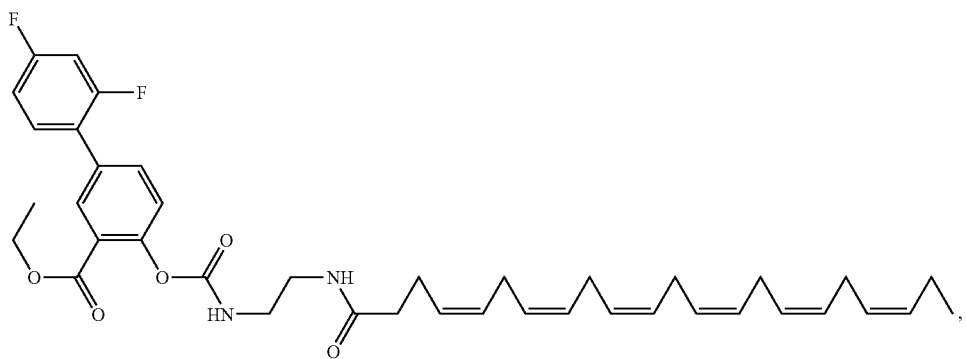

Ii-2

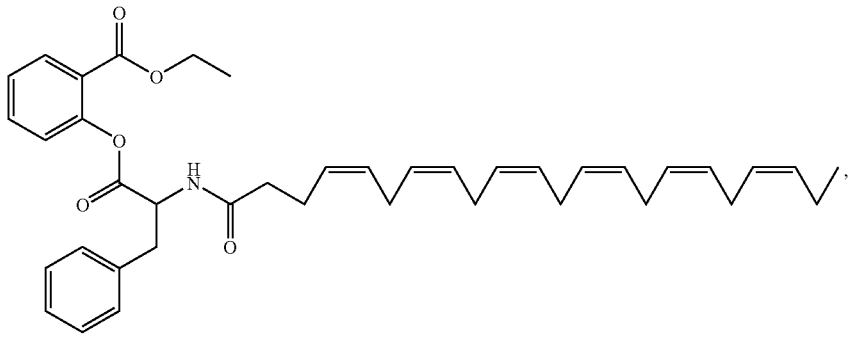

-continued
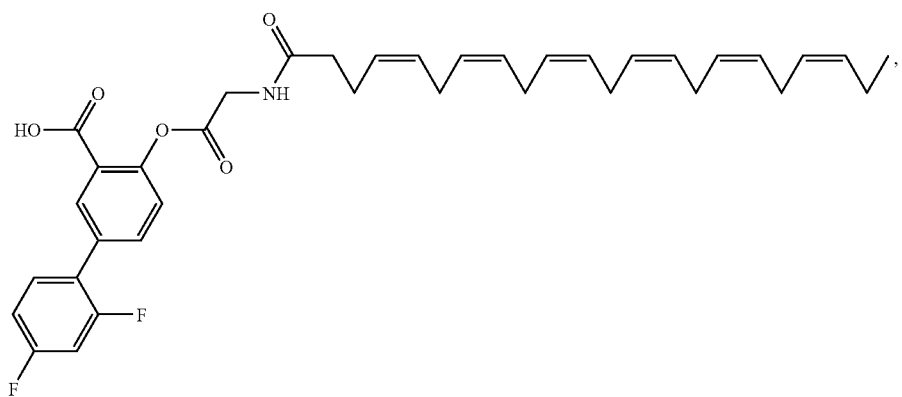
IVf-1
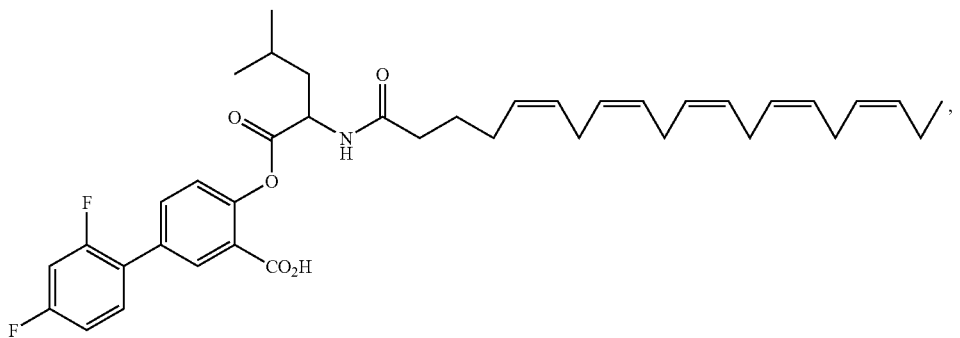
IVf-2
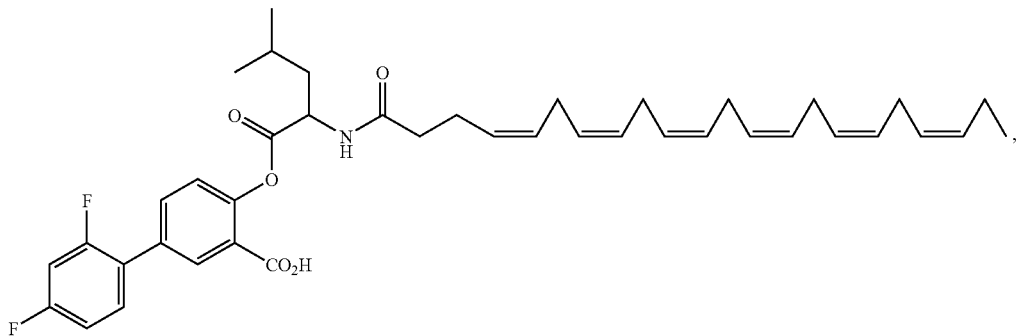
IVf-3
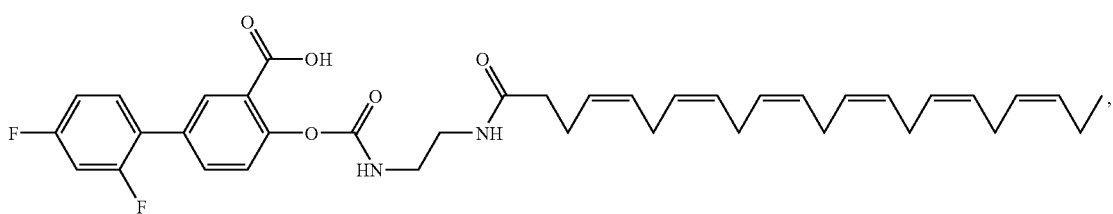
IVf-4

-continued
IVg-1
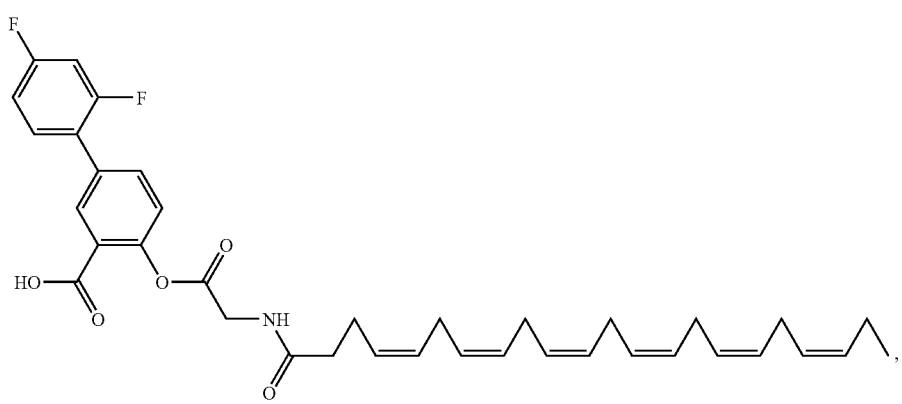
IVg-2
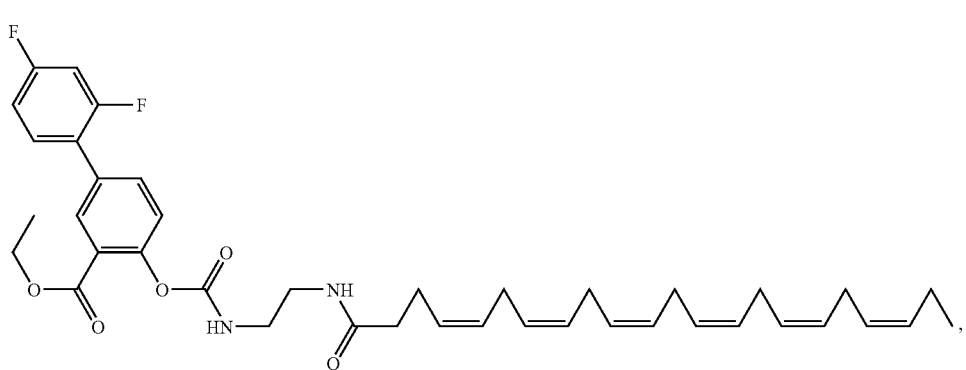
VIf-1
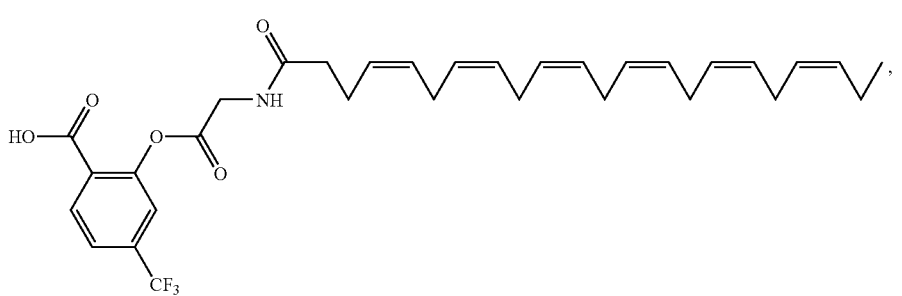
VIf-2
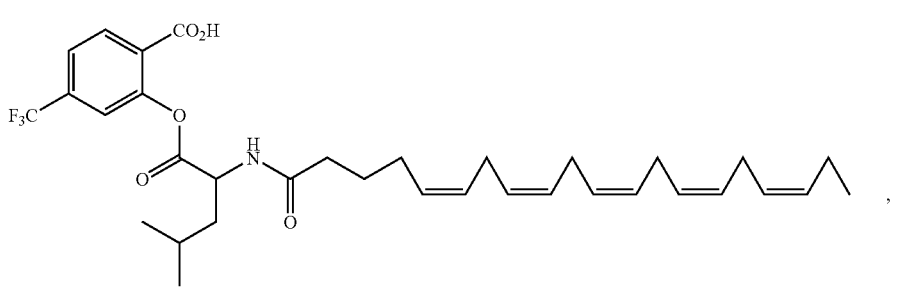
VIf-3
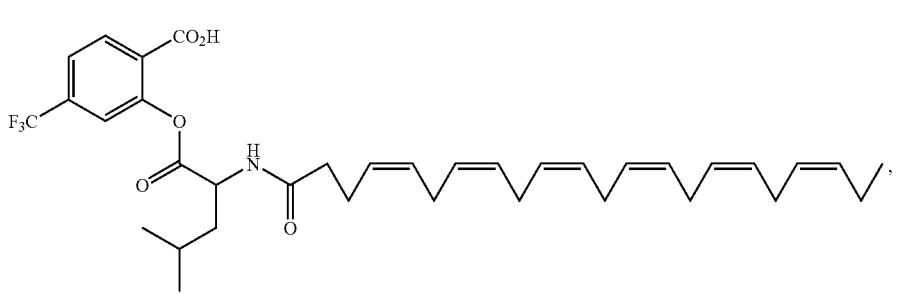

-continued

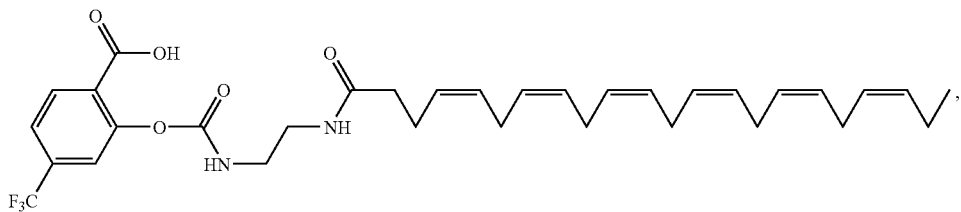
VIf-4

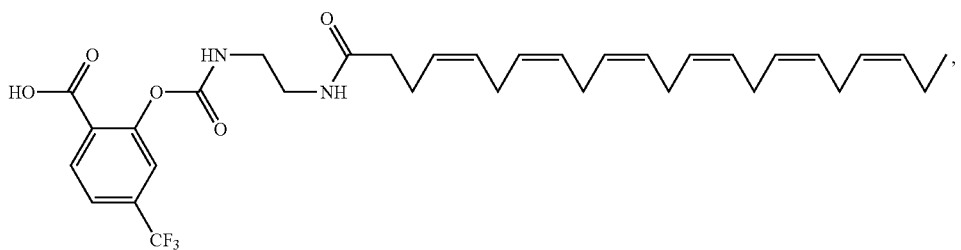
VIg-1

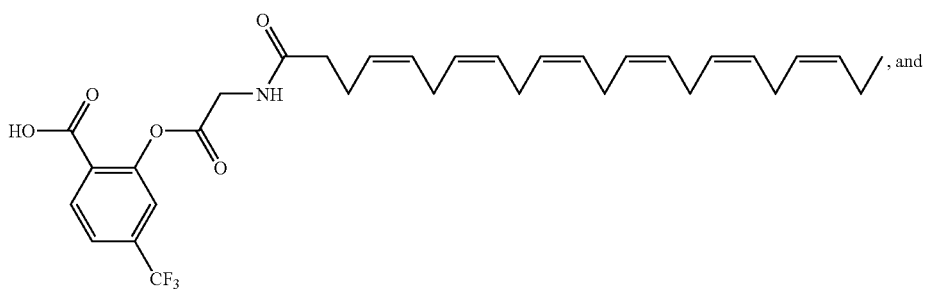
VIg-3
, and

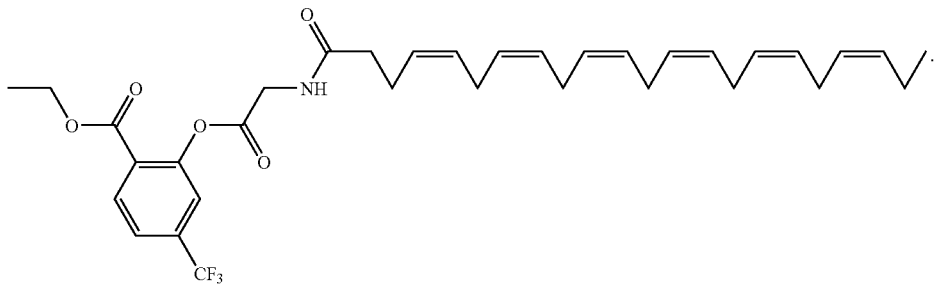
VIg-4

In another aspect, compounds of the Formula II are described

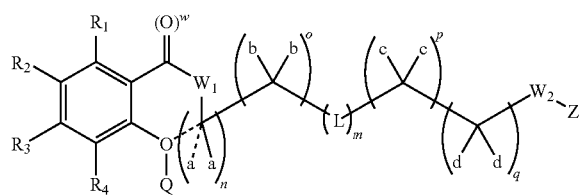
Formula II and pharmaceutically acceptable salts, hydrates, solvates, prodrugs, enantiomers, and stereoisomers thereof; wherein $R_1$, $R_2$, $R_3$, $R_4$, $R_7$, $R_8$, R, $W_1$, $W_2$, $W_3$, a, b, c, d, e, g, h, the symbol -----, L, Z, m, n, o, p, q, r, s, t, w, Q, and T are as defined above for compounds of Formula II.

In some embodiments, $R_2$ is Cl or F.
In some embodiments, $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, one symbol ----- represents a bond. In some embodiments, the bond is present between the phenolic oxygen and the methylene containing substituent a. In other embodiments, the bond is present between substituent a and the carbon of the methylene containing substituent a.

In some embodiments, each a and c is independently H, $CH_3$, —$OCH_3$, or C(O)OR.

In some embodiments, one b is O—Z, Z is

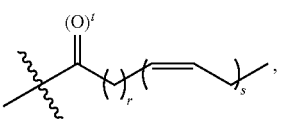

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

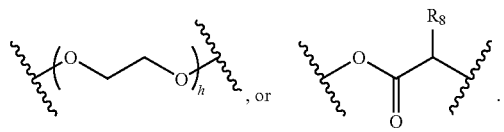
, or .

In some embodiments, each L is independently

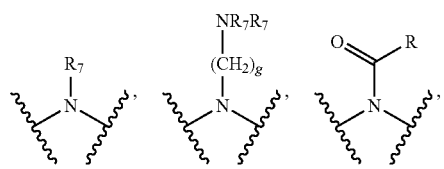

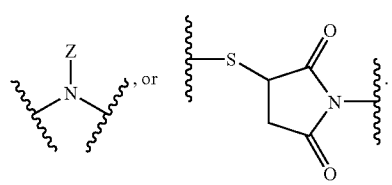
, or .

In some embodiments, each L is independently

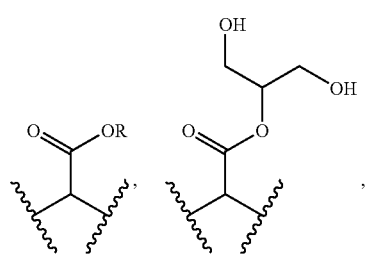
, ,

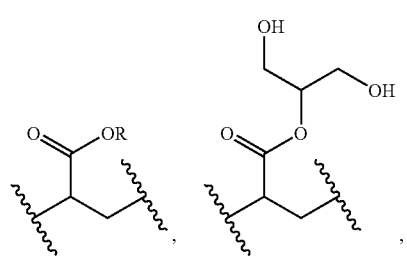
, ,

-continued

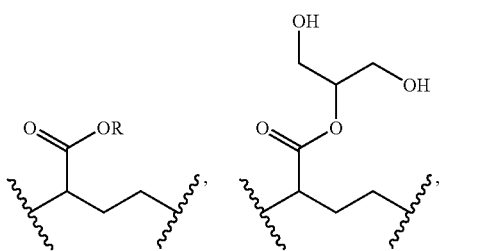
, ,

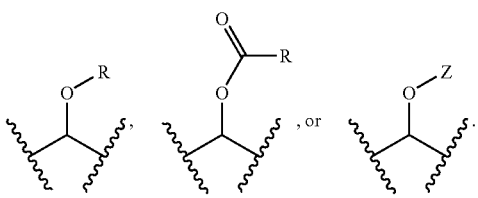
, , or .

In some embodiments, each L is independently

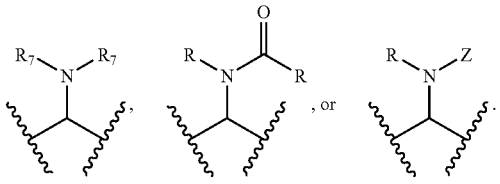
, , or .

In some embodiments, R$_8$ is e.

In some embodiments, t is 1.

In some embodiments, w is 1.

In some embodiments, Q is C(O)CH$_3$

In some embodiments, Q is Z.

In some embodiments, Q is

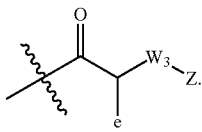

In some embodiments, Q is

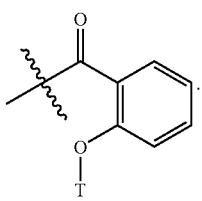 [SMILES: *C(=O)c1ccccc1O[3H] ; "."]

In some embodiments, T is H. In other embodiments, T is C(O)CH$_3$. In other embodiments, T is Z.

In some embodiments, each e is independently any one of the side chains of the naturally occurring amino acids. In other embodiments, e is H.

In another aspect, compounds of Formula III are described:

Formula III

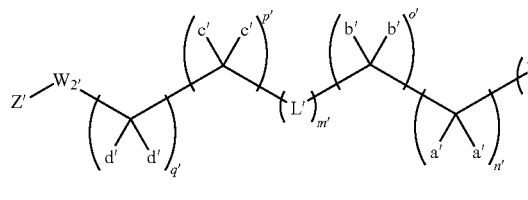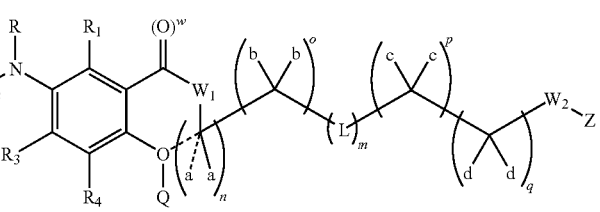

and pharmaceutically acceptable salts, hydrates, solvates, prodrugs, enantiomers, and stereoisomers thereof;
wherein
$R_1$, $R_3$, $R_4$, $R_7$, $R_8$, R, $W_1$, $W_{1'}$, $W_2$, $W_{2'}$, $W_3$, the symbol -----, L, L', a, a', b, b', c, c', d, d', e, g, h, m, m', n, n', o, o', p, p', q, Z, Z', r, s, t, u, w, Q, and T are as defined above for compounds of Formula III.

In some embodiments, $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, $W_{1'}$ is O, NH, N substituted with a $C_1$-$C_6$ alkyl, or an oxidized N.

In some embodiments, $W_{2'}$ is O, NH, N substituted with a $C_1$-$C_6$ alkyl, or an oxidized N.

In some embodiments, one symbol ----- represents a bond. In some embodiments, the bond is present between the phenolic oxygen and the methylene containing substituent a. In other embodiments, the bond is present between substituent a and the carbon of the methylene containing substituent a.

In some embodiments, each a and c is independently H, $CH_3$, —$OCH_3$, —$OCH_2CH_3$, or C(O)OR.

In some embodiments, each a' and c' is independently H, $CH_3$, —$OCH_3$, —$OCH_2CH_3$, or C(O)OR.

In some embodiments, one b is O—Z, Z is

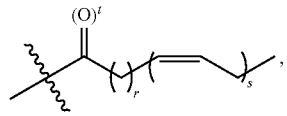

and t is 1.

In some embodiments, one b' is O—Z, Z is

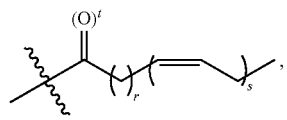

and t is 1.

In some embodiments, one d is C(O)OR.
In some embodiments, one d' is C(O)OR.
In some embodiments n, o, p, and q are each 1.
In some embodiments n', o', p', and q' are each 1.
In some embodiments, two of n, o, p, and q are each 1. In other embodiments, three of n, o, p, and q are each 1.
In some embodiments, two of n', o', p', and q' are each 1. In other embodiments, three of n', o', p', and q' are each 1.

In some embodiments, m is 0.
In some embodiments, m' is 0.
In some embodiments, each L is independently —S—, —S(O)—, —S(O)$_2$—, or —S—S—.
In some embodiments, each L' is independently —S—, —S(O)—, —S(O)$_2$—, or —S—S—.
In some embodiments, each L is independently —O—,

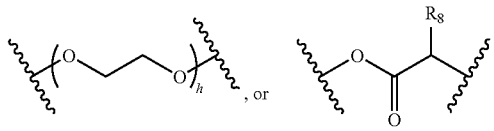

In some embodiments, each L' is independently —O—,

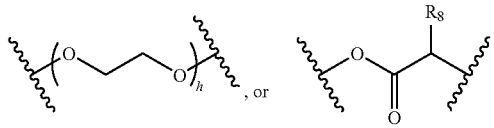

In some embodiments, each L is independently

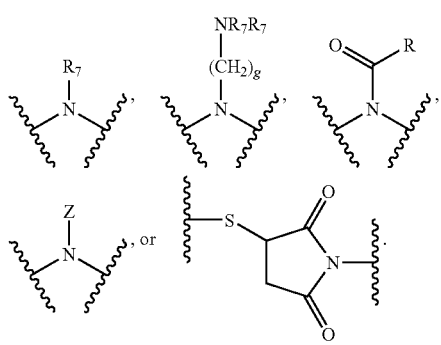

In some embodiments, each L' is independently

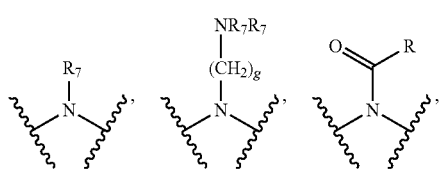

-continued
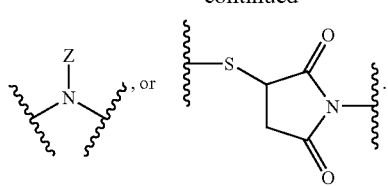
In some embodiments, each L is independently
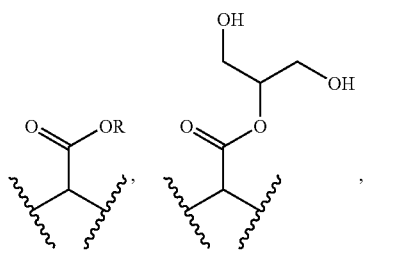
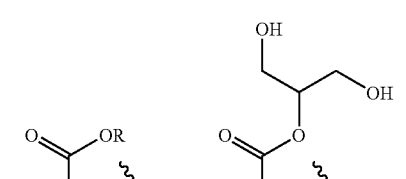
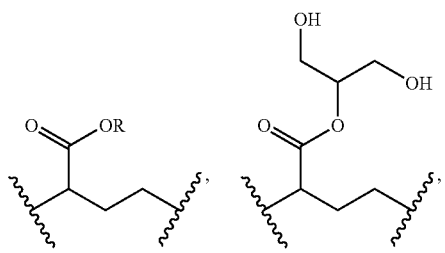
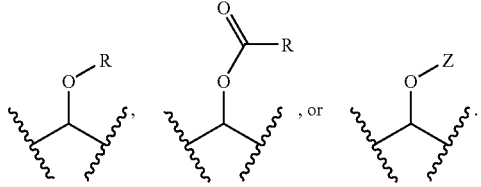
In some embodiments, each L' is independently
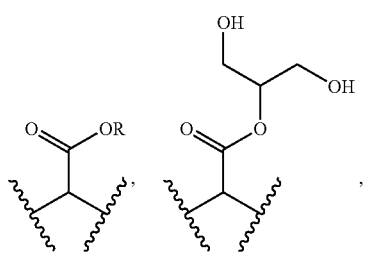
-continued
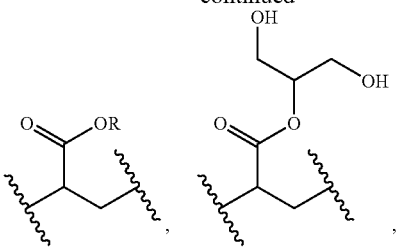
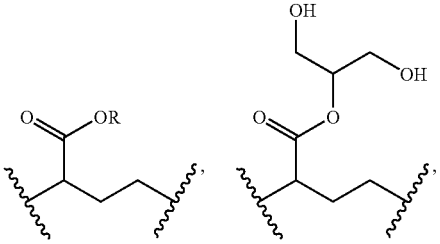
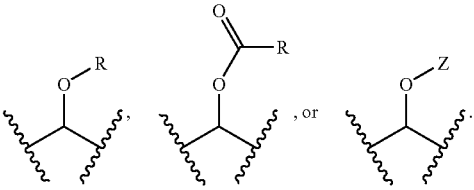
In some embodiments, each L is independently
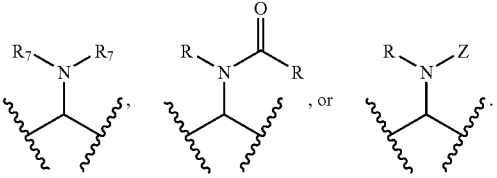
In some embodiments, each L' is independently
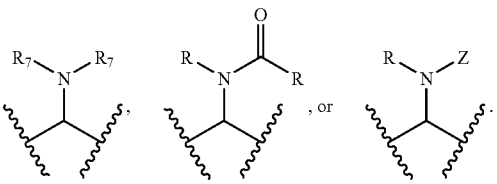
In some embodiments, $R_8$ is e.
In some embodiments, t is 1.
In some embodiments, w is 1.
In some embodiments, Q is $C(O)CH_3$
In some embodiments, Q is Z.
In some embodiments, Q is
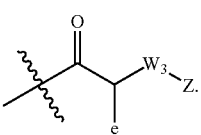

In some embodiments, each e is independently any one of the side chains of the naturally occurring amino acids. In other embodiments, e is H.
In other illustrative embodiments, compounds of Formula III are as set forth below:
III-1
III-2
III-3
III-4
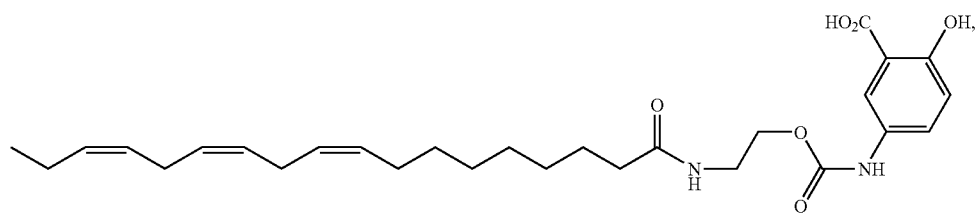
III-5
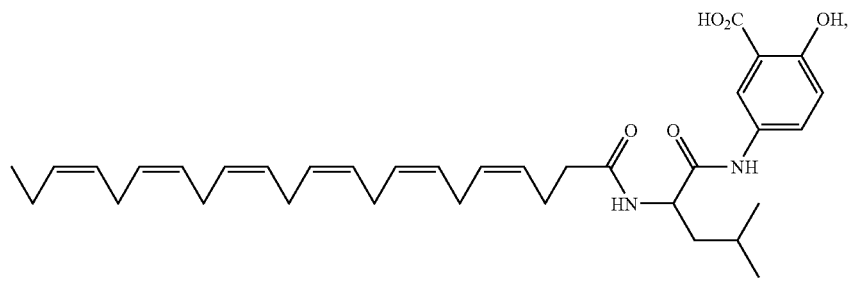
III-6
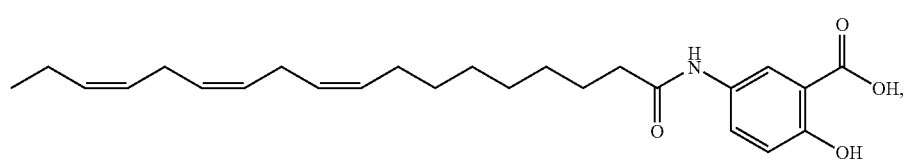
III-7

-continued

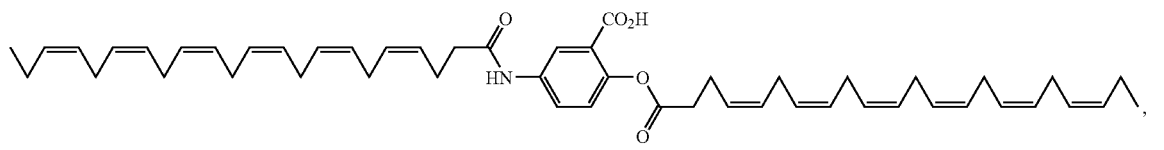
III-8

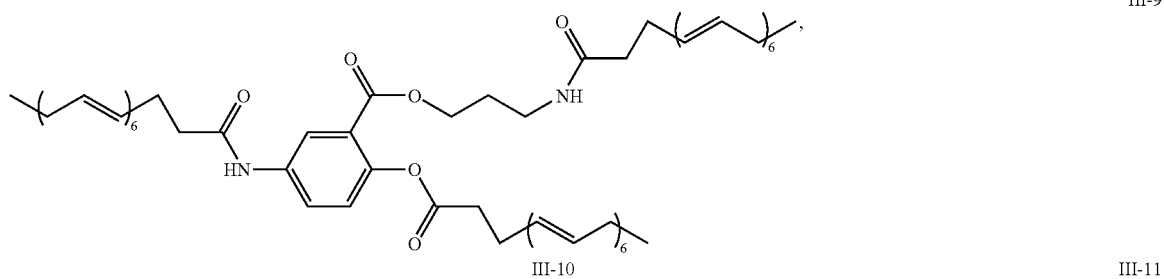
III-9

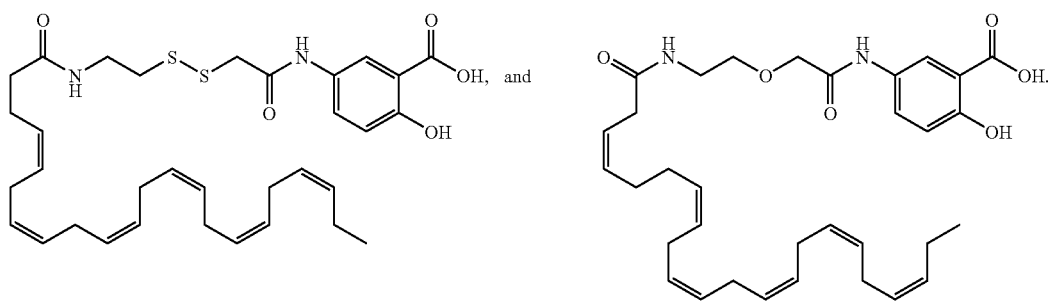
III-10

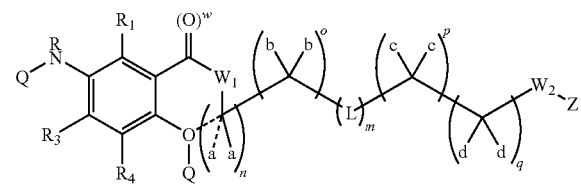
III-11, and

In yet another aspect, compounds of the Formula IIIa are described:

Formula IIIa

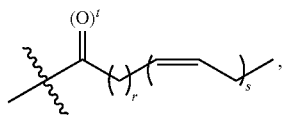

and pharmaceutically acceptable salts, hydrates, solvates, prodrugs, enantiomers, and stereoisomers thereof;
wherein
$R_1$, $R_3$, $R_4$, $R_7$, $R_8$, R, $W_1$, $W_2$, $W_3$, the symbol -----, L, a, b, c, d, e, g, h, m, n, o, p, q, Z, r, s, t, Q, and T are as defined above for compounds of Formula IIIa.

In some embodiments, $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, one symbol ----- represents a bond. In some embodiments, the bond is present between the phenolic oxygen and the methylene containing substituent a. In other embodiments, the bond is present between substituent a and the carbon of the methylene containing substituent a.
In some embodiments, each a and c is independently H, $CH_3$, —$OCH_3$, —$OCH_2CH_3$, or C(O)OR.
In some embodiments, one b is O—Z, Z is

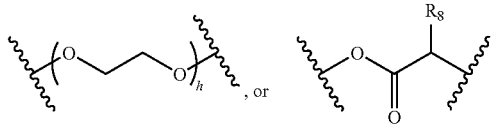

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —S(O)$_2$—, or —S—S—.
In some embodiments, each L is independently —O—,

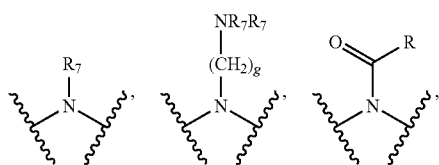

In some embodiments, each L is independently

-continued

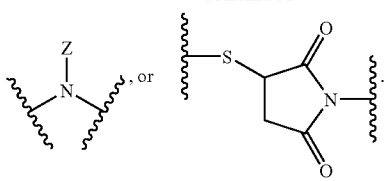

In some embodiments, each L is independently

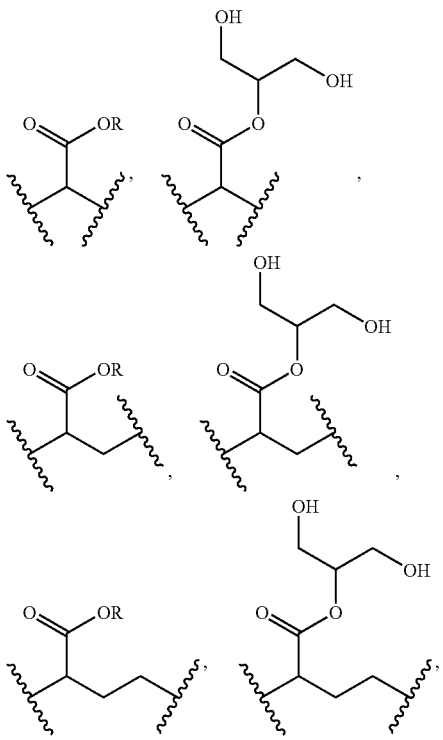

-continued

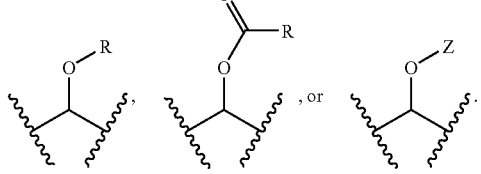

In some embodiments, each L is independently

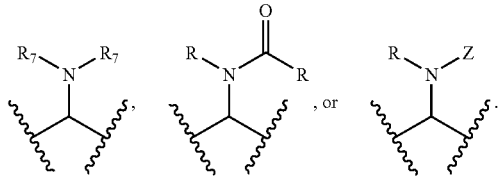

In some embodiments, $R_8$ is e.
In some embodiments, t is 1.
In some embodiments, w is 1.
In some embodiments, Q is $C(O)CH_3$. In other embodiments, Q is Z. In other embodiments, Q is

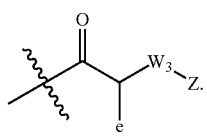

In some embodiments, $W_3$ is O. In other embodiments, $W_3$ is —N(R)—.

In some embodiments, each e is independently any one of the side chains of the naturally occurring amino acids. In some embodiments, e is H.

In other illustrative embodiments, compounds of Formula IIIa are as set forth below:

IIIa-1

IIIa-2

IIIa-3

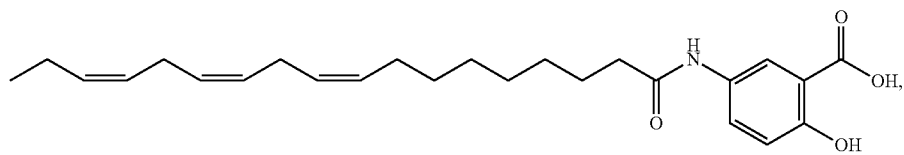

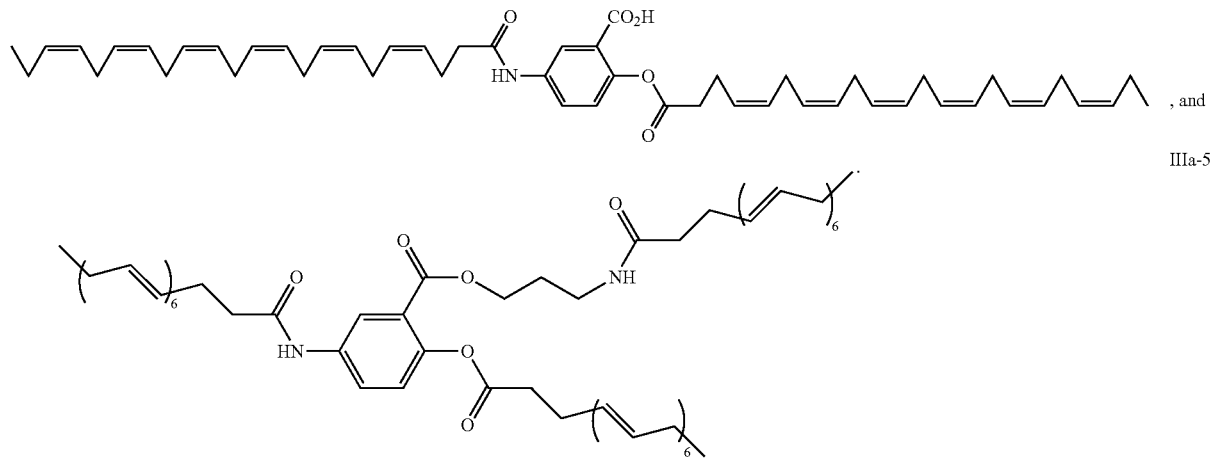

In yet another aspect, compounds of the Formula IIIb are described:

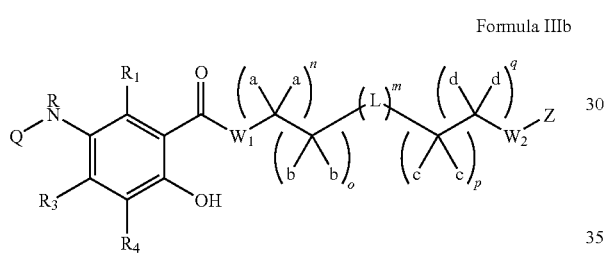

and pharmaceutically acceptable salts, hydrates, solvates, prodrugs, enantiomers, and stereoisomers thereof;
wherein
$R_1$, $R_3$, $R_4$, $R_7$, $R_8$, R, $W_1$, $W_2$, $W_3$, L, a, b, c, d, e, g, h, m, n, o, p, q, Z, r, s, t, Q, and T are as defined above for compounds of Formula IIIb.

In some embodiments, $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, each a and c is independently H, $CH_3$, —$OCH_3$, —$OCH_2CH_3$, or C(O)OR.
In some embodiments, one b is O—Z, Z is

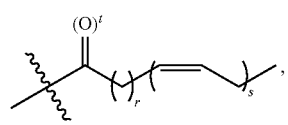

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —S(O)$_2$—, or —S—S—.

In some embodiments, each L is independently —O—,

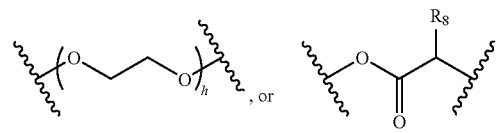

In some embodiments, each L is independently

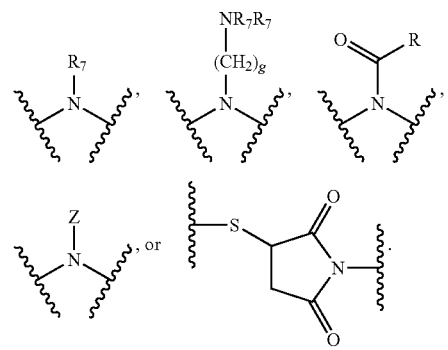

In some embodiments, each L is independently

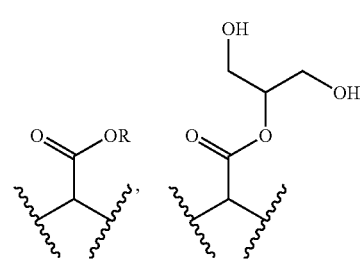

-continued

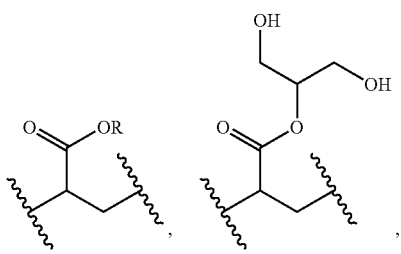

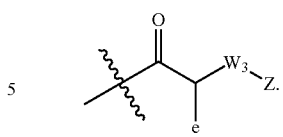

In some embodiments, $W_3$ is O. In other embodiments, $W_3$ is —N(R)—.

In some embodiments, each e is independently any one of the side chains of the naturally occurring amino acids. In some embodiments, e is H.

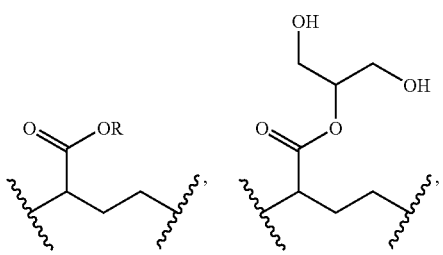

In another illustrative embodiment, a compound of Formula IIIb is as set forth below:

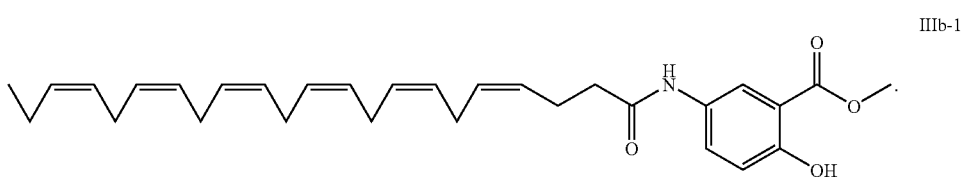 [SMILES: CC/C=C\C/C=C\C/C=C\C/C=C\C/C=C\C/C=C\CCC(=O)Nc1ccc(O)c(C(=O)OC)c1 ; "."]

IIIb-1

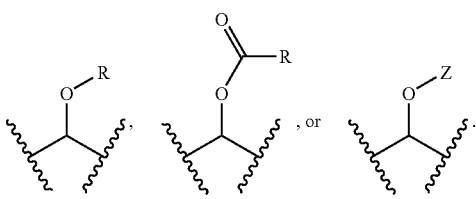

In some embodiments, each L is independently

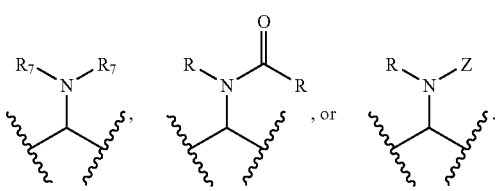

In some embodiments, $R_8$ is e.
In some embodiments, t is 1.
In some embodiments, Q is $C(O)CH_3$. In other embodiments, Q is Z. In other embodiments, Q is In yet another aspect, compounds of the Formula IIIc are described:

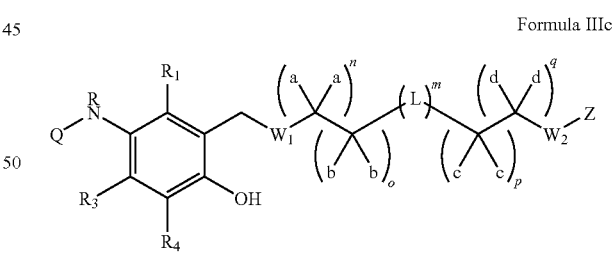

Formula IIIc and pharmaceutically acceptable salts, hydrates, solvates, prodrugs, enantiomers, and stereoisomers thereof;
wherein
$R_1$, $R_3$, $R_4$, $R_7$, $R_8$, R, $W_1$, $W_2$, $W_3$, L, a, b, c, d, e, g, h, m, n, o, p, q, Z, r, s, t, Q, and T are as defined above for compounds of Formula IIIc.

In some embodiments, $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.

In some embodiments, each a and c is independently H, $CH_3$, $-OCH_3$, $-OCH_2CH_3$, or C(O)OR.

In some embodiments, one b is O—Z. Z is

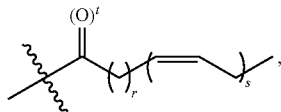

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

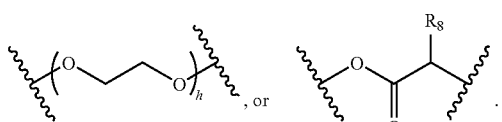

In some embodiments, each L is independently

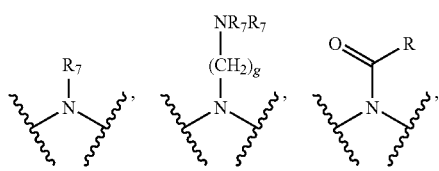

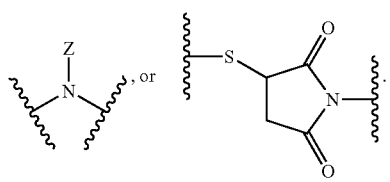

In some embodiments, each L is independently

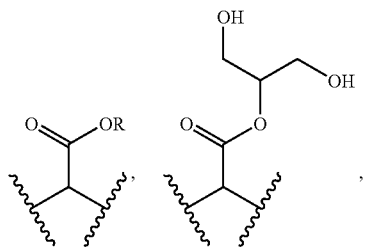

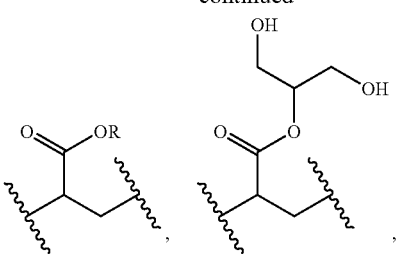

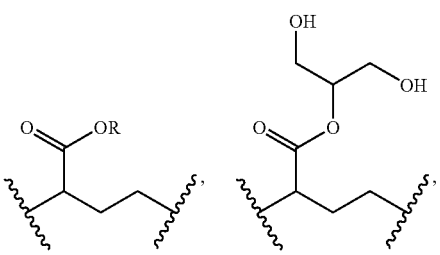

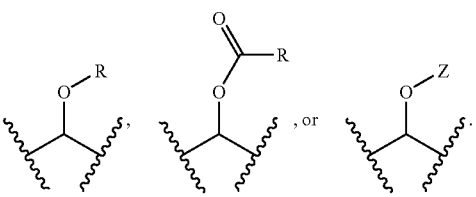

In some embodiments, each L is independently

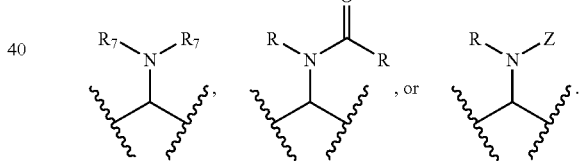

In some embodiments, $R_8$ is e.

In some embodiments, t is 1.

In some embodiments, Q is $C(O)CH_3$. In other embodiments, Q is Z. In other embodiments, Q is

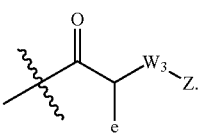

In some embodiments, $W_3$ is O. In other embodiments, $W_3$ is —N(R)—.

In some embodiments, each e is independently any one of the side chains of the naturally occurring amino acids. In some embodiments, e is H.

In yet another aspect, compounds of the Formula IIId are described:

Formula IIId

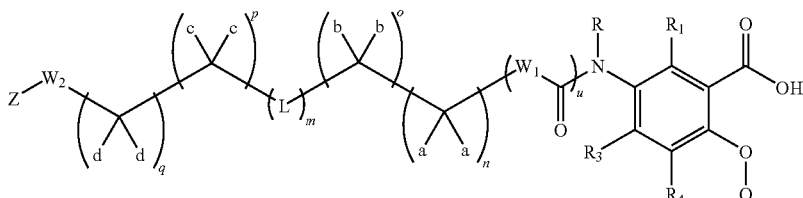

and pharmaceutically acceptable salts, hydrates, solvates, prodrugs, enantiomers, and stereoisomers thereof;

wherein $R_1$, $R_3$, $R_4$, $R_7$, $R_8$, R, $W_1$, $W_2$, $W_3$, L, a, b, c, d, e, g, h, m, n, o, p, q, Z, r, s, t, u, Q, and T are as defined above for compounds of Formula IIId.

In some embodiments, $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, —$OCH_2CH_3$, or C(O)OR.

In some embodiments, one b is O—Z, Z is

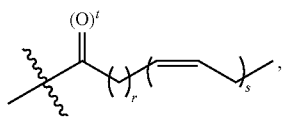

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

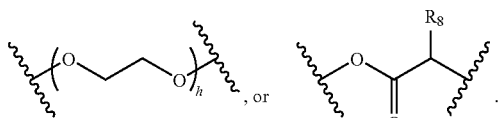

In some embodiments, each L is independently

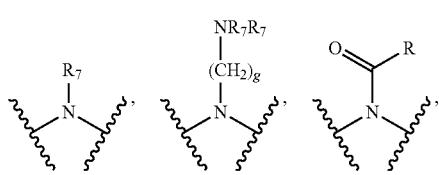

-continued

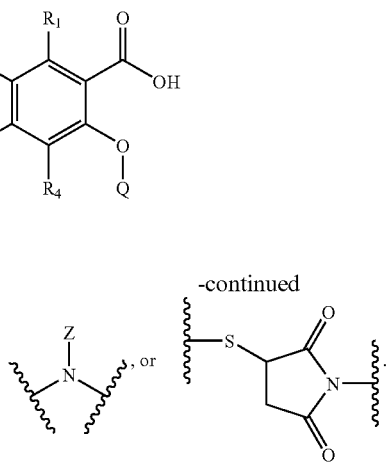

In some embodiments, each L is independently

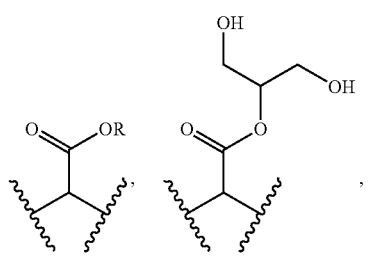

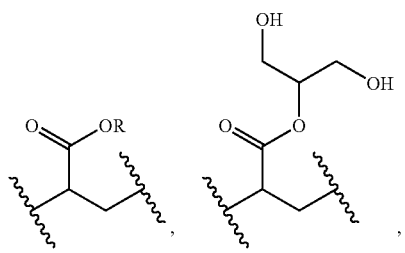

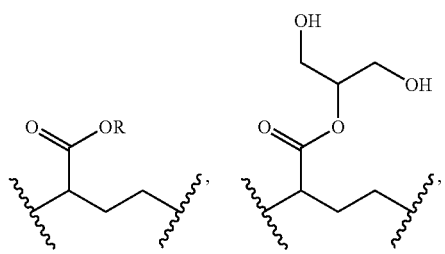

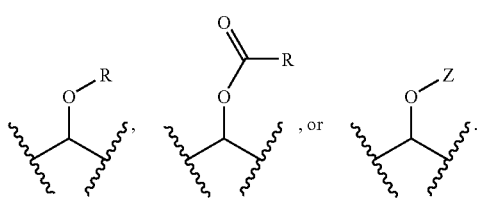

In some embodiments, each L is independently

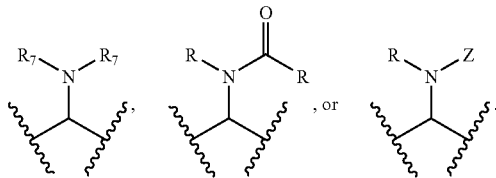

In some embodiments, $R_8$ is e.
In some embodiments, t is 1.
In some embodiments, Q is $C(O)CH_3$. In other embodiments, Q is Z. In other embodiments, Q is

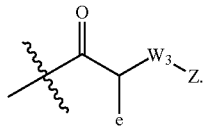

In some embodiments, $W_3$ is O. In other embodiments, $W_3$ is —N(R)—.

In some embodiments, each e is independently any one of the side chains of the naturally occurring amino acids. In some embodiments, e is H.

In yet another aspect, compounds of the Formula IIIe are described:

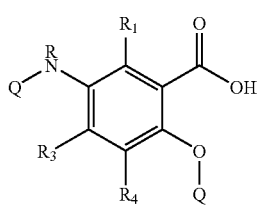

Formula IIIe and pharmaceutically acceptable salts, hydrates, solvates, prodrugs, enantiomers, and stereoisomers thereof;
wherein
$R_1$, $R_3$, $R_4$, R, $W_3$, e, Z, r, s, t, Q, and T are as defined above for compounds of Formula IIIe.

In some embodiments, $R_3$ is Cl or F.
In some embodiments, Q is $C(O)CH_3$. In other embodiments, Q is Z. In other embodiments, Q is

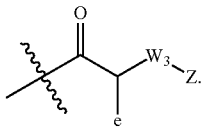

In some embodiments, $W_3$ is O. In other embodiments, $W_3$ is —N(R)—.
In some embodiments, t is 1.
In some embodiments, each e is independently any one of the side chains of the naturally occurring amino acids. In some embodiments, e is H.

In yet another aspect, compounds of the Formula IIIf are described:

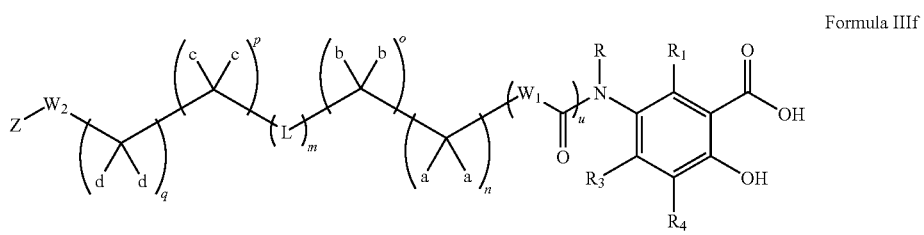

Formula IIIf and pharmaceutically acceptable salts, hydrates, solvates, prodrugs, enantiomers, and stereoisomers thereof;
wherein
$R_1$, $R_3$, $R_4$, $R_7$, $R_8$, R, $W_1$, $W_2$, L, a, b, c, d, e, g, h, m, n, o, p, q, Z, r, s, t, and u are as defined above for compounds of Formula IIIf.

In some embodiments, $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, each a and c is independently H, $CH_3$, —$OCH_3$, —$OCH_2CH_3$, or C(O)OR.
In some embodiments, one b is O—Z, Z is

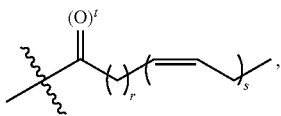

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —$S(O)_2$—, or —S—S—.
In some embodiments, each L is independently —O—,

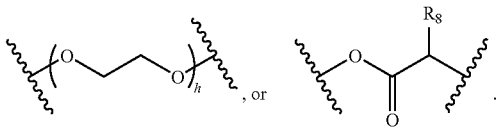

In some embodiments, each L is independently

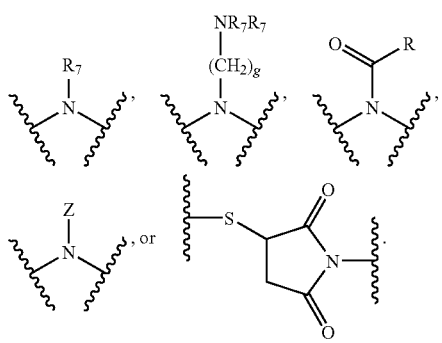

In some embodiments, each L is independently

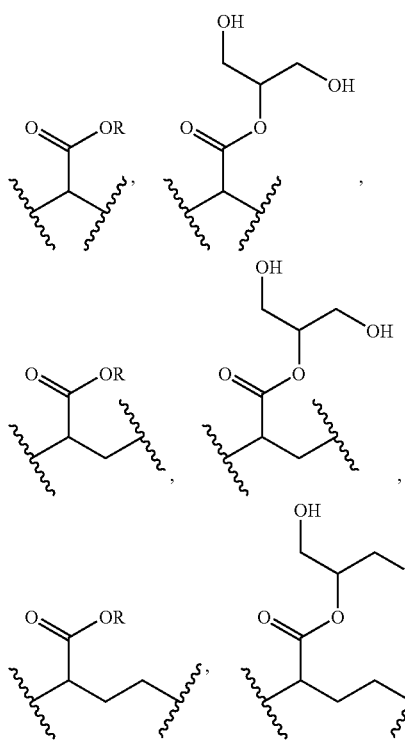

In some embodiments, each L is independently

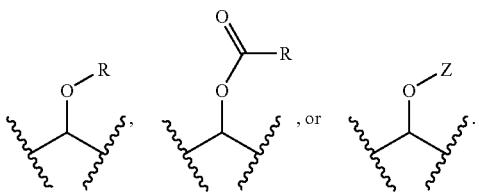

In some embodiments, each L is independently

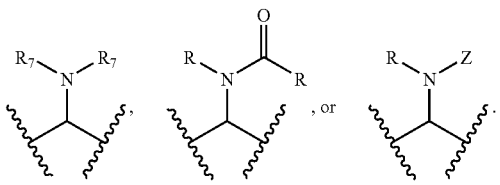

In some embodiments, $R_8$ is e.

In some embodiments, t is 1.

In some embodiments, each e is independently any one of the side chains of the naturally occurring amino acids. In some embodiments, e is H.

In some embodiments, the compounds have the formula:

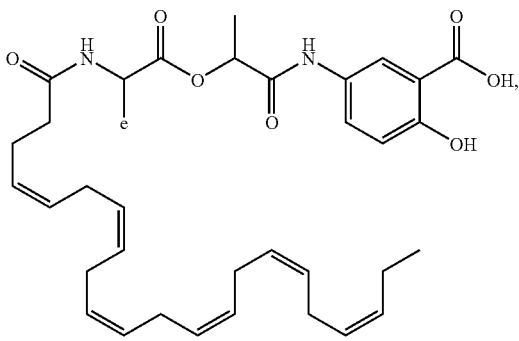

wherein e is as defined above for Formula IIIf.

Illustrative compounds of Formula IIIf include:

IIIf-1

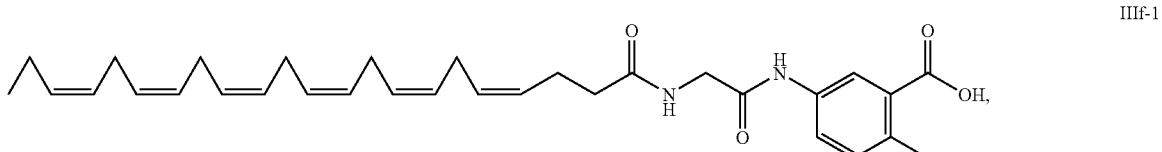

IIIf-2

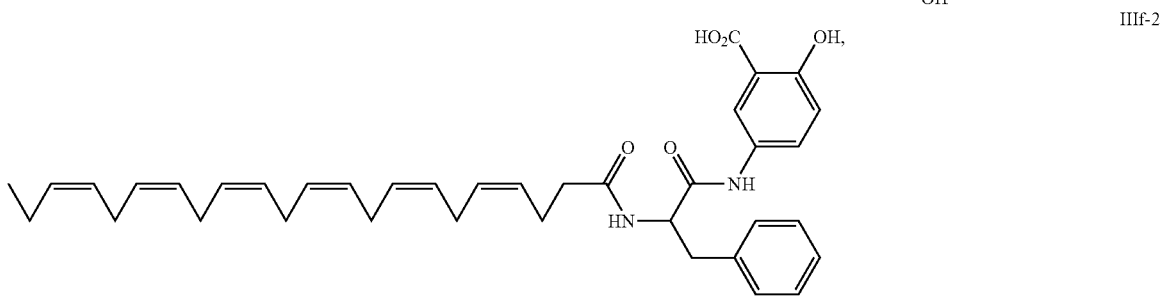

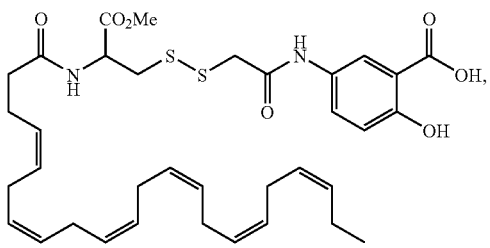

IIIf-3

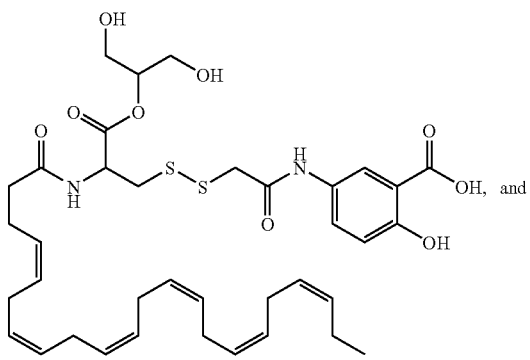

IIIf-4

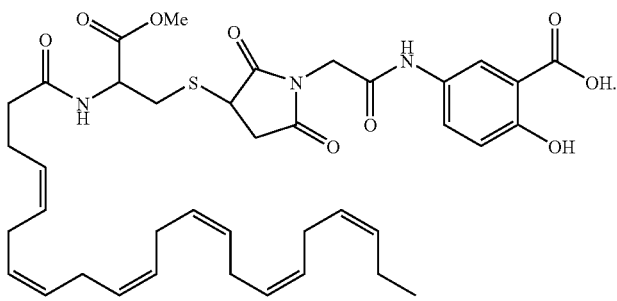

IIIf-5

In yet another aspect, compounds of the Formula IIIg are described:

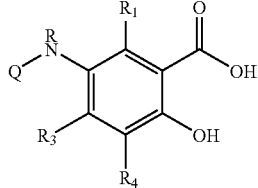

Formula IIIg and pharmaceutically acceptable salts, hydrates, solvates, prodrugs, enantiomers, and stereoisomers thereof; wherein
$R_1$, $R_3$, $R_4$, R, $W_3$, e, Z, r, s, t, Q, and T are as defined above for compounds of Formula IIIg.

In some embodiments, $R_3$ is Cl or F.

In some embodiments, Q is $C(O)CH_3$. In other embodiments, Q is Z. In other embodiments, Q is

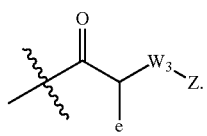

In some embodiments, $W_3$ is O. In other embodiments, $W_3$ is —N(R)—.

In some embodiments, t is 1.

In some embodiments, each e is independently any one of the side chains of the naturally occurring amino acids. In some embodiments, e is H.

Illustrative compounds of Formula IIIg include:

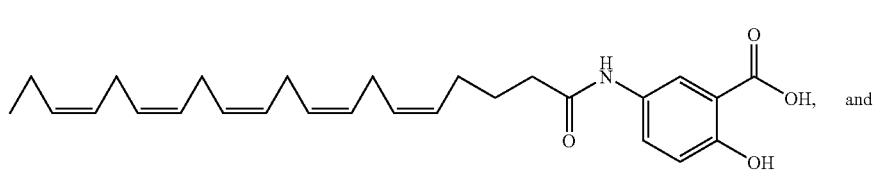

IIIg-1 and

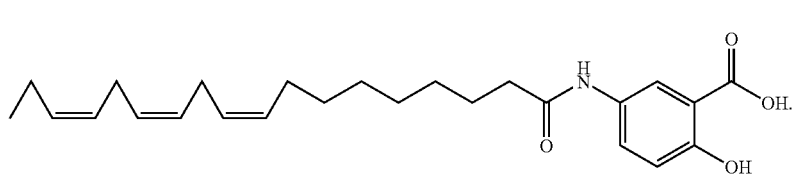

IIIg-2

In a further aspect, compounds of the Formula I' are described:

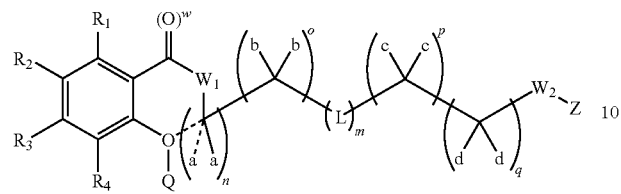

Formula I' and pharmaceutically acceptable salts, hydrates, solvates, prodrugs, enantiomers, and stereoisomers thereof;

wherein $R_1$, $R_2$, $R_3$, $R_4$, $R_5$, $R_6$, $R_7$, $R_8$, R, L, $W_1$, $W_2$, $W_3$, Z, the symbol -----, Q, a, b, c, d, e, g, h, m, n, o, p, q, r, s, t, v, w, and T are as defined above for Formula I'.

In some embodiments, $R_2$ or $R_3$ is Cl or F.

In some embodiments, $R_2$ is difluorophenyl.

In other embodiments, $R_3$ is trifluoromethyl.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, one symbol - - - - - represents a bond. In some embodiments, the bond is present between the phenolic oxygen and the methylene containing substituent a. In other embodiments, the bond is present between substituent a and the carbon of the methylene containing substituent a.

In some embodiments, each a and c is independently H, $CH_3$, —$OCH_3$, —$OCH_2CH_3$, or C(O)OR.

In some embodiments, one b is O—Z, Z is

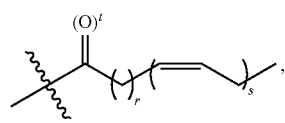

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

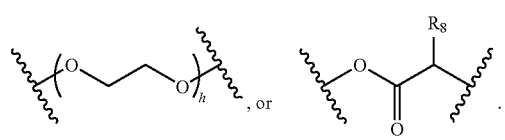

In some embodiments, each L is independently

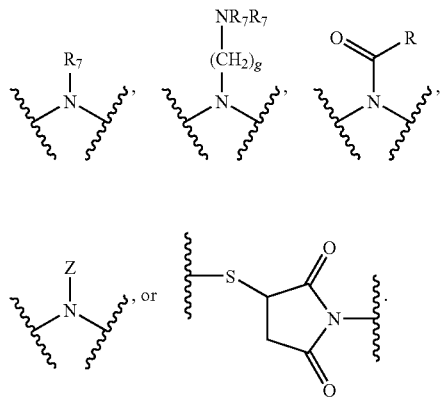

In some embodiments, each L is independently

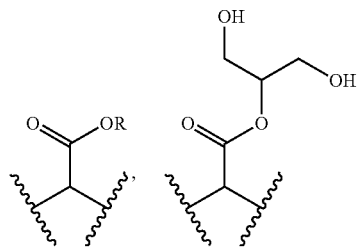

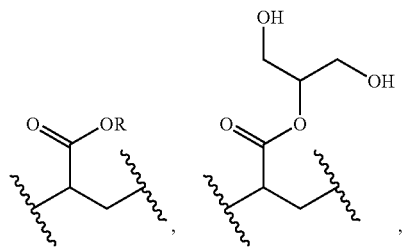

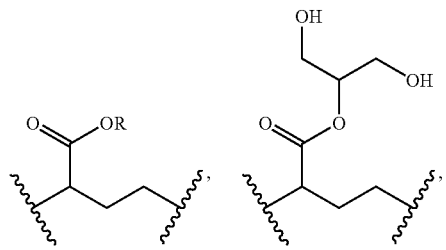

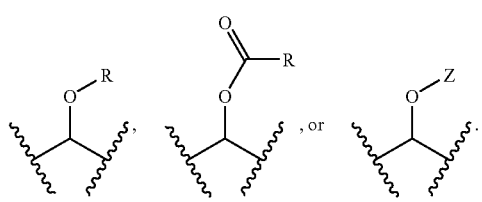

185

In some embodiments, each L is independently

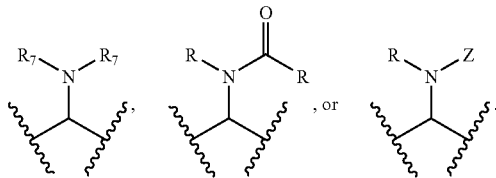

In some embodiments, $R_8$ is e.
In some embodiments, t is 1.
In some embodiments, w is 1.
In some embodiments, Q is $C(O)CH_3$. In other embodiments, Q is Z. In other embodiments, Q is

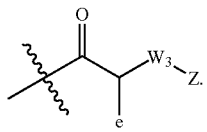

In some embodiments, each e is independently any one of the side chains of the naturally occurring amino acids. In some embodiments, e is H.

In a further aspect, compounds of the Formula Ia' are described:

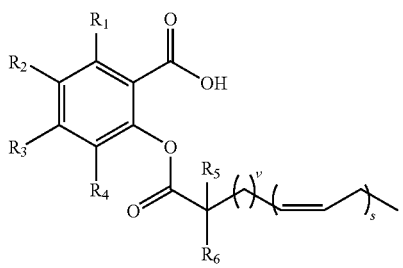

Formula Ia' and pharmaceutically acceptable salts, hydrates, solvates, prodrugs, enantiomers, and stereoisomers thereof;
wherein
$R_1$, $R_2$, $R_3$, $R_4$, $R_5$, $R_6$, s, and v are as defined above for Formula Ia'.
In some embodiments, $R_2$ or $R_3$ is Cl or F.
In some embodiments, $R_2$ is difluorophenyl.
In other embodiments, $R_3$ is trifluoromethyl.
In some embodiments, r is 2, and s is 6.
In some embodiments, r is 3, and s is 5.
In another aspect compounds of the Formula Ib' are described:

186

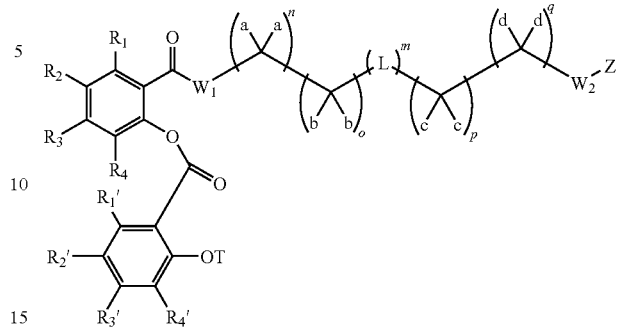

Formula Ib' and pharmaceutically acceptable salts, hydrates, solvates, prodrugs, enantiomers, and stereoisomers thereof;
wherein
$R_1$, $R_2$, $R_3$, $R_4$, $R_5$, $R_6$, $R_7$, $R_8$, $R_{1'}$, $R_{2'}$, $R_{3'}$, $R_{4'}$, R, L, $W_1$, $W_2$, Z, a, b, c, d, e, g, h, m, n, o, p, q, r, s, t, T, and v are as defined above for Formula Ib'.
In some embodiments, $R_2$ or $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, each a and c is independently H, $CH_3$, —$OCH_3$, —$OCH_2CH_3$, or C(O)OR.
In some embodiments, one b is O—Z, Z is

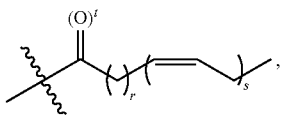

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —$S(O)_2$—, or —S—S—.
In some embodiments, each L is independently —O—,

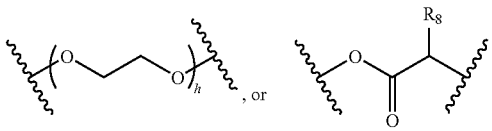

In some embodiments, each L is independently

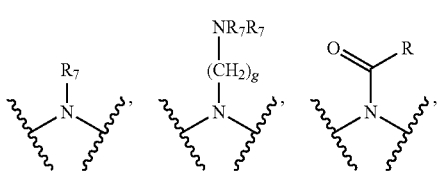

-continued

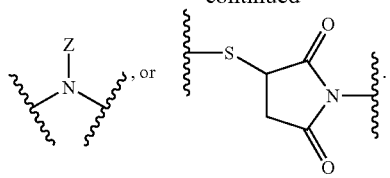

In some embodiments, each L is independently

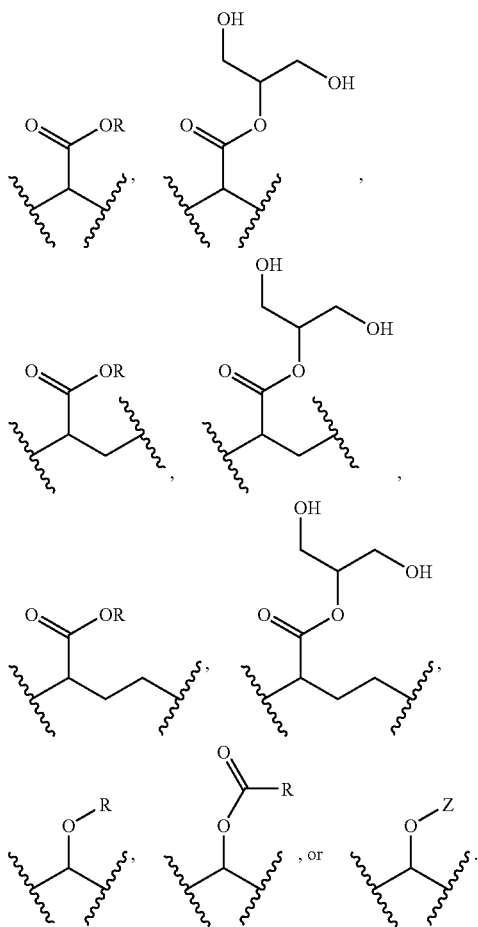

In some embodiments, each L is independently

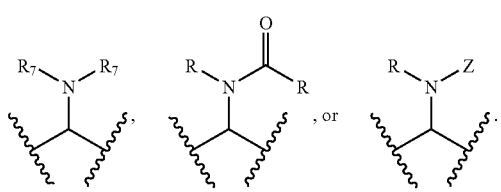

In some embodiments, $R_8$ is e.

In some embodiments, t is 1.

In some embodiments, T is H. In some embodiments, T is $C(O)CH_3$. In some embodiments, T is Z.

In another aspect compounds of the Formula Ic' are described:

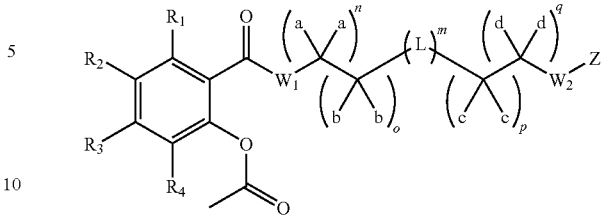

Formula Ic' and pharmaceutically acceptable salts, hydrates, solvates, enantiomers, and stereoisomers thereof, wherein $R_1$, $R_2$, $R_3$, $R_4$, $R_5$, $R_6$, $R_7$, $R_8$, R, L, $W_1$, $W_2$, Z, a, b, c, d, e, g, h, m, n, o, p, q, r, s, t, and v are as defined above for Formula Ic'.

In some embodiments, $R_2$ or $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, $—OCH_3$, $—OCH_2CH_3$, or C(O)OR.

In some embodiments, one b is O—Z, Z is

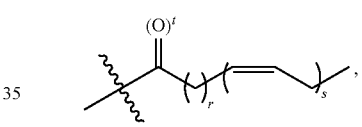

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

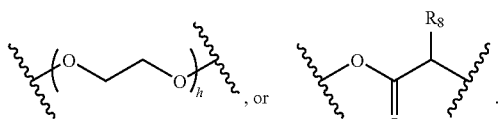

In some embodiments, each L is independently

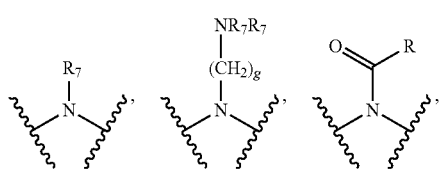

-continued

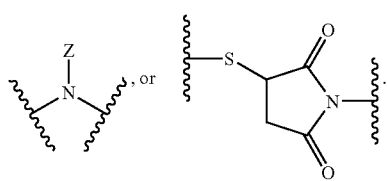

In some embodiments, each L is independently

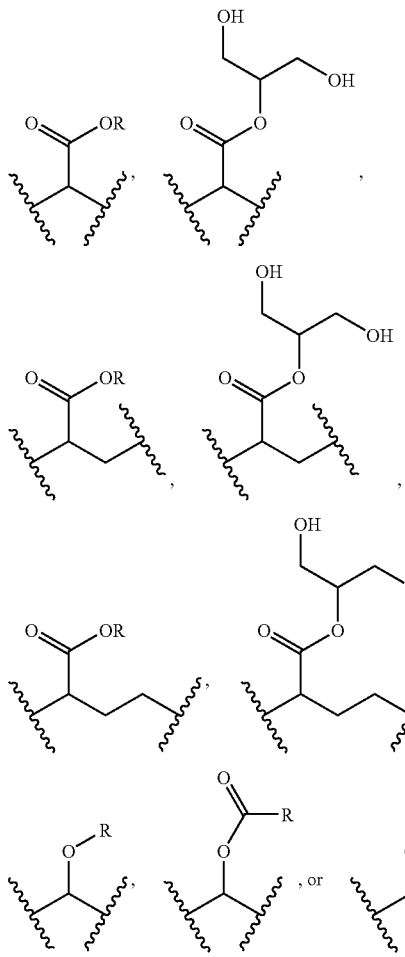

In some embodiments, each L is independently

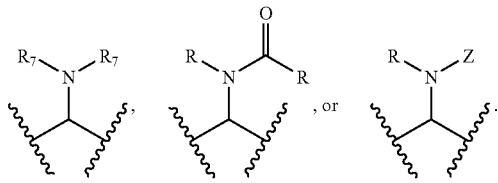

In some embodiments, $R_8$ is e.

In some embodiments, t is 1.

In another aspect, compounds of the Formula Id' are described:

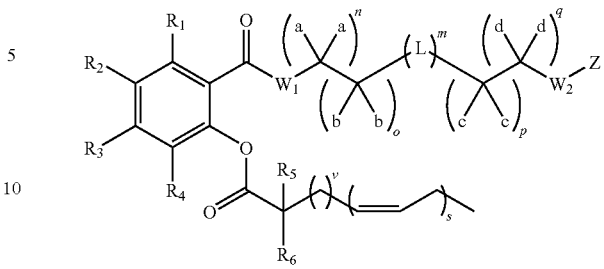

Formula Id' and pharmaceutically acceptable salts, hydrates, solvates, prodrugs, enantiomers, and stereoisomers thereof;

wherein $R_1$, $R_2$, $R_3$, $R_4$, $R_5$, $R_6$, $R_7$, $R_8$, R, L, $W_1$, $W_2$, a, b, c, d, e, g, h, m, n, o, p, q, Z, r, s, t, and v are as defined above for Formula Id'.

In some embodiments, $R_2$ or $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, —$OCH_2CH_3$, or C(O)OR.

In some embodiments, one b is O—Z, Z is

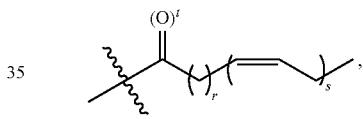

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

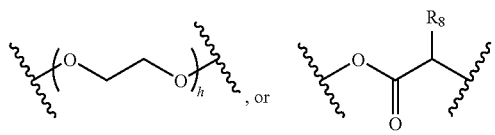

In some embodiments, each L is independently

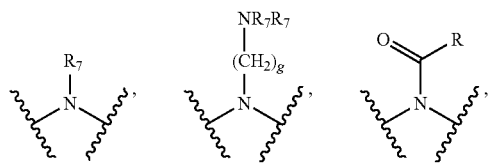

-continued

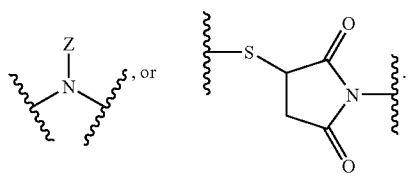

In some embodiments, each L is independently

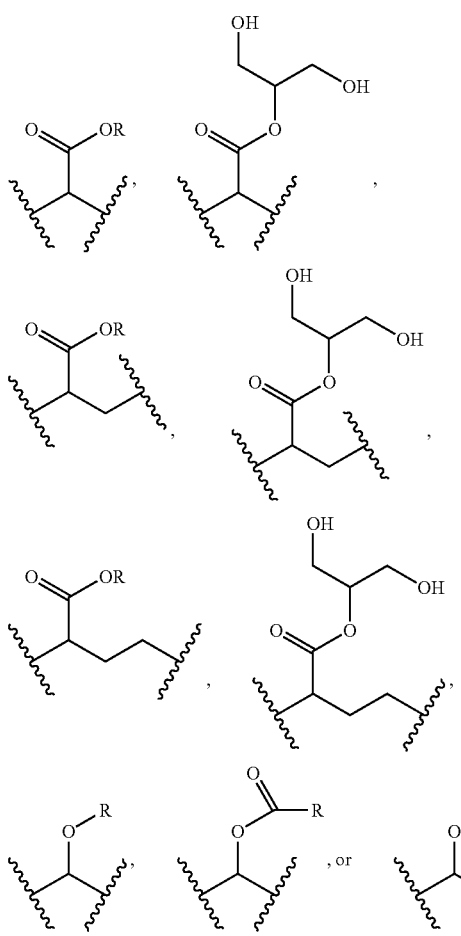

In some embodiments, each L is independently

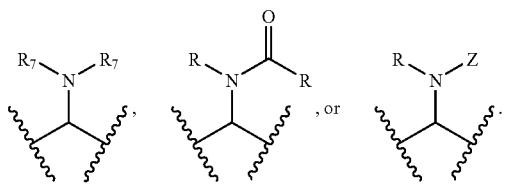

In some embodiments, $R_8$ is e.
In some embodiments, t is 1.

In another aspect, compounds of the Formula If' are described:

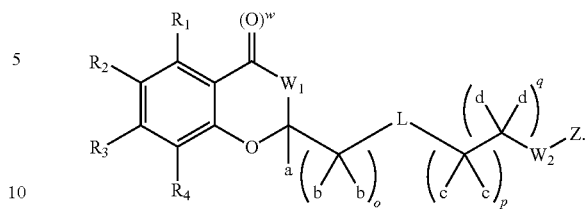

Formula If' and pharmaceutically acceptable salts, hydrates, solvates, prodrugs, enantiomers, and stereoisomers thereof;
wherein
$R_1$, $R_2$, $R_3$, $R_4$, $R_5$, $R_6$, $R_7$, $R_8$, R, L, $W_1$, $W_2$, Z, a, b, c, d, e, g, h, m, o, p, q, r, s, t, v, and w are as defined above for Formula If'.
In some embodiments, $R_2$ or $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, each a and c is independently H, $CH_3$, —$OCH_3$, —$OCH_2CH_3$, or C(O)OR.
In some embodiments, one b is O—Z, Z is

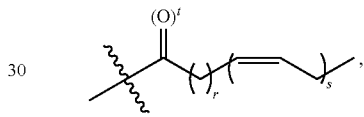

and t is 1.
In some embodiments, one d is C(O)OR.
In some embodiments, one of o, p, and q is 1. In other embodiments, two of o, p, and q are each 1.
In some embodiments, m is 0.
In some embodiments, each L is independently —S—, —S(O)—, —S(O)$_2$—, or —S—S—.
In some embodiments, each L is independently —O—,

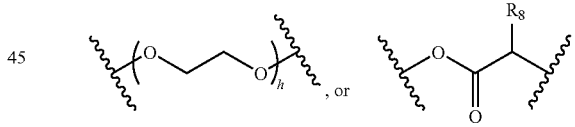

In some embodiments, each L is independently

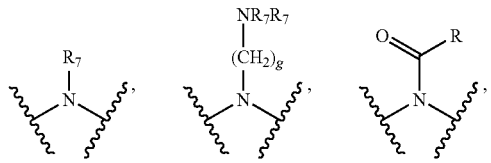

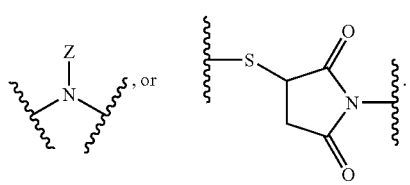

In some embodiments, each L is independently

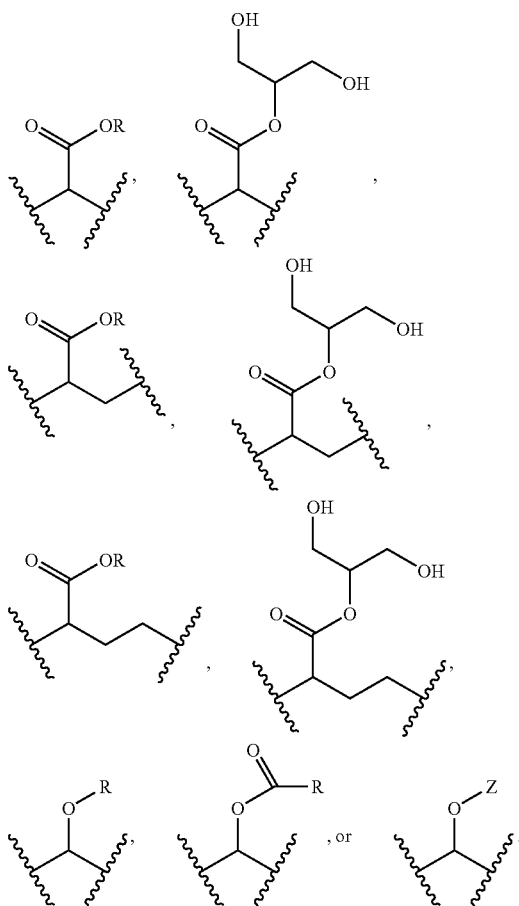

In some embodiments, each L is independently

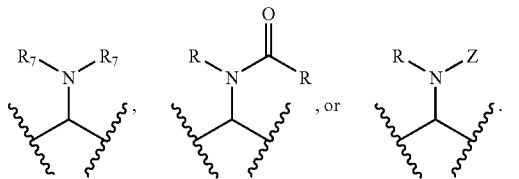

In some embodiments, $R_8$ is e.
In some embodiments, t is 1.
In some embodiments, w is 1.
In another aspect, compounds of the Formula Ih' are described:

Formula Ih'

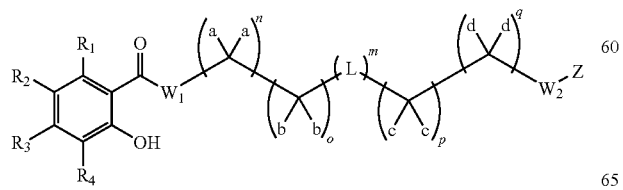

and pharmaceutically acceptable salts, hydrates, solvates, prodrugs, enantiomers, and stereoisomers thereof;

wherein $R_1$, $R_2$, $R_3$, $R_4$, $R_5$, $R_6$, $R_7$, $R_8$, R, L, $W_1$, $W_2$, Z, a, b, c, d, e, g, h, m, n, o, p, q, r, s, t, and v are as defined above for Formula Ih'.

In some embodiments, $R_2$ or $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, —$OCH_2CH_3$, or C(O)OR.

In some embodiments, one b is O—Z, Z is

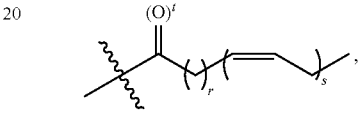

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

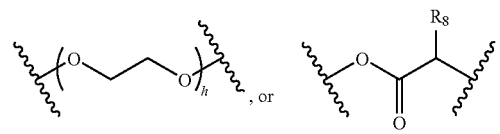

In some embodiments, each L is independently

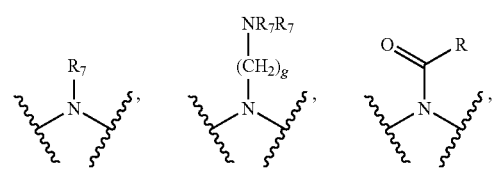

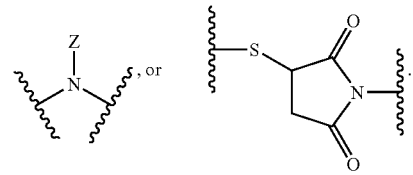

In some embodiments, each L is independently

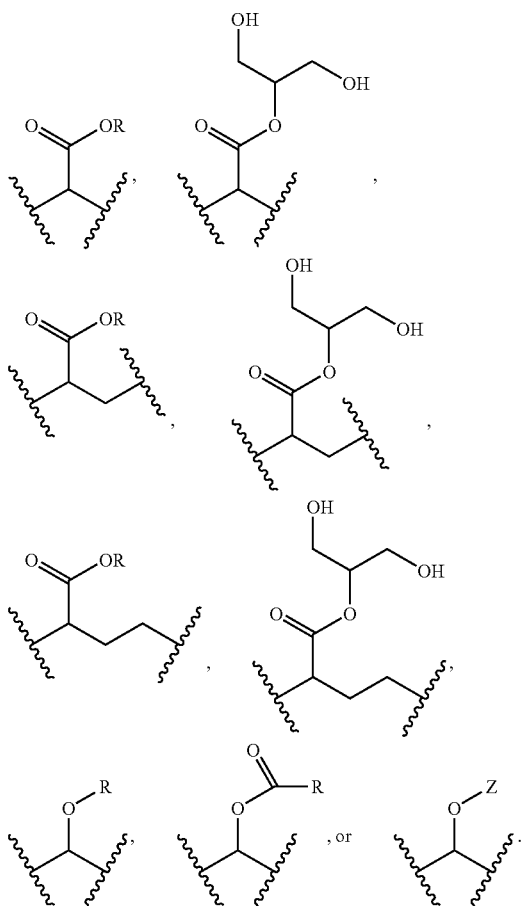

In some embodiments, each L is independently

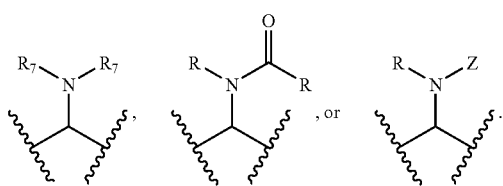

In some embodiments, $R_8$ is e.
In some embodiments, t is 1.
In another aspect, compounds of the Formula Ii' are described:

Formula Ii'

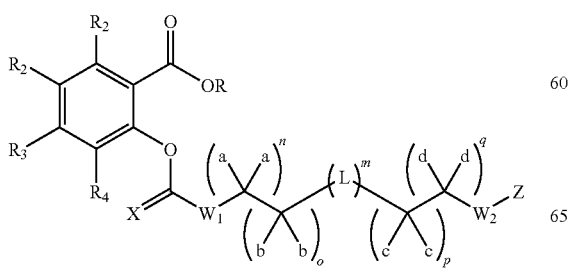

and pharmaceutically acceptable salts, hydrates, solvates, prodrugs, enantiomers, and stereoisomers thereof;

wherein $R_1$, $R_2$, $R_3$, $R_4$, $R_5$, $R_6$, $R_7$, $R_8$, R, L, $W_1$, $W_2$, X, Z, a, b, c, d, e, g, h, m, n, o, p, q, r, s, t, and v are as defined above for Formula Ii'.

In some embodiments, $R_2$ or $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, $CH_3$, —$OCH_3$, —$OCH_2CH_3$, or C(O)OR.

In some embodiments, one b is O—Z, Z is

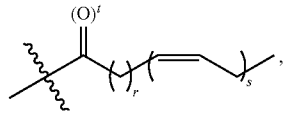

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

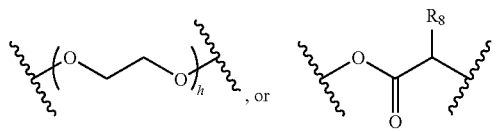

In some embodiments, each L is independently

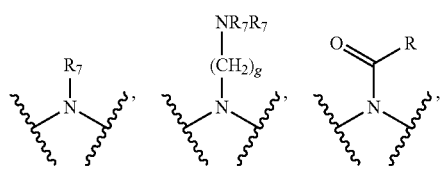

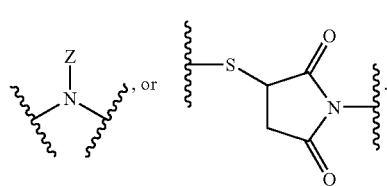

In some embodiments, each L is independently

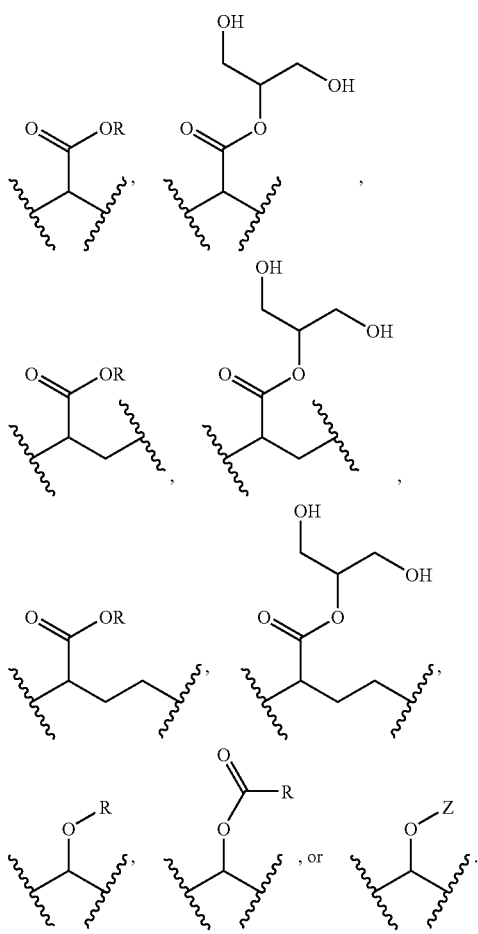

In some embodiments, each L is independently

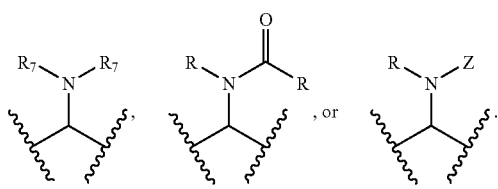

In some embodiments, $R_8$ is e.
In some embodiments, t is 1.
In another aspect, compounds of the Formula II' are described:

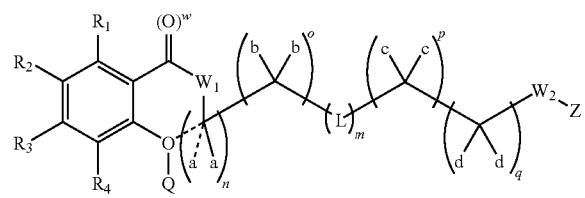

Formula II' and pharmaceutically acceptable salts, hydrates, solvates, prodrugs, enantiomers, and stereoisomers thereof;
wherein
$R_1$, $R_2$, $R_3$, $R_4$, $R_5$, $R_6$, $R_7$, $R_8$, R, L, $W_1$, $W_2$, $W_3$, Z, the symbol -----, Q, a, b, c, d, e, g, h, m, n, o, p, q, r, s, t, v, w, and T are as defined above for Formula II'.

In some embodiments, $R_2$ or $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, one symbol ----- represents a bond. In some embodiments, the bond is present between the phenolic oxygen and the methylene containing substituent a. In other embodiments, the bond is present between substituent a and the carbon of the methylene containing substituent a.
In some embodiments, each a and c is independently H, $CH_3$, —$OCH_3$, —$OCH_2CH_3$, or C(O)OR.
In some embodiments, one b is O—Z, Z is

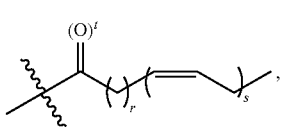

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —S(O)$_2$—, or —S—S—.
In some embodiments, each L is independently —O—,

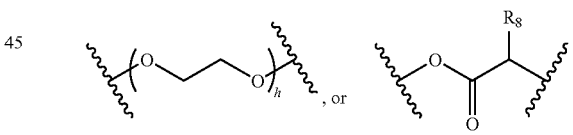

In some embodiments, each L is independently

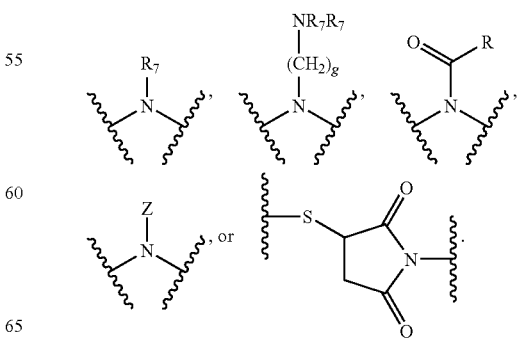

In some embodiments, each L is independently

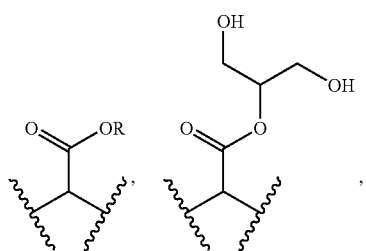

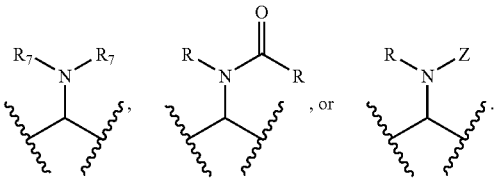

In some embodiments, $R_8$ is e.

In some embodiments, t is 1.

In some embodiments, w is 1.

In some embodiments, Q is $C(O)CH_3$. In other embodiments, Q is Z. In other embodiments, Q is

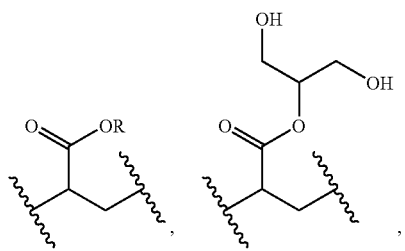

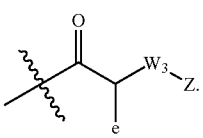

In some embodiments, Q is

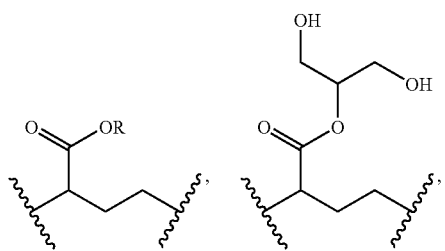

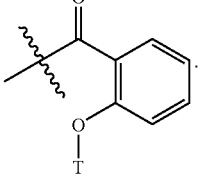

In some embodiments, T is H. In other embodiments, T is $C(O)CH_3$. In other embodiments, T is Z.

In some embodiments, each e is independently any one of the side chains of the naturally occurring amino acids. In other embodiments, e is H.

In another aspect, compounds of the Formula III' are described:

In some embodiments, each L is independently

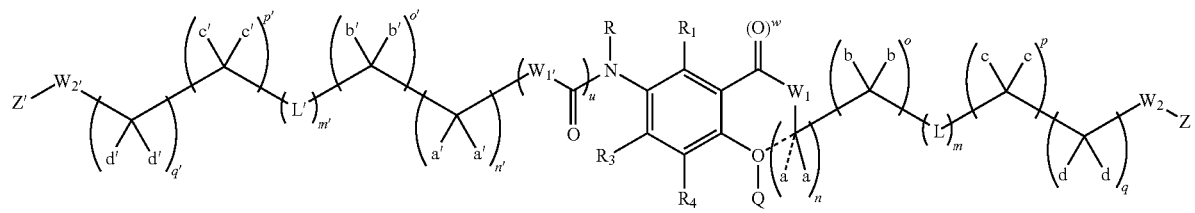

Formula III' and pharmaceutically acceptable salts, hydrates, solvates, prodrugs, enantiomers, and stereoisomers thereof;

wherein $R_1$, $R_3$, $R_4$, $R_5$, $R_6$, $R_7$, $R_8$, R, L, L', $W_1$, $W_{1'}$, $W_2$, $W_{2'}$, $W_3$, Z, Z', the symbol -----, Q, a, a', b, b', c, c', d, d', e, g, h, m, m', n, n', o, o', p, p', q, q', r, s, t, u, v, w, and T are as defined above for Formula III'.

In some embodiments, $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, $W_{1'}$ is O, NH, N substituted with a $C_1$-$C_6$ alkyl, or an oxidized N.

In some embodiments, $W_{2'}$ is O, NH, N substituted with a $C_1$-$C_6$ alkyl, or an oxidized N.

In some embodiments, one symbol ----- represents a bond. In some embodiments, the bond is present between the phenolic oxygen and the methylene containing substituent a. In other embodiments, the bond is present between substituent a and the carbon of the methylene containing substituent a.

In some embodiments, each a and c is independently H, $CH_3$, —$OCH_3$, —$OCH_2CH_3$, or C(O)OR.

In some embodiments, each a' and c' is independently H, $CH_3$, —$OCH_3$, —$OCH_2CH_3$, or C(O)OR.

In some embodiments, one b is O—Z, Z is

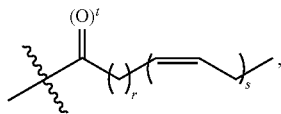

and t is 1.

In some embodiments, one b' is O—Z, Z is

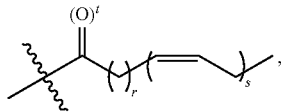

and t is 1.

In some embodiments, one d is C(O)OR.

In some embodiments, one d' is C(O)OR.

In some embodiments n, o, p, and q are each 1.

In some embodiments n', o', p', and q' are each 1.

In some embodiments, two of n, o, p, and q are each 1. In other embodiments, three of n, o, p, and q are each 1.

In some embodiments, two of n', o', p', and q' are each 1. In other embodiments, three of n', o', p', and q' are each 1.

In some embodiments, m is 0.

In some embodiments, m' is 0.

In some embodiments, each L is independently —S—, —S(O)—, —S(O)$_2$—, or —S—S—.

In some embodiments, each L' is independently —S—, —S(O)—, —S(O)$_2$—, or —S—S—.

In some embodiments, each L is independently —O—,

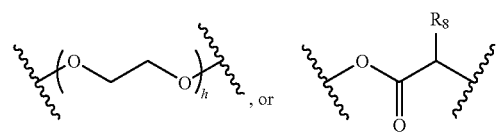

In some embodiments, each L' is independently —O—,

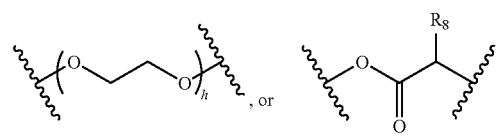

In some embodiments, each L is independently

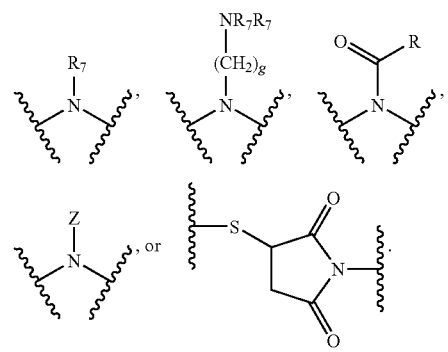

In some embodiments, each L' is independently

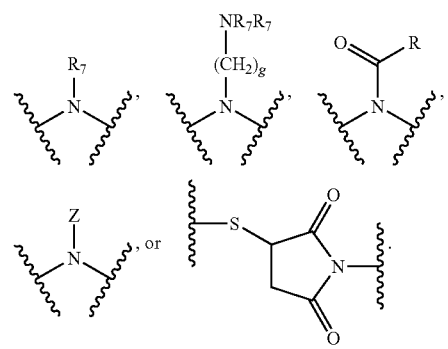

In some embodiments, each L is independently

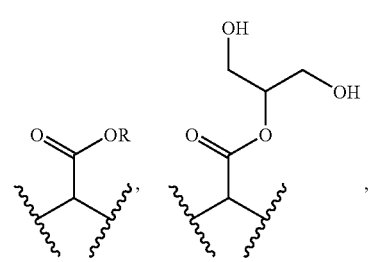

-continued

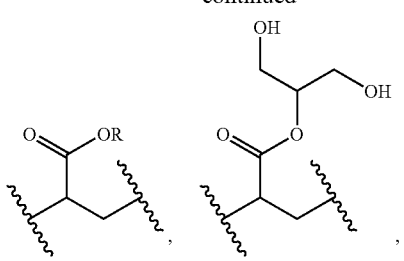

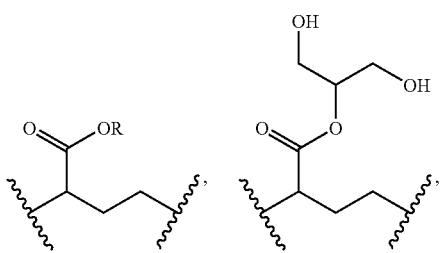

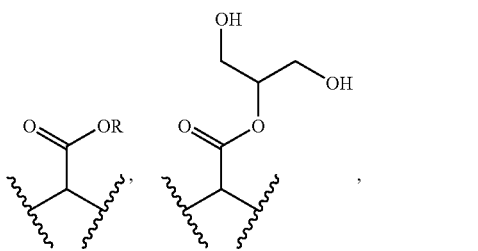

In some embodiments, each L' is independently

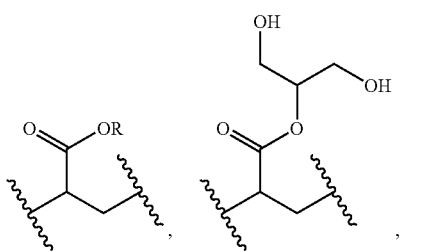

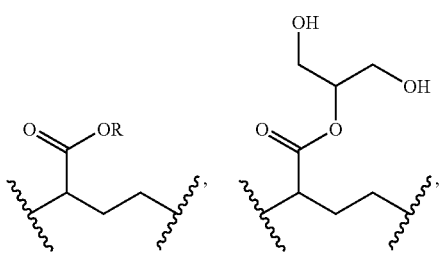

-continued

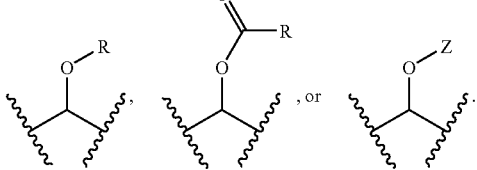

In some embodiments, each L is independently

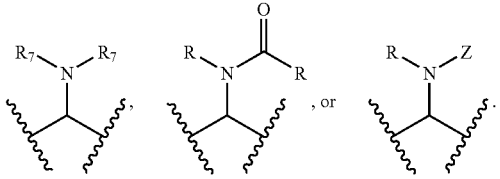

In some embodiments, each L' is independently

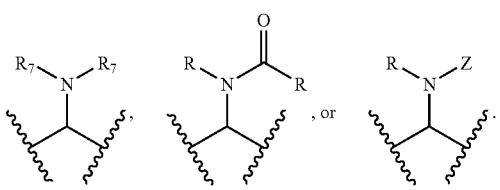

In some embodiments, $R_8$ is e.
In some embodiments, t is 1.
In some embodiments, w is 1.
In some embodiments, Q is $C(O)CH_3$. In other embodiments, Q is Z. In other embodiments, Q is

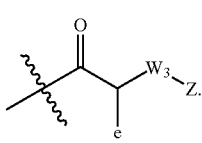

In some embodiments. Q is

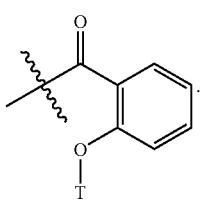 [SMILES: *C(=O)c1ccccc1O[3H] ; "."]

In some embodiments, T is H. In other embodiments, T is $C(O)CH_3$. In other embodiments, T is Z.

In some embodiments, each e is independently any one of the side chains of the naturally occurring amino acids. In other embodiments, e is H.

In yet another aspect, compounds of the Formula IIIa' are described:

Formula IIIa'

[Chemical structure of Formula IIIa']

and pharmaceutically acceptable salts, hydrates, solvates, prodrugs, enantiomers, and stereoisomers thereof;
wherein
$R_1, R_3, R_4, R_5, R_6, R_7, R_8, R, L, W_1, W_2, W_3, Z$, the symbol -----, Q, a, b, c, d, e, g, h, m, n, o, p, q, r, s, t, v, w, and T are as defined above for Formula IIIa'.

In some embodiments, $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, one symbol ----- represents a bond. In some embodiments, the bond is present between the phenolic oxygen and the methylene containing substituent a. In other embodiments, the bond is present between substituent a and the carbon of the methylene containing substituent a.
In some embodiments, each a and c is independently H, $CH_3$, —$OCH_3$, —$OCH_2CH_3$, or C(O)OR.
In some embodiments, one b is O—Z, Z is

[Chemical structure]

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —S(O)$_2$—, or —S—S—.
In some embodiments, each L is independently —O—,

[Chemical structures]

In some embodiments, each L is independently

[Chemical structures]

In some embodiments, each L is independently

[Chemical structures]

In some embodiments, each L is independently

[Chemical structures]

In some embodiments, each L is independently

[Chemical structures]

In some embodiments, $R_8$ is e.
In some embodiments, t is 1.
In some embodiments, w is 1.
In some embodiments, Q is C(O)$CH_3$. In other embodiments, Q is Z. In other embodiments, Q is

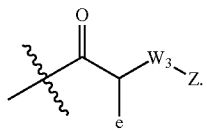

In some embodiments, $W_3$ is O. In other embodiments, $W_3$ is —N(R)—.

In some embodiments, each e is independently any one of the side chains of the naturally occurring amino acids. In other embodiments, e is H.

In some embodiments, Q is

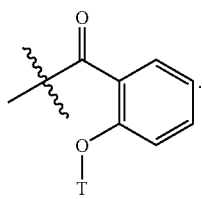 [SMILES: *C(=O)c1ccccc1O[3H] ; "."]

In some embodiments, T is H. In some embodiments, T is $C(O)CH_3$. In some embodiments, T is Z.

In yet another aspect, compounds of the Formula IIIb' are described:

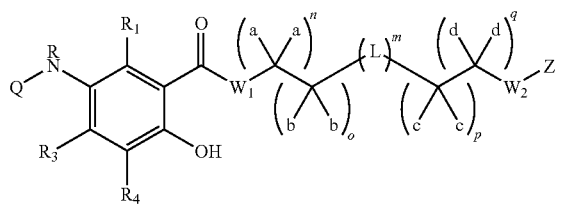

Formula IIIb' and pharmaceutically acceptable salts, hydrates, solvates, prodrugs, enantiomers, and stereoisomers thereof;
wherein
$R_1$, $R_3$, $R_4$, $R_5$, $R_6$, $R_7$, $R_8$, R, L, $W_1$, $W_2$, $W_3$, Z, Q, a, b, c, d, e, g, h, m, n, o, p, q, r, s, t, v, and T are as defined above for Formula IIIb'.

In some embodiments, $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, each a and c is independently H, $CH_3$, —$OCH_3$, —$OCH_2CH_3$, or C(O)OR.
In some embodiments, one b is O—Z, Z is

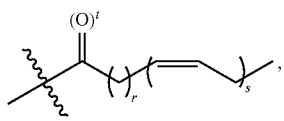

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.

In some embodiments, m is 0.
In some embodiments, each L is independently —S—, —S(O)—, —S(O)$_2$—, or —S—S—.
In some embodiments, each L is independently —O—,

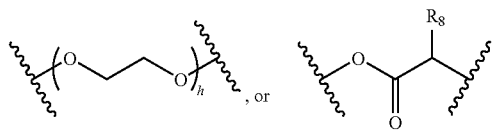

In some embodiments, each L is independently

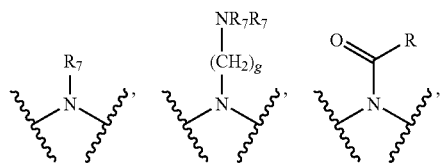

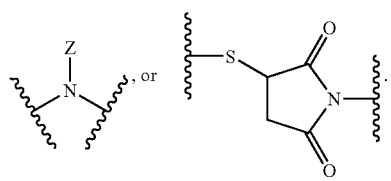

In some embodiments, each L is independently

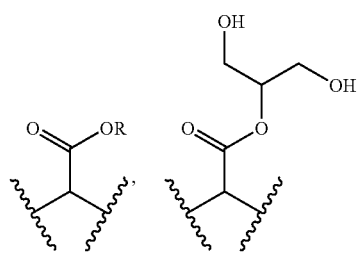

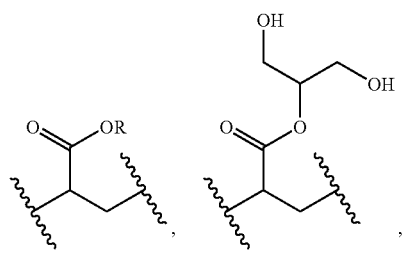

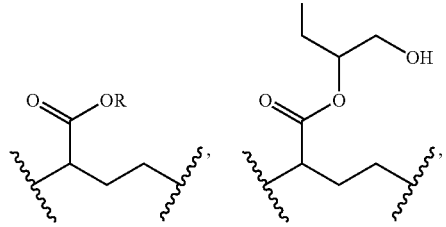

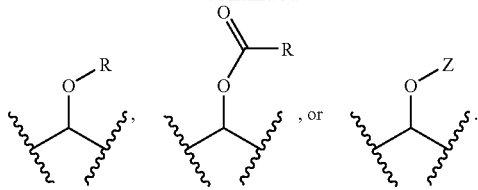

In some embodiments, each L is independently

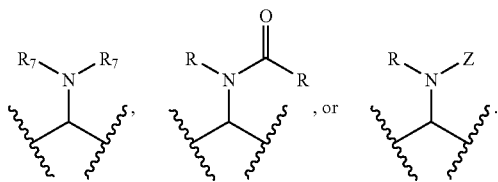

In some embodiments, $R_8$ is e.
In some embodiments, t is 1.
In some embodiments, Q is $C(O)CH_3$. In other embodiments, Q is Z. In other embodiments, Q is

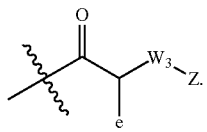

In some embodiments, $W_3$ is O. In other embodiments, $W_3$ is —N(R)—.

In some embodiments, each e is independently any one of the side chains of the naturally occurring amino acids. In other embodiments, e is H.

In yet another aspect, compounds of the Formula IIIc' are described:

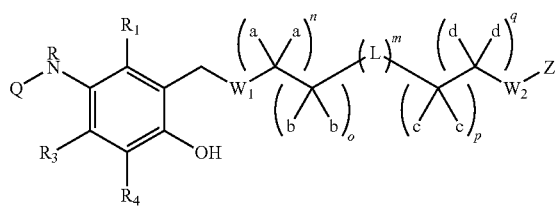

Formula IIIc' and pharmaceutically acceptable salts, hydrates, solvates, prodrugs, enantiomers, and stereoisomers thereof;
wherein
$R_1$, $R_3$, $R_4$, $R_5$, $R_6$, $R_7$, $R_8$, R, L, $W_1$, $W_2$, $W_3$, Z, Q, a, b, c, d, e, g, h, m, n, o, p, q, r, s, t, v, and T are as defined above for Formula IIIc'.

In some embodiments, $R_3$ is Cl or F.
In some embodiments, $W_1$ is O, NH, N substituted with a $C_1$-$C_6$ alkyl, or an oxidized N.
In some embodiments, $W_2$ is O, NH, N substituted with a $C_3$-$C_6$ alkyl, or an oxidized N.
In some embodiments, each a and c is independently H, $CH_3$, —$OCH_3$, —$OCH_2CH_3$, or C(O)OR.
In some embodiments, one b is O—Z, Z is

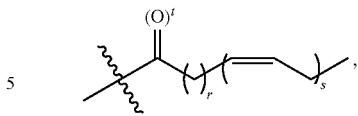

and t is 1.

In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —S(O)$_2$—, or —S—S—.
In some embodiments, each L is independently —O—,

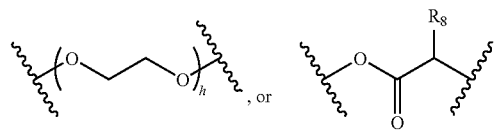

In some embodiments, each L is independently

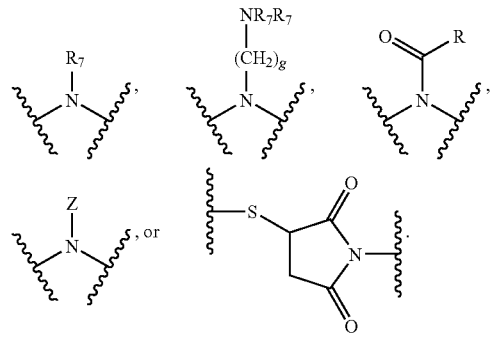

In some embodiments, each L is independently

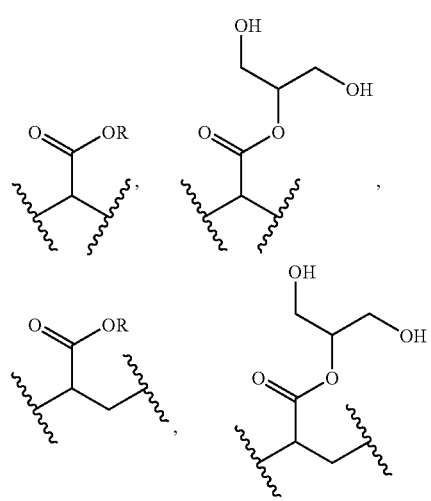

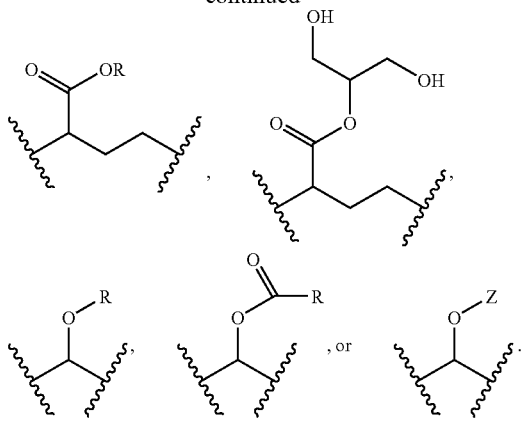

In some embodiments, each L is independently

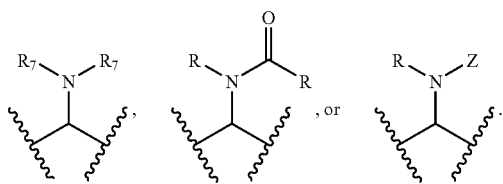

In some embodiments, $R_8$ is e.
In some embodiments, t is 1.
In some embodiments, Q is $C(O)CH_3$. In other embodiments, Q is Z. In other embodiments, Q is

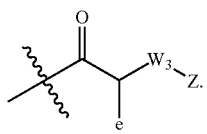

In some embodiments, $W_3$ is O. In other embodiments, $W_3$ is —N(R)—.
In some embodiments, each e is independently any one of the side chains of the naturally occurring amino acids. In other embodiments, e is H.
In yet another aspect, compounds of the Formula IIId' are described:

Formula IIId'

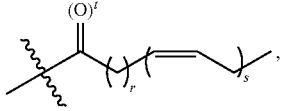

and pharmaceutically acceptable salts, hydrates, solvates, prodrugs, enantiomers, and stereoisomers thereof;
wherein
$R_1$, $R_3$, $R_4$, $R_5$, $R_6$, $R_7$, $R_8$, R, L, $W_1$, $W_2$, $W_3$, Z, Q, a, b, c, d, e, g, h, m, n, o, p, q, r, s, t, v, and T are as defined above for Formula IIId'.

In some embodiments, R is Cl or F.
In some embodiments, $W_1$ is O, NH, N substituted with a $C_1$-$C_6$ alkyl, or an oxidized N.
In some embodiments, $W_2$ is O, NH, N substituted with a $C_1$-$C_6$ alkyl, or an oxidized N.
In some embodiments, each a and c is independently H, $CH_3$, —$OCH_3$, —$OCH_2CH_3$, or C(O)OR.
In some embodiments, one b is O—Z, Z is

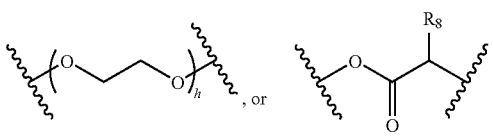

and t is 1.
In some embodiments, one d is C(O)OR.
In some embodiments n, o, p, and q are each 1.
In some embodiments, two of n, o, p, and q are each 1. In other embodiments, three of n, o, p, and q are each 1.
In some embodiments, m is 0.
In some embodiments, each L is independently —S—, —S(O)—, —S(O)$_2$—, or —S—S—.
In some embodiments, each L is independently —O—,

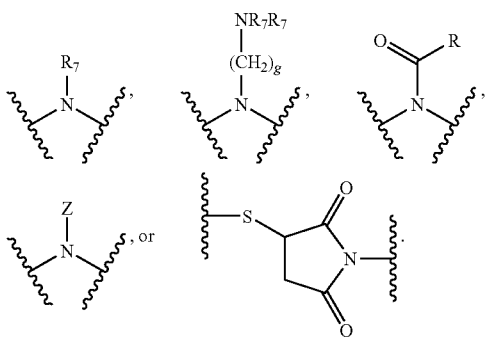

In some embodiments, each L is independently

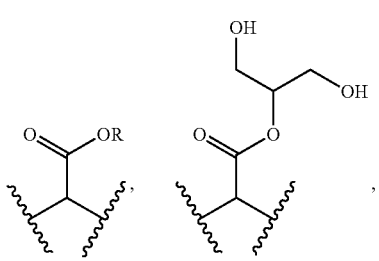

In some embodiments, each L is independently

-continued

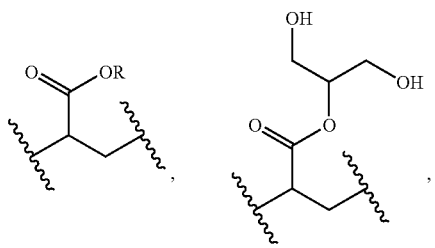

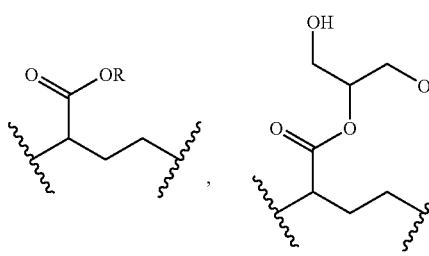

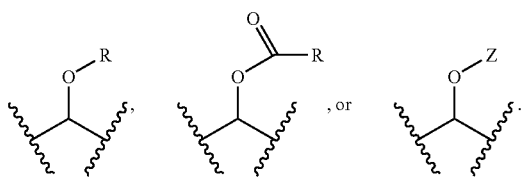

In some embodiments, each L is independently

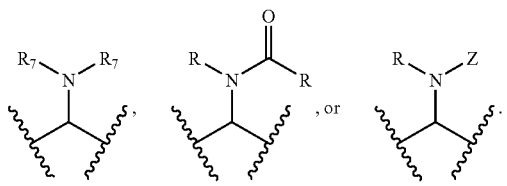

In some embodiments, $R_8$ is e.

In some embodiments, t is 1.

In some embodiments, Q is C(O)CH$_3$. In other embodiments, Q is Z. In other embodiments, Q is

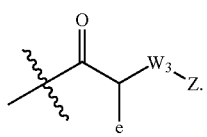

In some embodiments, $W_3$ is O. In other embodiments, $W_3$ is —N(R)—.

In some embodiments, each e is independently any one of the side chains of the naturally occurring amino acids. In other embodiments, e is H.

In yet another aspect, compounds of the Formula IIIe' are described:

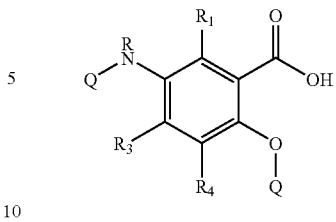

Formula IIIe' and pharmaceutically acceptable salts, hydrates, solvates, prodrugs, enantiomers, and stereoisomers thereof;

wherein $R_1$, $R_3$, $R_4$, $R_5$, $R_6$, R, $W_3$, Z, Q, e, r, s, t, v, and T are as defined above for Formula IIIe'.

In some embodiments, $R_3$ is Cl or F.

In some embodiments, t is 1.

In some embodiments, Q is C(O)CH$_3$. In other embodiments, Q is Z. In other embodiments, Q is

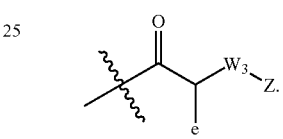

In some embodiments, $W_3$ is O. In other embodiments, $W_3$ is —N(R)—.

In some embodiments, each e is independently any one of the side chains of the naturally occurring amino acids. In other embodiments, e is H.

In yet another aspect, compounds of the Formula IIIf' are described:

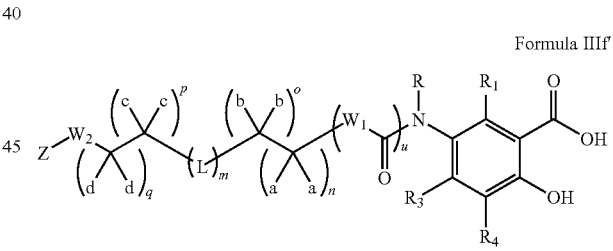

Formula IIIf' and pharmaceutically acceptable salts, hydrates, solvates, prodrugs, enantiomers, and stereoisomers thereof;

wherein $R_1$, $R_3$, $R_4$, $R_5$, $R_6$, $R_7$, $R_8$, R, L, $W_1$, $W_2$, Z, a, b, c, d, e, g, h, m, n, o, p, q, r, s, t, u, and v are as defined above for Formula IIIf'.

In some embodiments, $R_3$ is Cl or F.

In some embodiments, $W_1$ is O, NH, N substituted with a $C_1$-$C_6$ alkyl, or an oxidized N.

In some embodiments, $W_2$ is O, NH, N substituted with a $C_1$-$C_6$ alkyl, or an oxidized N.

In some embodiments, each a and c is independently H, CH$_3$, —OCH$_3$, —OCH$_2$CH$_3$, or C(O)OR.

In some embodiments, one b is O—Z, Z is

215

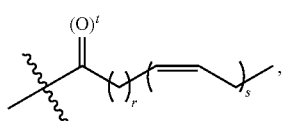

and t is 1.

In some embodiments, one d is C(O)OR.

In some embodiments n, o, p, and q are each 1.

In some embodiments, two of n, o, p, and q are each 1. In other embodiments, three of n, o, p, and q are each 1.

In some embodiments, m is 0.

In some embodiments, each L is independently —S—, —S(O)—, —S(O)$_2$—, or —S—S—.

In some embodiments, each L is independently —O—,

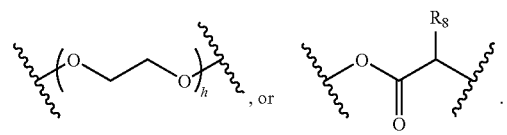

In some embodiments, each L is independently

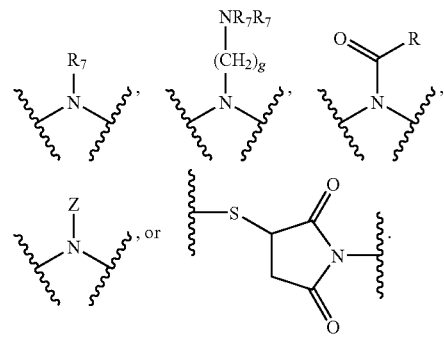

In some embodiments, each L is independently

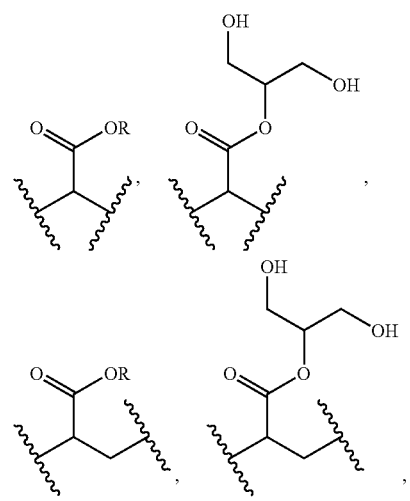

216

-continued

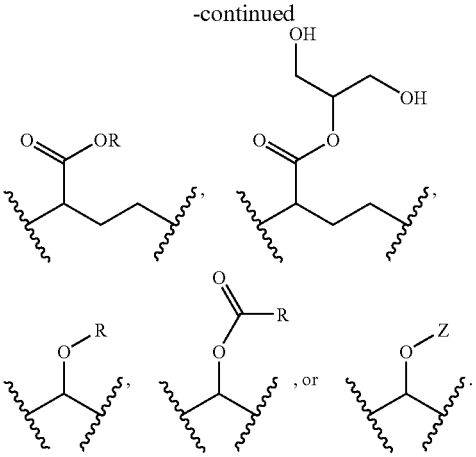

In some embodiments, each L is independently

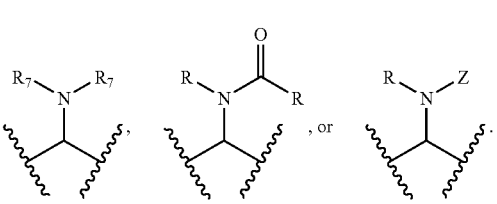

In some embodiments, $R_8$ is e.

In some embodiments, t is 1.

In some embodiments, each e is independently any one of the side chains of the naturally occurring amino acids. In other embodiments, e is H.

In yet another aspect, compounds of the Formula IIIg' are described:

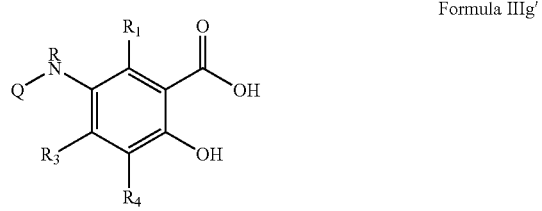

Formula IIIg' and pharmaceutically acceptable salts, hydrates, solvates, prodrugs, enantiomers, and stereoisomers thereof; wherein $R_1$, $R_3$, $R_4$, $R_5$, $R_6$, R, $W_3$, Z, Q, e, r, s, t, v, and T are as defined above for Formula IIIg'.

In some embodiments, $R_3$ is Cl or F.

In some embodiments, t is 1.

In some embodiments, Q is C(O)CH$_3$. In other embodiments, Q is Z. In other embodiments, Q is

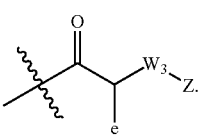

In some embodiments, $W_3$ is O. In other embodiments, $W_3$ is —N(R)—.

In some embodiments, each e is independently any one of the side chains of the naturally occurring amino acids. In other embodiments, e is H.

In any of the above Formulae, any one or more of H may be substituted with a deuterium. It is also understood in any of the above Formulae that a methyl substituent can be substituted with a $C_1$-$C_6$ alkyl.

The following embodiments are descriptive of the following Formulae: Formula I, Formula Ia, Formula Ib, Formula Ic, Formula Id, Formula If, Formula Ih, and Formula Ii.

In some embodiments, one Z is

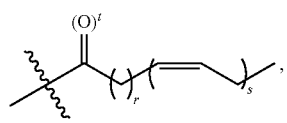

and r is 2.

In some embodiments, one Z is

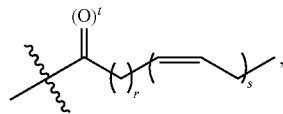

and r is 3.

In some embodiments, one Z is

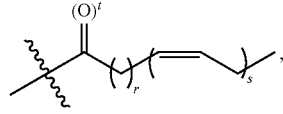

and r is 7.

In some embodiments, one Z is

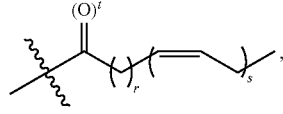

and s is 3.

In some embodiments, one Z is

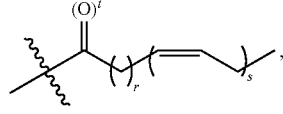

and s is 5.

In some embodiments, one Z is

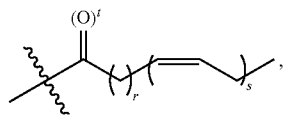

and s is 6.

In some embodiments of Formula II, one Z is

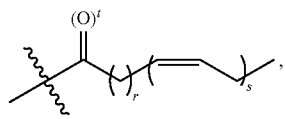

r is 7 and s is 3.

The following embodiments are descriptive of the following Formulae: Formula III, Formula IIIa, Formula IIIb, Formula IIIc, Formula IIId, Formula IIIe, Formula IIIf, and Formula IIIg.

In some embodiments, Z or Z' is

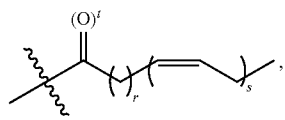

and r is 2.

In some embodiments, Z or Z' is

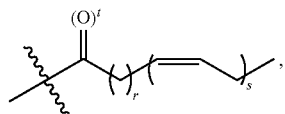

and r is 3.

In some embodiments, Z or Z' is

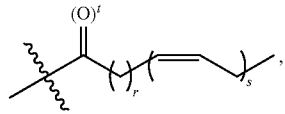

and r is 7.

In some embodiments, Z or Z' is

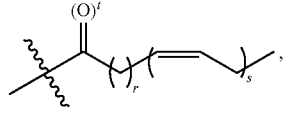

and s is 3.

In some embodiments, Z or Z' is

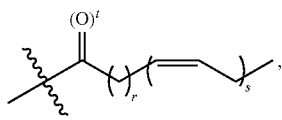

and s is 5.

In some embodiments, Z or Z' is

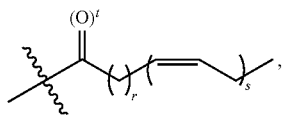

and s is 6.

The following embodiments are descriptive of the following Formulae: Formula I', Formula Ia', Formula Ib', Formula Ic', Formula Id', Formula If', Formula Ih', and Formula Ii'.

In some embodiments, one Z is

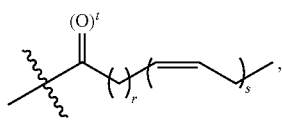

and r is 2.

In some embodiments, one Z is

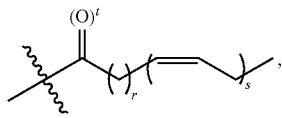

and r is 3.

In some embodiments, one Z is

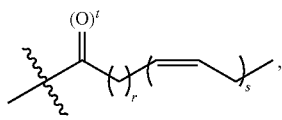

and r is 7.

In some embodiments, one Z is

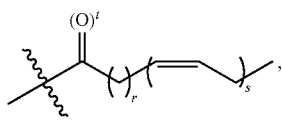

and s is 3.

In some embodiments, one Z is

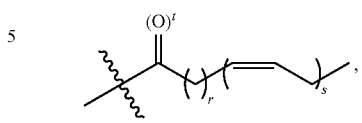

and s is 5.

In some embodiments, one Z is

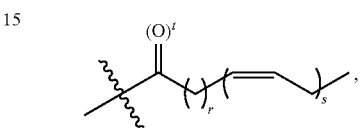

and s is 6.

In some embodiments, one Z is

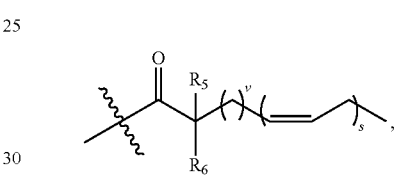

and v is 1.

In some embodiments, one Z is

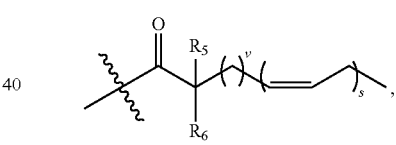

and v is 2.

In some embodiments, one Z is

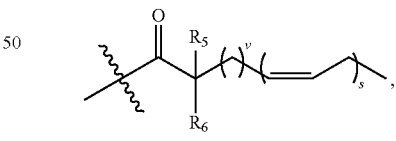

and v is 6.

In other embodiments, one Z is

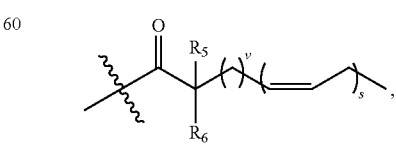

and s is 3.

In some embodiments, one Z is

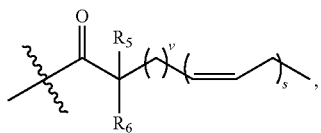

and s is 5.

In other embodiments, one Z is

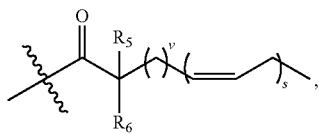

and s is 6.

In some embodiments of Formula II', one Z is

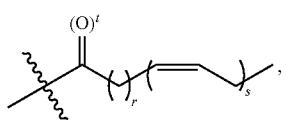

r is 7 and s is 3.

In some embodiments of Formula II', one Z is

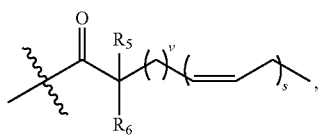

r is 6 and s is 3.

The following embodiments are descriptive of the following Formulae: Formula III', Formula IIIa', Formula IIIb', Formula IIIc', Formula IIId', Formula IIIe', Formula IIIf', and Formula IIIg'.

In some embodiments, Z or Z' is

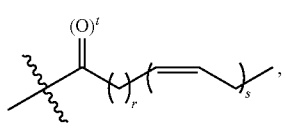

and r is 2.

In some embodiments, Z or Z' is

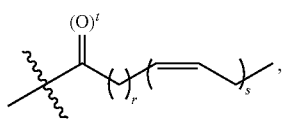

and r is 3.

In some embodiments, Z or Z' is

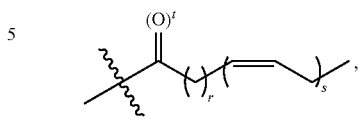

and r is 7.

In some embodiments, Z or Z' is

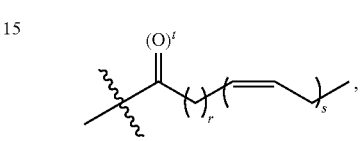

and s is 3.

In some embodiments, Z or Z' is

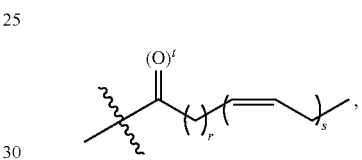

and s is 5.

In some embodiments, Z or Z' is

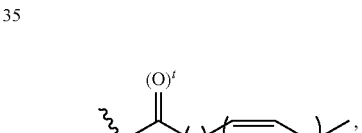

and s is 6.

In some embodiments, Z or Z' is

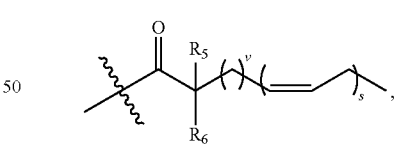

and v is 1.

In some embodiments, Z or Z' is

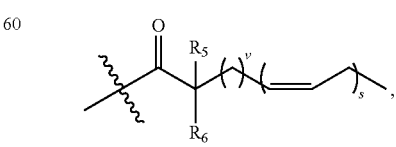

and v is 2.

In some embodiments, Z or Z' is

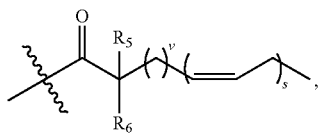

and v is 6.

In other embodiments, Z or Z' is

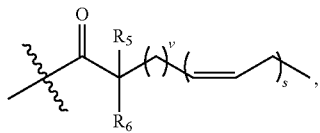

and s is 3.

In some embodiments, Z or Z' is

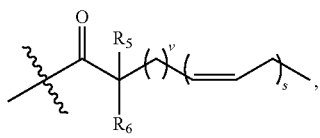

and s is 5.

In other embodiments, Z or Z' is

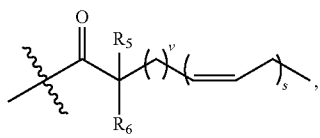

and s is 6.

Methods for Using Compounds of the Invention

The invention also includes methods for upregulating an anti-inflammatory pathway and downregulating a proinflammatory pathway in a cell.

In one embodiment, the method comprises contacting a cell with a compound of the invention in an amount sufficient to upregulate an anti-inflammatory pathway and down regulate a proinflammatory pathway in the cell. In general, any cell having, or capable of having, inflammatory activity or capable of expressing NFκB can be used. The cell can be provided in any form. For example, the cell can be provided in vitro, ex vivo, or in vivo. Inflammatory activity can be measured using any method known in the art, e.g., methods as described in Tran P. O. et al *Diabetes* 2002, 51, 1772-1778. Illustrative examples of cells capable of inflammatory activity include, but are not limited to, immune cells including monocytes, macrophages, T-cell, Th-1, Th-2, Th-17, Treg, lymphocytes, spleen cells, muscle, adipose or fat, vascular cells such as endothelial or pericyte, bone, gum, nerve, brain, glial, astrocytes, nerve, liver, kidney, pancreas including islet cells such as beta cells, lung, heart, breast, bladder, stomach, colon, rectal, small intestine, skin, esophageal, eye, larynx, uterine, ovarian, prostate, tendon, bone marrow, blood, lymph, testicular, vaginal and neoplastic cells.

Also provided in the invention is a method for inhibiting, preventing, or treating inflammation or an inflammatory disease in a subject. The inflammation can be associated with an inflammatory disease or a disease where inflammation contributes to the disease. Inflammatory diseases can arise where there is an inflammation of the body tissue. These include local inflammatory responses and systemic inflammation. Examples of such diseases include, but are not limited to: organ transplant rejection; reoxygenation injury resulting from organ transplantation (see Grupp et al. *J. Mol. Cell. Cardiol.* 1999, 31, 297-303) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, chronic obstructive airway disease, and cystic fibrosis; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis. Metabolic disease such as type II diabetes mellitus; the prevention of type I diabetes; dyslipidemia; hypertriglyceridemia; diabetic complications, including, but not limited to glaucoma, retinopathy, macula edema, nephropathy, such as microalbuminuria and progressive diabetic nephropathy, polyneuropathy, diabetic neuropathy, atherosclerotic coronary arterial disease, peripheral arterial disease, nonketotic hyperglycemichyperosmolar coma, mononeuropathies, autonomic neuropathy, joint problems, and a skin or mucous membrane complication, such as an infection, a shin spot, a candidal infection or necrobiosis lipoidica diabeticorum; immune-complex vasculitis, systemic lupus erythematosus; inflammatory diseases of the heart such as cardiomyopathy, ischemic heart disease hypercholesterolemia, and atherosclerosis; as well as various other diseases that can have significant inflammatory components, including preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, arrhythmia, prevention of sudden death, muscle wasting diseases such as Duchenne's Muscular Dystrophy, inflammatory myopathies such as dermatomositis, inclusion body myositis, and polymyositis, and cancer cachexia. Also inflammation that results from surgery and trauma can be treated with compound of the invention.

In some embodiments, the subject is administered an effective amount of a compound of the invention.

The invention also includes pharmaceutical compositions useful for treating or preventing an inflammatory disease, or for inhibiting inflammation activity, or more than one of these activities. The compositions can be suitable for internal use and comprise an effective amount of a compound of the invention and a pharmaceutically acceptable carrier. The compounds of the invention are especially useful in that they demonstrate very low peripheral toxicity or no peripheral toxicity.

The compounds of the invention can each be administered in amounts that are sufficient to treat or prevent an inflammatory disease or a reperfusion disease and/or prevent the development thereof in subjects.

Administration of the compounds of the invention can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a compound of the invention and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the compound of the invention is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the compounds of the invention.

The compounds of the invention can be also formulated as a suppository that can be prepared from fatty emulsions or suspensions; using polyalkylene glycols such as propylene glycol, as the carrier.

The compounds of the invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the conterts of which are herein incorporated by reference in their entirety.

compounds of the invention can also be delivered by the use of monoclonal antibodies as individual carriers to which the compounds of the invention are coupled. The compounds of the invention can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the compounds of the invention can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, compounds of the invention are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the compound of the invention by weight or volume.

The dosage regimen utilizing the compound of the invention is selected in accordance with a variety of factors including type, species, age, weight, sex and medical condition of the patient; the severity of the condition to be treated; the route of administration; the renal or hepatic function of the patient; and the particular compound of the invention employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 5,000 mg of the compound of the invention per day. Compositions for in vivo or in vitro use can contain about 20, 50, 75, 100, 150, 250, 500, 750, 1,000, 1,250, 2,500, 3,500, or 5,000 mg of the compound of the invention. In one embodiment, the compositions are in the form of a tablet that can be scored. Effective plasma levels of the compound of the invention can range from about 0.002 mg to about 100 mg per kg of body weight per day. Appropriate dosages of the compounds of the invention can be determined as set forth in Goodman, L. S.; Gilman, A. *The Pharmacological Basis of Therapeutics,* $5^{th}$ ed.; MacMillan: New York, 1975; 201-226.

compounds of the invention can be administered in a single daily dose, or the total daily dosage can be administered in divided doses of two, three or four times daily. Furthermore, compounds of the invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the compound of the invention ranges from about 0.1% to about 15%, w/w or w/v.

Methods for Making the Compounds of the Invention

Examples of synthetic pathways useful for making compounds of the invention are set forth in the Examples below and generalized in Schemes 1-18.

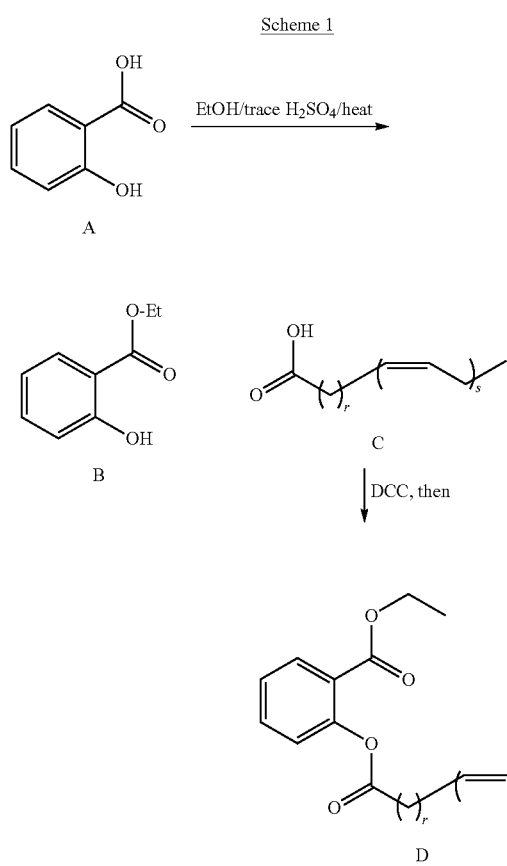

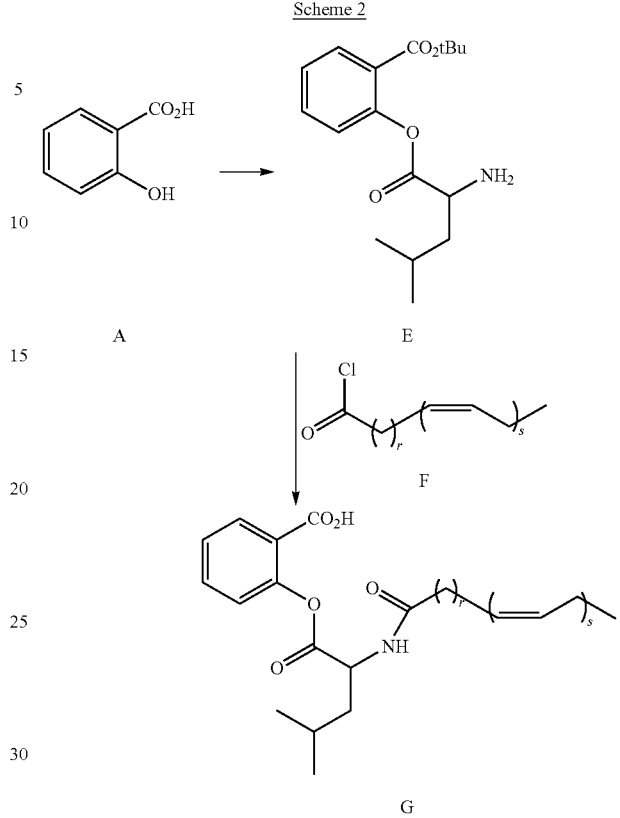

wherein r and s are as defined above.

Compound A can be esterified in the presence of acid catalyst and a suitable protecting alcohol such as, e.g., tert-butanol, followed by coupling to an activated amino acid to give compound E. Condensation of the amino compound E with a fatty acid chloride of formula F affords compounds of formula G. The ester may be deprotected using methods disclosed in Greene et al. *Protecting Groups in Organic Chemistry*, 4th ed.; Wiley & Sons: Hoboken, N.J., 2007; Chapter 5.

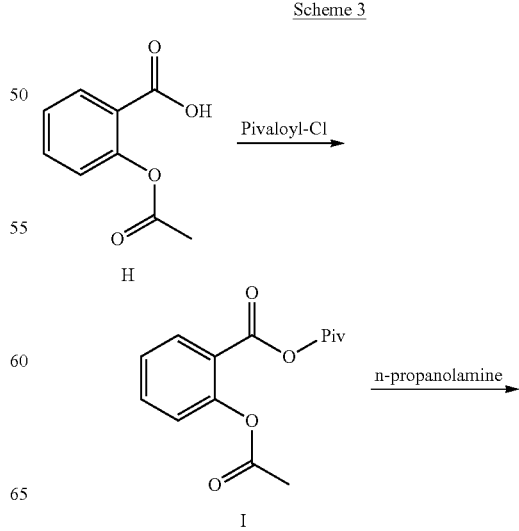

wherein r and s are as defined above.

Compound A can be esterified in the presence of acid catalyst and a suitable alcohol, e.g., ethanol to give ester B. Activation of compound B with a coupling reagent such as for example DCC, CDI, or EDC, optionally with a tertiary amine base and/or catalyst, e.g., DMAP, followed by addition of a fatty acid of formula C affords compounds of formula D. Alternatively, compound A can be esterified with benzyl bromide in the presence of base, e.g., CsCO$_3$, then subjected to the remaining steps of Scheme 1. Hydrogenolysis of the benzyl ester derived from A, for example using Pd/C and H$_2$, can yield the free acid of compounds of formula D.

-continued

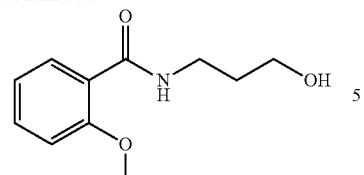
J

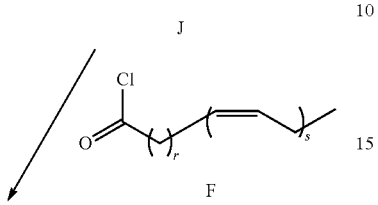
F

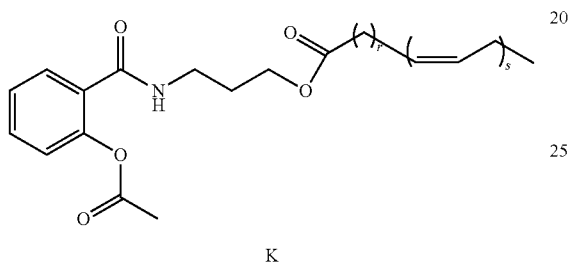
K wherein r and s are as defined above.

Acid H can be activated by esterification with a suitable activating agent such as, e.g., pivaloyl chloride, followed by condensation with an amino alcohol such as for example n-propanolamine, to give compound J. Condensation of the alcohol compound J with a fatty acid chloride of formula F affords compounds of formula K. Diacylated compounds of the invention can be made by subjecting compound A to the above procedure.

Scheme 4

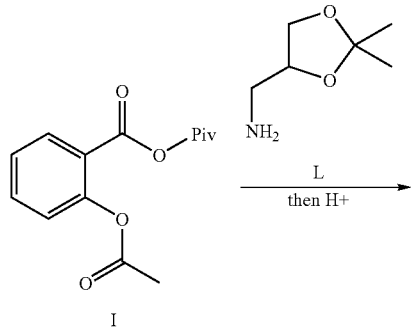

-continued

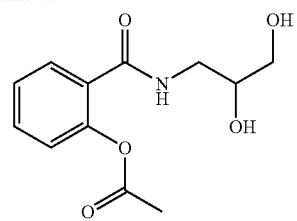
M

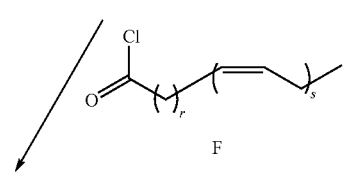
F

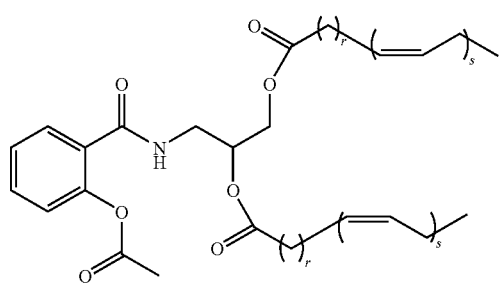
N wherein r and s are as defined above.

Activated ester I (see Scheme 3) can be condensed with an amino-masked diol L, which after acid workup gives the unmasked diol compound M. Condensation of the diol compound M with a fatty acid chloride of formula F affords compounds of formula N.

Scheme 5

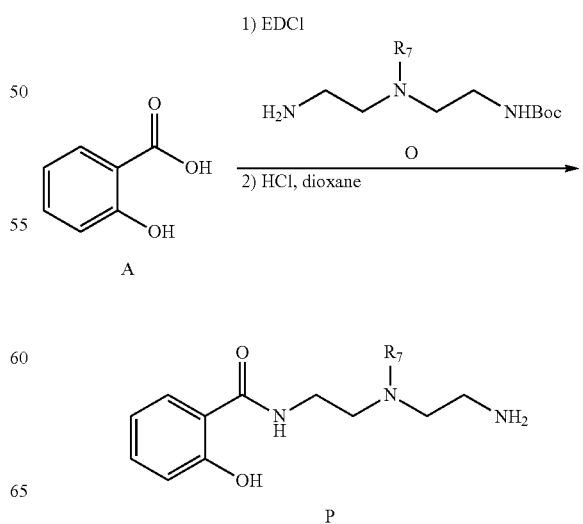

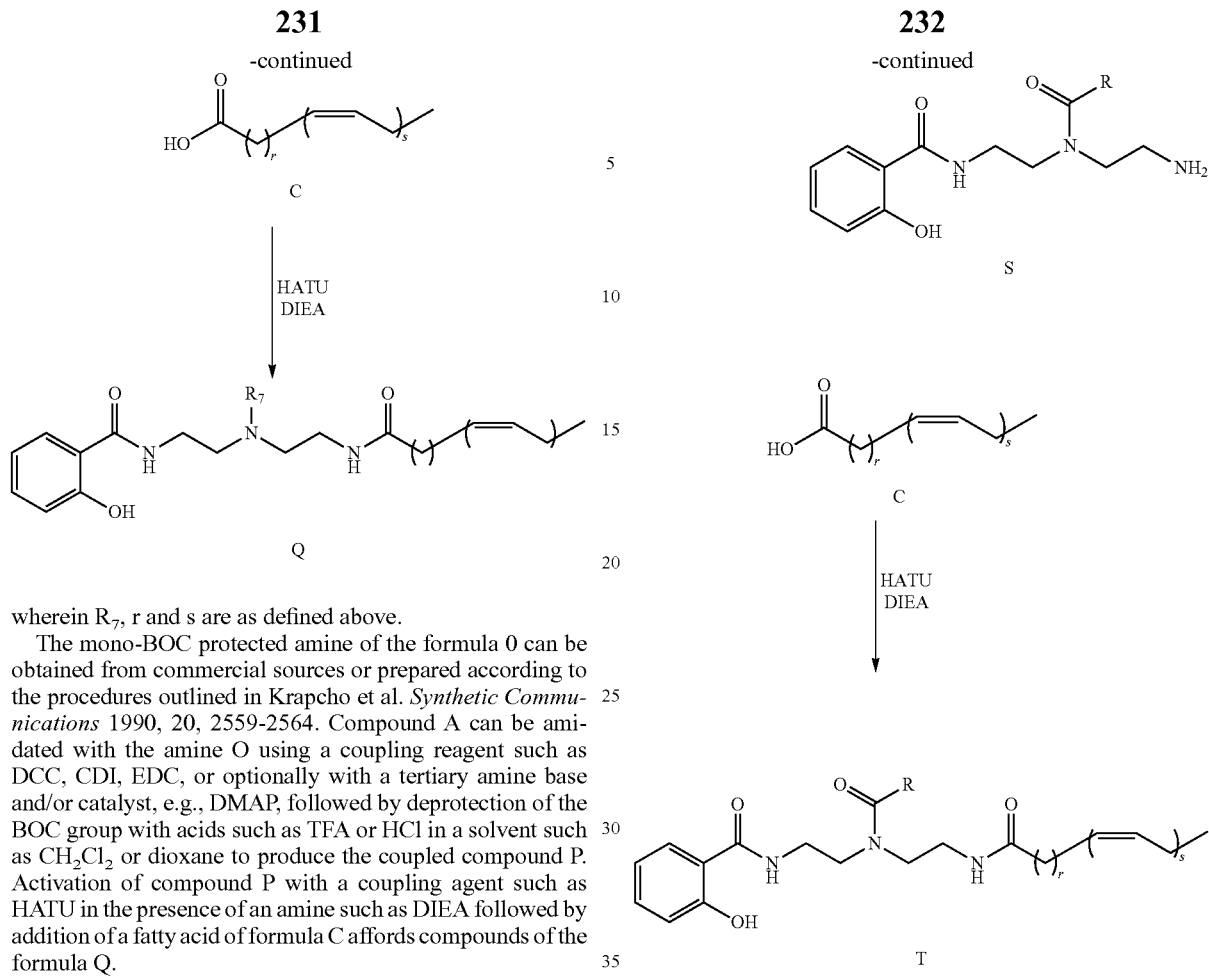

wherein $R_7$, r and s are as defined above.

The mono-BOC protected amine of the formula O can be obtained from commercial sources or prepared according to the procedures outlined in Krapcho et al. *Synthetic Communications* 1990, 20, 2559-2564. Compound A can be amidated with the amine O using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound P. Activation of compound P with a coupling agent such as HATU in the presence of an amine such as DIEA followed by addition of a fatty acid of formula C affords compounds of the formula Q.

wherein R, r and s are as defined above.

The acylated amine of the formula R can be prepared using the procedures outlined in Andruszkiewicz et al. *Synthetic Communications* 2008, 38, 905-913. Compound A can be amidated with the amine R using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound S. Activation of compound S with a coupling agent such as HATU in the presence of an amine such as DIEA followed by addition of a fatty acid of formula C affords compounds of the formula T.

Scheme 6

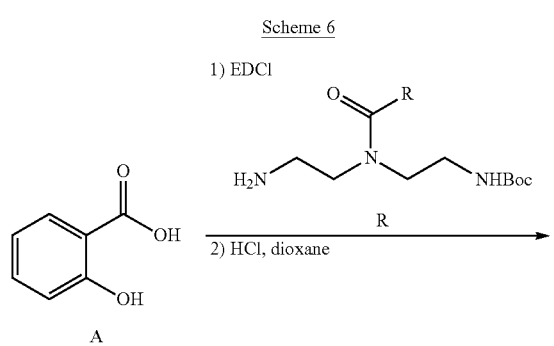

Scheme 7

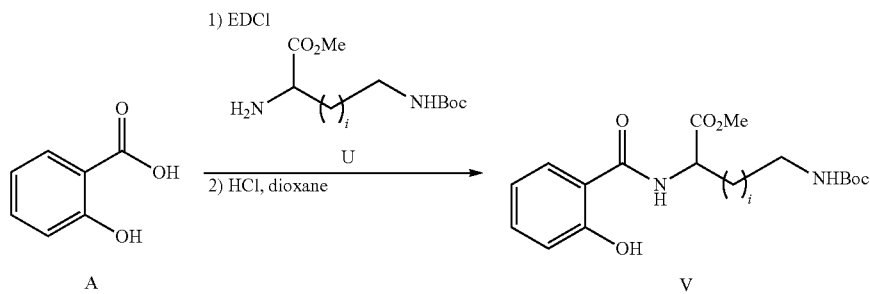

wherein r and s are as defined above.

Compound A can be amidated with the corresponding amine U (where i=0, 1, 2 or 3) using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound V. Activation of compound V with a coupling agent such as HATU in the presence of an amine such as DIEA followed by addition of a fatty acid of formula C affords compounds of the formula W. Hydrolysis of the ester under basic conditions such as NaOH or LiOH produces the corresponding acid, which can be coupled with glycidyl to afford compounds of the formula X.

wherein r and s are as defined above.

The amine Y can be prepared according to the procedures outlined in Dahan et al. *J. Org. Chem.* 2007, 72, 2289-2296. Compound A can be coupled with the amine Y using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound Z. Activation of compound Z with a coupling agent such as HATU in the presence of an amine such as DIEA followed by addition of a fatty acid of formula C affords compounds of the formula AA.

Scheme 9

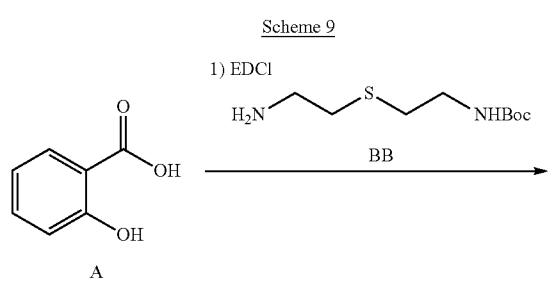

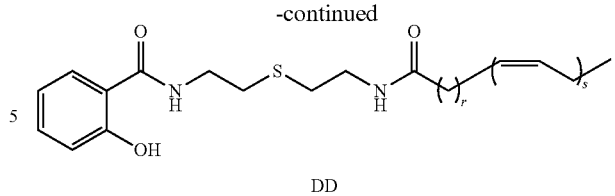

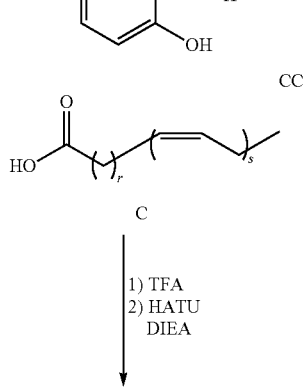

wherein r and s are as defined above.

Compound A can be amidated with the commercially available amine BB using a coupling reagent such as DCC, CDI, EDC, or optionally with a tertiary amine base and/or catalyst, e.g., DMAP, to afford compound CC. The BOC group in compound CC can be removed with acids such as TFA or HCl in a solvent such as $CH_2Cl_2$ or dioxane and the resulting amine can be coupled with a fatty acid of formula C using a coupling agent such as HATU in the presence of an amine such as DIEA to afford compounds of the formula DD. To those skilled in the art, the sulfur group in formula CC can be oxidized to the corresponding sulfoxide or sulfone using an oxidizing agent such as $H_2O_2$ or oxone.

Scheme 10

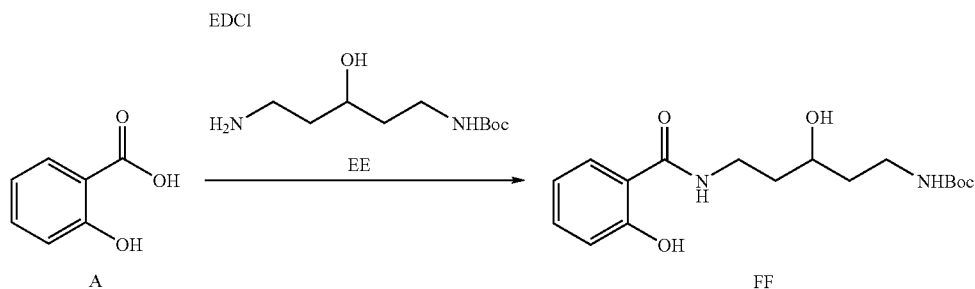

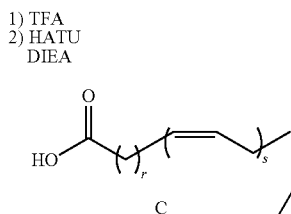

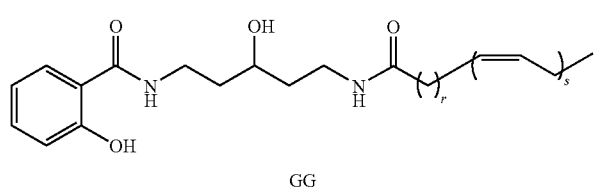

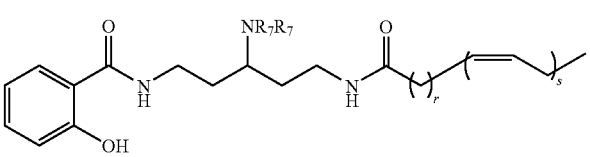

wherein $R_7$, r and s are as defined above.

The amine EE can be prepared from the commercially available diamine according to the procedures outlined in Dahan et al. *J. Org. Chem.* 2007, 72, 2289-2296. Compound A can be amidated with the amine EE using a coupling reagent such as DCC, CDI, EDC, or optionally with a tertiary amine base and/or catalyst, e.g., DMAP, to afford compound FF. The BOC group of compound FF can be removed with acids such as TFA or HCl in a solvent such as $CH_2Cl_2$ or dioxane and the resulting amine can be coupled with a fatty acid of formula C using HATU in the presence of an amine such as DIEA to afford compounds of the formula GG. To those skilled in the art, the hydroxyl group in compound FF can be further acylated or converted to an amino group by standard mesylation chemistry followed by displacement with sodium azide and hydrogenation over a catalyst such as Pd/C. The amine can be further acylated or alkylated, followed by the removal of the BOC group. The resulting amine can be coupled with a fatty acid of the formula C to afford compounds of the formula HH.

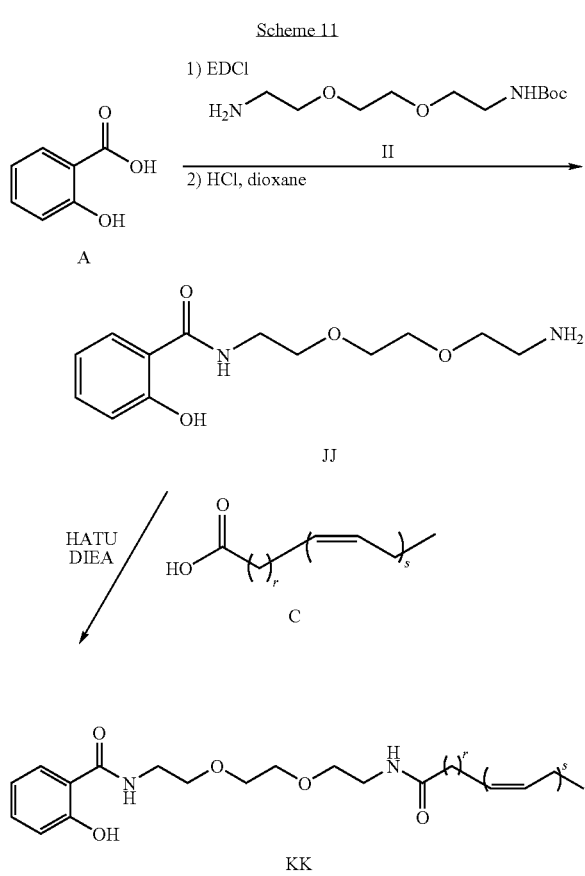

wherein r and s are as defined above.

Compound A can be amidated with the commercially available amine II using a coupling reagent such as DCC, CDI, EDC, optionally with a tertiary amine base and/or catalyst, e.g., DMAP to afford compound JJ. The BOC group in compound JJ can be removed with acids such as TFA or HCl in a solvent such as $CH_2Cl_2$ or dioxane. The resulting amine can be coupled with a fatty acid of the formula C using a coupling agent such as HATU in the presence of an amine such as DIEA to afford compounds of the formula KK.

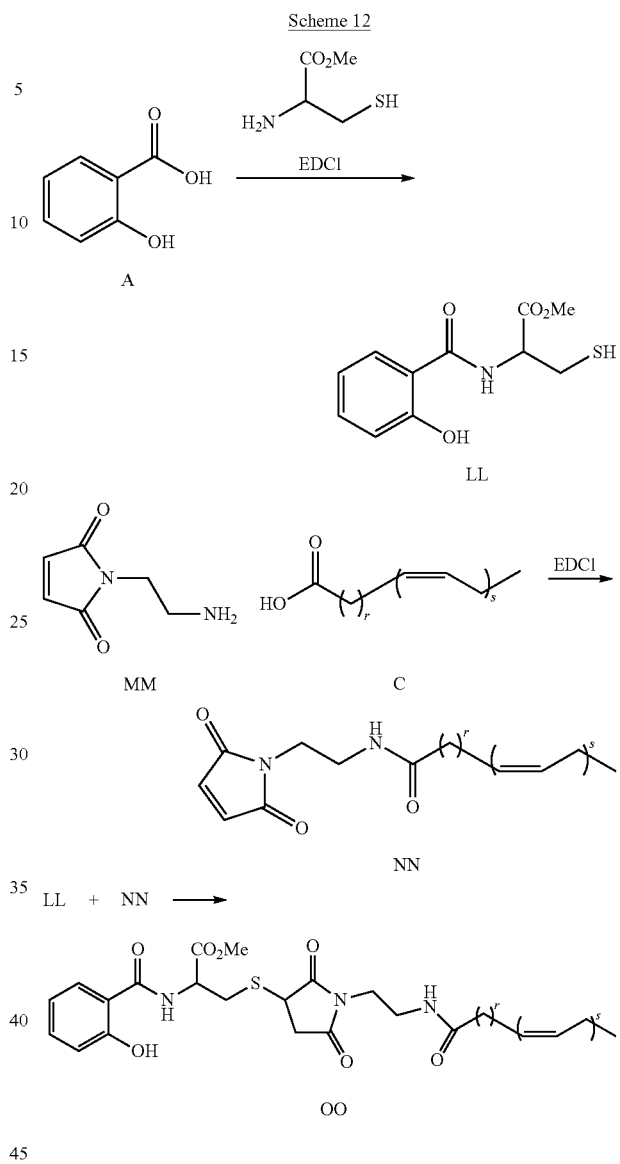

wherein r and s are as defined above.

Compound A can be amidated with the commercially available cysteine methyl ester using a coupling reagent such as DCC, CDI, EDC, or optionally with a tertiary amine base and/or catalyst, e.g., DMAP, to afford compound LL. The commercially available maleimide derivative MM can be coupled with a fatty acid of the formula C using a coupling agent such as HATU or EDCI to afford compounds of the formula CC. Compound LL can be coupled to compounds of the formula NN in a solvent such as acetonitrile to afford compounds of the formula OO.

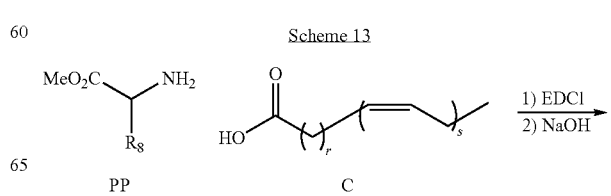

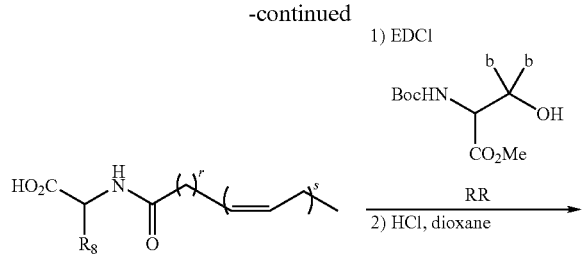
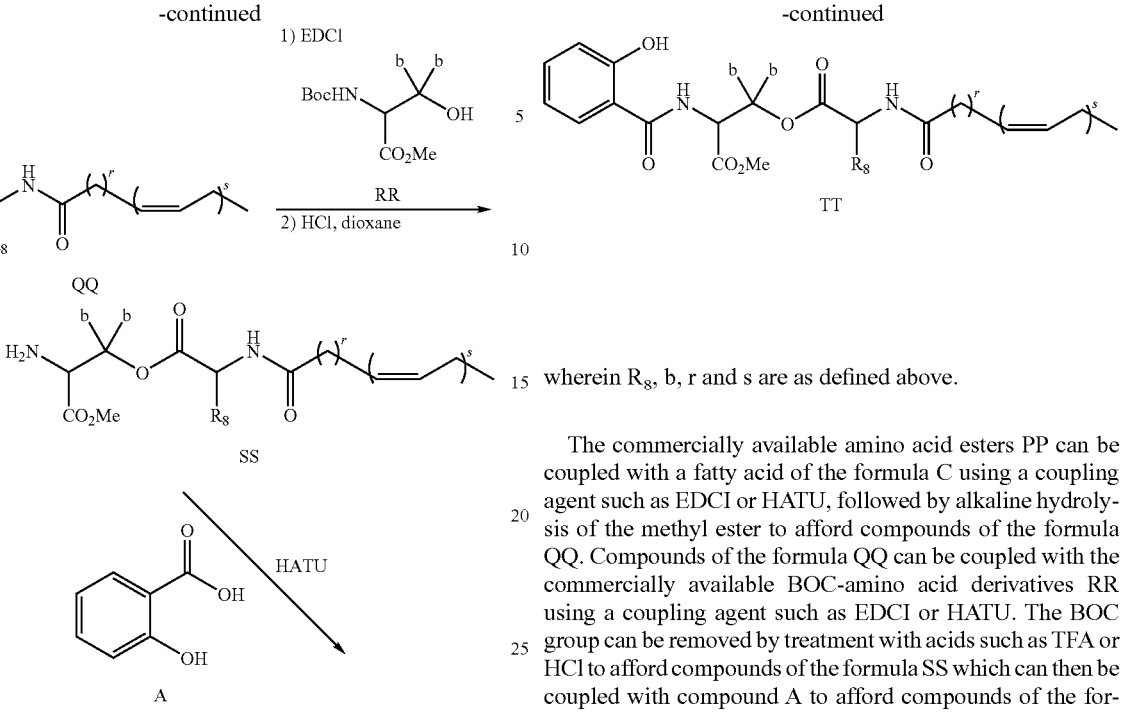

wherein $R_8$, b, r and s are as defined above.

The commercially available amino acid esters PP can be coupled with a fatty acid of the formula C using a coupling agent such as EDCI or HATU, followed by alkaline hydrolysis of the methyl ester to afford compounds of the formula QQ. Compounds of the formula QQ can be coupled with the commercially available BOC-amino acid derivatives RR using a coupling agent such as EDCI or HATU. The BOC group can be removed by treatment with acids such as TFA or HCl to afford compounds of the formula SS which can then be coupled with compound A to afford compounds of the formula TT.

Scheme 14

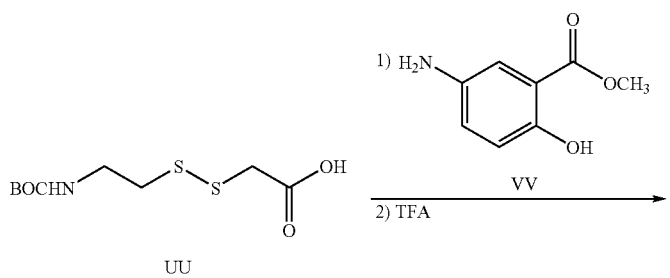

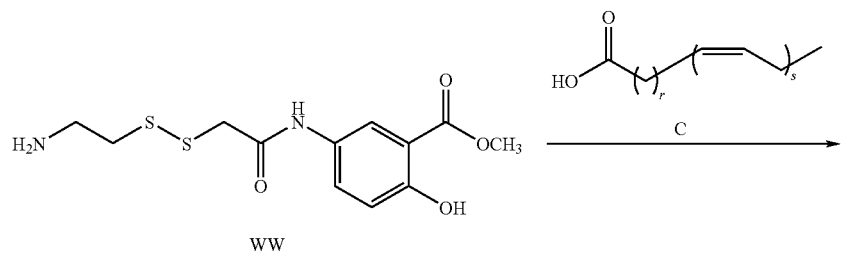

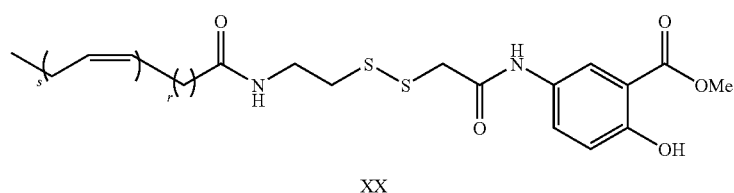

wherein r and s are as defined above.

The acid UU can be prepared using literature procedures (Jacobson, K. et al. *Bioconjugate Chem.* 1995, 6, 255-263) Compound UU can be coupled with aniline VV using a suitable coupling agent such as DCC, CDI, EDC, or optionally with a tertiary amine base and/or catalyst, e.g., DMAP, which, after deprotection with an acid such as TFA or HCl provides Compound WW. Compound WW can be coupled with a fatty acid of the formula C using a suitable coupling agent such as HATU, CDI, EDC, or optionally with a tertiary amine base and/or catalyst, e.g., DMAP, to produce compounds XX. Compounds XX can be hydrolyzed to the free benzoic acid analogs using standard basic saponification methods such as NaOH or LiOH.

Scheme 15

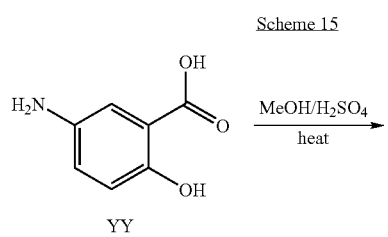

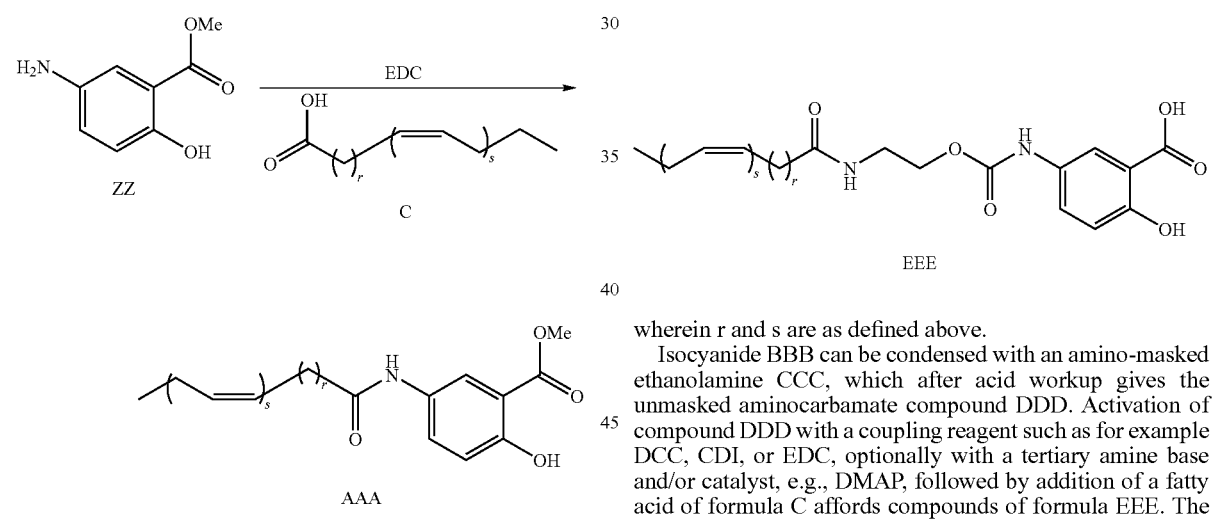

wherein r and s are as defined above.

Compound YY can be esterified in the presence of acid catalyst and a suitable alcohol, e.g., methanol to give ester ZZ. Activation of compound ZZ with a coupling reagent such as for example DCC, CDI, or EDC, optionally with a tertiary amine base and/or catalyst, e.g., DMAP, followed by addition of a fatty acid of formula C affords compounds of formula AAA. Saponification of the esters of formula AAA with a suitable base, such as for example NaOH, can yield the free acid of compounds of formula AAA. Alternatively, compound YY can be esterified with benzyl bromide in the presence of base, e.g., CsCO₃, then subjected to the remaining steps of Scheme 15. Hydrogenolysis of the benzyl ester derived from YY, for example using Pd/C and H₂, can yield the free acid of compounds of formula AAA. Diacylated compounds of the invention can be made by subjecting compound YY to the above procedure.

Scheme 16

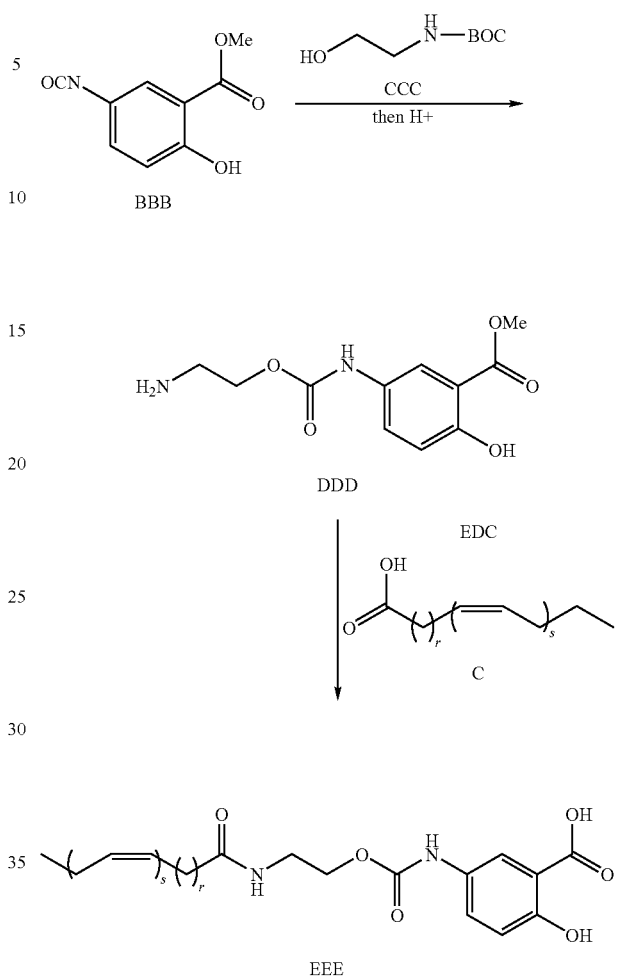

wherein r and s are as defined above.

Isocyanide BBB can be condensed with an amino-masked ethanolamine CCC, which after acid workup gives the unmasked aminocarbamate compound DDD. Activation of compound DDD with a coupling reagent such as for example DCC, CDI, or EDC, optionally with a tertiary amine base and/or catalyst, e.g., DMAP, followed by addition of a fatty acid of formula C affords compounds of formula EEE. The ester may be deprotected using methods disclosed in Greene et al. *Protecting Groups in Organic Chemistry,* 4th ed.; Wiley & Sons: Hoboken, N.J., 2007; Chapter 5.

Scheme 17

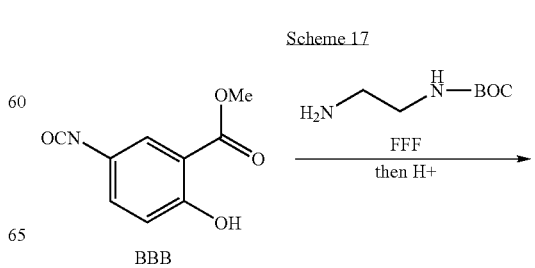

243
-continued

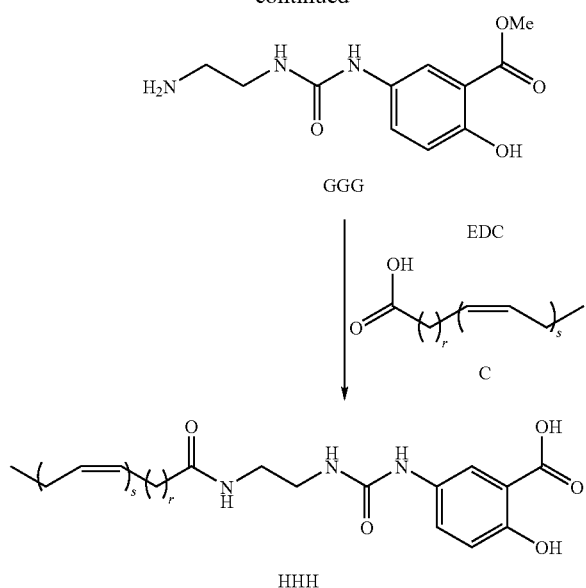

wherein r and s are as defined above.

Isocyanide BBB can be condensed with an mono amino-masked ethylenediamine FFF, which after acid workup gives the unmasked urea compound GGG. Activation of compound GGG with a coupling reagent such as for example DCC, CDI, or EDC, optionally with a tertiary amine base and/or catalyst, e.g., DMAP, followed by addition of a fatty acid of formula C affords compounds of formula HHH. The ester may be deprotected using methods disclosed in Greene et al. *Protecting Groups in Organic Chemistry*, 4th ed.; Wiley & Sons: Hoboken, N.J., 2007; Chapter 5.

Scheme 18

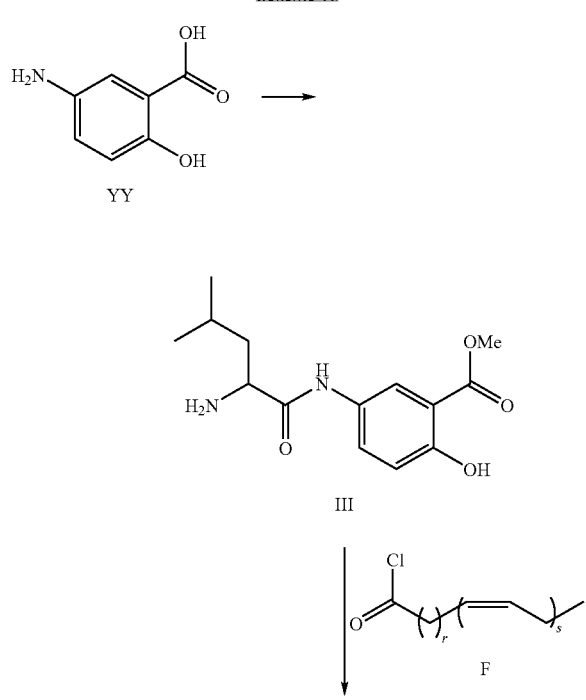

244
-continued

JJJ wherein r and s are as defined above.

Compound YY can be esterified in the presence of acid catalyst and a suitable protecting alcohol such as, e.g., methanol, followed by coupling to an activated amino acid to give compound III. Condensation of the amino compound III with a fatty acid chloride of formula F affords compounds of formula JJJ. The ester may be deprotected using methods disclosed in Greene et al. *Protecting Groups in Organic Chemistry*, 4th ed.; Wiley & Sons: Hoboken, N.J., 2007; Chapter 5.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Effect of Illustrative Compounds of the Invention on Inflammatory Activity in Adipose Tissue in Mice Demonstration of the ability of illustrative compounds of the invention to mediate serum adiponectin concentrations in a rodent obesity model was shown using methods described in Itoh, M. et al. *Arterioscler. Thromb. Vasc. Biol.* 2007, 27 (9), 1918-1925. Male C57BL/6J ob/ob mice and their wild-type (WT) littermates are purchased from Charles River Laboratories (Wilmington, Mass.). The animals are housed in individual cages in a temperature-, humidity-, and light-controlled room (12-hour light and 12-hour dark cycle) and allowed free access to water and fish meal-free diet (fish meal-free F1 (Funabashi Farm, Chiba, Japan) supplemented with; 362 kcal/100 g, 4.4% energy as fat).

Six-week-old male ob/ob mice and WT littermates are allowed unrestricted access to the fish meal-free diet (control group) or fish meal-free diet supplemented with 5% EPA (wt/wt) (EPA-treated group) for 4 weeks (n=10 to 14). In the short-term administration protocol, 8-week-old male ob/ob mice are treated with the compound of the invention for 2 weeks (n=7 to 8). All diets are changed every day and served with nonmetallic feeder to prevent oxidization of fatty acids. At the end of the experiments, mice are euthanized after 5-hour starvation under intraperitoneal pentobarbital anesthesia (30 mg/kg). Blood glucose and serum concentrations of triglyceride (TG) and free fatty acid (FFA) are measured as described in Kouyama R. et al. *Endocrinology* 2005, 146, 3481-3489. Serum fatty acid and salicylate concentrations are measured by gas chromatography.

Example 2

In Vivo Effects of Compounds of the Invention in Zucker Fatty Rats and Ob/Ob Mice Twelve-week-old male Zucker fa/fa rats and 8-week-old ob/ob (Lepob/ob) and ob/1 mice are given free access to food and water. A compound of the invention (120 mg/kg/day) is dosed orally by gavage once per day. For glucose tolerance tests, glucose (2.0 g/kg) is administered by oral gavage (rats) or intraperitoneal injection (mice) after an overnight fast. Blood glucose and serum insulin concentrations are determined during oral glucose tolerance tests in Zucker fa/fa rats or fa/1 rats. For insulin tolerance tests, insulin (2.0 U/kg) is injected intraperitoneally after an overnight fast. Cholesterol, triglyceride, long-chain FFA, and ALT concentrations are measured in sera from fasting Zucker fa/fa rats.

Example 3

Effects of Compounds of the Invention on Insulin Signaling in 3T3-L1 Adipocytes

3T3-L1 adipocytes are serum starved for 16 hours and treated or not treated with 5 mM aspirin for 2 hours and either 6.0 nM mTNFα (20 minutes) or the phosphatasen inhibitor calyculin A (Axxora, San Diego, USA) (at 2.0 nM for 30 minutes) as described in Yuan, M. et al. *Science* 2001, 293, 1673-1677. After a 5 minute stimulation with 10 nM insulin, the cells are chilled and solubilized and proteins are immunoprecipitated with anti-IR or anti-IRS1. Proteins are separated by SDS-PAGE and identified by Western blotting with anti-pY, anti-IR, or anti-IRS1.

Example 4

Effects of Compounds of the Invention on IL-10 Levels in 3T3-L1 Adipocytes

IL-10 production in 3T3-L1 adipocytes is measured using a modification of the method described by Bradley et al. *Obesity* 2008, 16, 938-944. Fully differentiated 3T3-L1 adipocytes are serum starved for 18 hours in DMEM containing 0.2% fatty acid free bovine serum albumin (BSA) and 0.1 mM pyruvate. A stock of 5 mM test compound is prepared in 100% ethanol and then is diluted 1:100 in 2% fatty acid free BSA in DMEM (with 0.1 mM pyruvate), yielding a 50 µM solution of compound. Starvation media is removed from cells and is replaced by the 50 µM compound solution in DMEM or Vehicle (0.1% ethanol, 0.2% fatty acid free BSA in DMEM with 0.1 mM pyruvate). Test compound or Vehicle is incubated with cells for 48 hours. Subsequently, RNA is purified from cells and reverse transcribed to cDNA. IL-10 message levels are then measured by quantitative real-time PCR (Applied Biosystems Step-One) using gene-specific oligoneucleotide primers and fluorescently labeled probe. IL-10 levels are normalized to the house-keeping gene GAPDH, which was measured using the same method. IL-10 levels in compound of the invention treated samples are expressed as a fold increase over IL-10 levels in Vehicle treated samples. (**$p<0.005$ by 2-tailed t-test). A sample graph showing the data obtained by using Compound III-1 described above in Example 4 is shown in FIG. 1.

Example 5

Effects of Compounds of the Invention in Fao Hepatoma Cells

Fao cells are serum starved for 16 hours followed by 2-hour incubations at 37° C. with 5 mM-25 mM a compound of the invention according to the method described in Yuan, M. et al. *Science* 2001, 293, 1673-1677. Cells are then stimulated sequentially with 6.0 nM mTNFα for 20 minutes and 10 nM insulin for 5 minutes. Cells are chilled and solubilized and proteins are then immunoprecipitated with anti-IR and detected by Western blotting using anti-pY. Phosphorylation is quantified by densitometry.

Example 6

TNFα Release Assay in RAW 264.7 Macrophages

The purpose of this assay is to measure the ability of small molecules to inhibit the secretion of TNFα in cultured macrophages stimulated with lipopolysaccharide (LPS). Treatment of macrophages with LPS activates inflammatory cytokine pathways primarily through the TLR4-NFκB signaling axis. Compounds of the invention inhibit the transcriptional activation of NFκB and thus decrease the production and release of TNFα. Dexamethasone, a potert agonist of the glucocorticoid receptor is used a positive control for inhibition of TNFα release.

Day 1: Seed RAW 264.7 macrophages into 96 well culture plates. Remove culture media from RAW 264.7 cell growing in a 75 $mm^2$ tissue culture flask (cells should be at ~70% confluence) and add 10 mL of warmed complete growth media (DMEM+10% FBS+1× pen/step). The cells are scraped into suspension using a sterile plate scraper and homogenized by pipetting up and down with a 10 mL serological pipette. The cell concentration is determined using a clinical hematoctyometer. Cells are then diluted to 150,000 cells per mL into growth media. The diluted cells are then transferred to a sterile reagent reservoir and 100 µl of cell suspension is pipetted into each well of a 96 well culture plate using a multichannel pipette (15,000 cells/well). Plates are then incubated at 37° C. under normal tissue culture growth conditions (37° C., humidified $CO_2$ chamber).

Day 2: The test compound sample plate is prepared. Test compounds are prepared in growth media. Compounds are delivered to media from 1000× stocks in 100% DMSO (e.g. for a 10 µM final concentration of test compound, deliver 2 µl of 10 mM test compound to 2 mL of media). At least 150 µl of 1× compound in media is added to 96 well sample plate. The perimeter wells of the 96 well plate are not used to avoid edge effects. Twelve sample wells are prepared with media plus 0.1% DMSO (these samples will serve as the vehicle controls; LPS-stimulated and non-stimulated; 10 µM dexamethasone, is used as a positive control). Culture plates are then returned to the growth incubator for 2 hours. Cells are stimulated afterwards by adding 25 µl of 50 ng/mL LPS is added to every well (except the 6 unstimulated vehicle control wells: final concentration of 10 ng/mL LPS. Plates are returned to growth incubator for 3 hours. Afterwards, 100 µl of media supernatant is removed and transferred to a 96 well v-bottom sample plate. The media supernatant plate is centrifuged for 5 minutes at 1,000 rpm in a swing-bucket centrifuge, pelleting any cellular debris that may remain in supernatant. 80 µl of supernatant is removed from sample plate and transferred to a fresh v-bottom 96 well plate. Cell viability is measured using Celltiter-glo kit. By measuring cell viability, a given compound's effects on TNFα secretion can determine whether effects are due to cytotoxicity or to true inhibition of inflammatory signaling. Add 100 μl of Celltiter-glo reagent to each well of the cell culture plate and afterwards measure the luminescence signal (CPS) of the plate using the Victor 5 plate reader (0.3 second read; 60 second plate shaking prior to read). Cell viability of a given compound at a given concentration is computed as follows:

Cell viability=CPS Sample/(Average CPS unstimulated controls)*100

Use 20 μl of media supernatant per well for TNFα ELISA. Follow Invitrogen/Biosource manufacture's protocol for the mouse TNFα ELISA. Chromogen development is typically conducted for 20-30 minutes as described in the manufacturer's protocol. After addition of stop solution, measure OD 450 nm using the Victor 5 plate reader (0.1 second/well scan). Determine the TNFα secretion percent of control. The following formula is used to determine the TNFα secretion percent of control:

$$\frac{100 \times (OD\ 450\ \text{nm Sample } X) - (\text{Average } OD\ 450\ \text{nm unstimulated vehicle controls})}{(\text{Average } OD\ 450\ \text{nm } LPS\ \text{stimulated vehicle controls}) - (\text{Average } OD\ 450\ \text{nm unstimulated vehicle controls})}$$

For each test compound, TNFα secretion percent of control can be plotted as a function of compound concentration using a four parameter dose-response curve fit equation (XLFIT Model #205):

$$\text{fit}=(A+((B-A)/(1+((C/x)^D))))$$

$$\text{inv}=(C/((((B-A)/(y-A))-1)^{(1/D)}))$$

$$\text{res}=(y-\text{fit})$$

For compounds which cause greater than 50% inhibition of TNFα secretion, determine the $IC_{50}$ (concentration of compound which causes 50% inhibition of TNFα secretion A sample graph showing the data obtained by using Compounds III-1, Ih-2 and III-6 in the procedure described above in Example 6 is shown in FIG. 2.

Figure 2:
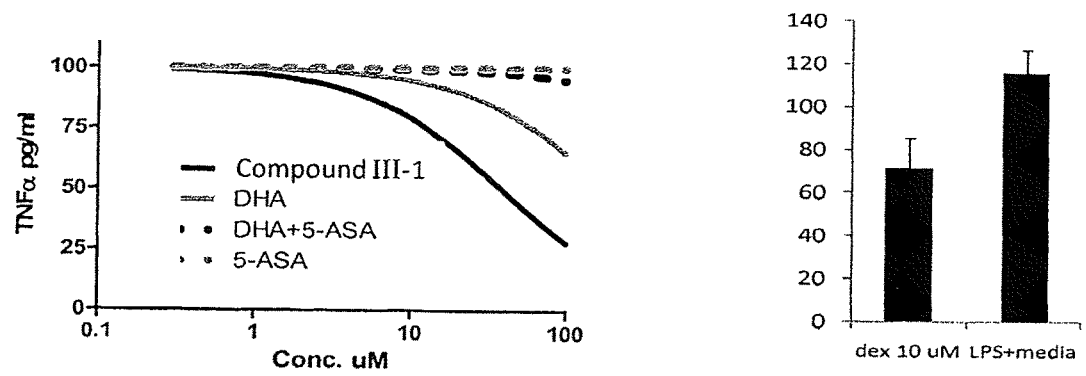
FIG. 2 is a graphic representation of the data showing the effects of the Compound III-1 of the invention on TNFα release.

As seen in FIG. 2, salicylate alone, fatty acid alone, and the simple combination of salicylate and fatty acid administered together do not appreciably inhibit the production of TNFα. In contrast the fatty acid acylated salicylate significantly inhibits the production of TNFα. This demonstrates that the fatty acid acylated salicylate is the species responsible for the inhibition of TNFα production and not either of the individual components alone or in simple combination.

A sample table showing the data obtained by using additional compounds of the invention in the procedure described above in Example 6 is shown in Table 1, below:

TABLE 1

| Compound Number | TNFα Secrection, $IC_{50}$ μM |
|---|---|
| Ia-1 | 69.2 |
| III-1 | 145.6 |
| Ic-1 | NT |
| Ih-1 | 15.0 |
| 5-ASA | >100 |
| Ih-2 | NT |
| DHA | >100 |

TABLE 1-continued

| Compound Number | TNFα Secrection, $IC_{50}$ μM |
|---|---|
| III-6 | 65.3 |
| I-1 | 24.4% Inhibition at 6.2 μM |

Example 7

Figure 3:
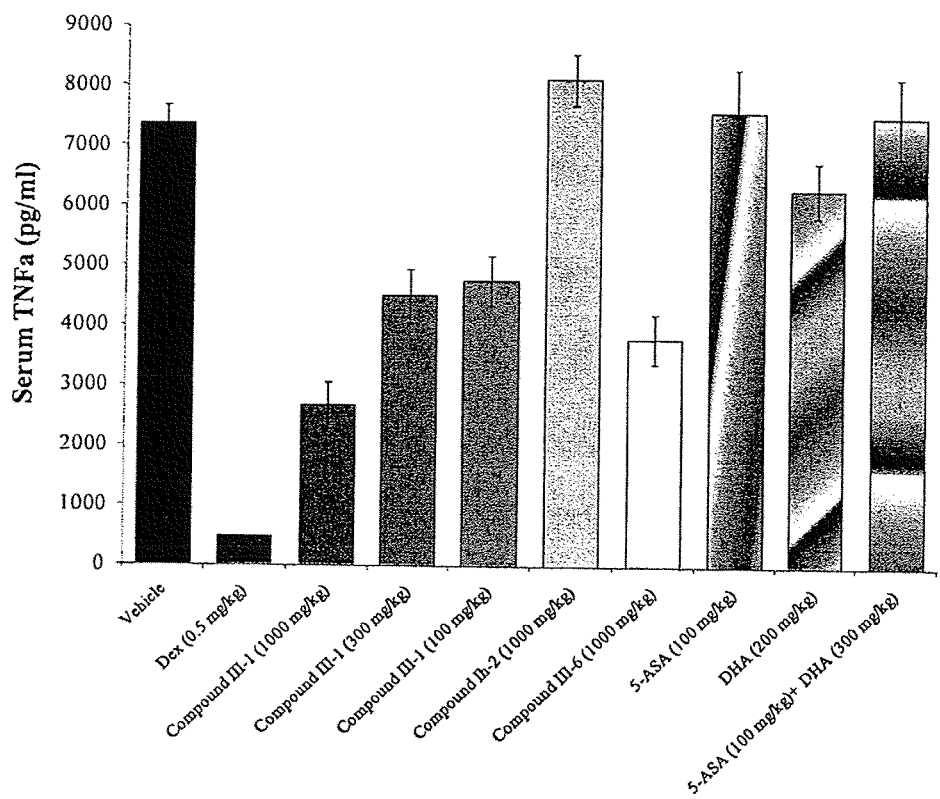
FIG. 3 is graphic representation of the data showing the in vivo effects of the Compounds III-1, Ih-2 and III-6 of the invention in an LPS-challenge TNFα mouse model.

In Vivo Effects of Compounds of the Invention in an LPS-Challenge TNFα Mouse Model To measure the effects of compounds on TNFα secretion in vivo, Male Swiss Webster mice (n=10 animals per group) are dosed by oral gavage with each test compound. All compounds are formulated in an aqueous solution of 0.5% carboxymethylcellulose and 0.05% TWEEN-80 (Vehicle). One hour after compound dosing, animals are treated with 0.2 mg/kg LPS (lipopolysaccharide) by intraperitoneal (IP) injection. Ninety minutes after LPS challenge, mice are anesthetized and bled by cardiac puncture into serum separator tubes (with sodium heparin). Bleeds are allowed to clot at room temperature for 2 hours, and tubes are then spun for 20 minutes at 2,000×g. Serum is harvested from tubes (100-150 μl per animal) and frozen at −70° C. TNFα serum levels are measured using commercially available TNFα ELISA kits (*p<0.05 using a 2-tailed t-test). A sample graph showing the data obtained by using Compound III-1 in the procedure described above in Example 7 is shown in FIG. 3.

Example 8

Effects of Compounds of the Invention on NFκB Levels in RAW 264.7 Macrophages

RAW 264.7 cells transfected with an NFκB-driven luciferase reporter are plated in 96 well plates. Cells are treated with Vehicle (0.1% ethanol) or test compounds for 2 hours. As a positive control for inhibition of NFκB signaling, 6 wells are treated with 10 μM dexamethasone. Cells are then challenged with 200 ng/mL LPS for 3 hours in the presence of test compounds. A subset of wells treated with vehicle should remain unstimulated with LPS to determine the floor signal of the assay. NFκB driven luciferase activity is developed by addition of BriteLite luciferase kit (Perkin-Elmer) and measured using a Victor V plate reader. NFκB activity (luciferase activity) for each treatment was normalized to Vehicle wells treated with LPS (% NFκB Response). AlamarBlue was used to monitor cell viability to ensure that inhibition of luciferase signal was not a result of compound cytotoxicity.

A sample table showing the data obtained by using additional compounds of the invention in the procedure described above in Example 8 is shown in Table 2, below:

TABLE 2

| Compound | NFκB Inhibitory Activity, $IC_{50}$ μM |
|---|---|
| Ia-1 | − |
| III-1 | + |
| IIIb-1 | + |
| Ic-1 | − |
| Ih-1 | + |
| Ih-2 | − |
| III-6 | + |
| I-1 | + |

TABLE 2-continued

| Compound | NFκB Inhibitory Activity, IC$_{50}$ μM |
|---|---|
| Ic-12 | + |
| IIIg-2 | + |
| Ih-3 | + |
| Ih-4 | + |
| Ih-5 | + |
| Ih-6 | + |
| Ih-7 | + |
| 16 | − |
| 17 | + |
| 18 | − |
| IIIf-1 | − |
| 20 | − |
| Ih-8 | − |
| Ii-3 | + |
| IIIf-2 | − |
| IIIg-1 | + |
| Ih-9 | + |
| Ih-10 | + |
| IVc-2 | + |
| VIc-3 | + |
| Ii-4 | − |
| Ii-5 | + |
| I-2 | + |
| I-3 | + |
| I-4 | + |
| Ih-12 | + |
| Ih-11 | + |
| I-7 | + |
| Ih-14 | + |
| Ih-15 | + |
| 5-ASA | − |
| DHA | − |
| DHA + SA | − |
| SA | − |

A − indicates that the compound showed no inhibitory activity up to 200 μM. A + indicates that the compound showed inhibitory activity less than 200 μM.

In Table 2, compounds 16, 17, 18, and 20 have structures as shown below:

Example 9

Luciferase Activity of NF-κB Reporter Gene in RAW Cells

RAW 264.7 cells stably expressing a 3×NF-κB response element-driven luciferase reporter were seeded into 96 well plates. After 18 hours, cells were pre-treated with compounds of the invention for 2 hours, and then stimulated with LPS (lipopolysaccharide, 200 ng/mL) or vehicle control for 3 h in the presence of the compounds of the invention. A set of six vehicle was left unstimulated with LPS in order to measure the assay floor. AlamarBlue viability dye (Invitrogen) was added to cells simultaneously with the delivery of LPS (final AlamarBlue concentration of 10%). After the 3 h incubation period with LPS, cell viability was measured by reading fluorescence (excitation 550 nm, emission 595 nm) with a Perkin Elmer Victor V plate reader. Then cell media was aspirated from each well. Luciferase signal was then developed by addition of the Britelite Plus reagent (Perkin Elmer). Luciferase activity was measured with the Perkin Elmer Victor V plate reader. NF-κB activity was expressed as a percent of the vehicle control wells (stimulated with LPS). Compounds were tested at 6 dose point titrations in triplicate to determine IC$_{50}$ values.

Compounds

The following non-limiting compound examples serve to illustrate further embodiments of the compounds of the invention. It is to be further understood that any embodiments listed in the Examples section are embodiments of the compounds of the invention and, as such, are suitable for use in the methods and compositions described above.

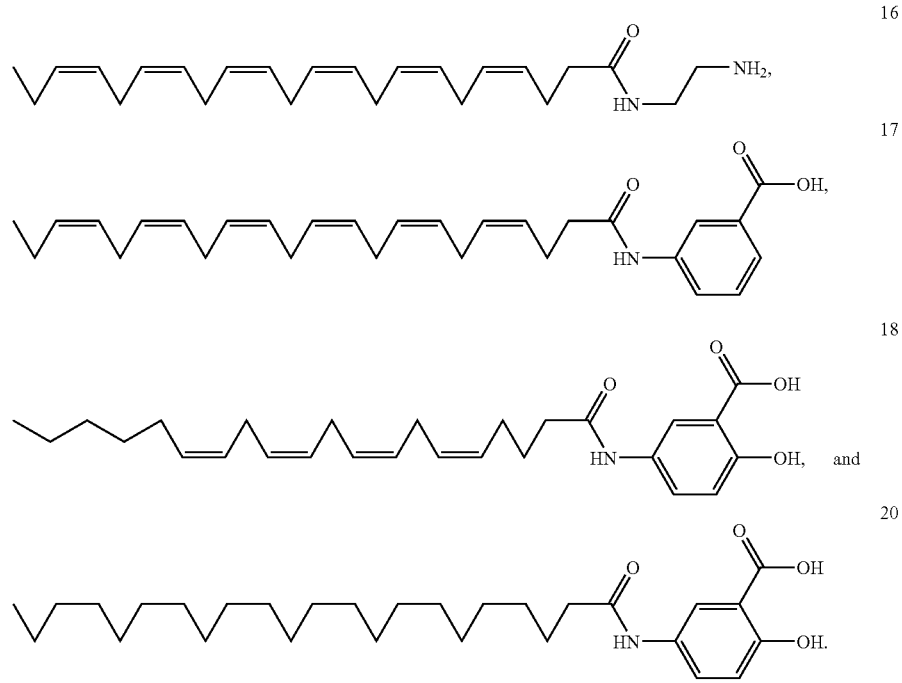

Example 10

Preparation of 2-((4Z,7Z,10Z,13Z,16Z,19Z)-docosa-4,7,10,13,16,19-hexaenoyloxy)benzoic acid (Ia-1)

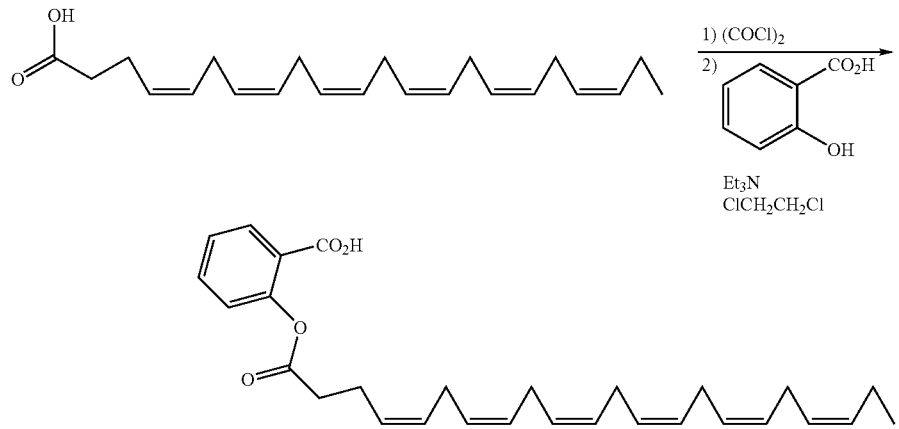

To a mixture of DHA (6.0 g, 18.3 mmol) in dichloroethane (30 mL) and DMF (0.05 mL) was slowly added oxalyl chloride (5.0 mL, 56.9 mmol). The reaction mixture was stirred (RT, 2 h) and concentrated under reduced pressure to obtain DHA-Cl as a yellow liquid. To a mixture of salicylic acid (3.78 g, 27.4 mmol) and triethylamine (3.80 mL, 27.5 mmol) in dichloroethane (35 mL) at 0° C. was slowly added the DHA-Cl in dichloroethane (35 mL). The reaction mixture was stirred (RT, 16 h), washed with 1N HCl and brine, dried over MgSO$_4$, filtered and concentrated under reduced pressure. The crude material was purified by silica gel chromatography (PE-EtOAc, 19:1) to afford 2-(docosa-4,7,10,13,16,19-hexaenoyloxy)benzoic acid (5.83 g, 71%) as a light yellow oil. Mass calculated for $C_{29}H_{36}O_4$=448.59; found: [M−H]$^+$=447.7.

Example 11

Preparation of 5-(4Z,7Z,10Z,13Z,16Z,19Z)-docosa-4,7,10,13,16,19-hexaenamido-2-hydroxybenzoic acid (IIIa-1)

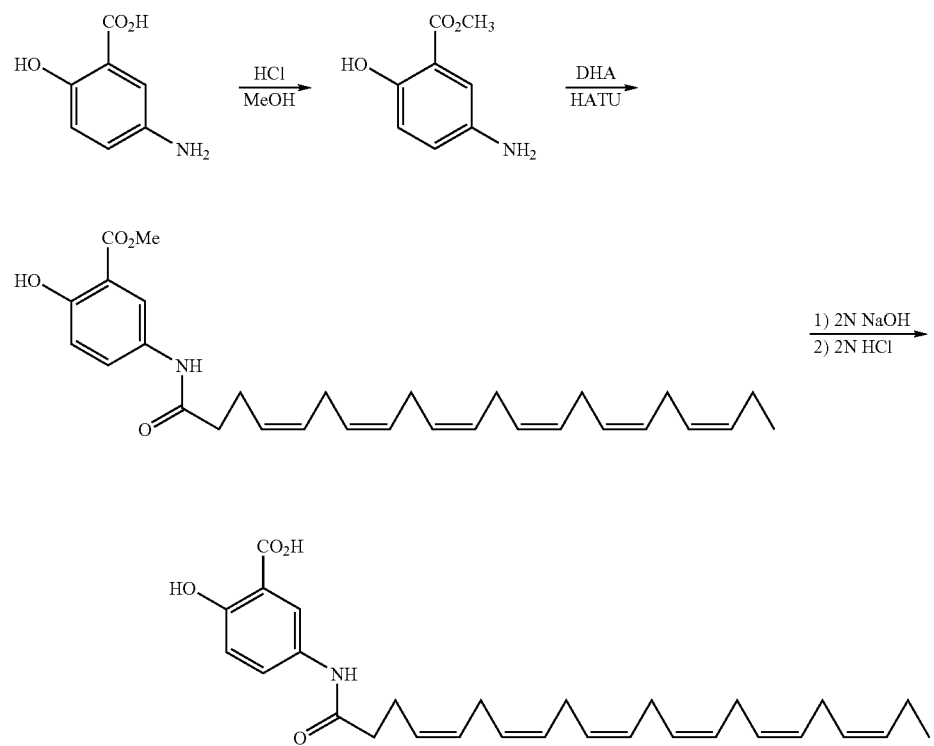

afford methyl 5-amino-2-hydroxybenzoate as a pale yellow solid (1.72 g, 78.5%). Mass calculated for $C_8H_9NO_3$=167.16; found: $[M+H]^+$=168.2.

To a mixture of methyl 5-amino-2-hydroxybenzoate (52.9 mg, 0.317 mmol), DHA (100 mg, 0.305 mmol) and $Et_3N$ (61.7 mg, 0.61 mmol) in $CH_3CN$ (2 mL) was added HATU (120 mg, 0.260 mmol). The mixture was stirred (RT, 4.5 h). The solvent was removed under reduced pressure and the residue was extracted with EtOAc (4×20 mL). The combined organic layer was washed with 1N HCl, water, 5% $NaHCO_3$, water, and dried over $MgSO_4$. The solvent was removed under reduced pressure. The crude product was purified by silica gel chromatography (EtOAc-PE, 1:10 to 2:3) to afford methyl 5-docosa-4,7,10,13,16,19-hexaenamido-2-hydroxybenzoate IIIb-1 as a light yellow oil (104.5 mg, 72.1%). Mass calculated for $C_{30}H_{39}NO_4$=477.63; found: $[M+H]^+$=478.5.

A mixture of methyl 5-docosa-4,7,10,13,16,19-hexaenamido-2-hydroxybenzoate (0.1 g, 0.2 mmol) in 2N NaOH (5 mL) and $CH_3OH$ (2.5 mL) was stirred (50° C., 24 h). The mixture was cooled and acidified to pH 1 with 2N HCl, then extracted with EtOAc (3×10 mL). The organic layer was washed with brine, dried over $MgSO_4$, filtered and concentrated under reduced pressure. The residue was purified by silica gel chromatography ($CH_2Cl_2$-EtOAc, 20:1 to 1:1) to afford 5-docosa-4,7,10,13,16,19-hexaenamido-2-hydroxybenzoic acid as a white solid (90.4 mg, yield: 90%). Mass calculated for $C_{29}H_{37}NO_4$=463.61; found: $[M+H]^+$=464.3.

Example 12

Preparation of 3-(4Z,7Z,10Z,13Z,16Z,19Z)-docosa-4,7,10,13,16,19-hexaenamidopropyl 2-acetoxybenzoate (Ic-1)

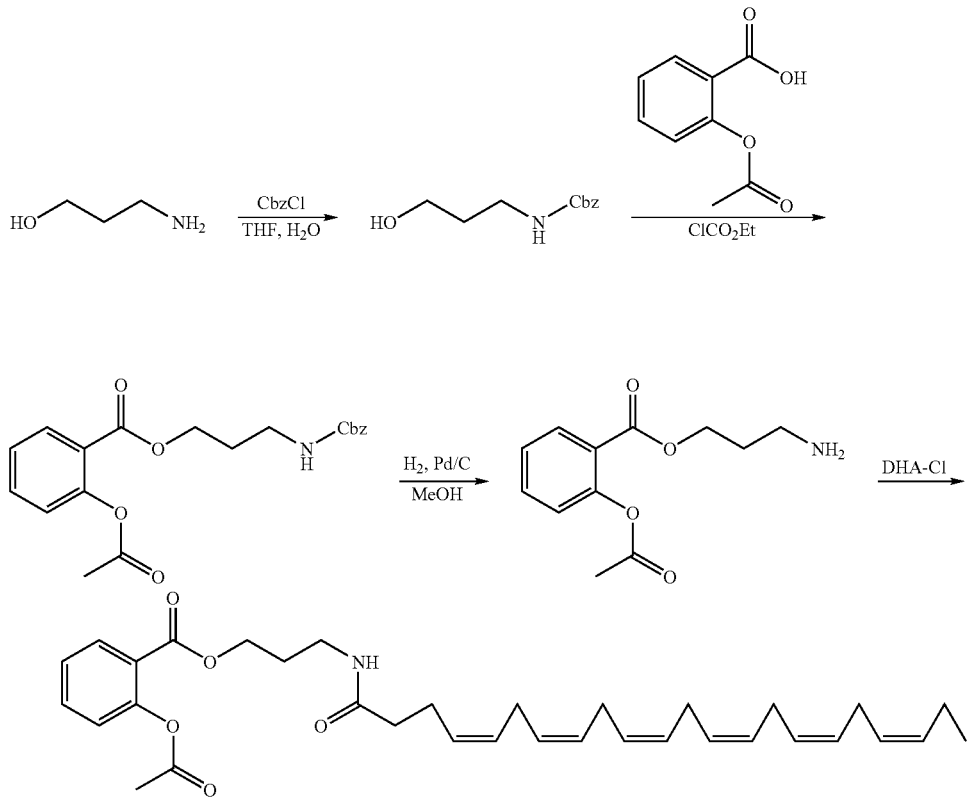

To a mixture of 3-aminopropan-1-ol (5.0 g, 67 mmol), $Na_2CO_3$ (8.8 g, 83 mmol) in THF (40 mL) and $H_2O$ (130 mL) at 0° C. was added Cbz-Cl (14.8 g, 87 mmol). The reaction mixture was stirred (RT, 1 h). Water (500 mL) and $CH_2Cl_2$ (500 mL) were added, and the layers were separated. The organic layer was dried over $MgSO_4$ and concentrated under reduced pressure. The residue was purified by silica gel chromatography (PE:EtOAc, 5:1) to afford benzyl 3-hydroxypropylcarbamate as a white solid (12.6 g, 90.5%).

To a solution of 2-acetoxybenzoic acid (2.0 g, 11.1 mmol) and triethylamine (1.8 mL, 11.1 mmol) in $CH_2Cl_2$ (40 mL) at 0° C. was slowly added $ClCO_2Et$ (1.1 mL, 167 mmol). The reaction mixture was stirred (0° C., 2 h) and filtered. The filtrate was added to a solution of benzyl 3-hydroxypropylcarbamate (2.1 g, 10.0 mmol) and triethylamine (15 mL) in $CH_2Cl_2$ (40 mL). The reaction mixture was stirred (RT, 4 h) and quenched with $H_2O$ (50 mL). The organic layer was washed with 1M aqueous HCl, saturated aqueous $Na_2CO_3$ (30 mL) and $H_2O$ (50 mL). The organic solution was dried over $MgSO_4$ and concentrated under reduced pressure. The residue was purified by silica gel chromatography, (PE-EtOAc, 5:1) to afford 3-(benzyloxycarbonylamino)propyl 2-acetoxybenzoate (2.0 g, 54%) as a colorless oil. Mass calculated for $C_{20}H_{21}NO6_4$=371.38; found: $[M+H]^+$=372.3.

To a solution of saturated HCl in $CH_3OH$ (20 mL) at RT was slowly added 5-amino-2-hydroxybenzoic acid (2 g, 13.06 mmol). The resulting mixture was stirred at (RT, 16 h) and then heated (reflux, 24 h). The mixture was cooled and the solvent was removed under reduced pressure. The residue was diluted with EtOAc (50 mL) and washed with saturated aqueous $NaHCO_3$. The organic solution was dried over $MgSO_4$, filtered, concentrated under reduced pressure to A mixture of 3-(benzyloxycarbonylamino)propyl 2-acetoxybenzoate (2.0 g, 5.4 mmol), 10% Pd/C (0.2 g) and CH$_3$OH (50 mL) was stirred under a H$_2$ atmosphere (RT, 16 h). The mixture was filtered and concentrated under reduced pressure to afford a colorless oil. Purification by silica gel chromatography afforded 3-aminopropyl 2-acetoxybenzoate as a colorless oil. Mass calculated for C$_{12}$H$_{15}$NO$_4$=237.25; found: [M+H]$^+$=238.3.

To a solution of DHA (500 mg, 1.52 mmol) in ClCH$_2$CH$_2$Cl (10 mL) and one drop of DMF at 0° C. was slowly added oxalyl chloride (0.3 mL, 3.42 mmol). The reaction mixture was stirred (RT, 2 h) and concentrated under reduced pressure. The residue was treated with toluene (5 mL) and the solvent was removed under reduced pressure to obtain the DHA acid chloride as a yellow liquid. To a solution of 3-aminopropyl-2-acetoxybenzoate (360 mg, 1.52 mmol) and NEt$_3$ (0.36 g, 3.56 mmol) in ClCH$_2$CH$_2$Cl (10 mL) at 0° C. was added a solution of DHA-Cl in ClCH$_2$CH$_2$Cl. The reaction mixture was stirred (0° C., 2 h, then warmed to RT, 12 h). Purification by silica gel chromatography afforded 3-docosa-4,7,10,13,16,19-hexaenamidopropyl 2-acetoxybenzoate. Mass calculated for C$_{34}$H$_{45}$NO$_5$=547.72; found: [M+H]$^+$=548.3.

Example 13

Preparation of N-(2-(4Z,7Z,10Z,13Z,16Z,19Z)-docosa-4,7,10,13,16,19-hexaenamidoethyl)-2-hydroxybenzamide (Ih-1)

the volatiles. The residue was shaken with water (20 mL) and filtered. The filtrate was then washed with toluene (3×50 mL), basified with excess 40% aqueous NaOH and extracted with toluene (3×50 mL). The organic layer was washed with brine (50 mL), dried over Na$_2$SO$_4$ and evaporated to give benzyl 2-aminoethylcarbamate as an oil (1.65 g, 51%). Mass calculated for C$_{10}$H$_{14}$N$_2$O$_2$=194.23; found: [M−H]$^+$=193.3.

To a mixture of benzyl 2-aminoethylcarbamate (1.65 g, 8.5 mmol), imidazole (0.58 g, 8.5 mmol), salicylic acid (1.73 g, 8.5 mmol) in ethyl acetate (30 mL) was added a solution of DCC (1.75 g, 8.5 mmol) in ethyl acetate (50 mL). The mixture was stirred (RT, 16 h) and filtered. The solution was concentrated under reduced pressure and the crude product was purified by silica gel chromatography (EtOAc-PE, 0-50%) to afford benzyl 2-(2-hydroxybenzamido)ethylcarbamate as a white solid (1.84 g, 66%). Mass calculated for C$_{17}$H$_{18}$N$_2$O$_4$=314.34; found: [M+H]$^+$=315.2.

A mixture of benzyl 2-(2-hydroxybenzamido)ethylcarbamate (1.84 g, 5.86 mmol) and Pd/C (0.18 g) in MeOH (30 mL) was stirred under a H$_2$ atmosphere (16 h). The mixture was filtered and concentrated under reduced pressure. The crude product was purified by silica gel chromatography (EtOAc-MeOH—NH$_3$OH (5:1:0.01) to afford N-2-(aminoethyl)-2-hydroxybenzamide as a white powder (0.68 g, 65%). Mass calculated for C$_9$H$_{12}$N$_2$O$_2$=180.20; found: [M+H]$^+$=181.2.

To a mixture of N-2-(aminoethyl)-2-hydroxybenzamide (58 mg, 0.32 mmol), DHA (100 mg, 0.3 mmol) and Et$_3$N (0.1 mL, 0.7 mmol) in CH$_3$CN (2 mL) was added HATU (115 mg,

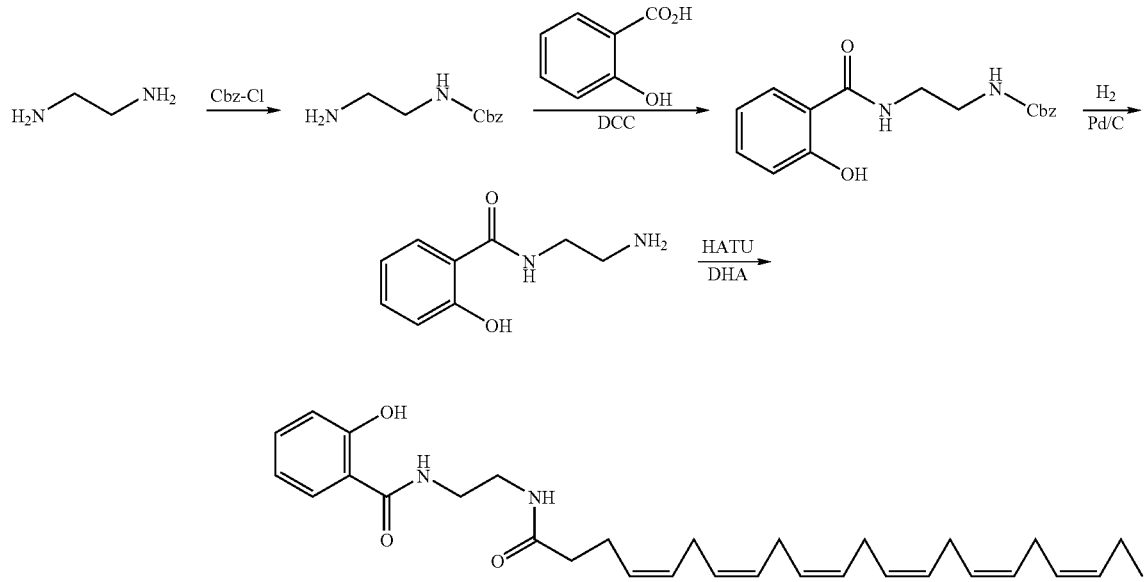

Ethylenediamine (1.0 g, 16.7 mmol) is dissolved in water (3.0 mL) containing bromocresol green as an indicator. Methane sulfonic acid (2.8 g, 31 mmol) in water (3.0 mL) is added until a blue to pale yellow color transition is just achieved. The solution is diluted with ethanol (8.0 mL) and vigorously stirred. To the mixture was added the solution of Cbz-Cl (2.8 g, 16.7 mmol) in dimethoxyethane (4 mL) and 50% w/v aqueous AcOK (10 mL) at 20° C. simultaneously to maintain the pale yellow-green color of the indicator. After the additions are complete the mixture was stirred (RT, 1 h) and concentrated at low temperature under vacuum to removed 0.3 mmol). The mixture was stirred (RT, 24 h) and concentrated under reduced pressure. The residue was treated with brine (15 mL) and extracted with EtOAc (3×30 mL). The combined organic layers were washed with 1M HCl, brine, 5% NaHCO$_3$ and brine. The organic solution was dried over MgSO$_4$ and concentrated under reduced pressure. The crude product was purified by silica gel chromatography (EtOAc: PE, 1:1) to afford N-(2-docosa-4,7,10,13,16,19-hexaenamidoethyl)-2-hydroxybenzamide (94 mg, 64%) as light yellow oil. Mass calculated for C$_{31}$H$_{42}$N$_2$O$_3$=490.68; found: [M+H]$^+$=491.4.

Example 14

Preparation of (4Z,7Z,10Z,13Z,16Z,19Z)-1-(4-(2-hydroxybenzoyl)piperazin-1-yl)docosa-4,7,10,13,16,19-hexaen-1-one (Ih-2)

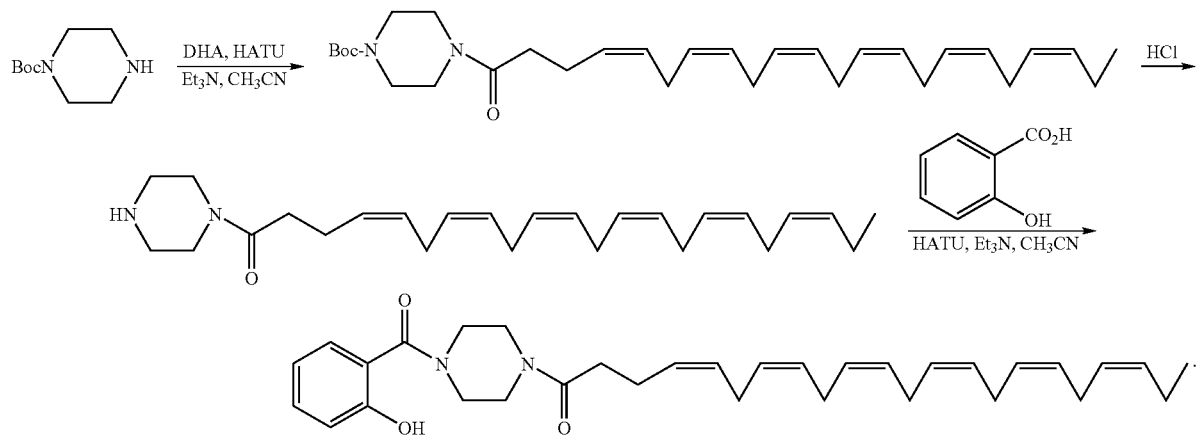

To a mixture of tert-butylpiperazine-1-carboxylate (0.57 g, 3.05 mmol), DHA (1 g, 3.05 mmol) and Et$_3$N (0.61 g, 6.1 mmol) in CH$_3$CN (20 mL) was added HATU (1.16 g, 3.05 mmol), and the mixture was stirred (RT, 16 h). The solvent was removed under reduced pressure and the residue was extracted with EtOAc (4×30 mL). The combined organic layers were washed successively with 1N HCl, water, 5% NaHCO$_3$ and water, and dried over MgSO$_4$. The solvent was removed under reduced pressure and the crude product was purified by silica gel chromatography (EtOAc-PE, 1:10 to 1:1) to afford tert-butyl 4-docosa-4,7,10,13,16,19-hexaenoylpiperazine-1-carboxylate (1.5 g, 99%) as a colorless oil. Mass calculated for C$_{31}$H$_{48}$N$_2$O$_3$=496.72; found: [M+H]$^+$=497.6.

To a mixture of tert-butyl 4-docosa-4,7,10,13,16,19-hexaenoylpiperazine-1-carboxylate (1.5 g, 3 mmol) in CH$_2$Cl$_2$ (20 mL) at 0° C. was added CF$_3$CO$_2$H (7 mL, 91 mmol). The mixture solution was stirred (0° C., 2 h) and then 10% Na$_2$CO$_3$ was added to adjust to pH 10. The mixture was extracted with CH$_2$Cl$_2$ (3×30 mL). The combined organic layers were dried over MgSO$_4$, filtered and concentrated under reduced pressure. The crude product was purified by silica gel chromatography (CH$_2$Cl$_2$:CH$_3$OH, 20:1) to afford 1-(piperazin-1-yl)-docosa-4,7,10,13,16,19-hexaen-1-one (1.17 g, 97.5%) as a colorless oil. Mass calculated for C$_{26}$H$_{40}$N$_2$O=396.61; found: [M+H]$^+$=396.7, 398.2.

To a mixture of 1-(piperazin-1-yl)-docosa-4,7,10,13,16,19-hexaen-1-one (1.17 g, 2.95 mmol), salicylic acid (0.61 g, 4.43 mmol) and Et$_3$N (0.89 g, 8.85 mmol) in CH$_3$CN (10 mL) was added HATU (1.68 g, 4.43 mmol), and the mixture was stirred (RT, 16 h). The solvent was removed under reduced pressure and the residue was extracted with EtOAc (4×50 mL). The combined organic layers were washed successively with 1N HCl, water, 5% NaHCO$_3$ and water, and dried over MgSO$_4$. The solvent was removed under reduced pressure. Purification of the crude product by preparative HPLC afforded 1-(4-(2-hydroxybenzoyl)piperazin-1-yl)docosa-4,7,10,13,16,19-hexaen-1-one (300 mg, 19.6%) as a light yellow oil. Mass calculated for C$_{33}$H$_{44}$N$_2$O$_3$=516.71; found: [M+H]$^+$517.6.

Example 15

Preparation of 5-(2-(4Z,7Z,10Z,13Z,16Z,19Z)-docosa-4,7,10,13,16,19-hexaenamido-4-methylpentanamido)-2-hydroxybenzoic acid (III-6)

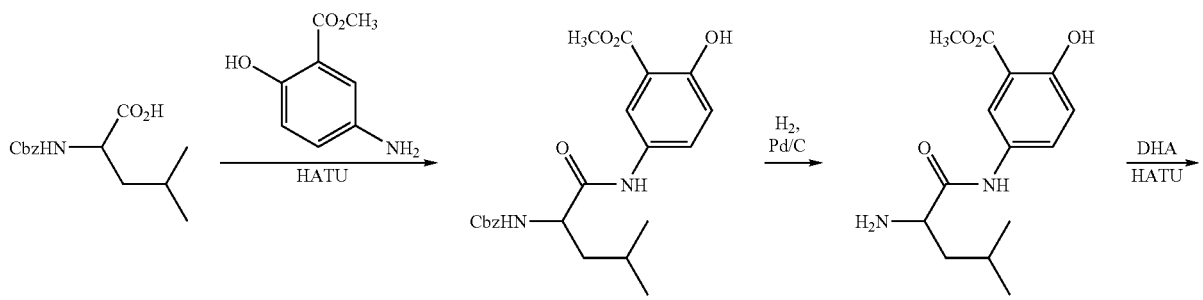

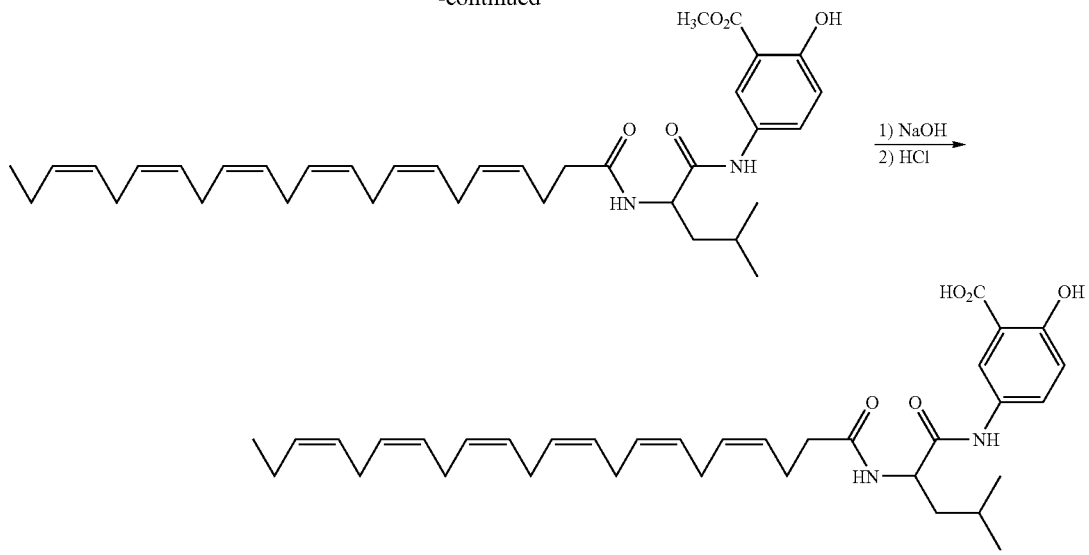

A mixture of 2-(benzyloxycarbonylamino)-4-methylpentanoic acid (1.0 g, 3.8 mmol), methyl 5-amino-2-hydroxybenzoate (0.66 g, 3.95 mmol) and Et$_3$N (0.76 g, 7.6 mmol) were dissolved in CH$_3$CN (10 mL) and HATU (1.50 g, 3.95 mmol) was added. The mixture was stirred (RT, 16 h). The solvent was removed under reduced pressure. Brine (50 mL) was added to the resulting residue, and the mixture was extracted with EtOAc (3×50 mL). The combined organic layers were washed successively with 2N HCl (3×50 mL), brine (50 mL), 5% NaHCO$_3$ (50 mL×3), brine (50 mL), dried over MgSO$_4$, filtered, and concentrated under reduced pressure. The crude material was purified by silica gel chromatography (CH$_2$Cl$_2$) to give methyl 5-(2-(benzyloxycarbonylamino)-4-methylpentanamido)-2-hydroxybenzoate as a white solid (0.81 g, 51.8%).

The mixture of 5-(2-(benzyloxycarbonylamino)-4-methylpentanamido)-2-hydroxybenzoate (0.81 g, 1.9 mmol) and 0.1 g Pd/C in MeOH (15 mL) was stirred under H$_2$ (RT, 16 h). The mixture was filtered and the filtrate was concentrated under reduced pressure. The crude product was purified by silica gel chromatography (MeOH/DCM, 0 to 5%) to afford methyl 5-(2-amino-4-methylpentanamido)-2-hydrozybenzoate as a white solid (0.53 g, 90%). Mass calculated for C$_{14}$H$_{20}$N$_2$O$_4$=280.32; found: [M+H]$^+$=281.2.

To a solution of methyl 5-(2-amino-4-methylpentanamido)-2-hydrozybenzoate (85 mg, 0.30 mmol), DHA (100 mg, 0.30 mmol), Et$_3$N (0.1 mL, 0.71 mmol) in CH$_3$CN (2 mL) was added HATU (114 mg, 0.30 mmol). The mixture was stirred (RT, 16 h) and the solvent was removed under reduced pressure. The residue was diluted with brine (20 mL) and extracted with ethyl acetate (50 mL). The combined organic layer was washed with 1M HCl (20 mL), brine (20 mL), 5% aqueous NaHCO$_3$ (20 mL) and brine (20 mL), dried over MgSO$_4$, and concentrated under reduced pressure. The crude product was purified by silica gel chromatography (EtOAc/DCM, 0 to 10%) to afford methyl 5-(2-docosa-4,7,10,13,16,19-hexaenamido-4-methylpentanamido)-2-hydroxybenzoate as light yellow oil (155 mg, 87%). Mass calculated for C$_{36}$H$_{50}$N$_2$O$_5$=590.79; found: [M+H]$^+$=591.6.

To a solution of methyl 5-(2-docosa-4,7,10,13,16,19-hexaenamido-4-methylpentanamido)-2-hydroxybenzoate (155 mg, 0.26 mmol) in MeOH (3 mL) was added 2M aqueous NaOH (5 mL). The mixture was heated (45-50° C., 16 h), and then cooled to RT. 2M aqueous HCl was added dropwise to adjust to pH 1. The mixture was then extracted by EtOAc (3×20 mL). The combined organic layers were washed with brine, dried over MgSO$_4$ and concentrated under reduced pressure. The crude product was purified by silica gel chromatography (MeOH/DCM, 0-10%) to afford of 5-(2-docosa-4,7,10,13,16,19-hexaenamido-4-methylpentanamido)-2-hydroxybenzoic acid as light yellow oil (92 mg, 61%). Mass calculated for C$_{35}$H$_{48}$N$_2$O$_5$=576.77; found: [M+H]$^+$=577.3.

Example 16

Preparation of ethyl 2-(2-(4Z,7Z,10Z,13Z,16Z,19Z)-docosa-4,7,10,13,16,19-hexaenamido-4-methylpentanoyloxy)benzoate (I-1)

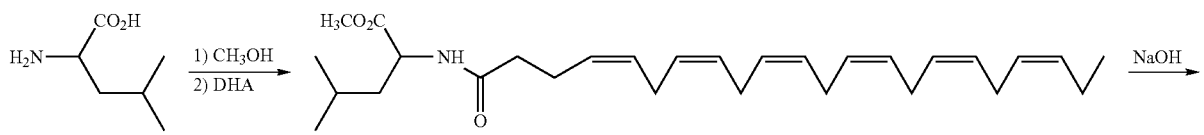

-continued

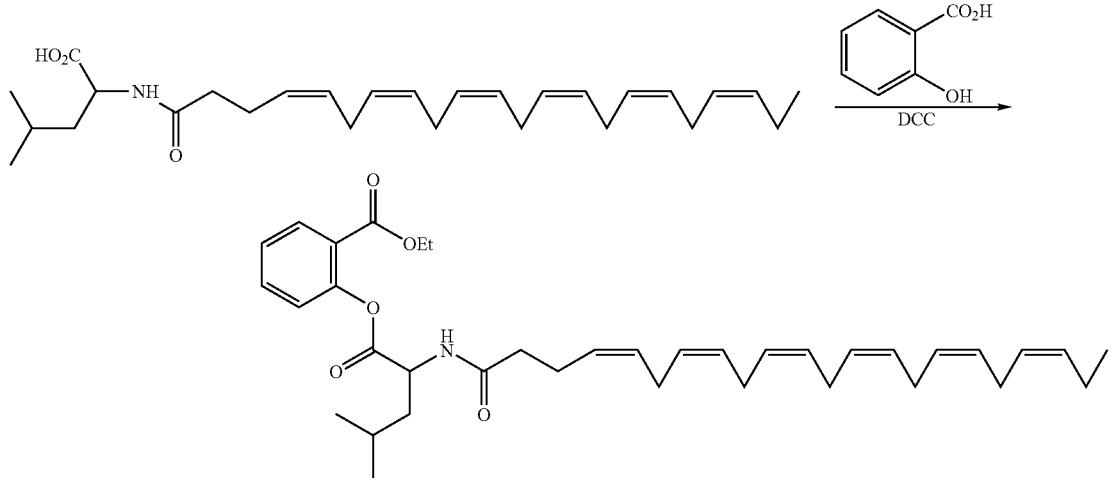

2-Amino-4-methylpentanoic acid (5.0 g 38.2 mmol) was slowly added to saturated HCl/MeOH (50 mL). The mixture was stirred (RT, 5 h) then heated to reflux (16 h). After the reaction, the solvent was removed under reduced pressure. The residue was diluted with water (50 mL), then NaHCO$_3$ was added to adjust to pH 7. The mixture was then extracted with DCM (3×50 mL), the combined organic layers were dried over MgSO$_4$, concentrated under reduced pressure to afford methyl 2-amino-4-methylpentanoate as a colorless liquid (5.3 g, 96%). Mass calculated for C$_7$H$_{15}$NO$_2$=145.20; found: [M+H]$^+$=145.9. The product was used in next step without further purification.

To a solution of methyl 2-amino-4-methylpentanoate (250 mg, 1.6 mmol), DHA (510 mg, 1.5 mmol), Et$_3$N (0.42 mL, 3 mmol) in CH$_3$CN (20 mL) at RT was added HATU (570 mg, 1.5 mmol). The mixture was stirred (RT, 16 h) and the solvent was removed under reduced pressure. The residue was diluted with brine and extracted with EtOAc. The organic layer was washed with 1M aqueous HCl (50 mL), brine (50 mL), 5% aqueous NaHCO$_3$ (50 mL) and brine (50 mL). The organic solution was dried over MgSO$_4$ and concentrated under reduced pressure. The crude product was purified by silica gel chromatography (EtOAc:PE, 0-25%) to afford methyl 2-docosa-4,7,10,13,16,19-hexaenamido-4-methylpentanoate (0.61 g, 85%) as a light yellow oil. Mass calculated for C$_{29}$H$_{45}$NO$_3$=455.67; found: [M+H]$^+$=456.2.

To a solution of methyl 2-docosa-4,7,10,13,16,19-hexaenamido-4-methylpentanoate (610 mg, 1.34 mmol) in MeOH (15 mL) was added 2M aqueous NaOH (30 mL). The reaction mixture was heated (50° C., 16 h), cooled (RT), and acidified with 2M aqueous HCl to pH 1. The mixture was extracted with EtOAc (3×50 mL). The combined organic layers were washed with brine, dried over MgSO$_4$, and concentrated under reduced pressure. The crude product was purified by silica gel chromatography, (MeOH:DCM, 0-10%) to afford 2-docosa-4,7,10,13,16,19-hexaenamido-4-methylpentanoic acid (0.51 g, 89%) as a light yellow solid. Mass calculated for C$_{28}$H$_{43}$NO$_3$=441.65; found: [M+H]$^+$=442.1.

To a solution of 2-docosa-4,7,10,13,16,19-hexaenamido-4-methylpentanoic acid (50 mg, 0.11 mmol) and ethyl 2-hydroxybenzoate (19 mg, 0.11 mmol) in CH$_3$CN/THF (1:1, 0.5 mL) at −10° C. was added DCC (12 mg, 0.11 mmol) and DMAP (1 mg). The mixture was stirred (RT, 16 h), filtered and concentrated under reduced pressure. The crude product was purified by silica gel chromatography (EtOAc-PE, 0-20%) to afford ethyl 2-(2-docosa-4,7,10,13,16,19-hexaenamido-4-methylpentanoyloxy)benzoate (40 mg, 67%) as colorless oil. Mass calculated for C$_{37}$H$_{51}$NO$_5$=589.80; found: [M+H]$^+$=590.4.

Example 17

Preparation of 1-((4Z,7Z,10Z,13Z,16Z,19Z)-docosa-4,7,10,13,16,19-hexaenoyloxy)ethyl 2-acetoxybenzoate (Ic-12)

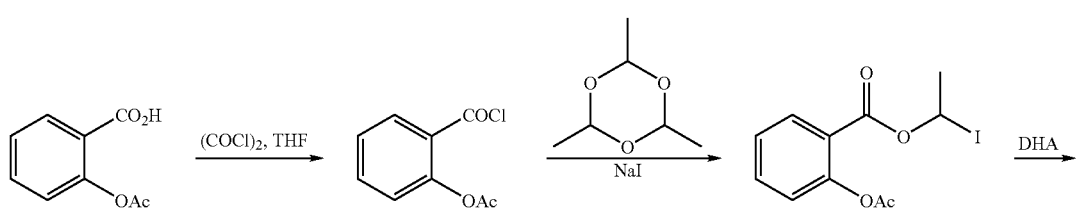

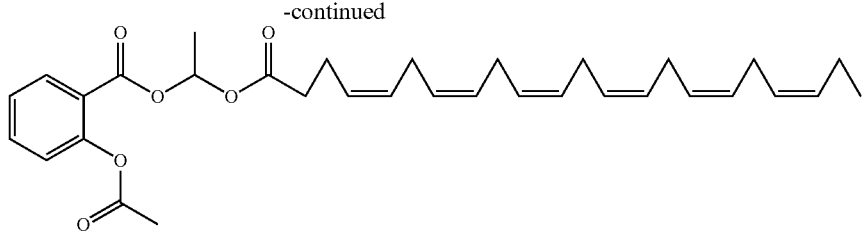

-continued

To a solution of compound 2-acetoxybenzoic acid (1.0 g, 5.5 mmol) in THF (30 mL) was added (COCl)$_2$ (0.8 mL, 9.1 mmol) at 0° C. The mixture was heated (reflux, 1.5 h) and concentrated under reduced pressure to afford 2-(chlorocarbonyl)-phenyl acetate.

To a mixture of 2,4,6-trimethyl-1,3,5-trioxane (245 mg, 1.85 mmol) and NaI (0.972 g, 6.48 mmol) in DCM (15 mL) was added a solution of 2-(chlorocarbonyl)-phenyl acetate in DCM (5 mL, 0° C.). The resulting mixture was allowed to stir (RT, 16 h). The mixture was filtrated and concentrated under reduced pressure. The crude was purified by silica gel chromatography (EtOAc-PE, 0-10%) to afford 1-iodoethyl 2-acetoxybenzoate (0.75 g, 40%) as a light yellow oil.

To a solution of DHA (0.1 g, 0.3 mmol) in CH$_3$CN (1 mL) was added K$_2$CO$_3$ (41.4 mg, 0.3 mmol) followed by Bu$_4$NBr (96.6 mg, 0.3 mmol). The mixture was stirred (RT, 0.5 h) and cooled to 0° C. To it was added 1-iodoethyl 2-acetoxybenzoate (0.1 g, 0.3 mmol) and the mixture was stirred (RT, 16 h). The mixture was filtered, washed with brine and concentrated under reduced pressure. The crude was purified by silica gel chromatography (PE:EtOAc, 20:1-15:1) to afford 1-(docosa-4,7,10,13,16,19-hexaenoyloxy)ethyl 2-acetoxybenzoate (85.3 mg, 53.3%) as a light yellow oil. Mass calculated for C$_{33}$H$_{42}$O$_6$=534.68; found: [M+Na]$^+$=557.2.

Example 18

Preparation of 2-hydroxy-5-(9Z,12Z,15Z)-octadeca-9,12,15-trienamidobenzoic acid (III-7)

To a solution of (9Z,12Z,15Z)-octadeca-9,12,15-trienoic acid (1.66 g, 5.98 mmol) and methyl 5-amino-2-hydroxybenzoate (1.0 g, 5.98 mmol) in methylene chloride (100 mL) was added 1-ethyl-3-(3-dimethylaminopropyl)carbodiimide hydrochloride (1.16 g, 6.0 mmol) and dimethylaminopyridine (100 mg). The mixture was stirred under N$_2$ (14 h) and then diluted with methylene chloride (100 mL) and washed successively with 3N HCl, saturated aqueous sodium bicarbonate solution and brine. The organic layer was dried over anhydrous magnesium sulfate, filtered and concentrated to give the corresponding amide (2.0 g).

To the amide was added 2N NaOH (100 mL) and methanol (100 mL) and the resulting slurry was heated to 40° C. and after 12 hours an additional 500 mg NaOH was added and the reaction stirred at 40° C. (12 hours). The reaction mixture was cooled to room temperature, acidified with 3N HCl and extracted with ethyl acetate (300 mL). The organic phase was washed successively with water and brine, dried over anhydrous magnesium sulfate, filtered and was concentrated to afford 2-hydroxy-5-(9Z,12Z,15Z)-octadeca-9,12,15-trienamidobenzoic acid (1.5 grams, 61%). Mass calculated for C$_{25}$H$_{35}$NO$_4$=413.55; found: [M−H]$^+$=412.3.

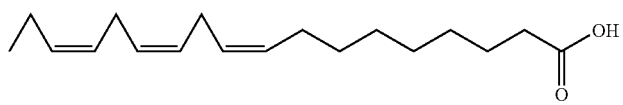
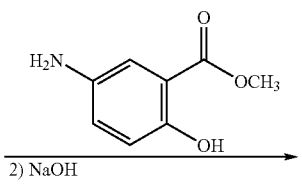
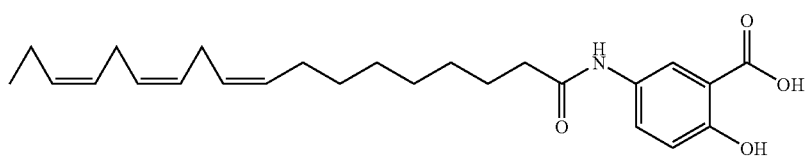

Example 19

Preparation of N-(2-(4Z,7Z,10Z,13Z,16Z,19Z)-docosa-4,7,10,13,16,19-hexaenamidoethyl)-2-hydroxy-N-methylbenzamide (Ih-3)

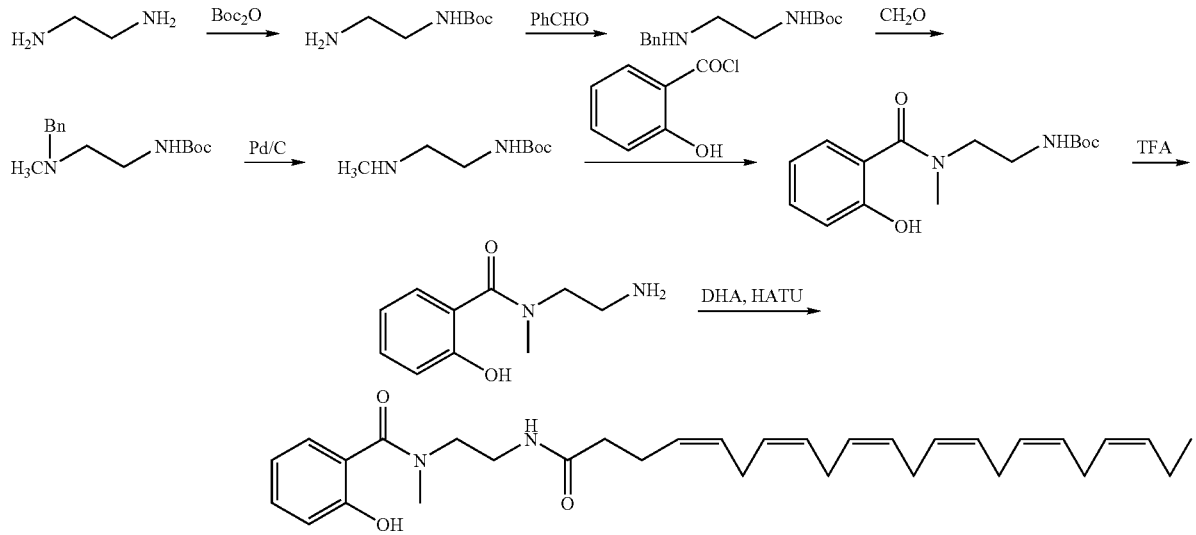

To a solution of ethylenediamine (20 mL, 0.28 mol) in CHCl$_3$ (300 mL) at 0° C. was slowly added a solution of Boc$_2$O (6.2 g, 0.028 mol) in CHCl$_3$ (150 mL). The mixture was allowed to warm to room temperature. After 16 h, the solution was filtered and washed with brine (6×100 mL) and water (100 mL). The organic solution was dried over MgSO$_4$, filtered and concentrated under reduced pressure to afford tert-butyl 2-aminoethylcarbamate (3.7 g, 78%) as a colorless oil.

To a solution of tert-butyl 2-aminoethylcarbamate (3.7 g, 22.3 mmol), benzaldehyde (2.36 g, 22.3 mmol) and MgSO$_4$ (1.33 g) in 1,2-dichoroethane (300 mL) and Et$_3$N (3.1 mL, 22.3 mmol) at RT was added NaHB(AcO)$_3$. The mixture was stirred (RT, 16 h) and filtered. The solution was washed with saturated aqueous NaHCO$_3$ (200 mL), dried over MgSO$_4$ and concentrated under reduced pressure. The crude product was purified by chromatography on silica gel, eluting with MeOH-DCM (0-10%) to afford tert-butyl 2-(benzylamino)ethylcarbamate (1.4 g, 23%). Mass calculated for C$_{14}$H$_{22}$N$_2$O$_2$=250.34; found: [M+H]$^+$=251.3.

To a mixture of tert-butyl 2-(benzylamino)ethylcarbamate (2.8 g, 11.2 mmol) and 37% aqueous CH$_2$O (1.0 mL, 11.2 mmol) in 1,2-dichoroethane (35 mL) at RT was added NaHB(AcO)$_3$ (3.7 g, 11.2 mmol). The mixture was stirred (RT, 16 h), diluted with saturated aqueous NaHCO$_3$ (400 mL) and extracted with EtOAc (3×300 mL). The organic layer was dried over MgSO$_4$ and concentrated under reduced pressure to afford tert-butyl 2-(benzyl(methyl)amino)ethylcarbamate (1.38 g, 46.8%). $^1$HNMR (CDCl$_3$): δ 7.25 (m, 5H, CH), 3.5 (s, 2H, CH$_2$), 3.3 (m, 2H, CH$_2$), 2.48 (m, 2H, CH$_2$), 2.2 (s, 3H, CH$_3$), 1.4 (s, 9H, CH$_3$).

A mixture of tert-butyl 2-(benzyl(methyl)amino)ethylcarbamate (1.20 g, 4.54 mmol), 10% Pd/C (0.90 g) and MeOH (60 mL) was stirred under a H$_2$ atmosphere (0.8 MPa, RT, 16 h). The mixture was filtered and concentrated under reduced pressure. The crude material was purified by column chromatography on silica gel, eluting with saturated N$_3$ in MeOH-DCM (0-10%) to afford tert-butyl 2-(methylamino)ethylcarbamate as a colorless oil (0.54 g, 68.3%). $^1$HNMR (CDCl$_3$): δ 3.25 (m, 2H, CH$_2$), 2.7 (m, 2H, CH$_2$), 2.49 (s, 3H, CH$_3$), 1.49 (s, 9H, CH$_3$).

To a mixture of tert-butyl 2-(methylamino)ethylcarbamate (0.348 g, 2 mmol), 2-hydroxybenzoyl chloride (0.276 g, 2 mmol) and imidazole (0.136 g, 2 mmol) in ethyl acetate (8 mL) at 0° C. was slowly added a solution of DCC (0.412 g, 2 mmol) in ethyl acetate (2 mL). The mixture was stirred (RT, 16 h), filtered and concentrated under reduced pressure. The crude material was purified by chromatography on silica gel, eluting with EtOAc/PE (20-50%) to afford tert-butyl 2-(2-hydroxy-N-methylbenzamido)ethylcarbamate (0.2 g, 34%) as a colorless oil. $^1$HNMR (CDCl$_3$): δ 7.5 (m, 2H, CH), 7.0 (d, 1H, CH), 6.8 (d, 1H, CH), 3.7 (m, 2H, CH$_2$), 3.48 (m, 2H, CH$_2$), 3.2 (m, 3H, CH$_3$), 1.5 (s, 9H, CH$_3$).

To a solution of tert-butyl 2-(2-hydroxy-N-methylbenzamido)ethylcarbamate (0.2 g, 0.68 mmol) in CH$_2$Cl$_2$ (5 mL) at 0° C. was added trifluoroacetic acid (1.8 mL, 23.4 mmol). The mixture was stirred (0° C., 16 h), concentrated under reduced pressure and neutralized with saturated NH$_3$ in CH$_3$OH. The mixture was concentrated under reduced pressure to afford N-(2-aminoethyl)-2-hydroxy-N-methylbenzamide as a colorless oil (0.5 g). This compound was used in the next step without further purification. Mass calculated for C$_{10}$H$_{14}$N$_2$O$_2$=194.23; found: [M+H]$^+$=195.1.

To a mixture of the crude N-(2-aminoethyl)-2-hydroxy-N-methylbenzamide, DHA (100 mg, 0.3 mmol) and Et$_3$N (92.3 mg, 0.9 mmol) in CH$_3$CN (2 mL) at RT was added HATU (115.8 mg, 0.3 mmol). The mixture was stirred (RT, 16 h) and concentrated under reduced pressure. The residue was diluted with 50 mL ethyl acetate, washed with brine, 1N HCl, saturated aqueous NaHCO$_3$ and brine. The organic layer was dried over MgSO$_4$, filtered and concentrated under reduced pressure. The residue was purified by chromatography on silica gel, eluting with CH$_2$Cl$_2$-EtOAc (1:1) to afford N-(2-(4Z,7Z,10Z,13Z,16Z,19Z)-docosa-4,7,10,13,16,19-hexaenamidoethyl)-2-hydroxy-N-methylbenzamide (40 mg, 26%) as a light yellow oil. Mass calculated for C$_{32}$H$_{44}$N$_2$O$_3$=504.70; found: [M+H]$^+$=505.5.

Example 20

Preparation of 2-hydroxy-N-(2-((4Z,7Z,10Z,13Z,16Z,19Z)—N-methyldocosa-4,7,10,13,16,19-hexaenamido)ethyl)benzamide (Ih-4)

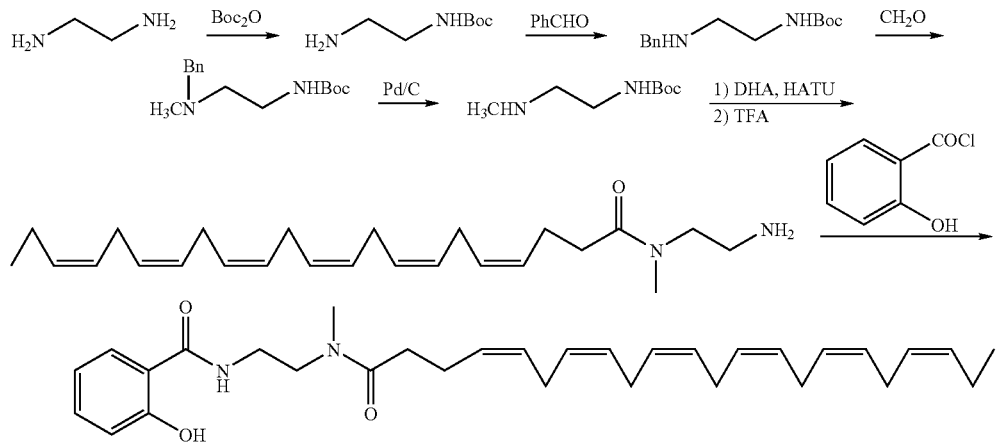

To a solution of tert-butyl 2-(methylamino)ethylcarbamate (0.82 g, 4.7 mmol), prepared as previously described, DHA (1.55 g, 4.7 mmol) and Et$_3$N (1.32 mL, 9.4 mmol) in CH$_3$CN (40 mL) was added HATU (1.79 g, 4.7 mmol). The mixture was stirred (RT, 16 h) and concentrated under reduced pressure. The residue was diluted with brine (150 mL) and extracted with ethyl acetate (2×150 mL). The combined organic layers were washed with saturated aqueous NaHCO$_3$ (150 mL) and brine (150 mL), dried over MgSO$_4$, and concentrated under reduced pressure. The crude product was purified by chromatography on silica gel, eluting with EtOAc-PE (0-50%) to afford tert-butyl 2-((4Z,7Z,10Z,13Z,16Z,19Z)—N-methyldocosa-4,7,10,13,16,19-hexaenamido)ethylcarbamate (1.71 g, 77%) as a light yellow oil. Mass calculated for C$_{30}$H$_{48}$N$_2$O$_3$=484.71; found: [M+H]$^+$=485.6.

To a solution of tert-butyl 2-((4Z,7Z,10Z,13Z,16Z,19Z)—N-methyldocosa-4,7,10,13,16,19-hexaenamido)ethylcarbamate (1.71 g, 3.5 mmol)) in dichloromethane (50 mL) at 0° C. was slowly added TFA (17 mL). The mixture was stirred (0° C., 2 h) basified to pH 10 with saturated aqueous Na$_2$CO$_3$ and extracted with EtOAc (3×150 mL). The combined organic layers were dried over MgSO$_4$ and concentrated under reduced pressure to afford (4Z,7Z,10Z,13Z,16Z,19Z)—N-(2-aminoethyl)-N-methyldocosa-4,7,10,13,16,19-hexaenamide (1.31 g, 97%) as a light yellow oil.

To a solution of (4Z,7Z,10Z,13Z,16Z,19Z)—N-(2-aminoethyl)-N-methyldocosa-4,7,10,13,16,19-hexaenamide (104 mg, 0.27 mmol), 2-hydroxybenzoyl chloride (37 mg, 0.27 mmol) and imidazole (19 mg, 0.27 mmol) in EtOAc (4 mL) at 0° C. was added dropwise a solution of DCC (0.57 g, 0.27 mmol) in EtOAc (4 mL). The mixture was stirred (RT, 16 h), filtered and concentrated under reduced pressure. The crude material was purified by chromatography on silica gel, eluting with EtOAc-PE (1:3) to afford 2-hydroxy-N-(2-((4Z,7Z,10Z,13Z,16Z,19Z)—N-methyldocosa-4,7,10,13,16,19-hexaenamido)-ethyl)-benzamide (100 mg, 73%) as a colorless oil. Mass calculated for C$_{32}$H$_{44}$N$_2$O$_3$=504.70; found: [M+H]$^+$=505.5.

Example 21

Preparation of N-(1-(4Z,7Z,10Z,13Z,16Z,19Z)-docosa-4,7,10,13,16,19-hexaenamidopropan-2-yl)-2-hydroxybenzamide (Ih-5)

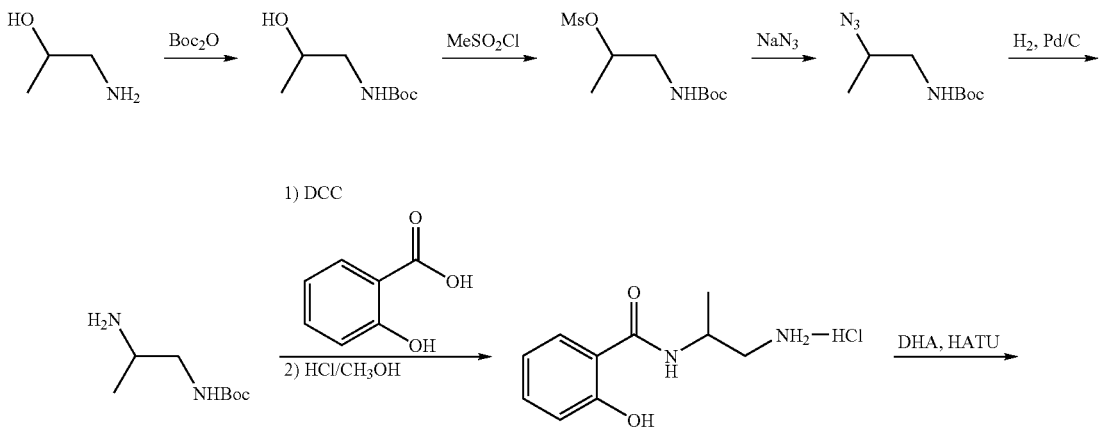

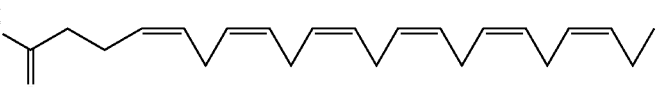

To a solution of 1-aminopropan-2-ol (7.5 g, 0.1 mol) in THF—H$_2$O (1:1, 150 mL) at RT was slowly added a solution of Boc$_2$O (21.8 g, 0.1 mol) in THF (50 mL). The mixture was stirred (RT, 2 h) and concentrated under reduced pressure. The residue was extracted with EtOAc (2×100 mL) and the combined organic layers were washed with citric acid (0.5 M, 2×50 mL) and brine (100 mL). The organic solution was dried over MgSO$_4$, filtered and concentrated under reduced pressure to afford tert-butyl 2-hydroxypropylcarbamate (15.3 g, 87.4%) as a colorless oil. Mass calculated for C$_8$H$_{17}$NO$_3$=175.23; found: [M+H]$^+$=176.3.

To a solution of tert-butyl 2-hydroxypropylcarbamate (14.3 g, 81.7 mmol) and Et$_3$N (35.6 mL, 245.1 mmol) in CH$_2$Cl$_2$ (250 mL) at 0° C. was slowly added a solution of methanesulfonyl chloride (9.5 mL, 122.6 mmol) in CH$_2$Cl$_2$ (250 mL). The mixture was stirred at 0° C. for 2 h, diluted with CH$_2$Cl$_2$ (300 mL) and washed with water, 1N HCl, 5% aqueous NaHCO$_3$ and brine. The organic layer was dried over MgSO$_4$ and concentrated under reduced pressure to afford 1-(tert-butoxycarbonylamino)propan-2-yl methanesulfonate (19.5 g, 94%) as a light yellow oil. Mass calculated for C$_9$H$_{19}$NO$_5$S=253.32; found: [M+H]$^+$=254.2.

To a solution of 1-(tert-butoxycarbonylamino)propan-2-yl methanesulfonate (10.0 g, 39.5 mmol) in DMF (100 mL) at RT was added NaN$_3$ (7.7 g, 118.5 mmol). The reaction mixture was stirred at 85° C. for 24 h, cooled to RT, diluted with cold water (300 mL) and extracted with diethyl ether (3×300 mL). The combined organic layers were washed with saturated aqueous NaHCO$_3$ (2×200 mL) and brine (200 mL), dried over MgSO$_4$, filtered and concentrated under reduced pressure to afford tert-butyl 2-azidopropylcarbamate (7.0 g, 88.6%) as a light yellow oil. $^1$HNMR (CDCl$_3$): δ 3.6 (m, 1H, CH), 3.25 (m, 1H, CH$_2$), 2.9 (m, 1H, CH$_2$), 1.49 (s, 9H, CH$_3$), 1.2 (d, 3H, CH$_3$).

A mixture of afford tert-butyl 2-azidopropylcarbamate (7.0 g, 3.6 mmol) and Pd/C (0.7 g) in MeOH (250 mL) was stirred under a H$_2$ (1 atm) atmosphere (RT, 16 h). The mixture was filtered and concentrated under reduced pressure. The crude product was purified by chromatography on silica gel, eluting with saturated NH$_3$ in MeOH-DCM (0-10%) to afford tert-butyl 2-aminopropylcarbamate (5.1 g, 83.7%) as a light yellow oil. $^1$HNMR (CDCl$_3$): δ 4.9 (bs, 1H, NH), 3.15 (m, 1H, CH), 3.0 (m, 1H, CH$_2$), 2.8 (m, 1H, CH$_2$), 1.7 (bs, 2H, NH$_2$), 1.5 (s, 9H, CH$_3$), 1.0 (d, 3H, CH$_3$).

To a solution of tert-butyl 2-aminopropylcarbamate (3.6 g, 20.6 mmol), 2-hydroxybenzoic acid (2.79 g, 20.6 mmol) and imidazole (1.41 g, 20.6 mmol) in EtOAc (100 mL) at 0° C. was slowly added a solution of DCC (4.26 g, 20.6 mmol) in EtOAc (50 mL). The reaction mixture was stirred (RT, 16 h), filtered and concentrated under reduced pressure. The crude product was purified by silica gel chromatography, EtOAc/PE (0-20%) to afford tert-butyl 2-(2-hydroxybenzamido)propylcarbamate (2.4 g, 40%) as a white solid.

A mixture of tert-butyl 2-(2-hydroxybenzamido)propylcarbamate (2.4 g, 8.16 mmol) in saturated HCl-MeOH (50 mL) was stirred (RT, 2 h) and concentrated under reduced pressure to afford N-(1-aminopropan-2-yl)-2-hydroxybenzamide (1.8 g, 96%) as a white solid. Mass calculated for C$_{10}$H$_{14}$N$_2$O$_2$=194.23; found: [M+H]$^+$=195.2.

To a solution of N-(1-aminopropan-2-yl)-2-hydroxybenzamide (1.7 g, 7.3 mmol), DHA (2.0 g, 6.1 mmol) and Et$_3$N (3.1 mL, 21.9 mmol) in CH$_3$CN (50 mL) at 0° C. was added HATU (2.77 g, 7.3 mmol). The mixture was allowed to warm to RT, stirred for 16 h and concentrated under reduced pressure. The residue was diluted with brine (150 mL) and extracted with EtOAc (2×200 mL). The combined organic layers were washed with 1N HCl (2×150 mL), saturated aqueous NaHCO$_3$ (2×150 mL) and brine (150 mL), dried over MgSO$_4$, filtered and concentrated under reduced pressure. The residue was purified by chromatography on silica gel, eluting with EtOAc-PE (0-25%) to afford the crude product, which was further purified by Preparative HPLC to afford N-(1-(4Z,7Z,10Z,13Z,16Z,19Z)-docosa-4,7,10,13,16,19-hexaenamidopropan-2-yl)-2-hydroxybenzamide (1.31 g, 42.6%) as a light yellow oil. Mass calculated for C$_{32}$H$_{44}$N$_2$O$_3$=504.70; found: [M+H]$^+$=505.5.

Example 22

Preparation of N-(2-(4Z,7Z,10Z,13Z,16Z,19Z)-docosa-4,7,10,13,16,19-hexaenamidopropyl)-2-hydroxybenzamide (Ih-6)

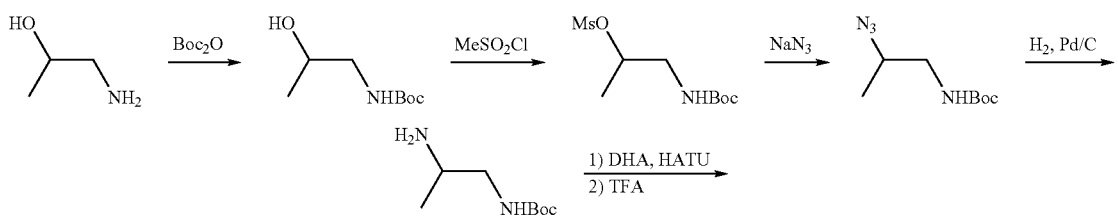

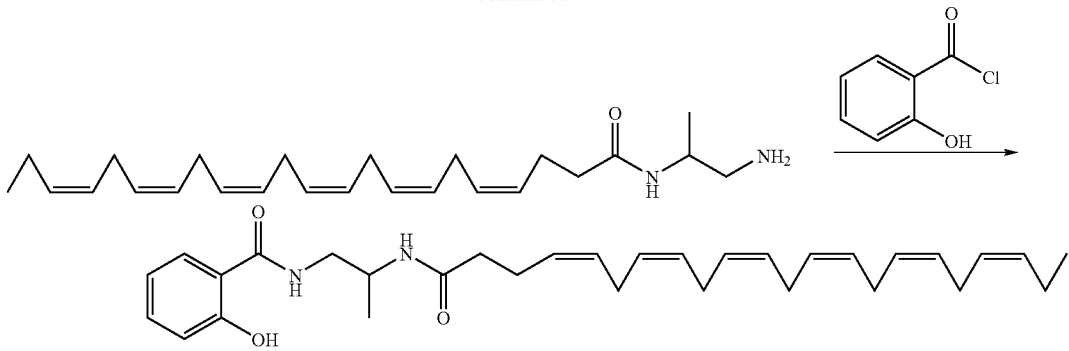

To a solution of tert-butyl 2-aminopropylcarbamate (1.06 g, 6.09 mmol, prepared as previously described), DHA (2.0 g, 6.09 mmol) and Et$_3$N (1.7 mL, 12.8 mmol) in CH$_3$CN (40 mL) at 0° C. was added HATU (2.31 g, 6.09 mmol). The mixture was stirred (RT, 16 h) and concentrated under reduced pressure. The residue was diluted with brine (100 mL) and extracted with EtOAc (2×100 mL). The combined organic layers were washed with saturated aqueous NaHCO$_3$ (100 mL) and brine (100 mL), dried over MgSO$_4$, filtered and concentrated under reduced pressure. The crude product was purified by chromatography on silica gel, eluting with EtOAc-PE (0-25%) to afford tert-butyl 2-(4Z,7Z,10Z,13Z,16Z,19Z)-docosa-4,7,10,13,16,19-hexaenamidopropylcarbamate (2.1 g, 70%) as a light yellow oil. Mass calculated for C$_{30}$H$_{48}$N$_2$O$_3$=484.71; found: [M+H]$^+$=485.6.

To a solution of tert-butyl 2-(4Z,7Z,10Z,13Z,16Z,19Z)-docosa-4,7,10,13,16,19-hexaenamidopropylcarbamate (2.10 g, 4.34 mmol) in DCM (100 mL) at 0° C. was slowly added TFA (30 mL). The mixture was stirred (0° C., 2 h), warmed to RT and stirred (16 h). The mixture was basified to pH 10 with saturated aqueous Na$_2$CO$_3$ and extracted with EtOAc (2×200 mL). The combined organic layers were dried over MgSO$_4$, filtered and concentrated under reduced pressure to afford (4Z,7Z,10Z,13Z,16Z,19Z)—N-(1-aminopropan-2-yl)-docosa-4,7,10,13,16,19-hexaenamide (1.60 g, 98%) as a light yellow oil. Mass calculated for C$_{25}$H$_{40}$N$_2$O=384.6; found: [M+H]$^+$=385.2.

To a solution of (4Z,7Z,10Z,13Z,16Z,19Z)—N-(1-aminopropan-2-yl)docosa-4,7,10,13,16,19-hexaenamide (1.60 g, 4.2 mmol), 2-hydroxybenzoic acid (0.57 g, 4.2 mmol) and imidazole (0.29 g, 4.2 mmol) in EtOAc (40 mL) at 0° C. was added a solution of DCC (0.87 g, 4.2 mmol) in EtOAc (40 mL). The mixture was allowed to warm to RT, stirred (16 h) and filtered. The solvent was removed under reduced pressure and the crude product was purified by chromatography on silica gel, eluting with EtOAc-PE (0-50%) to afford N-(2-(4Z,7Z,10Z,13Z,16Z,19Z)-docosa-4,7,10,13,16,19-hexaenamidopropyl)-2-hydroxybenzamide (1.07 g, 50.5%) as a light yellow oil. Mass calculated for C$_{32}$H$_{44}$N$_2$O$_3$=504.70; found: [M+H]$^+$=505.5.

Example 23

Preparation of N-(3-(4Z,7Z,10Z,13Z,16Z,19Z)-docosa-4,7,10,13,16,19-hexaenamidobutan-2-yl)-2-hydroxybenzamide (Ih-7)

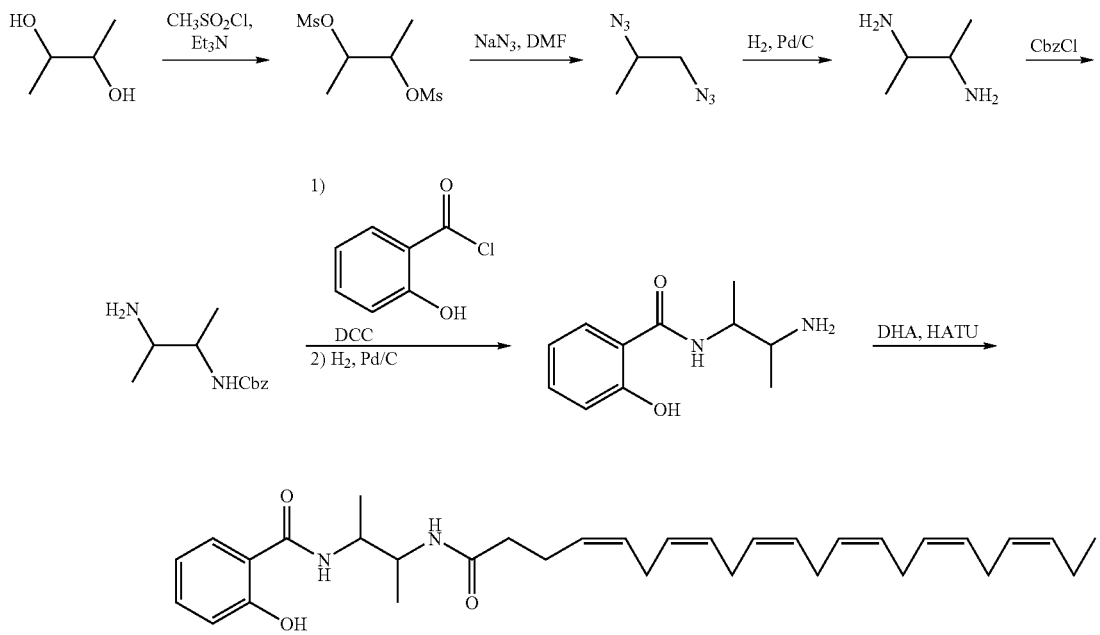

To a solution of butane 2,3-diol (15 g, 0.166 mol) and $Et_3N$ (57.7 mL, 0.415 mol) in $CH_2Cl_2$ (150 mL) at 0° C. was slowly added a solution of $CH_3SO_2Cl$ (32.1 mL, 0.415 mol) in $CH_2Cl_2$ (75 mL). The mixture was stirred at 0° C. for 2 h and diluted with $CH_2Cl_2$. The mixture was washed with water, 1N HCl, 5% aqueous $NaHCO_3$ and brine. The organic layer was dried over $MgSO_4$, filtered and concentrated under reduced pressure to afford butane-2,3-diol dimethanesulfonate (40 g, 98%) as a light yellow oil. $^1$HNMR ($CDCl_3$): δ 4.9 (m, 2H, CH), 3.05 (s, 6H, $CH_3$), 1.4 (m, 6H, $CH_3$).

To a solution of butane-2,3-diyldimethanesulfonate (15.0 g, 63.7 mmol) in DMF (150 mL) at RT was added $NaN_3$ (19.6 g, 301.5 mmol). The reaction mixture was stirred at 85° C. for 24 h, cooled to RT, diluted with cold water (100 mL) and extracted with diethyl ether (4×100 mL). The combined organic layers were washed with saturated aqueous $NaHCO_3$ (2×100 mL) and brine (100 mL), dried over $MgSO_4$, filtered and concentrated under reduced pressure. The crude product was purified by flash chromatography on silica gel, eluting with PE:EtOAc (5:1) to afford 2,3-diazidobutane (6.10 g, 68%) as a colorless oil.

A mixture of 2,3-diazidobutane (9.0 g, 64.3 mmol) and 10% Pd/C (0.90 g) in MeOH (300 mL) was stirred under a $H_2$ atmosphere (RT, 16 h). The mixture was filtered and concentrated under reduced pressure. The crude product was purified by column chromatography on silica gel, eluting with saturated $NH_3$ in MeOH-DCM (0-20%) to afford butane-2,3-diamine (4.8 g, 85%) as a yellow oil. $^1$HNMR ($CDCl_3$): δ 2.8 (m, 1H, CH), 2.6 (m, 1H, CH), 1.65 (s, 4H, $NH_2$), 1.0 (d, 6H, $CH_3$).

To a mixture of butane-2,3-diamine (4.8 g, 54.5 mmol) in water (50 mL) containing bromocresol green as indicator was slowly added a solution of methane sulfonic acid (10.46 g) in water (50 mL) until a blue to yellow color transition was observed. The mixture was diluted with ethanol (100 mL) and to it was added a solution of Cbz-Cl (7.61 g, 45.5 mmol) in DME (50 mL) and aqueous AcOK (w/v 50%) to maintain the pale-green color. The reaction mixture was stirred (RT, 1 h), concentrated under reduced pressure, treated with water and filtered. The solution was washed with toluene, basified with 40% aqueous NaOH and extracted with toluene (4×100 mL). The combined organic layers were washed with brine, dried over $MgSO_4$, filtered and concentrated under reduced pressure to afford benzyl 3-aminobutan-2-ylcarbamate (4.2 g, 35%) as a colorless oil. Mass calculated for $C_{12}H_{18}N_2O_2$=222.28; found: $[M-H]^+$=221.2.

To a mixture of benzyl 3-aminobutan-2-ylcarbamate (5.3 g, 23.8 mmol), 2-hydroxybenzoic acid (3.28 g, 23.8 mmol) and imidazole (1.62 g, 23.8 mmol) in EtOAc (180 mL) at 0° C. was slowly added a solution of DCC (4.90 g, 23.8 mmol) in EtOAc (20 mL). The reaction mixture was stirred (RT, 16 h), filtered and concentrated under reduced pressure. The crude product was purified by column chromatography on silica gel, eluting with PE-EtOAc (5:1) to afford benzyl 3-(2-hydroxybenzamido)butan-2-ylcarbamate (3.2 g, 40%) as a colorless oil. Mass calculated for $C_{19}H_{22}N_2O_4$=342.39; found: $[M+H]^+$=343.2.

A mixture of benzyl 3-(2-hydroxybenzamido)butan-2-ylcarbamate (3.2 g, 9.36 mmol) and 10% Pd/C (0.32 g) in MeOH (120 mL) was stirred under a $H_2$ (1 atm) atmosphere (RT, 16 h). The mixture was filtered and concentrated under reduced pressure. The crude product was purified by column chromatography on silica gel, eluting with MeOH-DCM (0-20%) to afford N-(3-aminobutan-2-yl)-2-hydroxybenzamide (1.67 g, 86%) as a yellow oil.

To a solution of N-(3-aminobutan-2-yl)-2-hydroxybenzamide (1.52 g, 7.3 mmol), DHA (2 g, 6.0 mmol) and $Et_3N$ (1.21 g, 12.0 mmol) in $CH_3CN$ (50 mL) at 0° C. was added HATU (2.37 g, 6.24 mmol). The mixture was stirred (RT, 16 h) and concentrated under reduced pressure. The residue was diluted with brine (50 mL) and extracted with EtOAc (3×50 mL). The combined organic layers were washed with 1N HCl (2×50 mL), saturated aqueous $NaHCO_3$ (2×50 mL) and brine (50 mL), dried over $MgSO_4$, and concentrated under reduced pressure. The crude product was purified by chromatography on silica gel, eluting with EtOAc-PE (0-25%) to afford N-(3-(4Z,7Z,10Z,13Z,16Z,19Z)-docosa-4,7,10,13,16,19-hexaenamidobutan-2-yl)-2-hydroxybenzamide (1.08 g, 34.3%) as a light yellow oil. Mass calculated for $C_{33}H_{46}N_2O_3$=518.73; found: $[M+H]^+$=519.6.

Example 24

Preparation of 3-(4Z,7Z,10Z,13Z,16Z,19Z)-docosa-4,7,10,13,16,19-hexaenamidobenzoic acid (17)

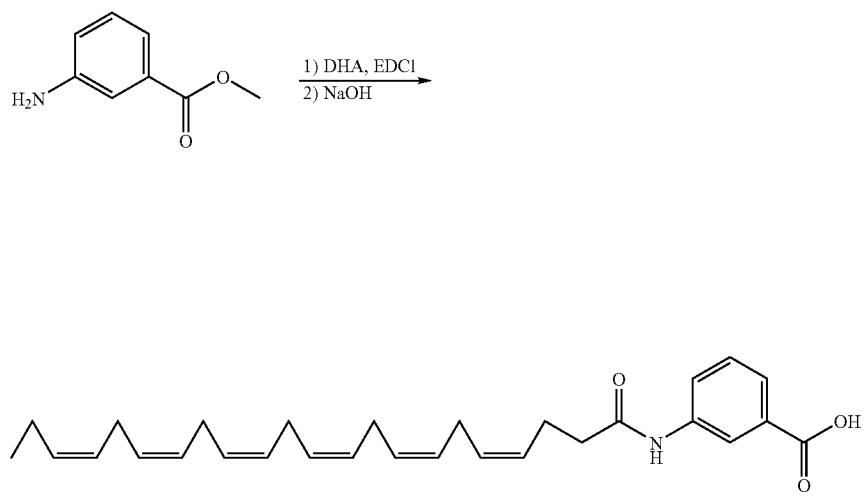

To a solution of DHA (0.10 g, 0.3 mmol) in dichloromethane (3 mL) was added methyl 3-aminobenzoate (0.046 g, 0.3 mmol), EDCI (0.064 g, 0.3 mmol) and dimethylaminopyridine (4 mg, 0.03 mmol). The reaction mixture was stirred (RT, 2 h) and then partitioned between $CH_2Cl_2$ and water. The aqueous layer was extracted with $CH_2Cl_2$, and the combined organic extracts were washed with 10% HCl, brine and dried over $MgSO_4$. The crude material was purified by silica gel chromatography (0-30% EtOAc/pentane) to afford methyl 3-(4Z,7Z,10Z,13Z,16Z,19Z)-docosa-4,7,10,13,16,19-hexaenamidobenzoate. Mass calculated for $C_{302}H_{39}NO_3$=461.64; found: $[M+H]^+$=462.3. This was then dissolved in MeOH (10 mL) and 5 N NaOH (2 mL). The mixture was stirred at reflux (4 h), and then concentrated. The aqueous solution was acidified to pH 3 with HCl, and the product was extracted with ethyl acetate. The organic layer was washed with water, brine and dried over $MgSO_4$. The crude product was purified by silica gel chromatography (0-30% ethyl acetate/pentane) to afford 0.066 g of 3-(4Z,7Z,10Z,13Z,16Z,19Z)-docosa-4,7,10,13,16,19-hexaenamidobenzoic acid as an off-white solid. Mass calculated for $C_{29}H_{37}NO_3$=447.61; found: $[M-H]^+$=446.2.

Example 25

Preparation of 2-hydroxy-5-(5Z,8Z,11Z,14Z)-icosa-5,8,11,14-tetraenamidobenzoic acid (18)

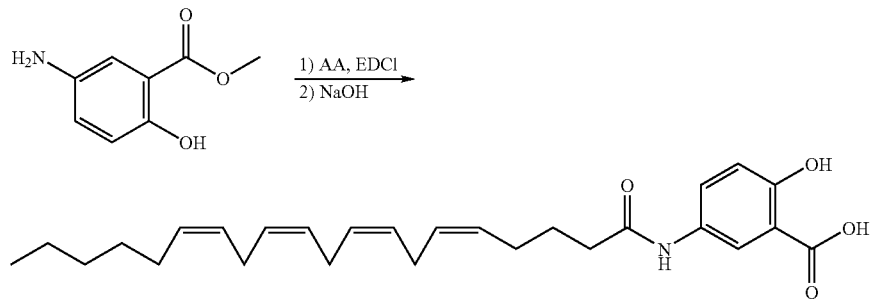

To a solution of methyl 5-amino-2-hydroxybenzoate (0.27 g, 1.6 mmol) in dichloromethane (10 mL) was added arachidonic acid (0.5 g, 1.6 mmol), EDCI (0.32 g, 1.7 mmol) and dimethylaminopyridine (0.020 g, 0.2 mmol). The reaction was stirred (RT, 2 h), and then partitioned between DCM and brine. The aqueous layer was extracted with DCM, and the combined organic layers were washed with 1N HCl, water, saturated aqueous $NaHCO_3$ and water, and then dried over $MgSO_4$. The crude product was purified by silica gel chromatography (0-5% MeOH/DCM) to afford 0.6 g of methyl 2-hydroxy-5-(5Z,8Z,11Z,14Z)-icosa-5,8,11,14-tetraenamidobenzoate as a brown oil. Mass calculated for $C_{28}H_{39}NO_4$=453.61; found: $[M+H]^+$=454.3.

The methyl 2-hydroxy-5-(5Z,8Z,11Z,14Z)-icosa-5,8,11,14-tetraenamidobenzoate was then dissolved in THF (15 mL) and 3N NaOH (5 mL). The mixture was heated (60° C., 2 h) and then concentrated and acidified to pH 3 with 2N HCl. The product was extracted with ethyl acetate, and the combined organic extracts were washed with brine and dried over $MgSO_4$. The crude product was purified by silica gel chromatography (0-15% MeOH/$CH_2Cl_2$) to afford 2-hydroxy-5-(5Z,8Z,11Z,14Z)-icosa-5,8,11,14-tetraenamidobenzoic acid (0.3 g) as an orange solid. Mass calculated for $C_{27}H_{37}NO_4$=439.59; found: $[M-H]^+$=438.3.

Example 26

Preparation of 5-(2-(4Z,7Z,10Z,13Z,16Z,19Z)-docosa-4,7,10,13,16,19-hexaenamidoacetamido)-2-hydroxybenzoic acid (IIIf-1)

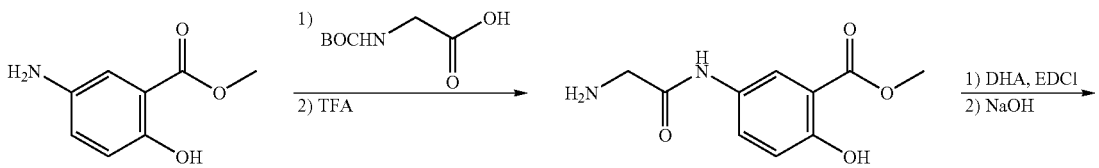

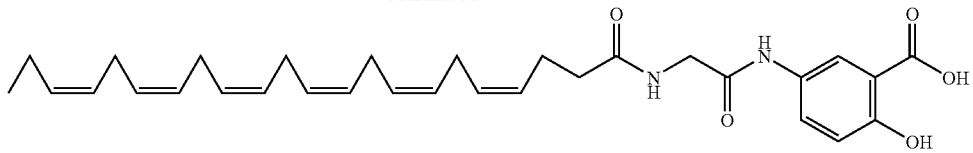

To a solution of methyl 5-amino-2-hydroxybenzoate (1.5 g, 9.0 mmol) in dichloromethane (50 mL) was added BOC-glycine (1.57 g, 9.0 mmol), EDCI (1.89 g, 9.9 mmol) and dimethylaminopyridine (0.11 g, 0.9 mmol). The reaction was stirred (RT, 2.5 h), and then partitioned between $CH_2Cl_2$ and brine. The aqueous layer was extracted with $CH_2Cl_2$ and the combined organic layers were washed with brine and dried over $MgSO_4$. The crude product was purified by silica gel chromatography (0-5% MeOH/$CH_2Cl_2$) to afford methyl 5-(2-(tert-butoxycarbonylamino)-acetamido)-2-hydroxybenzoate (1.37 g). Mass calculated for $C_{15}H_{20}N_2O_6$=324.33; found: $[M+Na]^+$=347.2.

The methyl 5-(2-(tert-butoxycarbonylamino)-acetamido)-2-hydroxybenzoate (1.3 g, 4.0 mmol) was dissolved in $CH_2Cl_2$ (15 mL) and TFA (8 mL). The reaction was stirred (RT, 2.5 h) and then concentrated to afford methyl 5-(2-aminoacetamido)-2-hydroxybenzoate as a clear oil. Found $[M+H]+$=225.1. The oil was dissolved in $CH_2Cl_2$ (20 mL) and to this was added DHA (1.3 g, 4.0 mmol), EDCI (0.84 g, 4.4 mmol) and triethylamine (2.0 g, 20.0 mmol). The reaction was stirred (RT, 4 h) and then partitioned between $CH_2Cl_2$ and brine. The aqueous layer was extracted with $CH_2Cl_2$, and the combined organic layers were dried over $MgSO_4$. The crude material was purified by silica gel chromatography (0-5% MeOH/$CH_2Cl_2$) to afford methyl 5-(2-(4Z,7Z,10Z,13Z,16Z,19Z)-docosa-4,7,10,13,16,19-hexaenamidoacetamido)-2-hydroxybenzoate (0.9 g) as a tan solid. Mass calculated for $C_{10}H_{12}N_2O_4$=534.69; found: $[M+H]^+$=535.4.

Methyl 5-(2-(4Z,7Z,10Z,13Z,16Z,19Z)-docosa-4,7,10,13,16,19-hexaenamidoacetamido)-2-hydroxybenzoate (0.9 g, 1.7 mmol) was dissolved in THF (15 mL) and 1N NaOH (8 mL). The reaction was stirred (50° C., 5 h), and then acidified to pH 3 with 2N HCl. The product was extracted with ethyl acetate, and the combined organic extracts were washed with water, brine and dried over $MgSO_4$. The crude material was purified by silica gel chromatography (0-5% MeOH/$CH_2Cl_2$) to afford 5-(2-(4Z,7Z,10Z,13Z,16Z,19Z)-docosa-4,7,10,13,16,19-hexaenamidoacetamido)-2-hydroxybenzoic acid (0.40 g) as a yellow solid. Mass calculated for $C_{31}H_{40}N_2O_5$=520.66; found: $[M+H]+$=521.3.

Example 27

Preparation of N-(2-(4Z,7Z,10Z,13Z,16Z,19Z)-docosa-4,7,10,13,16,19-hexaenamidoethyl)-2-hydroxy-4-(trifluoromethyl)benzamide (Ih-8)

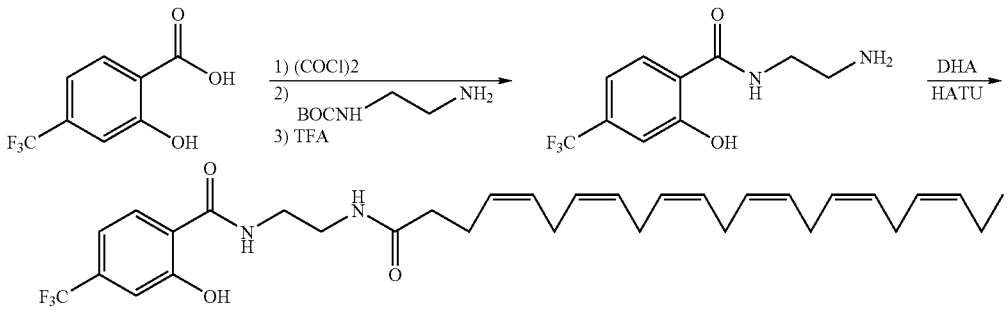

To a solution of 2-hydroxy-4-(trifluoromethyl)benzoic acid (0.5 g, 2.4 mmol) in $CH_2Cl_2$ (8 mL) was added oxalyl chloride (0.46 g, 3.6 mmol) and 2 drops of DMF. The reaction was stirred (RT, 2 h) and then concentrated under reduced pressure. The resulting residue was dissolved in $CH_2Cl_2$ (8 mL) and tert-butyl 2-aminoethylcarbamate (0.39 g, 2.4 mmol) and diisopropylethylamine (0.41 g, 3.2 mmol) were added. The reaction was stirred (RT, 16 h) and then partitioned between $CH_2Cl_2$ and brine. The aqueous layer was extracted with $CH_2Cl_2$ and the combined organic extracts were dried over $MgSO_4$. The crude material was purified by silica gel chromatography (0-10% MeOH/$CH_2Cl_2$) to afford tert-butyl 2-(2-hydroxy-4-(trifluoromethyl)benzamido)ethylcarbamate (0.55 g). Mass calculated for $C_{15}H_{19}F_3N_2O_4$=348.32; found: $[M+Na]^+$=371.1. This was then dissolved in $CH_2Cl_2$ (10 mL) and TFA (4 mL). The reaction was stirred (RT, 3 h) and concentrated and dried to afford N-(2-aminoethyl)-2-hydroxy-4-(trifluoromethyl)benzamide (0.7 g) as a clear oil. Mass calculated for $C_{10}H_{11}F_3N_2O_2$=248.20; found: $[M+H]^+$=249.1.

The N-(2-aminoethyl)-2-hydroxy-4-(trifluoromethyl)benzamide (0.7 g, 1.5 mmol) was dissolved in CH$_2$Cl$_2$ (10 mL) and to this was added DHA (0.48 g, 1.5 mmol), HATU (0.67 g, 1.8 mmol) and triethylamine (0.59 g, 5.9 mmol). The reaction was stirred (RT, 16 h) and then partitioned between CH$_2$Cl$_2$ and brine. The aqueous layer was extracted with CH$_2$Cl$_2$ and the combined organic extracts were dried over MgSO$_4$. The crude material was purified by silica gel chromatography (0-10% MeOH/CH$_2$Cl$_2$) to afford N-(2-(4Z,7Z,10Z,13Z,16Z,19Z)-docosa-4,7,10,13,16,19-hexaenamidoethyl)-2-hydroxy-4-(trifluoromethyl)benzamide (0.28 g) as a yellow oil. Mass calculated for C$_{32}$H$_{41}$F$_3$N$_2$O$_3$=558.67; found: [M+H]$^+$=559.3.

Example 28

Preparation of ethyl 2-(2-(4Z,7Z,10Z,13Z,16Z,19Z)-docosa-4,7,10,13,16,19-hexaenamido-3-phenylpropanoyloxy)benzoate (Ii-3)

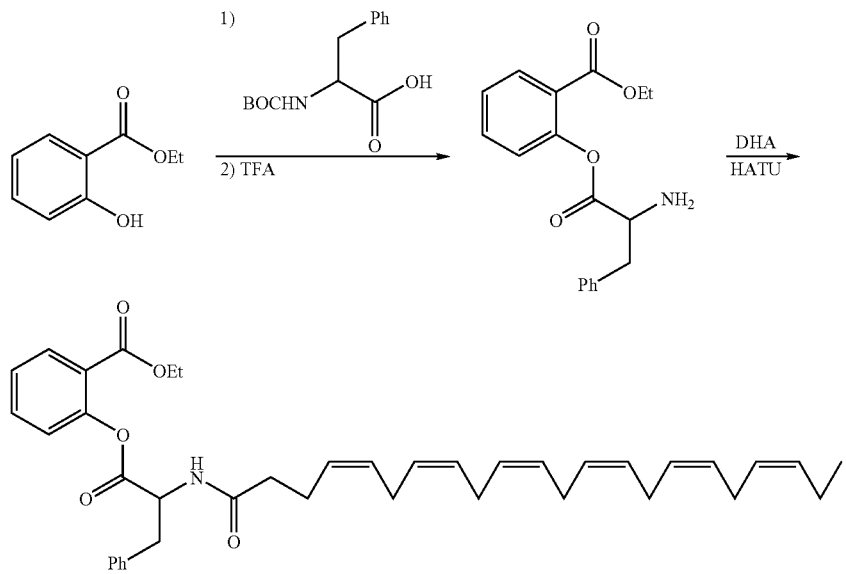

To a solution of ethyl 2-hydroxybenzoate (0.5 g, 3.0 mmol) in CH$_2$Cl$_2$ (8 mL) was added 2-(tert-butoxycarbonylamino)-3-phenylpropanoic acid (0.8 g, 3.0 mmol), EDCI (0.63 g, 3.3 mmol) and dimethylaminopyridine (0.037 g, 0.3 mmol). The reaction was stirred (RT, 3 h) and then partitioned between CH$_2$Cl$_2$ and brine. The aqueous layer was extracted with CH$_2$Cl$_2$ and the combined organic extracts were dried over MgSO$_4$. The crude material was purified by silica gel chromatography (0-10% MeOH/CH$_2$Cl$_2$) to afford ethyl 2-(2-(tert-butoxycarbonylamino)-3-phenylpropanoyloxy)benzoate (1.2 g). Mass calculated for C$_{23s}$H$_{27}$NO$_6$=413.46; found: [M+Na]$^+$=437.1.

The ethyl 2-(2-(tert-butoxycarbonylamino)-3-phenylpropanoyloxy)benzoate (1.2 g, 2.9 mmol) was dissolved in CH$_2$Cl$_2$ (10 mL) and TFA (4 mL). The reaction was stirred (RT, 3 h) and then concentrated under reduced pressure. The crude material was purified by silica gel chromatography (0-10% MeOH/CH$_2$Cl$_2$) to afford ethyl 2-(2-amino-3-phenylpropanoyloxy)benzoate (0.63 g). Mass calculated for C$_{18}$H$_{19}$NO$_4$=313.35; found: [M+H]$^+$=314.1

Ethyl 2-(2-amino-3-phenylpropanoyloxy)benzoate (0.24 g, 0.8 mmol) and DHA (0.25 g, 0.8 mmol) were combined in CH$_2$Cl$_2$ (10 mL) and to this was added HATU (0.35 g, 0.9 mmol) and diisopropylethylamine (0.30 g, 2.3 mmol). The reaction was stirred (RT, 3 h) and then partitioned between CH$_2$Cl$_2$ and brine. The aqueous layer was extracted with CH$_2$Cl$_2$ and the combined organic extracts were dried over MgSO$_4$. The crude material was purified by silica gel chromatography (0-10% MeOH/CH$_2$Cl$_2$) to afford ethyl 2-(2-(4Z,7Z,10Z,13Z,16Z,19Z)-docosa-4,7,10,13,16,19-hexaenamido-3-phenylpropanoyloxy)benzoate as a tan solid. Mass calculated for C$_{40}$H$_{49}$NO$_5$=623.82; found: [M+H]$^+$=624.2.

Example 29

Preparation of 5-(2-(4Z,7Z,10Z,13Z,16Z,19Z)-docosa-4,7,10,13,16,19-hexaenamido-3-phenylpropanamido)-2-hydroxybenzoic acid (IIIf-2)

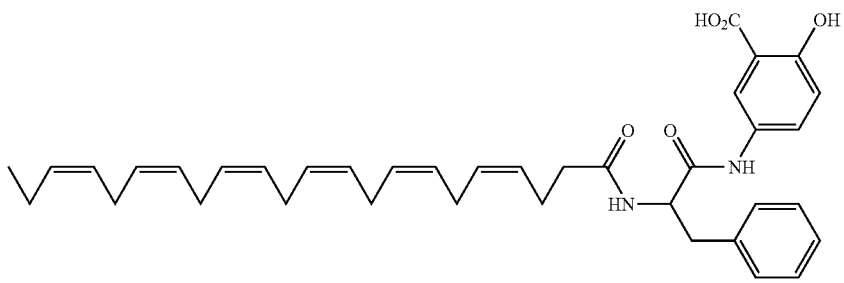 [SMILES: CC/C=C\C/C=C\C/C=C\C/C=C\C/C=C\C/C=C\CCC(=O)NC(Cc1ccccc1)C(=O)Nc1ccc(O)c(C(=O)O)c1]

5-(2-(4Z,7Z,10Z,13Z,16Z,19Z)-Docosa-4,7,10,13,16,19-hexaenamido-3-phenylpropanamido)-2-hydroxybenzoic acid was prepared in a similar fashion as 5-(2-(4Z,7Z,10Z,13Z,16Z,19Z)-docosa-4,7,10,13,16,19-hexaenamido-4-methylpentanamido)-2-hydroxybenzoic acid, using the appropriate phenylalanine starting material. Mass calculated for $C_{38}H_{46}N_2O_5$=610.78; found: $[M-H]^+$=609.3.

Example 30

Preparation of 2-hydroxy-5-(5Z,8Z,11Z,14Z,17Z)-icosa-5,8,11,14,17-pentaenamidobenzoic acid (IIIg-1)

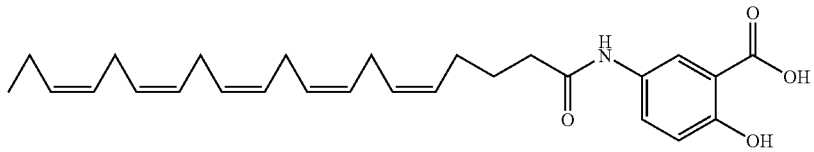 [SMILES: CC/C=C\C/C=C\C/C=C\C/C=C\C/C=C\CCCC(=O)Nc1ccc(O)c(C(=O)O)c1]

2-Hydroxy-5-(5Z,8Z,11Z,14Z,17Z)-icosa-5,8,11,14,17-pentaenamidobenzoic acid was prepared in a similar fashion as 5-(4Z,7Z,10Z,13Z,16Z,19Z)-docosa-4,7,10,13,16,19-hexaenamido-2-hydroxybenzoic acid, using the appropriate EPA starting material. Mass calculated for $C_{27}H_{35}NO_4$=437.57; found: $[M-H]^+$=436.2.

Example 31

Preparation of N-(2-(4Z,7Z,10Z,13Z,16Z,19Z)-docosa-4,7,10,13,16,19-hexaenamidoethyl)-2',4'-difluoro-4-hydroxybiphenyl-3-carboxamide (Ih-9)

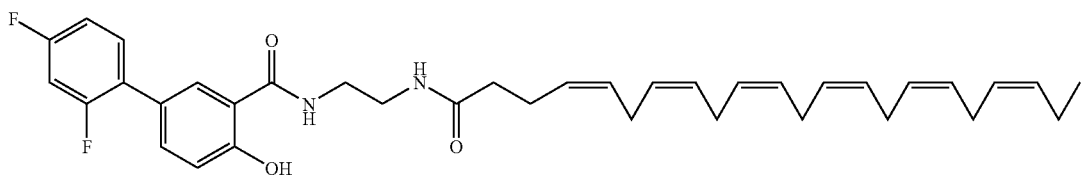

N-(2-(4Z,7Z,10Z,13Z,16Z,19Z)-docosa-4,7,10,13,16,19-hexaenamidoethyl)-2',4'-difluoro-4-hydroxybiphenyl-3-carboxamide was prepared in a similar fashion as N-(2-(4Z,7Z,10Z,13Z,16Z,19Z)-docosa-4,7,10,13,16,19- hexaenamidoethyl)-2-hydroxybenzamide, using the appropriate 2',4'-difluoro-4-hydroxybiphenyl-3-carboxylic acid starting material. Mass calculated for $C_{37}H_{44}F_2N_2O_3$=602.75; found: $[M+H]^+$=603.3.

Example 32

Preparation of 2',4'-difluoro-4-hydroxy-N-(2-(5Z,8Z,11Z,14Z,17Z)-icosa-5,8,11,14,17-pentaenamidoethyl)biphenyl-3-carboxamide (Ih-10)

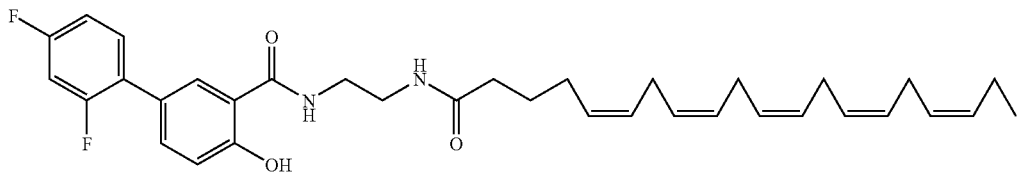 [SMILES: CC/C=C\C/C=C\C/C=C\C/C=C\C/C=C\CCCC(=O)NCCNC(=O)c1cc(-c2ccc(F)cc2F)ccc1O]

2',4'-Difluoro-4-hydroxy-N-(2-(5Z,8Z,11Z,14Z,17Z)-icosa-5,8,11,14,17-pentaenamidoethyl)biphenyl-3-carboxamide was prepared in a similar fashion as N-(2-(4Z,7Z,10Z,13Z,16Z,19Z)-docosa-4,7,10,13,16,19-hexaenamidoethyl)-2-hydroxybenzamide, using the appropriate 2',4'-difluoro-4-hydroxybiphenyl-3-carboxylic acid and EPA starting materials. Mass calculated for $C_{35}H_{42}F_2N_2O_3$=576.72; found: $[M+H]^+$=577.3.

Example 33

Preparation of ethyl 4-((4Z,7Z,10Z,13Z,16Z,19Z)-docosa-4,7,10,13,16,19-hexaenoyloxy)-2',4'-difluorobiphenyl-3-carboxylate (IVc-2)

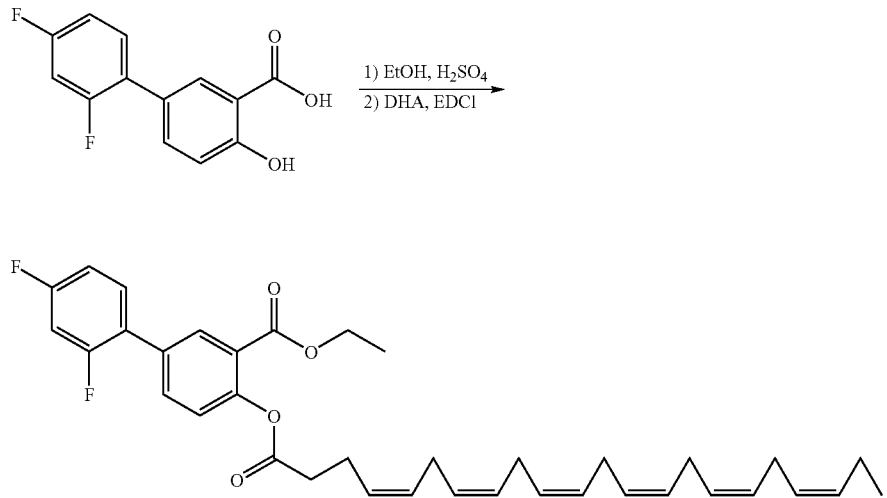 [SMILES: O=C(O)c1cc(-c2ccc(F)cc2F)ccc1O ; CC/C=C\C/C=C\C/C=C\C/C=C\C/C=C\C/C=C\CCC(=O)Oc1ccc(-c2ccc(F)cc2F)cc1C(=O)OCC]

2',4'-difluoro-4-hydroxybiphenyl-3-carboxylic acid (1.0 g, 4.0 mmol) was dissolved in ethanol (30 mL) and sulfuric acid (8 mL). The solution was stirred (80° C., 18 h) and then concentrated under reduced pressure. The residue was dissolved in ethyl acetate and washed with water, brine and dried over $MgSO_4$. Solvent evaporation afforded ethyl 2',4'-difluoro-4-hydroxybiphenyl-3-carboxylate (1.0 g). Mass calculated for $C_{15}H_{12}F_2O_3$=278.25; found: $[M+H]^+$=279.1.

Ethyl 2',4'-difluoro-4-hydroxybiphenyl-3-carboxylate (0.3 g, 1.1 mmol) was dissolved in $CH_2Cl_2$ (10 mL) and to this was added DHA (0.35 g, 1.1 mmol), EDCI (0.23 g, 1.2 mmol) and dimethylaminopyridine (0.13 g, 0.1 mmol). The reaction was stirred (RT, 3 h) and then partitioned between $CH_2Cl_2$ and brine. The aqueous layer was extracted with $CH_2Cl_2$ and the combined organic extracts were dried over $MgSO_4$. The crude material was purified by silica gel chromatography (0-40% ethyl acetate/pentane) to afford ethyl 4-((4Z,7Z,10Z,13Z,16Z,19Z)-docosa-4,7,10,13,16,19-hexaenoyloxy)-2',4'-difluorobiphenyl-3-carboxylate (0.1 g). Mass calculated for $C_{37}H_{42}F_2O_4$=588.72; found: $[M+H]^+$=589.3.

Example 34

Preparation of ethyl 2-((4Z,7Z,10Z,13Z,16Z,19Z)-docosa-4,7,10,13,16,19-hexaenoyloxy)-4-(trilluoromethyl)benzoate (VIc-3)

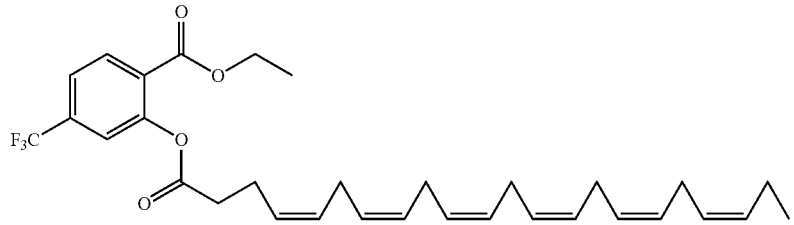 [SMILES: CC/C=C\C/C=C\C/C=C\C/C=C\C/C=C\C/C=C\CCC(=O)Oc1cc(C(F)(F)F)ccc1C(=O)OCC]

Ethyl 2-((4Z,7Z,10Z,13Z,16Z,19Z)-docosa-4,7,10,13,16,19-hexaenoyloxy)-4-(trifluoromethyl)benzoate was prepared in a similar fashion as ethyl 4-((4Z,7Z,10Z,13Z,16Z,19Z)-docosa-4,7,10,13,16,19-hexaenoyloxy)-2',4'-difluorobiphenyl-3-carboxylate, using the appropriate 2-hydroxy-4-(trifluoromethyl)benzoic acid starting material. Mass calculated for $C_{32}H_{39}F_3O_4$=544.64; found: $[M+Na]^+$= 567.3.

Example 35

Preparation of ethyl 4-(2-(4Z,7Z,10Z,13Z,16Z,19Z)-docosa-4,7,10,13,16,19-hexaenamido-4-methylpentanoyloxy)-2',4'-difluorobiphenyl-3-carboxylate (Ii-4)

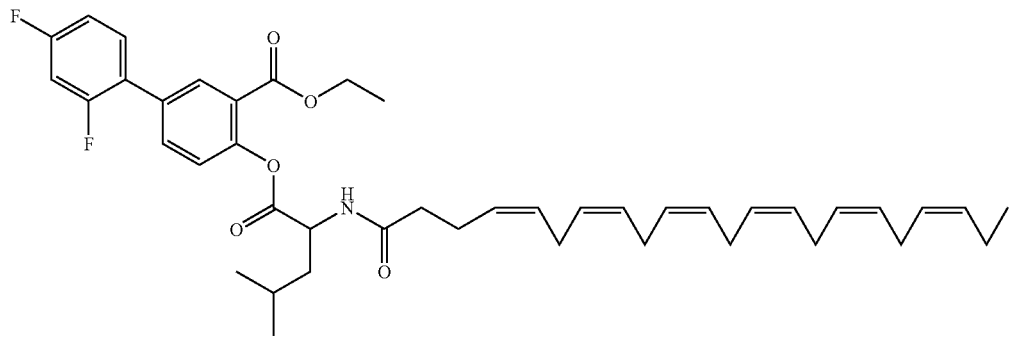 [SMILES: CC/C=C\C/C=C\C/C=C\C/C=C\C/C=C\C/C=C\CCC(=O)NC(CC(C)C)C(=O)Oc1ccc(-c2ccc(F)cc2F)cc1C(=O)OCC]

Ethyl 4-(2-(4Z,7Z,10Z,13Z,16Z,19Z)-docosa-4,7,10,13,16,19-hexaenamido-4-methylpentanoyloxy)-2',4'-difluorobiphenyl-3-carboxylate was prepared as described for ethyl 2-(2-(4Z,7Z,10Z,13Z,16Z,19Z)-docosa-4,7,10,13,16,19-hexaenamido-4-methylpentanoyloxy)benzoate, using the appropriate 2',4'-difluoro-4-hydroxybiphenyl-3-carboxylic acid starting material. Mass calculated for $C_{43}H_{53}F_2NO_5$=701.88; found: $[M+H]^+$=702.4.

Example 36

Preparation of ethyl 2-(2-(4Z,7Z,10Z,13Z,16Z,19Z)-docosa-4,7,10,13,16,19-hexaenamido-4-methylpentanoyloxy)-4-(trilluoromethyl)benzoate (Ii-5)

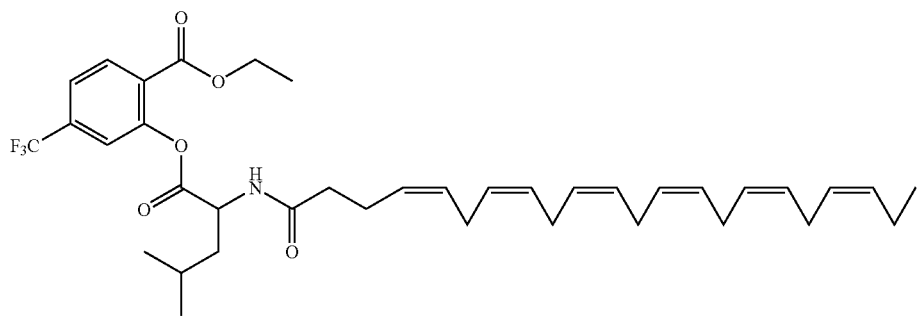 [SMILES: CC/C=C\C/C=C\C/C=C\C/C=C\C/C=C\C/C=C\CCC(=O)NC(CC(C)C)C(=O)Oc1cc(C(F)(F)F)ccc1C(=O)OCC]

Ethyl 2-(2-(4Z,7Z,10Z,13Z,16Z,19Z)-docosa-4,7,10,13,16,19-hexaenamido-4-methylpentanoyloxy)-4-(trifluoromethyl)benzoate was prepared as described for ethyl 2-(2-(4Z,7Z,10Z,13Z,16Z,19Z)-docosa-4,7,10,13,16,19-hexaenamido-4-methylpentanoyloxy)benzoate, using the appropriate 2-hydroxy-4-(trifluoromethyl)benzoic acid starting material. Mass calculated for $C_{38}H_{50}F_3NO_5$=657.80; found: $[M+H]^+$=658.4.

Example 37

Preparation of N-(2-(2-(2-(4Z,7Z,10Z,13Z,16Z,19Z)-docosa-4,7,10,13,16,19-hexaenamidoethyl)disulfanyl)ethyl)-2-hydroxybenzamide (I-2)

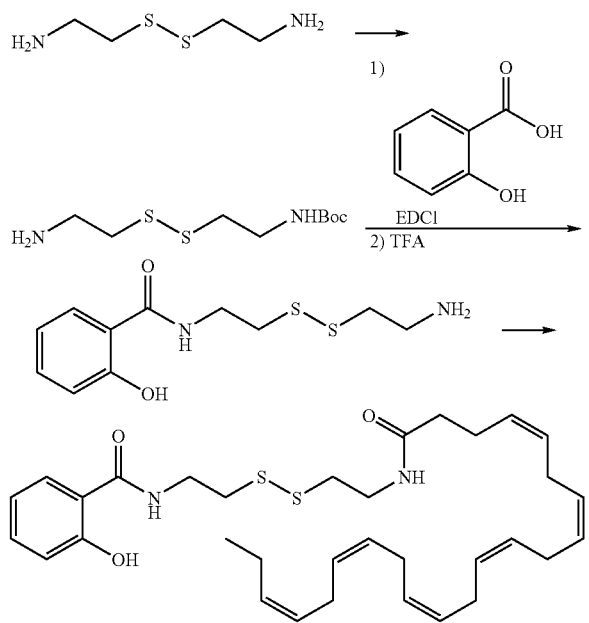

Cystamine dihydrochloride (1.0 g, 4.44 mmol) was dissolved in MeOH (50 mL). Triethylamine (1.85 mL, 3 eq) was added at room temperature, followed by dropwise addition of $Boc_2O$ (0.97 g, 4.44 mmol) as a solution in 5 mL of MeOH The resulting reaction mixture was stirred at room temperature for 3 h. It was then concentrated under reduced pressure and the resulting residue was taken up in 1M $NaH_2PO_4$ (20 mL). The aqueous layer was washed with 10 mL of a 1:1 solution of pentane/EtOAc, basified to pH 9 with 1M NaOH, and extracted with EtOAc. The combined organic layers were washed with brine, dried over $Na_2SO_4$ and concentrated under reduced pressure to afford tert-butyl 2-(2-(2-aminoethyl)disulfanyl)ethylcarbamate (500 mg, 44%).

tert-Butyl 2-(2-(2-aminoethyl)disulfanyl)ethylcarbamate (500 mg, 1.98 mmol) was taken up in $CH_2Cl_2$ (20 mL) along with salicylic acid (273 mg, 1.98 mmol) and EDCI (693 mmol, 2.2 mmol). The resulting reaction mixture was stirred at room temperature for 18 h. It was then diluted with $CH_2Cl_2$, washed with saturated aqueous $NaHCO_3$, brine, dried over $Na_2SO_4$ and concentrated under reduced pressure. Purification by chromatography (40% EtOAc, 60% pentane) afforded tert-butyl 2-(2-(2-(2-hydroxybenzamido)ethyl)disulfanyl)ethylcarbamate (400 mg, 54%). Mass calculated for $C_{16}H_{24}N_2O_4S_2$: 372.12; found: $[M+H]^+$=373.

tert-Butyl 2-(2-(2-(2-hydroxybenzamido)ethyl)disulfanyl)ethylcarbamate (400 mg, 1.08 mmol) was taken up in 25% TFA in $CH_2Cl_2$ (10 mL) and allowed to stand at room temperature for 3 h. The reaction mixture was concentrated under reduced pressure to afford a quantitative yield of N-(2-(2-(2-aminoethyl)-disulfanyl)-ethyl)-2-hydroxybenzamide as the TFA salt.

The TFA salt of N-(2-(2-(2-aminoethyl)-disulfanyl)-ethyl)-2-hydroxybenzamide (1.08 mmol) was taken up in anhydrous $CH_3CN$ (15 mL) along with (4Z,7Z,10Z,13Z,16Z,19Z)-docosa-4,7,10,13,16,19-hexaenoic acid (DHA, 352 mg, 1.08 mmol), HATU (450 mg, 1.2 mmol) and DIEA (0.550 mL). The resulting reaction mixture was stirred at room temperature for 2 h. It was then diluted with EtOAc and washed successively with saturated aqueous $NaHCO_3$ and brine. The organic layer was dried over $Na_2SO_4$ and concentrated under reduced pressure. Purification by chromatography (60% EtOAc, 40% pentane) afforded N-(2-(2-(2-(4Z,7Z,10Z,13Z,16Z,19Z)-docosa-4,7,10,13,16,19-hexaenamidoethyl)disulfanyl)ethyl)-2-hydroxybenzamide (280 mg, 44%). Mass calculated for $C_{33}H_{46}N_2O_3S_2$: 582.3; found: $[M+H]^+$=583.

Example 38

Preparation of N-(2-(2-(4Z,7Z,10Z,13Z,16Z,19Z)-docosa-4,7,10,13,16,19-hexaenamidoethoxy)ethyl)-2-hydroxybenzamide (I-3)

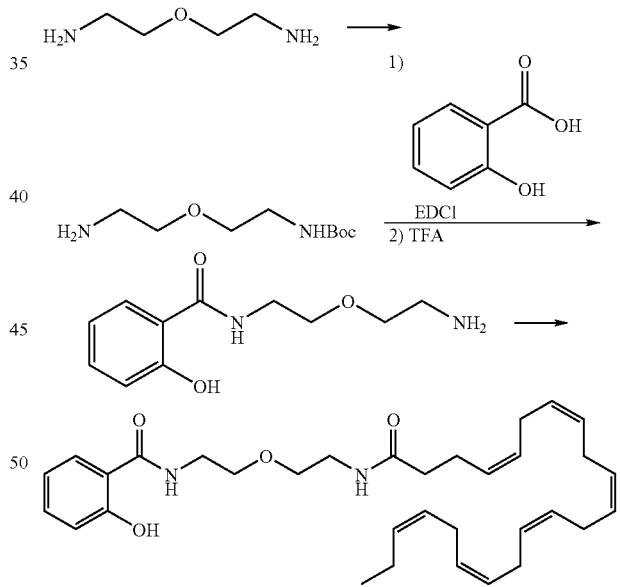

In a typical run, sodium hydroxide (400 mg, 10 mmol) was dissolved in MeOH (70 mL) and 2-(2-aminoethoxy)-ethanamine dihydrochloride (1.0 g, 5.65 mmol) was added. The resulting reaction mixture was stirred at room temperature for 30 minutes. A solution containing $Boc_2O$ (740 mg, 3.40 mmol) in THF (15 mL) was then added dropwise, at room temperature, over a period of 15 minutes. The resulting reaction mixture was stirred at room temperature for 18 h and then concentrated under reduced pressure. The resulting residue was taken up in $CH_2Cl_2$ (200 mL) and stirred vigorously at room temperature for 4 h. The mixture was filtered and the filtrate was concentrated under reduced pressure to afford tert-butyl 2-(2-aminoethoxy)ethylcarbamate (850 mg, 74%).

tert-Butyl 2-(2-aminoethoxy)ethylcarbamate was then taken up in $CH_2Cl_2$ (20 mL) along with salicylic acid (576 mg, 4.17 mmol) and EDCI (905 mg, 4.72 mmol). The resulting reaction mixture was stirred at room temperature for 18 h. It was then diluted with $CH_2Cl_2$ (20 mL), washed with saturated aqueous $NaHCO_3$, brine, dried over $Na_2SO_4$ and concentrated under reduced pressure. The resulting residue was purified by chromatography (9:1 $CH_2Cl_2$/MeOH) to afford tert-butyl 2-(2-(2-hydroxybenzamido)ethoxy)ethylcarbamate (450 mg, 33%). Mass, calculated for $C_{16}H_{24}N_2O_5$: 324.17; found: $[M+H]^+=325$.

tert-Butyl 2-(2-(2-hydroxybenzamido)ethoxy)ethylcarbamate (450 mg, 1.39 mmol) was taken up in 25% TFA in $CH_2Cl_2$ (5 mL). The reaction mixture was allowed to stand at room temperature for 2 h and then concentrated under reduced pressure to afford N-(2-(2-aminoethoxy)ethyl)-2-hydroxybenzamide as the TFA salt. This material was then taken up in $CH_3CN$ (10 mL) along with (4Z,7Z,10Z,13Z,16Z,19Z)-docosa-4,7,10,13,16,19-hexaenoic acid (DHA, 456 mg, 1.39 mmol), HATU (580 mg, 1.53 mmol) and DIEA (0.730 mL). The resulting reaction mixture was stirred at room temperature for 2 h. It was then diluted with EtOAc and washed successively with saturated aqueous $NaHCO_3$ and brine. The organic layer was dried over $Na_2SO_4$ and concentrated under reduced pressure. Purification by chromatography (60% EtOAc, 40% pentane) afforded N-(2-(2-(4Z,7Z,10Z,13Z,16Z,19Z)-docosa-4,7,10,13,16,19-hexaenamidoethoxy)ethyl)-2-hydroxybenzamide (150 mg, 20%). Mass calculated for $C_{33}H_{46}N_2O_4$: 534.35; found: $[M+H]^+=535$.

Example 39

Preparation of N-(1-(4Z,7Z,10Z,13Z,16Z,19Z)-docosa-4,7,10,13,16,19-hexaenamido-2-methylpropan-2-yl)-2-hydroxybenzamide (I-4)

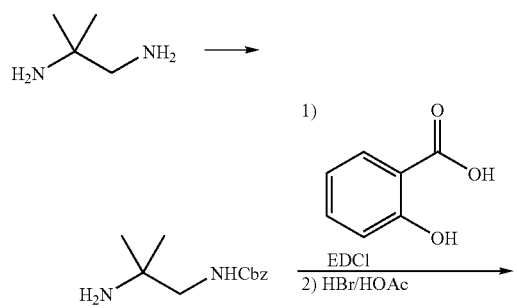

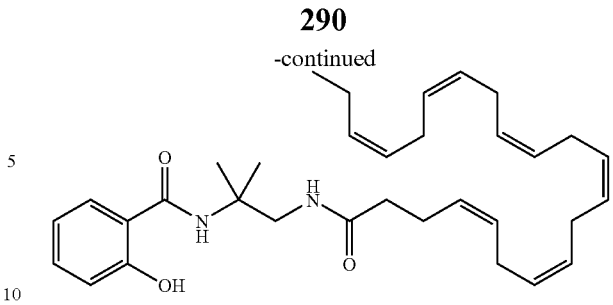

2-Methylpropane-1,2-diamine (1.52 g, 14.5 mmol) was dissolved in $CH_2Cl_2$ (50 mL) and cooled to 0° C. Benzyl chloroformate (2.0 mL, 14.5 mmol) was then added dropwise at 0° C. over a period of 10 minutes. The resulting reaction mixture was warmed to room temperature, stirred for 4 h and then concentrated under reduced pressure to afford benzyl 2-amino-2-methylpropylcarbamate as the HCl salt.

The HCl salt of benzyl 2-amino-2-methylpropylcarbamate (1.0 g, 3.87 mmol) was taken up in $CH_3CN$ (15 mL) along with HATU (1.60 g, 4.2 mmol), salicylic acid (535 mg, 3.87 mmol) and DIEA (2.0 mL, 11.6 mmol). The resulting reaction mixture was stirred at room temperature for 18 h. It was then concentrated under reduced pressure and diluted with EtOAc. The organic layer was washed with saturated aqueous $NaHCO_3$, brine, dried over $Na_2SO_4$ and concentrated under reduced pressure. The resulting residue was purified by chromatography (30% EtOAc/pentane) to afford benzyl 2-(2-hydroxybenzamido)-2-methylpropylcarbamate (340 mg, 26%). Mass calculated for $C_{19}H_{22}N_2O_4$: 342.16; found: $[M+H]^+=343$.

Benzyl 2-(2-hydroxybenzamido)-2-methylpropylcarbamate (340 mg, 0.99 mmol) was taken up in 33% HBr in glacial acetic acid (1.5 mL). The reaction mixture was allowed to stand at room temperature for 2 h and then concentrated under reduced pressure to afford the HBr salt of N-(1-amino-2-methylpropan-2-yl)-2-hydroxybenzamide. This material was taken up in $CH_3CN$ (10 mL) along with (4Z,7Z,10Z,13Z,16Z,19Z)-docosa-4,7,10,13,16,19-hexaenoic acid (326 mg, 0.99 mmol), HATU (415 mg, 1.1 mmol) and DIEA (0.26 mL). The resulting reaction mixture was stirred at room temperature for 2 h. It was then diluted with EtOAc and washed successively with saturated aqueous $NaHCO_3$ and brine. The organic layer was dried over $Na_2SO_4$ and concentrated under reduced pressure. Purification by chromatography (EtOAc-PE, 30%) afforded N-(1-(4Z,7Z,10Z,13Z,16Z,19Z)-docosa-4,7,10,13,16,19-hexaenamido-2-methylpropan-2-yl)-2-hydroxybenzamide (150 mg, 29%). Mass calculated for $C_{33}H_{46}N_2O_3$: 518.35; found: $[M+H]^+=519$.

Example 40

Preparation of (R)-methyl 3-(1-(2-(4Z,7Z,10Z,13Z,16Z,19Z)-docosa-4,7,10,13,16,19-hexaenamidoethyl)-2,5-dioxopyrrolidin-3-ylthio)-2-(2-hydroxybenzamido)propanoate (Ih-11)

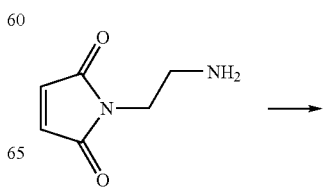

291
-continued

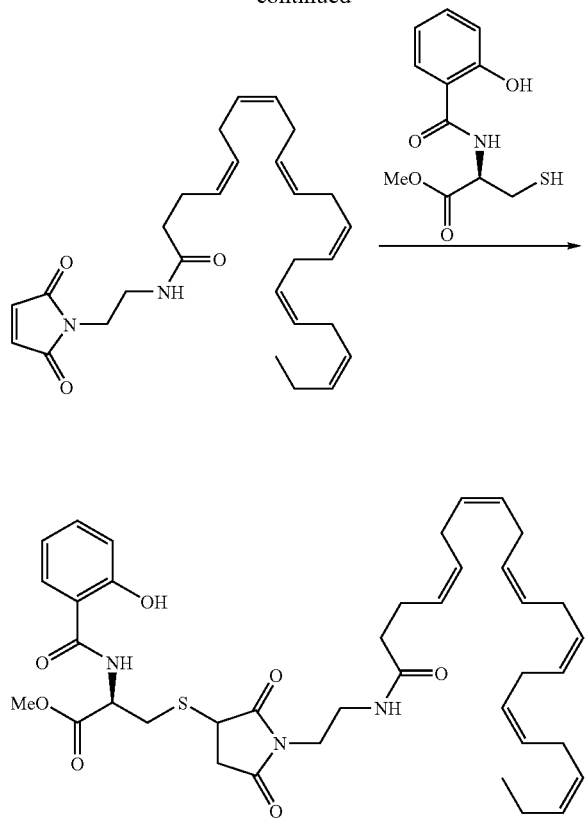

The TFA salt of 1-(2-aminoethyl)-1H-pyrrole-2,5-dione (Aldrich, 280 mg, 1.10 mmol) was taken up in $CH_3CN$ (10 mL) along with (4Z,7Z,10Z,13Z,16Z,19Z)-docosa-4,7,10,13,16,19-hexaenoic acid (360 mg, 1.1 mmol), HATU (460 mg, 1.2 mmol) and DIEA (0.58 mL). The resulting reaction mixture was stirred at room temperature for 3 h. It was then diluted with EtOAc and washed successively with saturated aqueous $NaHCO_3$ and brine. The organic layer was dried over $Na_2SO_4$ and concentrated under reduced pressure. Purification by chromatography ($CH_2Cl_2$) afforded (4Z,7Z,10Z,13Z,16Z,19Z)—N-(2-(2,5-dioxo-2H-pyrrol-1(5H)-yl)ethyl) docosa-4,7,10,13,16,19-hexaenamide (350 mg, 70%).

Separately, salicylic acid (152 mg, 1.10 mmol) was taken up in $CH_3CN$ (10 mL) along with L-cysteine methyl ester hydrochloride (189 mg, 1.10 mmol), EDCI (350 mg) and N-methylmorpholine (120 μL). The reaction mixture was stirred at room temperature for 3 h. It was then diluted with EtOAc. The organic layer was washed with saturated aqueous $NaHCO_3$ and brine. The organic layer was dried over $Na_2SO_4$ and concentrated under reduced pressure to afford crude (R)-methyl 2-(2-hydroxybenzamido)-3-mercaptopropanoate. This material was then taken up in $CH_3CN$ (3 mL) along with (4Z,7Z,10Z,13Z,16Z,19Z)—N-(2-(2,5-dioxo-2H-pyrrol-1(5H)-yl)ethyl)docosa-4,7,10,13,16,19-hexaenamide (315 mg, 0.7 mmol) and stirred at room temperature for 30 minutes. The reaction mixture was then concentrated under reduced pressure. Purification by silica gel chromatography ($CH_2Cl_2$) afforded (R)-methyl 3-(1-(2-(4Z,7Z,10Z,13Z,16Z,19Z)-docosa-4,7,10,13,16,19-hexaenamidoethyl)-2,5-dioxopyrrolidin-3-ylthio)-2-(2-hydroxybenzamido)propanoate (140 mg). Mass calculated for $C_{39}H_{51}N_3O_7S$: 705.34; found: $[M+H]^+=706$.

292
Example 41

Preparation of N-(2-((2-(4Z,7Z,10Z,13Z,16Z,19Z)-docosa-4,7,10,13,16,19-hexaenamidoethyl)(methyl)amino)ethyl)-2-hydroxybenzamide (I-7)

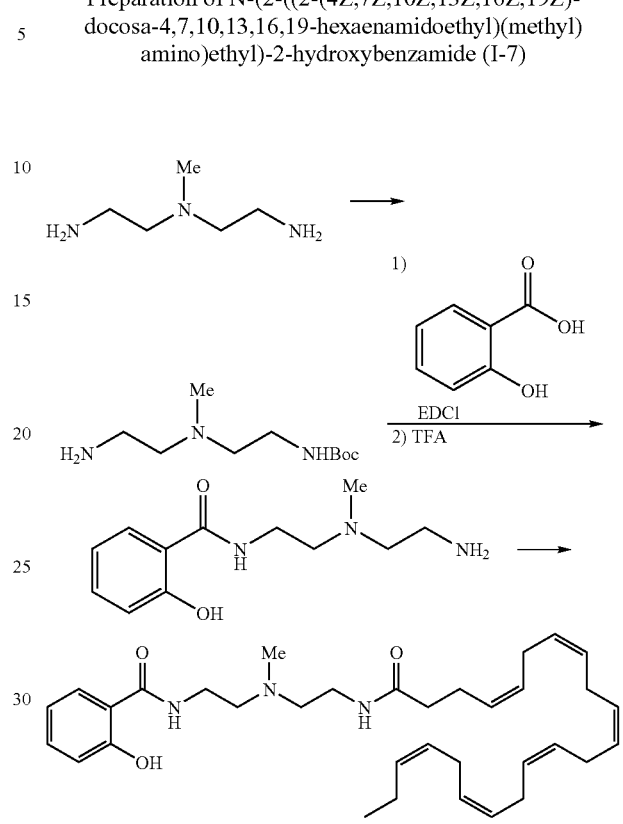

N-1-(2-Aminoethyl)-N1-methylethane-1,2-diamine (5.0 g, 42.7 mmol) was dissolved in $CH_2Cl_2$ (100 mL) and cooled to 0° C. A solution of di-tert-butylcarbonate (0.93 g, 4.27 mmol) in $CH_2Cl_2$ (10 mL) was then added dropwise at 0° C. over a period of 15 minutes. The resulting reaction mixture was stirred at 0° C. for 30 minutes and then warmed to room temperature. After stirring at room temperature for 2 h, the reaction mixture was diluted with $CH_2Cl_2$ (100 mL). The organic layer was washed with brine (3×25 mL), dried over $Na_2SO_4$ and concentrated under reduced pressure to afford 1.1 g of tert-butyl 2-((2-aminoethyl)(methyl)amino)ethylcarbamate.

tert-Butyl 2-((2-aminoethyl)(methyl)amino)ethylcarbamate (500 mg, 2.3 mmol) was taken up in $CH_3CN$ (10 mL) along with salicylic acid (310 mg, 2.3 mmol) and EDCI (485 mg, 2.53 mmol). The resulting reaction mixture was stirred at room temperature for 18 h and then diluted with EtOAc. The organic layer was washed with saturated aqueous $NaHCO_3$, brine, dried over $Na_2SO_4$ and concentrated under reduced pressure. The resulting residue was purified by chromatography (MeOH—$CH_2Cl_2$, 5%) to afford tert-butyl 2-((2-(2-hydroxybenzamido)ethyl)(methyl)amino)ethylcarbamate (380 mg, 49%). Mass calculated for $C_{17}H_{27}N_3O_4$: 337.2; found: $[M+H]^+=338$.

tert-Butyl 2-((2-(2-hydroxybenzamido)ethyl)(methyl)amino)ethylcarbamate (380 mg, 1.13 mmol) was taken up in 25% TFA in $CH_2Cl_2$ (5 mL) and allowed to stand at room temperature for 3 h. The reaction mixture was concentrated under reduced pressure to afford the TFA salt of N-(2-((2- aminoethyl)(methyl)amino)ethyl)-2-hydroxybenzamide.

This material was taken up in $CH_3CN$ (10 mL) along with (4Z,7Z,10Z,13Z,16Z,19Z)-docosa-4,7,10,13,16,19-hexaenoic acid (DHA, 370 mg, 1.13 mmol), HATU (472 mg, 1.24 mmol) and DIEA (0.59 mL). The resulting reaction mixture was stirred at room temperature for 2 h. It was then diluted with EtOAc and washed successively with saturated aqueous $NaHCO_3$ and brine. The organic layer was dried over $Na_2SO_4$ and concentrated under reduced pressure. Purification by chromatography (MeOH—$CH_2Cl_2$, 5%) afforded N-(2-((2-(4Z,7Z,10Z,13Z,16Z,19Z)-docosa-4,7,10,13,16,19-hexaenamidoethyl)(methyl)amino)ethyl)-2-hydroxybenzamide (420 mg). Mass calculated for $C_{34}H_{49}N_3O_3$: 547.38; found: $[M+H]^+=548$.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A synergistically active molecular conjugate comprising a salicylate and a fatty acid,
   wherein the salicylate is selected from the group consisting of substituted or unsubstituted salicylic acid, aminosalicylic acid, diflunisal, and triflusal, and the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid (DPA), docosahexaenoic acid (DHA), tetracosapentaenoic acid, and tetracosahexaenoic acid,
   with the proviso that when the molecular conjugate comprises a fatty acid containing seven contiguous unsubstituted methylene units, the methylene units must be preceded by an adjacent carbonyl moiety, and
   wherein the synergistic activity is derived from in vivo delivery of the salicylate and the fatty acid together to a target tissue or a target cell.

2. A compound of Formula I,

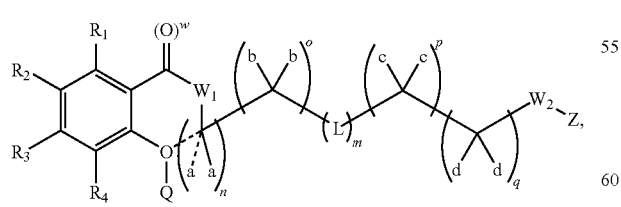

Formula I or a pharmaceutically acceptable salt, enantiomer, or stereoisomer thereof,
wherein:
$R_1$, $R_2$, $R_3$, and $R_4$ are each independently selected from the group consisting of H, Cl, F, CN, $NH_2$, —$NH(C_1-C_3$ alkyl), —$N(C_1-C_3$ alkyl)$_2$, —$NH(C(O)C_1-C_3$ alkyl), —$N(C(O)C_1-C_3$ alkyl)$_2$, —C(O)H, —$C(O)C_1-C_3$ alkyl, —$C(O)OC_1-C_3$ alkyl, —$C(O)NH_2$, —$C(O)NH(C_1-C_3$ alkyl), —$C(O)N(C_1-C_3$ alkyl)$_2$, —$C_1-C_3$ alkyl, —O—$C_1-C_3$ alkyl, difluorophenyl, and trifluoromethyl;

$W_1$ and $W_2$ are each independently null or NH, or when $W_1$ and $W_2$ are both NH, then both $W_1$ and $W_2$ can be taken together to form a piperidine moiety;

each symbol - - - - - represents an optional bond, which when present between the phenolic oxygen and the methylene containing substituent a, requires that Q is null, or when present between substituent a and the carbon of the methylene containing substituent a, requires that Q not be null;

each a and c is independently H, $CH_3$, —$OCH_3$, —$OCH_2CH_3$, C(O)OH, C(O)OR or benzyl;

each b is independently H, $CH_3$, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —$S(O)_2$—, —S—S—,

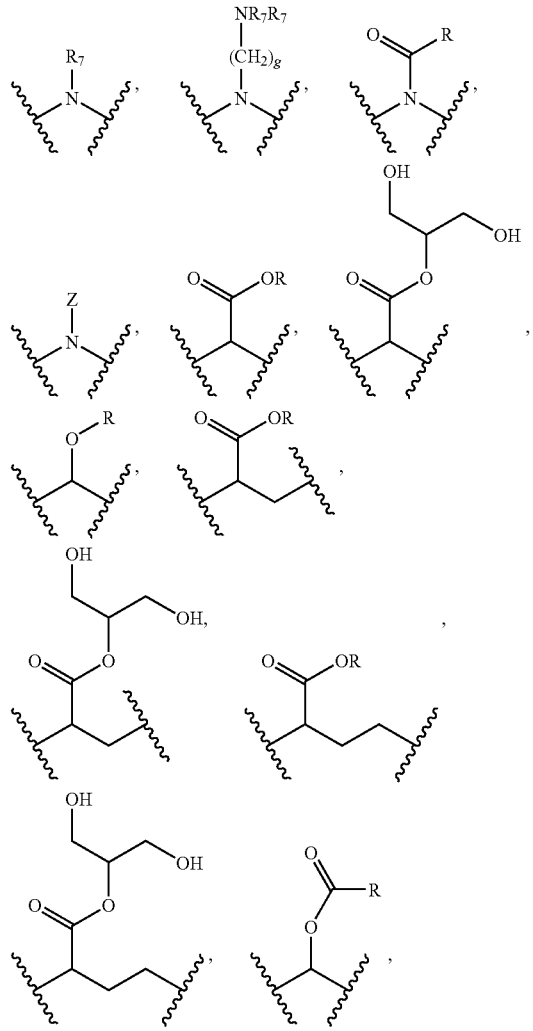

-continued

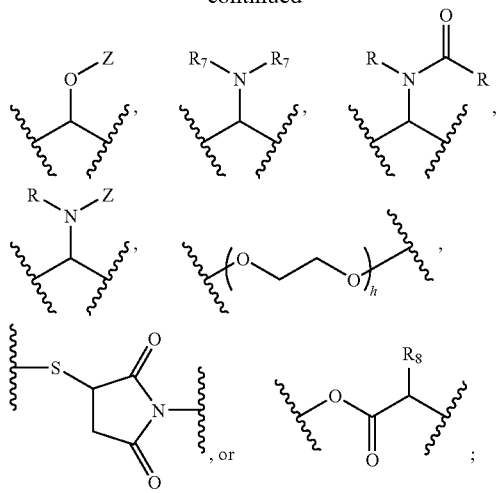

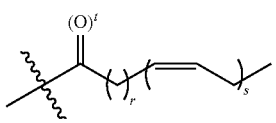

in the compound;
each r is independently 2 or 3;
each s is independently 5 or 6;
each t is independently 0 or 1;
w is 0 or 1;
Q is null, C(O)CH$_3$, Z,

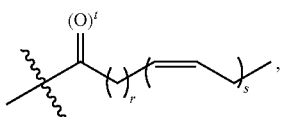

each e is independently H or any one of the side chains of a naturally occurring amino acid;
W$_3$ is null or —N(R)—; and
T is H, C(O)CH$_3$, or Z;
provided that when w is 0, then W$_1$ is NH.

3. A compound of claim 2, wherein W$_1$ and W$_2$ are each NH.

4. A compound of claim 3, wherein r is 2, s is 6, w is 1, Z is

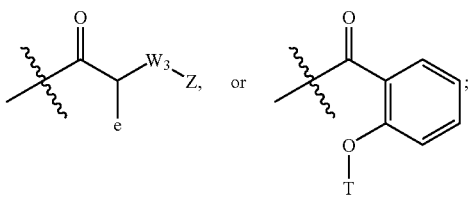

and t is 1.

5. A compound of claim 3, wherein the compound is selected from the group consisting of:

each g is independently 2, 3 or 4;
each h is independently 1, 2, 3 or 4;
m is 0, 1, 2, or 3;
each R$_7$ is independently H or C$_1$-C$_6$ alkyl, or both R$_7$ groups, when taken together with the nitrogen to which they are attached, can form a heterocycle;
each R$_8$ is independently e, H or straight or branched C$_1$-C$_{10}$ which can be optionally substituted with OH, NH$_2$, CO$_2$R, CONH$_2$, phenyl, C$_6$H$_4$OH, imidazole or arginine;
each R is independently H, —C(O)—C$_1$-C$_3$ alkyl, or straight or branched C$_1$-C$_4$ alkyl optionally substituted with halogen;
each Z is independently H or

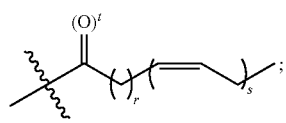

with the proviso that there is at least one

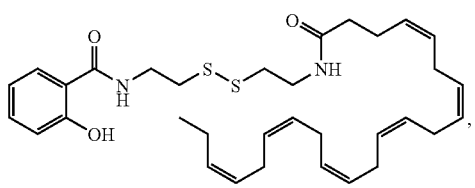

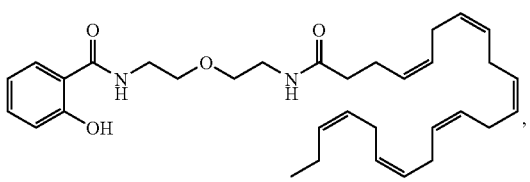 [SMILES: CC/C=C\C/C=C\C/C=C\C/C=C\C/C=C\C/C=C\CCC(=O)NCCOCCNC(=O)c1ccccc1O ; "."]

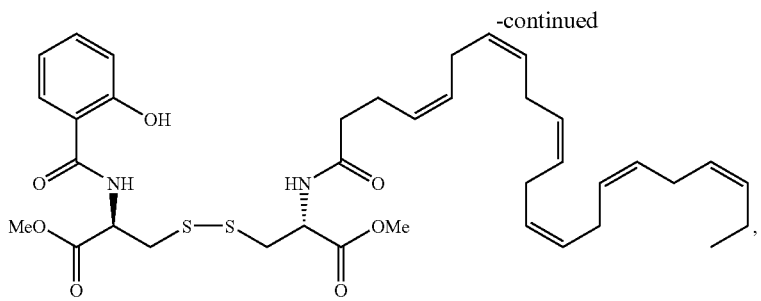
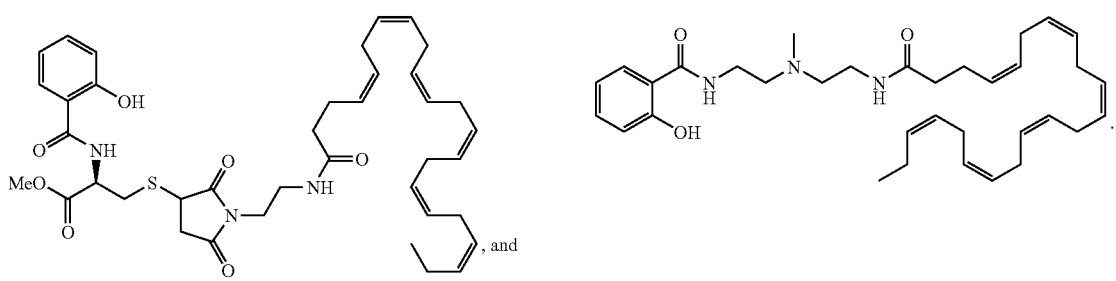
6. A compound of claim 4, wherein the compound is
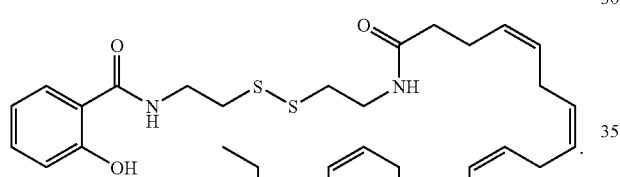
7. A compound of claim 4, wherein the compound is
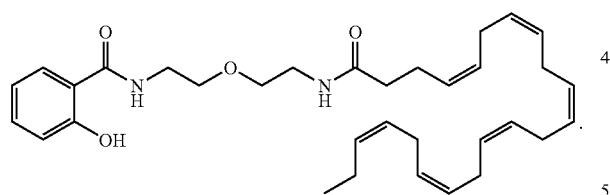
8. A compound of claim 2, wherein Q is Z.
9. A compound of claim 2, wherein Q is
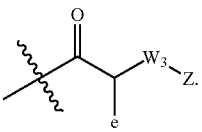
10. A compound of claim 2, wherein m is 1 and L is —S—S— or —O—.
11. A compound of Formula III:
Formula III
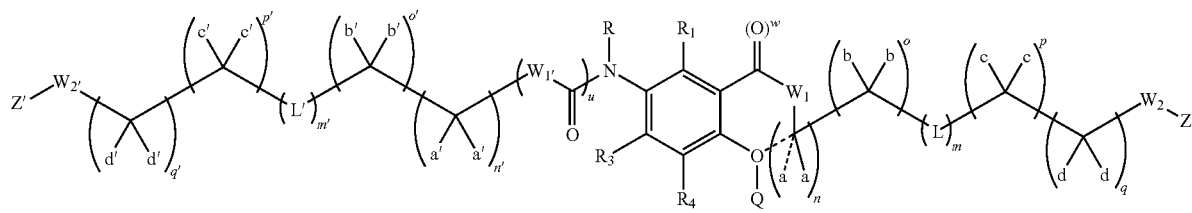

or a pharmaceutically acceptable salt, enantiomer, or stereoisomer thereof, wherein $R_1$, $R_3$, and $R_4$ are each independently selected from the group consisting of H, Cl, F, CN, $NH_2$, $-NH(C_1-C_3$ alkyl), $-N(C_1-C_3$ alkyl)$_2$, $-NH(C(O)C_1-C_3$ alkyl), $-N(C(O)C_1-C_3$ alkyl)$_2$, $-C(O)H$, $-C(O)C_1-C_3$ alkyl, $-C(O)OC_1-C_3$ alkyl, $-C(O)NH_2$, $-C(O)NH(C_1-C_3$ alkyl), $-C(O)N(C_1-C_3$ alkyl)$_2$, $-C_1-C_3$ alkyl, $-O-C_1-C_3$ alkyl, difluorophenyl, and trifluoromethyl;

each $W_1$, $W_{1'}$, $W_2$ and $W_{2'}$ is independently null, O, or NH, or when $W_1$ and $W_2$ or $W_{1'}$ and $W_{2'}$ are both NH, then both $W_1$ and $W_2$ or $W_{1'}$ and $W_{2'}$ can be taken together to form a piperidine moiety;

each symbol - - - - - represents an optional bond, which when present between the phenolic oxygen and the methylene containing substituent a, requires that Q is null, or when present between substituent a and the carbon of the methylene containing substituent a, requires that Q not be null;

each a, a', c, and c' is independently H, $CH_3$, $-OCH_3$, $-OCH_2CH_3$, C(O)OH, C(O)OR or benzyl;

each b and b' is independently H, $CH_3$, C(O)OH, O—Z, C(O)OR or benzyl;

each d and d' is independently H, C(O)OH, C(O)OR or benzyl;

each n, n', o, o', p, p', q, and q' is independently 0 or 1;

each L and L' is independently $-O-$, $-S-$, $-S(O)-$, $-S(O)_2-$, $-S-S-$,

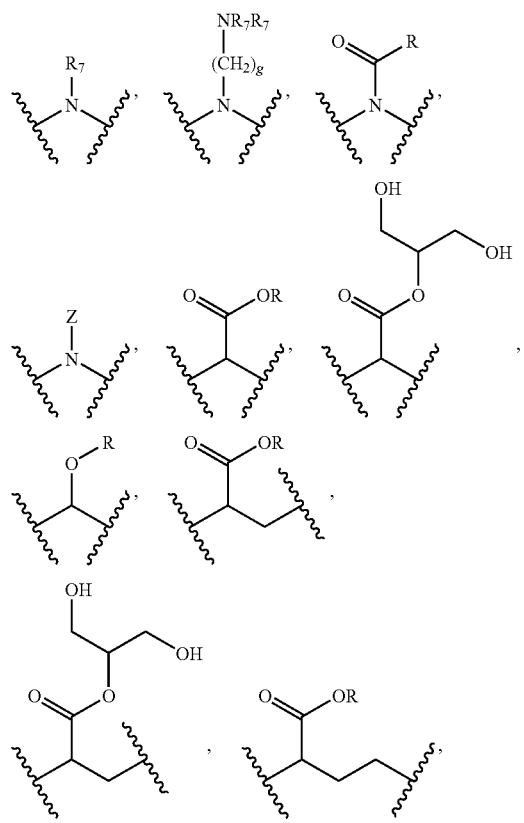

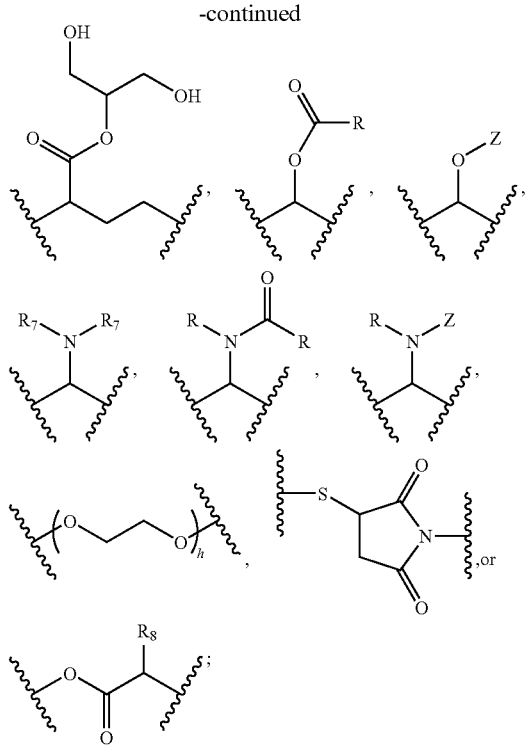

each g is independently 2, 3 or 4;
each h is independently 1, 2, 3 or 4;
each m and m' is independently 0, 1, 2, or 3;
each $R_7$ is independently H or $C_1-C_6$ alkyl, or both $R_7$ groups, when taken together with the nitrogen to which they are attached, can form a heterocycle;
each $R_8$ is independently e, H or straight or branched $C_1-C_{10}$ which can be optionally substituted with OH, $NH_2$, $CO_2R$, $CONH_2$, phenyl, $C_6H_4OH$, imidazole or arginine;
each R is independently H, $-C(O)-C_1-C_3$ alkyl, or straight or branched $C_1-C_4$ alkyl optionally substituted with halogen;
each Z and Z' is independently H, or

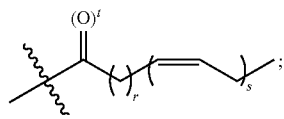

with the proviso that there is at least one

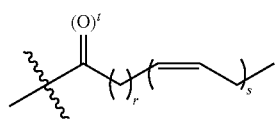

in the compound;
each r is independently 2, 3, or 7;
each s is independently 3, 5, or 6;
each t is independently 0 or 1;
w is 0 or 1;
u is 0 or 1;

Q is null, C(O)CH₃, Z,

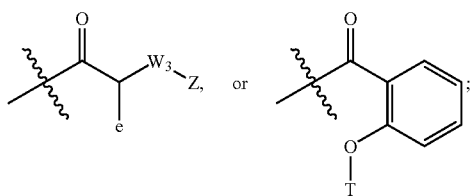

each e is independently H or any one of the side chains of a naturally occurring amino acid;
each W₃ is independently null, O, or —N(R)—; and
each T is independently H, C(O)CH₃, or Z;
provided that
when m, n, o, p, and q are each 0, W₁ and W₂ are each null, w is 1, and Z is

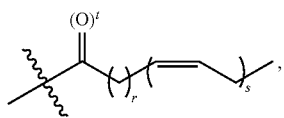

then t must be 0;
when m', n', o', p', and q' are each 0, u is 1, W₁' and W₂' are each null, and Z' is

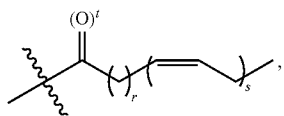

then t must be 0;
when w is 0, then W₁ is NH; and
when w is 1, Z is

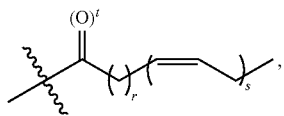

and r is 7, then t is 1.

12. A compound of claim 11, wherein Q is H.
13. A compound of Formula IIIa,

Formula IIIa

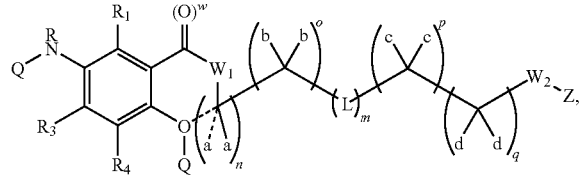

or a pharmaceutically acceptable salt, enantiomer, or stereoisomer thereof,
wherein
R₁, R₃, and R₄ are each independently selected from the group consisting of H, Cl, F, CN, NH₂, —NH(C₁-C₃ alkyl), —N(C₁-C₃ alkyl)₂, —NH(C(O)C₁-C₃ alkyl), —N(C(O)C₁-C₃ alkyl)₂, —C(O)H, —C(O)C₁-C₃ alkyl, —C(O)OC₁-C₃ alkyl, —C(O)NH₂, —C(O)NH(C₁-C₃ alkyl), —C(O)N(C₁-C₃ alkyl)₂, —C₁-C₃ alkyl, —O—C₁-C₃ alkyl, difluorophenyl, and trifluoromethyl;

each W₁ and W₂ is independently null, O, or NH, or when W₁ and W₂ are both NH, then both W₁ and W₂ can be taken together to form a piperidine moiety;

each symbol - - - - - represents an optional bond, which when present between the phenolic oxygen and the methylene containing substituent a, requires that Q is null, or when present between substituent a and the carbon of the methylene containing substituent a, requires that Q not be null;

each a and c is independently H, CH₃, —OCH₃, —OCH₂CH₃, C(O)OH, C(O)OR or benzyl;

each b is independently H, CH₃, C(O)OH, O—Z, C(O)OR or benzyl;

each d is independently H, C(O)OH, C(O)OR or benzyl;

each n, o, p, and q is independently 0 or 1;

each L is independently —O—, —S—, —S(O)—, —S(O)₂₋₅—S—S—,

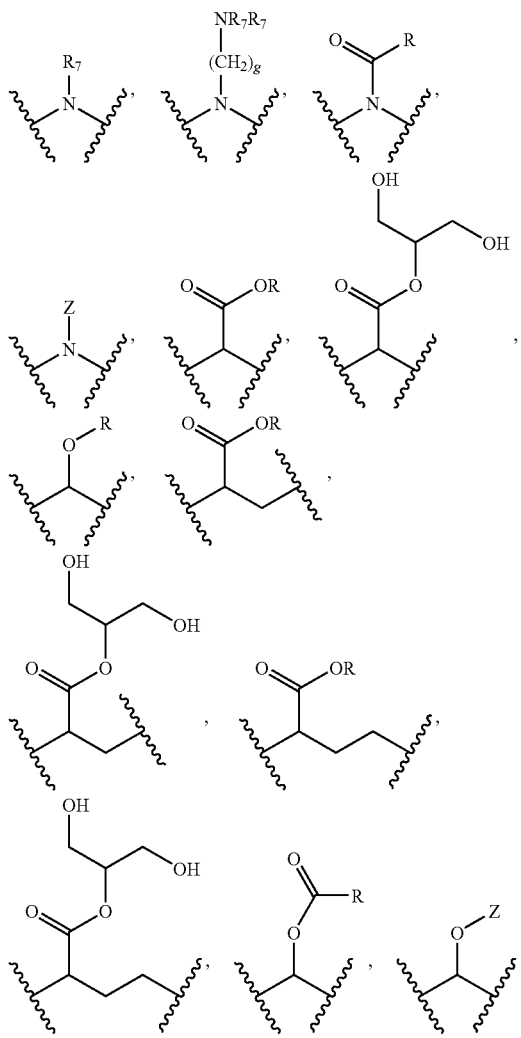

-continued

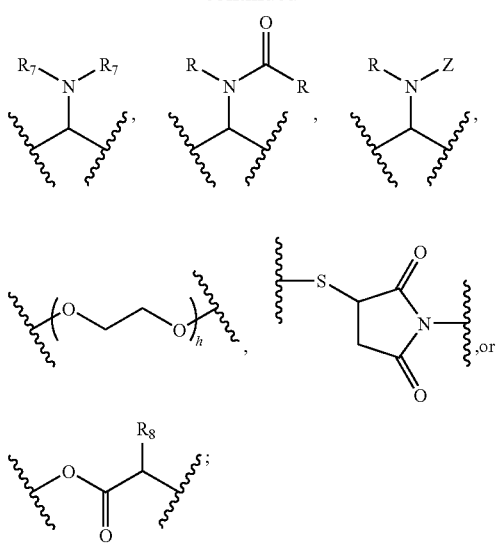

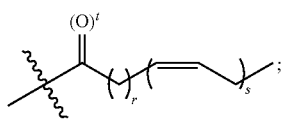

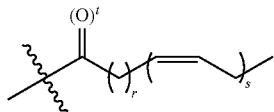

each g is independently 2, 3 or 4;
each h is independently 1, 2, 3 or 4;
m is 0, 1, 2, or 3;
each $R_7$ is independently H or $C_1$-$C_6$ alkyl, or both $R_7$ groups, when taken together with the nitrogen to which they are attached, can form a heterocycle;
each $R_8$ is independently e, H or straight or branched $C_1$-$C_{10}$ which can be optionally substituted with OH, $NH_2$, $CO_2R$, $CONH_2$, phenyl, $C_6H_4OH$, imidazole or arginine;
each R is independently H, —C(O)—$C_1$-$C_3$ alkyl, or straight or branched $C_1$-$C_4$ alkyl optionally substituted with halogen;
each Z is independently H, or

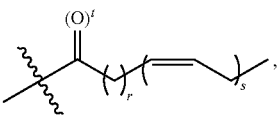

with the proviso that there is at least one

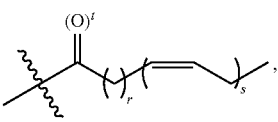

in the compound;
each r is independently 2, 3, or 7;
each s is independently 3, 5, or 6;
with the proviso that when r is 7, s is 3;
each t is independently 0 or 1;
w is 0 or 1;
each Q is independently null, H, $C(O)CH_3$, Z,

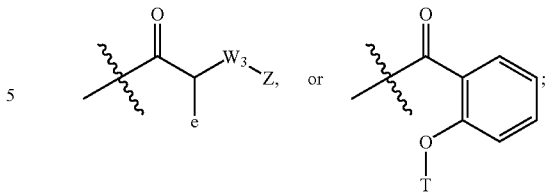

each e is independently H or any one of the side chains of a naturally occurring amino acid;
each $W_3$ is independently null, O, or —N(R)—; and
each T is independently H, $C(O)CH_3$, or Z;
provided that
when m, n, o, p, and q are each 0, $W_1$ and $W_2$ are each null, w is 1, and Z is

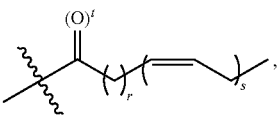

then t must be 0;
when w is 0, then $W_1$ is NH; and
when w is 1, Z is

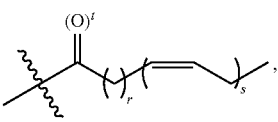

and r is 7, then t is 1.

14. A compound of claim 13, wherein at least one t is 1, and at least one Q is H.

15. A method of treating inflammation associated with a metabolic disorder selected from the group consisting of Type II diabetes, insulin resistance, atherosclerosis, dyslipidemia, retinopathy associated with diabetic complications, nephropathy associated with diabetic complications, neuropathy associated with diabetic complications, and macular edema associated with diabetic complications, the method comprising administering to a patient in need thereof an effective amount of a compound of claim 2.

16. The method of claim 15, wherein Q is H.

17. A method of treating inflammation associated with an inflammatory bowel disease selected from the group consisting of ileitis, ulcerative colitis, Barrett's syndrome, and Crohn's disease, comprising administering to a patient in need thereof an effective amount of a compound of claim 2.

18. A method of treating inflammation associated with a neurodegenerative disorder selected from the group consisting of Alzheimer's disease, amylotrophic lateral sclerosis, and multiple sclerosis, comprising administering to a patient in need thereof an effective amount of a compound of claim 2.

19. A method of treating inflammation associated with Duchenne's muscular dystrophy comprising administering to a patient in need thereof an effective amount of a compound of claim 2.

20. A pharmaceutical composition comprising a compound of claim 1 and a pharmaceutically acceptable carrier.

21. A method of treating inflammation associated with a metabolic disorder selected from the group consisting of Type II diabetes, insulin resistance, atherosclerosis, dyslipidemia, retinopathy associated with diabetic complications, nephropathy associated with diabetic complications, neuropathy associated with diabetic complications, and macular edema associated with diabetic complications, the method comprising administering to a patient in need thereof an effective amount of a compound of claim 11.

22. The method of claim 21, wherein Q is H.

23. A method of treating inflammation associated with an inflammatory bowel disease selected from the group consisting of ileitis, ulcerative colitis, Barrett's syndrome, and Crohn's disease, comprising administering to a patient in need thereof an effective amount of a compound of claim 11.

24. A method of treating inflammation associated with a neurodegenerative disorder selected from the group consisting of Alzheimer's disease and multiple sclerosis, comprising administering to a patient in need thereof an effective amount of a compound of claim 11.

25. A method of treating inflammation associated with Duchenne's muscular dystrophy comprising administering to a patient in need thereof an effective amount of a compound of claim 11.

26. The method of claim 23, wherein Q is H.

27. The method of claim 24, wherein Q is H.

28. The method of claim 25, wherein Q is H.

29. A method of treating inflammation associated with a metabolic disorder selected from the group consisting of Type II diabetes, insulin resistance, atherosclerosis, dyslipidemia, retinopathy associated with diabetic complications, nephropathy associated with diabetic complications, neuropathy associated with diabetic complications, and macular edema associated with diabetic complications, the method comprising administering to a patient in need thereof an effective amount of a compound of claim 13.

30. The method of claim 29, wherein at least one t is 1, and at least one Q is H.

31. A method of treating inflammation associated with an inflammatory bowel disease selected from the group consisting of ileitis, ulcerative colitis, Barrett's syndrome, and Crohn's disease, comprising administering to a patient in need thereof an effective amount of a compound of claim 13.

32. The method of claim 31, wherein at least one t is 1, and at least one Q is H.

33. A method of treating inflammation associated with a neurodegenerative disorder selected from the group consisting of Alzheimer's disease and multiple sclerosis, comprising administering to a patient in need thereof an effective amount of a compound of claim 13.

34. The method of claim 33, wherein at least one t is 1, and at least one Q is H.

35. A method of treating inflammation associated with Duchenne's muscular dystrophy comprising administering to a patient in need thereof an effective amount of a compound of claim 13.

36. The method of claim 35, wherein at least one t is 1, and at least one Q is H.

37. A method of treating inflammation associated with a metabolic disorder selected from the group consisting of Type II diabetes, insulin resistance, atherosclerosis, dyslipidemia, retinopathy associated with diabetic complications, nephropathy associated with diabetic complications, neuropathy associated with diabetic complications, and macular edema associated with diabetic complications, the method comprising administering to a patient in need thereof an effective amount of the conjugate of claim 1.

38. The method of claim 37, wherein the salicylate is unsubstituted salicylic acid, and wherein the fatty acid is docosahexaenoic acid (DHA) or eicosapentaenoic acid (EPA).

39. The method of claim 38, wherein the salicylate is unsubstituted salicylic acid, and wherein the fatty acid is docosahexaenoic acid (DHA).

40. A method of treating inflammation associated with an inflammatory bowel disease selected from the group consisting of ileitis, ulcerative colitis, Barrett's syndrome, and Crohn's disease, comprising administering to a patient in need thereof an effective amount of the conjugate of claim 1.

41. The method of claim 40, wherein the salicylate is aminosalicylic acid, and wherein the fatty acid is docosahexaenoic acid (DHA) or eicosapentaenoic acid (EPA).

42. The method of claim 41, wherein the salicylate is aminosalicylic acid, and wherein the fatty acid is docosahexaenoic acid (DHA).

43. A method of treating inflammation associated with a neurodegenerative disorder selected from the group consisting of Alzheimer's disease, amylotrophic lateral sclerosis, and multiple sclerosis, comprising administering to a patient in need thereof an effective amount of the conjugate of claim 1.

44. The method of claim 43, wherein the salicylate is unsubstituted salicylic acid, and wherein the fatty acid is docosahexaenoic acid (DHA) or eicosapentaenoic acid (EPA).

45. The method of claim 44, wherein the salicylate is unsubstituted salicylic acid, and wherein the fatty acid is docosahexaenoic acid (DHA).

46. A method of treating inflammation associated with Duchenne's muscular dystrophy comprising administering to a patient in need thereof an effective amount of the conjugate of claim 1.

47. The method of claim 46, wherein the salicylate is unsubstituted salicylic acid, and wherein the fatty acid is docosahexaenoic acid (DHA) or eicosapentaenoic acid (EPA).

48. The method of claim 47, wherein the salicylate is unsubstituted salicylic acid, and wherein the fatty acid is eicosapentaenoic acid (EPA).

49. A pharmaceutical composition comprising a compound of claim 2 and a pharmaceutically acceptable carrier.

50. A pharmaceutical composition comprising a compound of claim 11 and a pharmaceutically acceptable carrier.

51. A pharmaceutical composition comprising a compound of claim 13 and a pharmaceutically acceptable carrier.

52. The compound

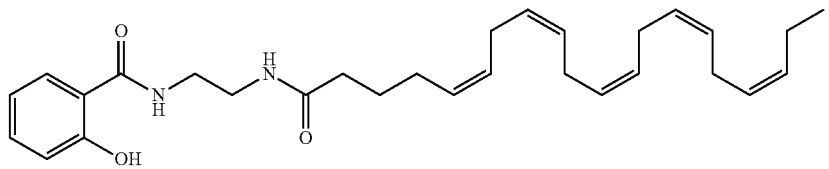 [SMILES: CC/C=C\C/C=C\C/C=C\C/C=C\C/C=C\CCCC(=O)NCCNC(=O)c1ccccc1O]

or a pharmaceutically acceptable salt thereof.

53. A pharmaceutical composition comprising the compound claim 52 or the pharmaceutically acceptable salt thereof; and a pharmaceutically acceptable carrier.

54. A method of treating inflammation associated with Duchenne's muscular dystrophy comprising administering to a patient in need thereof an effective amount of the compound of claim 52 or the pharmaceutically acceptable salt thereof.

* * * * *

UNITED STATES PATENT AND TRADEMARK OFFICE
CERTIFICATE OF CORRECTION

PATENT NO. : 9,085,527 B2
APPLICATION NO. : 12/714308
DATED : July 21, 2015
INVENTOR(S) : Chi B. Vu et al.

It is certified that error appears in the above-identified patent and that said Letters Patent is hereby corrected as shown below:

In the Claims

In claim 20 at column 304, lines 64-65, replace "a compound" with -- the molecular conjugate --.

In claim 53 at column 307, lines 1-2, replace "compound claim 52" with -- compound of claim 52 --.

Signed and Sealed this
Sixteenth Day of August, 2016

Michelle K. Lee
*Director of the United States Patent and Trademark Office*